US008680252B2

(12) United States Patent
Emalfarb et al.

(10) Patent No.: US 8,680,252 B2
(45) Date of Patent: Mar. 25, 2014

(54) EXPRESSION AND HIGH-THROUGHPUT SCREENING OF COMPLEX EXPRESSED DNA LIBRARIES IN FILAMENTOUS FUNGI

(75) Inventors: Mark A. Emalfarb, Jupiter, FL (US); Peter J. Punt, Houten (NL); Cornelia Van Zeijl, Vleuten-de-Meern (NL); Cornelius Van Den Hondel, Gouda (NL); Jan Verdoes, Zeist (NL); Richard P. Burlingame, Jupiter, FL (US)

(73) Assignee: Dyadic International (USA), Inc., Jupiter, FL (US)

( * ) Notice: Subject to any disclaimer, the term of this patent is extended or adjusted under 35 U.S.C. 154(b) by 465 days.

(21) Appl. No.: 12/518,595

(22) PCT Filed: Dec. 10, 2007

(86) PCT No.: PCT/US2007/087020
§ 371 (c)(1),
(2), (4) Date: Mar. 1, 2010

(87) PCT Pub. No.: WO2008/073914
PCT Pub. Date: Jun. 19, 2008

(65) Prior Publication Data
US 2012/0030839 A1 Feb. 2, 2012

Related U.S. Application Data

(60) Provisional application No. 60/869,341, filed on Dec. 10, 2006.

(51) Int. Cl.
*C12P 1/00* (2006.01)
*C12P 21/04* (2006.01)
*C07H 21/02* (2006.01)

(52) U.S. Cl.
USPC ........... 536/23.1; 435/41; 435/69.7; 435/71.1

(58) Field of Classification Search
None
See application file for complete search history.

(56) References Cited

U.S. PATENT DOCUMENTS

| | | |
|---|---|---|
| 2,974,001 A | 3/1961 | Windblicher et al. |
| 3,844,890 A | 10/1974 | Horikoshi et al. |
| 3,966,543 A | 6/1976 | Cayle et al. |
| 4,081,328 A | 3/1978 | Skinner et al. |
| 4,435,307 A | 3/1984 | Barbesgaard et al. |
| 4,443,355 A | 4/1984 | Murata et al. |
| 4,462,307 A | 7/1984 | Wells |
| 4,479,881 A | 10/1984 | Tai |
| 4,486,533 A | 12/1984 | Lambowitz |
| 4,610,800 A | 9/1986 | Durham et al. |
| 4,661,289 A | 4/1987 | Parslow et al. |
| 4,816,405 A | 3/1989 | Yelton et al. |
| 4,832,864 A | 5/1989 | Olson |
| 4,885,249 A | 12/1989 | Buxton |
| 4,912,056 A | 3/1990 | Olson |
| 4,935,349 A | 6/1990 | McKnight |
| 4,940,838 A | 7/1990 | Schilperoort et al. |
| 5,006,126 A | 4/1991 | Olson et al. |
| 5,120,463 A | 6/1992 | Bjork et al. |
| 5,122,159 A | 6/1992 | Olson et al. |
| 5,198,345 A | 3/1993 | Gwynne |
| 5,223,409 A | 6/1993 | Ladner |
| 5,252,726 A | 10/1993 | Woldike |
| 5,290,474 A | 3/1994 | Clarkson et al. |
| 5,362,638 A | 11/1994 | Dahiya |
| 5,364,770 A | 11/1994 | Berka |
| 5,436,158 A | 7/1995 | Takagi |
| 5,457,046 A | 10/1995 | Woldike et al. |
| 5,464,763 A | 11/1995 | Schilperoort et al. |
| 5,503,991 A | 4/1996 | Gwynne |
| 5,516,670 A | 5/1996 | Kuehnle |
| 5,536,661 A | 7/1996 | Boel |
| 5,565,332 A | 10/1996 | Hoogenboom |
| 5,578,463 A | 11/1996 | Berka |
| 5,602,004 A | 2/1997 | Jensen |
| 5,604,129 A | 2/1997 | Jensen |
| 5,605,793 A | 2/1997 | Stemmer |

(Continued)

FOREIGN PATENT DOCUMENTS

| | | |
|---|---|---|
| EP | 0194276 | 9/1986 |
| EP | 0239400 | 4/1989 |

(Continued)

OTHER PUBLICATIONS

*Myceliophthora thermophila* ATCC 42464 chromosome 1, complete sequence; Genbank record CP003002.1; Jul. 23, 2012.*
Lumbertozzi et al., Marker and promoter effects on heterologous expression in *Aspergillus nidulans*; Appl Microbiol Biotechnol, vol. 72, pp. 1014-1023, 2006.*
Joutsjoki et al., Transformation of *Trichoderma reesei* with the *Hormoconis resinae* glucoamylase P (gamP) gene: production of a heterologous glucoamylase by *Trichoderma reesei*; Curr Genet, vol. 24, p. 223-228, 1993.*

(Continued)

*Primary Examiner* — Celine Qian
*Assistant Examiner* — Addison D Ault
(74) *Attorney, Agent, or Firm* — Roetzel & Andress; Michael J. Keller; Verne A. Luckow

(57) ABSTRACT

The invention provides a method for the expression and subsequent screening of DNA libraries, particularly synthetic, genomic, and cDNA libraries, in filamentous fungal hosts. In particular, the invention provides vectors, host strains, and a method for the expression and screening of complex DNA libraries, including, but not limited to, combinatory (combinatorial) libraries expressing one, two or more variable constituents and/or prepared from two or more sublibraries (e.g., for the expression and screening of immunoglobulin (including fragments and derivatives of whole immunoglobulin proteins) and other receptor or complex DNA libraries or libraries of libraries). The invention is useful for the expression and screening for a large variety of proteins and protein complexes, including human proteins. The present invention also relates to novel fungal protease sequences.

43 Claims, 27 Drawing Sheets

(56) References Cited

U.S. PATENT DOCUMENTS

| | | |
|---|---|---|
| 5,627,052 A | 5/1997 | Schrader |
| 5,686,593 A | 11/1997 | Woldike et al. |
| 5,695,965 A | 12/1997 | Stuart |
| 5,695,985 A | 12/1997 | Jensen |
| 5,705,358 A | 1/1998 | Gouka |
| 5,728,547 A | 3/1998 | Gwynne |
| 5,753,477 A | 5/1998 | Chan |
| 5,763,192 A | 6/1998 | Kaufmann |
| 5,763,254 A | 6/1998 | Woldike et al. |
| 5,770,356 A | 6/1998 | Light, II |
| 5,776,730 A | 7/1998 | Stuart |
| 5,780,279 A | 7/1998 | Matthews |
| 5,783,385 A | 7/1998 | Treco |
| 5,783,431 A | 7/1998 | Peterson et al. |
| 5,811,381 A | 9/1998 | Emalfarb |
| 5,820,866 A | 10/1998 | Kappler |
| 5,824,485 A | 10/1998 | Thompson et al. |
| 5,830,696 A | 11/1998 | Short |
| 5,834,191 A | 11/1998 | Radforth |
| 5,834,251 A | 11/1998 | Maras |
| 5,837,847 A | 11/1998 | Royer |
| 5,849,541 A | 12/1998 | Vinci |
| 5,858,657 A | 1/1999 | Winter |
| 5,871,907 A | 2/1999 | Winter |
| 5,879,921 A | 3/1999 | Cherry |
| 5,939,250 A | 8/1999 | Short |
| 5,955,316 A | 9/1999 | Connelly |
| 5,958,672 A | 9/1999 | Short |
| 5,965,384 A | 10/1999 | Boel |
| 5,969,108 A | 10/1999 | McCafferty |
| 5,989,814 A | 11/1999 | Frankel |
| 6,015,707 A | 1/2000 | Emalfarb |
| 6,017,731 A | 1/2000 | Tekamp-Olson |
| 6,022,725 A | 2/2000 | Fowler |
| 6,025,185 A | 2/2000 | Christensen |
| 6,030,779 A | 2/2000 | Short |
| 6,046,021 A | 4/2000 | Bochner |
| 6,054,267 A | 4/2000 | Short |
| 6,057,103 A | 5/2000 | Short |
| 6,060,305 A | 5/2000 | Royer et al. |
| 6,066,493 A | 5/2000 | Shuster et al. |
| 6,121,034 A | 9/2000 | Laroche et al. |
| 6,174,673 B1 | 1/2001 | Short |
| 6,184,026 B1 | 2/2001 | Shuster et al. |
| 6,518,042 B1 | 2/2003 | Borchert et al. |
| 6,573,068 B1 | 6/2003 | Milne Edwards et al. |
| 6,573,086 B1 | 6/2003 | Emalfarb |
| 7,122,330 B2 | 10/2006 | Emalfarb et al. |
| 7,399,627 B2 | 7/2008 | Emalfarb et al. |
| 7,794,962 B2 | 9/2010 | Emalfarb et al. |
| 7,883,872 B2 | 2/2011 | Gusakov et al. |
| 7,892,812 B2 | 2/2011 | Emalfarb et al. |
| 7,906,309 B2 | 3/2011 | Emalfarb et al. |
| 2003/0157595 A1 | 8/2003 | Emalfarb et al. |
| 2003/0176672 A1 | 9/2003 | Salceda et al. |
| 2004/0002136 A1 | 1/2004 | Emalfarb et al. |
| 2005/0191736 A1 | 9/2005 | Brown et al. |
| 2005/0227324 A1* | 10/2005 | Huang et al. ............ 435/69.1 |
| 2006/0005279 A1 | 1/2006 | Dotson et al. |
| 2006/0053514 A1 | 3/2006 | Wu et al. |
| 2006/0105361 A1 | 5/2006 | Rothstein et al. |
| 2006/0134747 A1 | 6/2006 | Baldwin et al. |
| 2006/0218671 A1 | 9/2006 | Brown et al. |
| 2006/0257923 A1* | 11/2006 | Emalfarb et al. ............ 435/6 |
| 2007/0077630 A1 | 4/2007 | Harris et al. |
| 2009/0280105 A1 | 11/2009 | Gusakov et al. |

FOREIGN PATENT DOCUMENTS

| | | |
|---|---|---|
| EP | 0220016 B1 | 8/1991 |
| EP | 0451216 | 10/1991 |
| EP | 0460617 | 5/1992 |
| EP | 1022335 A1 | 7/2000 |
| EP | 0215594 B2 | 10/2003 |
| GB | 1368599 A | 10/1974 |
| GB | 2094826 A | 9/1982 |
| GB | 2289218 A | 11/1995 |
| JP | 50-132269 A | 10/1975 |
| JP | 11304666 | 5/1999 |
| WO | 9100920 A2 | 1/1991 |
| WO | WO 91/00092 | 1/1991 |
| WO | WO 91/09967 | 7/1991 |
| WO | WO 91/09968 | 7/1991 |
| WO | WO 92/13831 | 8/1992 |
| WO | WO 93/07277 | 4/1993 |
| WO | 9311249 A1 | 6/1993 |
| WO | 9404673 A1 | 3/1994 |
| WO | WO 94/13820 | 6/1994 |
| WO | WO 96/02563 | 2/1996 |
| WO | WO 96/29391 | 9/1996 |
| WO | WO 97/09438 | 3/1997 |
| WO | 9713853 A1 | 4/1997 |
| WO | 9727363 A1 | 7/1997 |
| WO | WO 97/26330 | 7/1997 |
| WO | WO 98/15633 | 4/1998 |
| WO | 9932617 A2 | 7/1999 |
| WO | WO 99/51756 | 10/1999 |
| WO | WO 99/64582 | 12/1999 |
| WO | WO 99/67639 | 12/1999 |
| WO | WO 00/00632 | 1/2000 |
| WO | WO 00/20555 | 4/2000 |
| WO | 0050567 A1 | 8/2000 |
| WO | 0056893 A1 | 9/2000 |
| WO | WO 00/56900 | 9/2000 |
| WO | WO 00/78997 | 12/2000 |
| WO | WO 01/09352 | 2/2001 |
| WO | WO 01/25468 | 4/2001 |
| WO | WO 0125468 A1 * | 4/2001 |
| WO | WO 01/79558 | 10/2001 |
| WO | 2004031367 A2 | 4/2004 |

OTHER PUBLICATIONS

Office Action, dated May 27, 2010, for U.S. Appl. No. 12/047,709, filed Mar. 13, 2008, entitled "Transformation System in the Field of Filamentous Fungal Hosts.".

Food and Drug Administration. Agency Response Letter GRAS Notice No. GRN 000292, dated Sep. 29, 2009, from Mitchell A. Cheesman, Acting Director, to Richard H. Jundzil, Dyadic International (USC), Inc. (hyper text transfer protocol://www.fda.gov).

Notice of Allowance and Fee(s) Due, dated Oct. 28, 2010, for U.S. Appl. No. 10/257,629, filed Apr. 11, 2003, entitled "Novel Expression-Regulating Sequences and Expression Products in the Field of Filamentous fungi.".

Notice of Allowance and Fee(s) Due, dated Dec. 1, 2010, for U.S. Appl. No. 11/833,133, filed Aug. 2, 2007, entitled "Novel Fungal Enzymes.".

Armesilla et al. 1994. CEL1: a novel cellulose binding protein secreted by *Agaricus bisporus* during growth on crystalline cellulose. FEMS Microbiol. Lett. vol. 116, pp. 293-300.

Bajpai et al.1998. Deinking with Enzymes: A Review. TAPPI Journal. vol. 81, No. 12, pp. 111-117.

Benen et al. 2000. Characterization of *Aspergillus niger* Pectate Lyase A. Biochemistry, vol. 39, pp. 15563-15569.

Bhatawadekar. 1983. Studies on Optimum Conditions of Dnzymatic Desizing of LTKP Sized Fabric by Cellulase—Steeping and Cellulase-Padding Methods. Journal of the Textile Association, May 1983, pp. 83-86.

Bukhtojarov et al. 2004. Cellulase Complex of the Fungus *Chrysosporium lucknowense*: Isolation and Characterization of Endoglucanases and Cellobiohydrolases. Biochemistry (MOSC), May 2004, vol. 69, No. 5, pp. 542-551 (Abstract).

Canevascini, G. et al. 1983. Fractionation and Identification of Cellulases and Other Extracellular Enzymes Produced by *Sporotrichum* (*chrysosporium*) Thermophile During Growth on Cellulose or Cellobiose. Can. J. Microbiol., vol. 29, pp. 1071-1080.

De Vries, R.P. and Visser, J., 2001. *Aspergillus* enzymes involved in degradation of plant cell wall polysaccharides. Microbiol. Mol. Biol. R., 65, 497-522.

Ding et al. Cloning of multiple cellulose cDNAs from *Volvariella volvacea* and their differential expression during substrate colonization and fruiting. FEMS Microbiol. Lett 2006, vol. 263, pp. 207-213.

(56) References Cited

OTHER PUBLICATIONS

Eriksson, K. et al. Extracellular Enzyme System Utilized by the Fungus *Sporotrichum pulverulentum* (*Chrysosporium lignorum*) for the Breakdown of Cellulose. 1, Separation, Purification, and Physico-Chemical Characterisation of Five Endo-1, 4-Beta-Glucanases. European Journal of Biochemistry, 1975, vol. 51, pp. 193-206.
Flanagan, P.W. et al. Physiological Groups of Decomposer Fungi on Tundra Plant Remains. In Soil Organisms and Decomposition in Tundra, A.J. Holding et al., Eds., Tundra Biome Steering Committee (Stockholm), 1974, pp. 159-181.
Foreman et al. Transcriptional Regulation of Biomass-Degrading Enzymes in the Filamentous Fungus *Trichoderma reesei*. J. Biol. Chem. 2003, vol. 278, pp. 31988-31997.
Gordillo et al. *Penicillium purpurogenum* Produces a Family 1 Acetyl Xylan Esterase Containing a Carbohydrate-Binding Module: Characterization of the Protein and Its Gene. Mycol. Res., 2006, vol. 110, p. 1129.
Goudar et al. Influence of microbial concentration on the rheology of non-Newtonian fermentation broths. Appl. Microbiol. Biiotechnol. 1999, vol. 51, pp. 310-315.
Gunf-Fusox, accession No. p46239, Nov. 1, 1995, P.O. Sheppard et al. The Use of Conserved Cellulase Family-Specific Sequences to Clone Cellulase Homologue cDNAs from *Fusarium oxysporum*.
Gusakov, A.V. et al. Design of Highly Efficient Cellulase Mixtures for Enzymatic Hydrolysis of Cellulose. Biotechnol. Bioeng., 2007, vol. 97, No. 5, pp. 1028-1038.
Gusakov, A.V. et al. Purification, Cloning and Characterization of Two Forms of Thermostable and Highly Active Cellobiohydrolase I (Cel7A) Produced by the Industrial Strain of *Chrysosporium lucknowense*. Enzyme Microb. Technol. 2005, vol. 36, pp. 57-69.
Gusakov, A.V. Microassays to Control the Results of Cellulase Treatment of Denim Fabrics. Textile Chemist and Colorist and American Dyestuff Reporter, 2000, vol. 32, No. 5, pp. 42-47.
Hahn-Hagerdal et al. Bio-ethanol—The Fuel of Tomorrow from the Residues of Today. Trends in Biotechnology, 2006, vol. 24, No. 12, pp. 549-556.
Harmsen Martin C. et al. 1992. Sequence Analysis of the Glyceraldehyde-3-phosphate dehydrogenase genes from the basidiomycetes *Schizopyllum commune*, *Phanerochaete chrysosporium* and *Agaricus bisporus*. Current Genetics, vol. 22, No. 6, pp. 447-454.
Hong et al. Unusual hydrophobic linker region of B-glucosidase (BGLII) from *Thermoascus aurantiacus* is required for hyper-activation by organic solvents. *Applied Microbiol. Biotechnol*., 2006, vol. 73, pp. 80-88.
Huertas-Gonzalez et al. Cloning and characterization of pl1 encoding an in planta-secreted secreted pectate lyase of *Fusarium oxysporum*. Curr Genet, 1999, vol. 35, pp. 36-40.
Hurst, J.L. et al Association between *Chrysosporium pannorum* and *Mucor hiemalis* in *Poa flabellata* Litter. Trans. Br. Mycol. Soc., 1983, vol. 81, No. 1, pp. 151-153.
Iikura, H. et al. Cloning of a Gene Encoding a Putative Xylanase with a Cellulose-Binding Domain from *Humicola grisea*. Bioscience Biotechnology and Biochemistry, 1997, vol. 61, No. 9, pp. 1593-1595.
Janeckova et al. Ceska Mykologie (1977), vol. 331, No. 4, pp. 206-213 (Abstract).
Johnstone et al. Cloning an *Aspergillus nidulans* developmental gene by transformation. EMBO J., 1985, vol. 4, pp. 1307-1311.
Kauppinen et al. Molecular Cloning and Characterization of a Rhamnogalacturonan Acetylesterase from *Aspergillus aculeatus*. J. Biol Chem, 1995, vol. 270, p. 27172-27178.
Kormelink F.J.M. et al. Mode of Action of the Xylan-Degrading Enzymes from *Aspergillus awamori* on Alkali-Extractable Cereal Arabinoxylans. Carbohydr. Res, 1993, vol. 249, pp. 355-367.
Kormelink et al. Purification and Characterization of Three Endo-(1,4)-B-xylanases and one B-xylosidase from *Aspergillus awamori*. J. Biotechnol. 1993, vol. 27, pp. 249-265.
Kotake et al. Molecular cloning and expression in *Escherichia coli* of a *Trichoderma viride* endo-B-(1-6)-galactanase gene. Biochem J.., 2004, vol. 377, pp. 749-755.

Kramer et al. Insect Chitinases: Molecular Biology and Potential Uses as Biopesticides. Insect Biochem Mol Biol., 1997, vol. 27, p. 887.
Mandels, M. et al. Induction of Cellulase in *Trichoderma viride* as Influenced by Carbon Sources and Metals. J. Bacteriol., 1957, vol. 73, pp. 269-278.
Mantyla et al. Production in *Trichoderma reesei* xylanases of three xylanases from *Chaetomium thermophilum*: a recombinant thermoxylanase for biobleaching of kraft pulp. Appl. Microbiol. Biotechnol., 2007, vol. 76, pp. 377-386.
Maras et al., "Filamentous fungi as production organisms for glycoproteins of bio-medical interest," Glycoconjugate Journal, vol. 16, pp. 99-107 (1999).
Martinez, D. et al. Genome Sequencing and Analysis of the Biomass-Degrading Fungus *Trichoderma reesei* (syn. *Hypocrea jecorina*), Nature Biotechnol., 2008, vol. 26, pp. 553-560.
Meynial-Salles et al. In vitro glycosylation of proteins: An enzymatic approach. J. Biotechnol., 1996, vol. 46, pp. 1-14.
Mielenz. Ethanol Production from Biomass: Technology and Commercialization Status. Current Opinion in Microbiology, 2001, vol. 4, pp. 324-329.
Oberson, J. et al. Comparative investigation of cellulose-degrading enzyme systems produced by different strains of *Myceliophthora thermophila* (Apinis) v. Oorschot. Enzyme Microb. Technol. 1992, vol. 14, pp. 303-312.
Pages et al. ARhamnogalacturonan Lyase in the *Clostridium cellulolyticum* Cellulosome. J. Bacteriol. vol. 185, pp. 4727-4733 (2003).
Qureshi, M.S.A. et al. Cellulolytic Activity of Some Thermophilic and Thermotolerant Fungi of Pakistan, Viologia, vol. 26, Nos. 1-2, 1980, pp. 201-217.
Reese, E.T. et al. Beta-D-1,3 Glucanases in Fungi. Can. J. Microbiol. 1959, vol. 5, pp. 173-185.
Ridder, R. et al. 1992. Sequence Analysis of the Gene Coding for Glyceraldehyde-3-Phosphate Dehydrogenase GPD of *Podospora-anserina* use of Homologous Regulatory Sequences to Improve Transformation Efficiency. Current Genetics, vol. 21, No. 3, pp. 207-213.
Roller et al. Biotechnology in the Production and Modification of Biopolymers for Foods. Critical Reviews in Biotechnology, 1992, vol. 12, No. 3, pp. 261-277.
Ruiz-Roldan, M.C. et al. *Fusarium oxysporum* f.s.p. lycopersici. Family F xylanase (XYL3). Accession No. 059937, Aug. 1, 1998.
Sakamoto et al. Molecular characterization of a *Penicillium chrysogenum* exo-1,5-a-L-arbinanase that is structurally distinct from other arabinan-degrading enzymes. FEBS Lett. 2004, vol. 506, pp. 199-204.
Saloheimo et al. cDNA cloning of a *Trichoderma reesei* cellulose and demonstration of endoglucanase activity by expression in yeast. Eur. J. Biochem, 1997, vol. 249, p. 584-591.
Seffernick, et al. 2001. Melamine deaminase and atrazine chloroydrolase: 98 percent identical but functionally different. Journal of Bacteriology, vol. 183, No. 8, pp. 2405-2410.
Sheehan et al. Enzymes, energy and the Environment: A Strategic Perspective on the U.S. Department of Energy's Research and Development Activities for Bioethanol. Biotechnology Progress, 1999, vol. 15, pp. 817-827.
Sheppard, P.O. et al. 1995. The Use of Conserved Cellulase Family-Specific Sequences to Clone Cellulase Homologue cDNAs from *Fusarium oxysporum*, XP002154884, Abstract.
Sheppard, P.O. et al. The Use of Conserved Cellulase Family-Specific Sequences to Clone Cellulase Homologue cDNAs from *Fusarium oxysporum*. Gene, 1994, vol. 150, pp. 163-167.
Shin et al. A comparison of the pectate lyase genes, pel-1 and pel-2, of *Colletotrichum gloeosporioides* f.sp. *malvae* and the relationship between their expression in culture and during necrotrophic infection. Gene, 2000, vol. 243, pp. 139-150.
Søorensen et al. Efficiencies of Designed Enzyme Combinations in Releasing Arabinose and Xylose from Wheat Arabinoxylan in an Industrial Ethanol Fermentation Residue. Enzyme Microb. Technol., 2005, vol. 36, pp. 773-784.
Søorensen et al. A Novel GH43 alpha-L-arabinofuranosidase from *Humicola insolens*: Mode of Action and Synergy with GH51 alpha-

(56) References Cited

OTHER PUBLICATIONS

L-arabinofuranosidases on wheat arabinoxylan. Appl. Microbiol. Biotechnol. 2006, vol. 73, pp. 850-861.

Søorensen et al. Enzymatic Hydrolysis of Wheat Arabinoxylan by a Recombinant "Minimal" Enzyme Cocktail Containing B-Xylosidase and Novel Endo-1,4-B-Xylanase and a-L-Arabinofuranosidase Activities. Biotechnol. Progr., 2007, vol. 23, pp. 100-107.

Takami et al. Complete genome sequence of the alkaliphilic bacterium *Bacillus halodurans* and genomic sequence comparison with *Bacillus subtilis*. Nucleic Acid Res, 2000, vol. 28, pp. 4317-4331.

Takishima, S. et al. Cloning, Sequencing, and Expression of the Cellulase Genes of *Humicola grisea* Var. Thermoida. Accession No. D63515, Aug. 21, 1995.

Takashima, S. et al. Cloning, Sequencing, and Expression of the Cellulase Genes of *Humicola grisea* Var. Thermoidea. Journal of Biotechnology, 1996, vol. 50, pp. 137-147.

Unkles, S.E. et al. The development of a homologous transformation system for *Aspergillus oryzae* based on the nitrate assimilation pathway: A convenient and general selection system for filamentous fungal transformation. Mol. Gen. Genet., 1989, vol. 218, pp. 99-104.

Uzcategui et al. The 1,4-b-d-glucan glucanohydrolases from *Phanerochaete chrysosporium*. Re-assessment of their significance in cellulose degradation mechanisms. Journal of Biotechnology, 1991, vol. 21, pp. 143-160.

Van Den Broek L.A.M. et al. Cloning and Chracterization of Arabinoxylan arabinofuranosidase-D3 (AXHd3) from *Bifidobacterium adolescentis* DSM 20083. Appl. Microbiol. Biotechnol, 2005, vol. 67, pp. 641-647.

Van Laere, D.M.J. et al. A New Arabinofuranohydrolase from *Bifidobacterium adolescentis* Able to Remove Arabinosyl Residues from Double-Substitutes Xylose Units in Arabinoxylan. Appl. Microbiol. Biotechnol, 1997, vol. 47, pp. 231-235.

Van Oorschot, A Revision of *Chrysosporium* and Allied Genera. Studies in Mycology, 1980, No. 20, pp. 1-3, 8-9 and 32-35.

Vllkari et al. Use of Cellulases in Pulp and Paper Applications. In Carbohydrates from *Trichoderma reesei* and Other Microorganisms. Structure, Biochemistry, Genetics, and Applications. Claessens, M. et al. eds. The Royal Society of Chemistry, 1998, pp. 245-254.

Xu et al. Humicola insolens cellobiose dehydrogenase: cloning, redox chemistry, and "logic gate"-like dual functionality. Enzyme Microb. Technol., 2001, vol. 28, p. 744-753.

Yano et al. Cloning and Expression of an a-1,3-Glucanase Gene from *Bacillus circulans* KA-304: The Enzyme Participates in Protoplast Formation of *Schizophyllum commune*. Biosci Biotechnol. Biochem., 2006, vol. 70, pp. 1754-1763.

International Search Report prepared by the United States Patent & Trademark Office on Jul. 1, 2008, for International Application No. PCT/US07/87020.

Written Opinion prepared by the United States Patent & Trademark Office on Jul. 1, 2008, for International Application No. PCT/US07/87020.

Barreau, C. et al. "Use of Linear Plasmid Containing Telomeres as an Efficient Vector for Direct Cloning in the Filamentous Fungus *Podospora anserine*." Fungal Genetics and Biology, 1998, vol. 25, pp. 22-30.

Aleksenko et al., "Gene expression from replicating plasmids in *Aspergillus nidulans*," Mol. Gen. Genet. vol. 253, pp. 242-246 (1996).

Aleksenko et al., "Autonomous Plasmid Replication in *Aspergillus nidulans*: AMA1 and MATE Elements," Fungal Genetics and Biology, vol. 21, pp. 373-387 (1997).

Aleksenko et al., "In vivo linearization and autonomous replication of plasmids containing human telemetric DNA in *Aspergillus nidulans*," Mol. Gen. Genet., vol. 260, pp. 159-164 (1998).

Archer et al., "The Molecular Biology of Secreted Enzyme Production by Fungi," Critical Reviews in Biotechnology, vol. 17, No. 4, pp. 273-306 (1997).

Arnau et al., "Integrative transformation by homologous recombination in the zygomycete *Mucor circinelloides*," Mol. Gen. Genet., vol. 225, pp. 193-198 (1991).

Arnold et al., "Directed evolution of biocatalysts," Current Opinion in chemical Biology, vol. 3, pp. 54-59 (1999).

Asgeirsdottir et al., "A Sandwiched-Culture Technique for Evaluation of Heterologous Protein Production in a Filamentous Fungus," Applied and Environmental Microbiology, vol. 65, No. 5, pp. 2250-2252 (1999).

Barcellos et al., "Genetic analysis of *Aspergillus niduians* unstable transformants obtained by the biolistic process," Can. J. Microbiol., vol. 44, pp. 1137-1141 (1998).

Barreau et al., "Use of a Linear Plasmid containing Telomeres as an Efficient Vector for Direct Cloning in The Filamentous Fungus *Podospora anserina*," Fungal Genetics and biology, vol. 25, pp. 22-30 (1998).

Berges et al., "Cloning of an *Aspergillus niger* invertase gene by expression in *Trichoderma reesei*," Curr. Genet., vol. 24, pp. 53-59 (1993).

Beydon et al., "Microbiological High Throughout Screening: An Opportunity for the Lead Discovery Process," Journal of Biomolecular Screening, vol. 5, No. 1, pp. 13-21 (2000).

Bretthauer et al., "Glycosylation of *Pichia pastoris*-derived proteins," Biotechnol. Appl. Biochem., vol. 30, pp. 193-200 (1999).

Bruckner et al., "Transformation of *Gibberella fujikuroi*: effect of the *Aspergillus nidulans* AMA1 sequence on frequency and integration," Curr. Genet., vol. 22, pp. 313-316 (1992).

Buxton et al., "The transformation of mycelial spheroplasts of *Neurospora crassa* and the attempted isolation of an autonomous replicator," Mol. Gen. Genet, vol. 196, pp. 339-344 (1984).

Chakraborty et al., "Transformation of filamentous fungi by electroporation," Nucleic Acids Research, vol. 18, No. 22, p. 6637 (1990).

Christensen et al., "High Level Expression of Recombinant Genes in *Aspergillus otyzae*," Bio/Techology, vol. 6, pp. 1419-1422 (1988).

Christiansen et al., "Biolistic transformation of the obligate plant pathogenic fungus, *Erysiphe graminis* f.sp. *hordei*," Curr. Genet., vol. 29, pp. 100-102 (1995).

Dalboge et al., "A novel method for efficient expression cloning of fungal enzyme genes," Mol. Gen. Gent., vol. 243, pp. 253-260 (1994).

Dantas-Barbosa et al., "Genetic transformation of germinated conidia of the thermophilic fungus *Humicola grisea* var. *therrnoidea* to hygromycin B resistance," FEMS Microbiology Letters, vol. 169, pp. 185-190 (1998).

Degroot et al., *Agrobacterium tumefaciens*-mediated transformation of filamentous fungi, Nature Biotechnology, vol. 16, pp. 839-842 (1998).

Deutsch et al., "Intron-exon structures of eukaryotic model organisms," Nucleic Acids Research, vol. 27, No. 15, .1. 3219-3228 1999.

Devchand et al., "Expression of heterologous proteins in *Aspergillus*," Journal of Biotechnology, vol. 17, pp. 3-10 (1991).

Durand et al., Transient expression of the β-glucuronidase gene after biolistic transformation of the anaerobic fungus *Neocallimastix frontalis*, Curr. Genet., vol. 31, pp. 159-161 (1997).

Fierro et al., "Automonously replicating plasmids carrying the *AMA1* region in *Penicillium chrysogenum*," Curr. Genet, vol. 29, pp. 482-489 (1996).

Fu et al., "A microfabricated fluorescence-activated cell sorter," Nature Biotechnology, vol. 17, pp. 1109-1111 (1999).

Gems et al., "An autonomously replicating plasmid transforms *Aspergillus nidulans* at high frequency," Gene, vol. 98, pp. 61-67 (1991).

Gems et al., "Co-transformation with autonomously-replicating helper plasmids facilitates gene cloning from an *Aspergillus nidulans* gene library," Curr. Genet., vol. 24, pp. 520-524 (1993).

Gems et al., "An 'instant gene bank' method for gene closing by mutant complementation," Mol. Gen. Genet, vol. 242, pp. 467-471 (1994).

Giver et al., "Directed evolution of a thermostable esterase," Proc. Natl. Acad. Sci. USA, vol. 95, pp. 12809-12813 (1998).

Gouka et al., "Efficient production of secreted proteins by *Aspergillus*: progress, limitations and prospects," Appl. Microbiol. Biotechnol., vol. 47, pp. 1-11 (1997).

Hu et al., "Hydrogen Bonding and Circular Dichroism of Bacteriochlorophylls in the *Rhodobacter capsulatus* Light-Harvest-

(56) References Cited

OTHER PUBLICATIONS ing 2 Complex Altered by Combinatorial Mutagenesis," *Biochemistry*, vol. 37, pp. 10006-10015 (1998).
Hynes et al., "The Genetic analysis of Regulation of Amidase Synthesis in *Aspergillus nidulans*," *Molec. Gen. Genetics*, vol. 108, pp. 107-116 (1970).
Hynes et al., "Isolation of Genomic Clones containing the *amdS* Gene of *Aspergillus nidulans* and Their Use in the Analysis of Structural and Regulatory Mutations," *Molecular and Cellular Biology*, vol. 3, No. 8, pp. 1430-1439 (1983).
Innis et al., "Expression, glycosylation, and Secretion of an *Aspergillus glucoamylase* by *Saccharaomyces cerevisiae*," *Science*, vol. 228, pp. 21-26 (1985).
Ishibashi et al., "Nonhomologous chromosomal integration of foreign DNA is completely dependent on MUS-53 (human Lig4 homolog) in *Neurospora*," *PNAS*, vol. 103, No. 40, pp. 14871-14876 (2006).
Javerzat et al., "Isolation of telomeric DNA from the filamentous fungus *Podospora anserine* and construction of a self-replicating linear plasmid showing High transformation frequency," *Nucleic Acids Research*, vol. 21, No. 3, pp. 497-504 (1993).
Jayawickreme et al., "Gene expression systems in the development of high-throughput screens," *Current Biology*, vol. 8, pp. 629-634 (1997).
Jeenes et al., "Heterologous Protein Production by Filamentous Fungi," *Biotechnology & Genetic Engineering Reviews*, vol. 9, pp. 327-367 (1991).
Joo et al., "A high-throughput digital imaging screen for the discovery and directed evolution of oxygenases," *Chemistry & Biology*, vol. 6, pp. 699-706 (1999).
Joo et al., "Laboratory evolution of peroxide-mediated cytochrome P450 hydroxylation," *Nature*, vol. 399, pp. 670-673 (1999).
Judelson et al., "Transformation of the Oomycete Pathogen, *Phytophthora infestans*," *Molecular Plant-Microbe Interactions*, vol. 4, No. 6, pp. 602-607 (1991).
Kistler et al., "Autonomously replicating plasmids and chromosome rearrangement during transformation of *Nectria haematococca*," *Gene*, vol. 117, pp. 81-89 (1992).
Klein et al., "Selection for genes encoding secreted proteins and receptors," *Proc. Natl. Acad. Sci. USA*, vol. 93, pp. 7108-7113 (1996).
Kruszewska, "Heterologous expression of genes in filamentous fungi," *Acta Biochimica Polonica*, vol. 46, No. 1, pp. 181-195 (1999).
Kuchner et al., "Directed evolution of enzyme catalysts," *Tibtech*, vol. 15, pp. 523-530 (1997).
Liao et al., "Isolation of a thermostable enzyme variant by cloning and selection in a thermophile," *Proc. Natl. Acad. Sci. USA*, vol. 83, pp. 576-580 (1986).
Liou et al., "Transformation of a Leu Mutant of *Rhizopus niveus* with the *leuA* Gene of *Mucor circinelloides*," *Biosci. Biotech. Biochem.*, vol. 56, No. 9, pp. 1503-1504 (1992).
Mabashi et al., "Development of a Versatile Expression Plasmid construction System for *Aspergillus oryzae* and Its Application to Visualization of Mitochondria," *Biosci. Biotech. Biochem.*, vol. 70, No. 8, pp. 1882-1889 (2006).
Maras et al., "In vitro conversion of the carbohydrate moiety of fungal glycoproteins to mammalian-type oligosaccharides. Evidence for N-acetylglucosaminyltransferase-I-accepting glycans from *Trichoderma reesei*," *Eur. J. Biochem.*, vol. 249, pp. 701-707 (1997).
Maras et al,, "Filamentous fungi as production organisms for glycoproteins of bio-medical interest," *Glycoconjugate Journal*, vol. 16, pp. 99-107 (1999).
May et al., "Inverting enantioselectivity by directed evolution of hydantoinase for improved production of L-methionine," *Nature Biotechnology*, vol. 18, pp. 317-320 (2000).
Minshull et al., "Protein evolution by molecular breeding," *Current Opinion in Chemical Biology*, vol. 3, pp. 284-290 (1999).
Miyazaki et al., "Directed Evolution Study of Temperature Adaptation in a Psychrophilic Enzyme," *J. Mol. Biol.*, vol. 297, pp. 1015-1026 (2000).

Munoz et al., "Hydrophobin gene srh1, expressed during sporulation of the biocontrol agent *Trichoderma harzianum*," Curr. Genet., vol. 32, pp. 225-230 (1997).
Munoz-Rivas et al., "Transformation of the basidiomycete, *Schizophyllum commune*." *Mol. Gen. Gent.*, vol. 205, pp. 103-106 (1986).
Nakari-Setala et al., "Genetic and biochemical characterization of the *Trichoderma reesei* hydrophobin HFBI," *Eur. J. Biochem.*, vol. 235, pp. 248-255 (1996).
Ninomiya et al., "Highly efficient gene replacements in *Neurospora* strains deficient for nonhomologous end-joining," *PNAS*, vol. 101, No. 33, pp. 12248-12253 (2004).
Parta et al., "*HYP1*, a Hydrophobin Gene from *Aspergillus fumigatus*, complements the *rodletless* Phenotype in *Aspergillus nidulans*," *Infection and Immunity*, vol. 62, No. 10, pp. 4389-4395 (1994).
Peberdy, "Extracellular Proteins in Fungi: A Cytological and Molecular Perspective," *Acta Microbiologica et Immunologica Hungarica*, vol. 46, pp. 165-174 (1999).
Powell et al., "In Vivo Rearrangement of Foreign DNA by *Fusarium oxysporum* Produces Linear Self-Replicating Plasmids," *Journal of Bacteriology*, vol. 172, No. 6, pp. 3163-3171 (1990).
Punt et al., "Transformation of Filamentous Fungi Based on Hygromycin B and Phleomycin Resistance Markers," *Methods in Enzymology*, vol. 216, pp. 447-457 (1992).
Rajpal et al., "A general method for greatly improving the affinity of antibodies by using combinatorial libraries," *PNAS*, vol. 102, No. 24, pp. 8466-8471 (2005).
Record et al., "Expression of the *Pycnoporus cinnabarinus* laccase gene in *Aspergillus niger* and characterization of the recombinant enzyme," *Eur. J. Biochem.*, vol. 269, pp. 602-609 (2002).
Schmidt-Dannert et al., "Directed evolution of industrial enzymes," *Tibtech*, vol. 17, pp. 135-136 (1999).
Shao et al., "Random-priming in vitro recombination: an effective tool for directed evolution," *Nucleic Acids Research*, vol. 26, No. 2, pp. 681-683 (1998).
Sohn et al., "A Novel Autonomously replicating Sequence (ARS) for Multiple Integration in the Yeast *Hansenula polymorpha* DL-1," *Journal of Bacteriology*, vol. 178, No. 15, pp. 4420-4428 (1996).
Song et al., "Simultaneous Enhancement of Thermostability and Catalytic Activity of Phospholipase A1 by Evolutionary Molecular Engineering," *Applied and Environmental Microbiology*, vol. 66, No. 3, pp. 890-894 (2000).
Stemmer, "DNA shuffling by random fragmentation and reassembly: In vitro recombination for molecular evolution," *Proc. Natl. Acad. Sci. USA*, vol. 91, pp. 10747-10751 (1994).
Stinchcomb et al., "Isolation and characterization of a yeast chromosomal replicator," *Nature*, vol. 282, pp. 3943 (1979).
Stringer et al., "*dewA* encodes a fungal hydrophobin component of the *Aspergillus* spore wall," *Molecular Microbiology*, vol. 16, No. 1, pp. 33-44 (1995).
Van De Rhee et al., "Transformation of the cultivated mushroom, *Agaricus bisponis*, to hygromycin B resistance," *Mol. Gen. Genet.*, vol. 250. pp. 252-258 (1996).
Van Zeijl et al., "An improved colony-PCR method for filamentous fungi for amplification of PCR-fragments of several kilobases," *Journal of Biotechnology*, vol. 59, pp. 221-224 (1998).
Verdoes et al., "characterization of an efficient gene cloning strategy for *Aspergillus niger* based on an autonomously replicating plasmid: cloning of the *nicB* gene of *A. niger*," *Gene*, vol. 146, pp. 159-165 (1994).
Volkov et al., "Recombination and chimeragenesis by in vitro heteroduplex formation and in vivo repair," *Nucleic Acids Research*, vol. 27, No. 18, pp. i-vi (1999).
Von Stein et al., "A high throughput screening for rarely transcribed differentially expressed genes," *Nucleic Acids Research*, vol. 25, No. 13, pp. 2598-2602 (1997).
Youvan et al., "Digital Imaging spectroscopy for Massively Parallel Screening of Mutants," *Methods in Enzymology*, vol. 246, pp. 732-752 (1995).
Zhao et al., "Molecular evolution by staggered extension process (StEP) in vitro recombination," *Nature biotechnology*, vol. 16, pp. 258-261 (1998).

(56) References Cited

OTHER PUBLICATIONS

Yelton, Melanie M., et al., "Development regulation of the *Aspergillus nidulans* trpC gene", Proc. Natl. Acad. Sci. USA., Department of Plant Pathology, University of California, Davis, CA, Dec. 1983, pp. 7576-7580, vol. 80.

Yelton, Melanie M., et al., "Transformation of *Aspergillus nidulans* by using a trpC plasmid", Proc. Natl. Acad. Sci. USA., Department of Plant Pathology, University of California, Davis, CA, 95616, Mar. 1984, pp. 1470-1474, vol. 81.

Mullaney, Edward J., et al., "Primary structure of the trpC gene from *Aspergillus nidulans*", Mol Gen Genet, Department of Plant Pathology, University of California, Davis, CA, 95616, USA, 1985, pp. 37-45, vol. 199.

Punt, Peter J., et al., "Isolation and characterization of the glyceraldehyde-3-phosphate dehydrogenase gene of *Aspergillus nidulans*", Elsevier Science Publishers B.V. (Biomedical Division), TNO Medical Biological Laboratory, Rijswijk (The Netherlands), May 1988, pp. 49-57, Gene. 69.

Punt, Peter J., et al., "Functional elements in the promoter region of the *Aspergillus nidulans* gpdA gene encoding glyceraldehyde-3-phosphate dehydrogenase", Elsevier Science Publishers B.V. (Biomedical Division), TNO Medical Biological Laboratory, Rijswijk (The Netherlands), May 1990, pp. 101-109, Gene. 93.

Gusakov, Alexander V., et al., "Purification, cloning and characterisation of two forms of thermostable and highly active cellobiohydrolase I (Cel7A) produced by the industrial strain of *Chrysosporium lucknowense*", Elsevier, Science Direct, Enzyme and Microbial Technology, 2005, pp. 57-69, vol. 36.

* cited by examiner

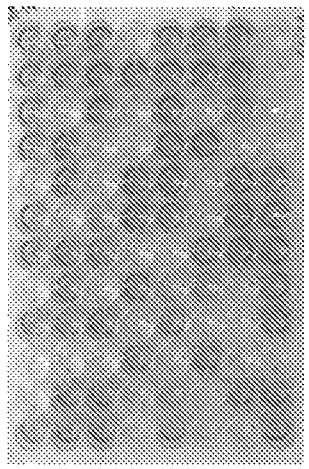
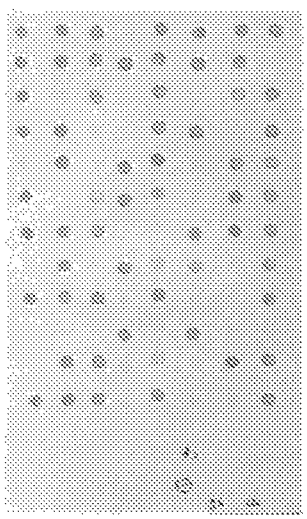
FIG. 21

```
        SalI
  1  tgctgtcgac tattctattt gctcaaatgg agagcacatt catcggcgca gggatacacg
 61  gtttatggac cccaagagtg taaggactat tattagtaat attatatgcc tctaggcgcc
121  ttaacttcaa caggcgagca ctactaatca acttttggta gacccaatta caaacgacca
181  tacgtgccgg aaatttggg attccgtccg ctctcccccaa ccaagctaga agaggcaacg
241  aacagccaat cccggtgcta attaaattat atggttcatt tttttaaaa aaattttttc
                                                 BclI
301  ttcccatttt cctctcgctt ttcttttcg catcgtagtt gatcaaagtc caagtcaagc
361  gagctatttg tgctatagct cggtgctat aatcagtaca gcttagagag gctgtaaagg
421  tatgacca cagcagtatt cgcgctataa gcggcactcc tagctaatt gtacggtct
481  acagaagtag gtaataaag cgttaattgt tctaaatact agagcactt agagaagcta
541  tctaaatata tattgaccct agctattat ccctattagt aagttagtta gctctaacct
            NotI
601  atagatagat gcatgcgggcc gc
```

FIG. 23

SEQUENCE LISTING

```
<160> NUMBER OF SEQ ID NOS: 17

<210> SEQ ID NO 1
<211> LENGTH: 4200
<212> TYPE: DNA
<213> ORGANISM: Chrysosporium lucknowense
<220> FEATURE:
<221> NAME/KEY: CDS
<222> LOCATION: (1588)..(1869)
<220> FEATURE:
<221> NAME/KEY: CDS
<222> LOCATION: (1976)..(2161)
<220> FEATURE:
<221> NAME/KEY: CDS
<222> LOCATION: (2230)..(2402)
<220> FEATURE:
```

<220> FEATURE:
<221> NAME/KEY: CDS
<222> LOCATION: (2480)..(2825)
<220> FEATURE:
<221> NAME/KEY: CDS
<222> LOCATION: (2943)..(3131)

<400> SEQUENCE: 1

```
gcatggaaat tccctcccc ccacggccag acttggacca aggaaaagag ataccacctg      60
ccgaacgtgg ctctcgctcc agcatttcga gagcgtacct cagccaacca ctcggctccc     120
cgtgtcgagc gatcggcact tgcggccttt gcaatgcccc atccttgaac tccaccaaat     180
aggctaccac cacaccaccc ctccatttct tgttcctcgg cttcctcgct cgaggtaccg     240
atccagggtg ggccgattgc gatggtgcca ttgctgccct tgctttggct tcacctaggc     300
gatgtcacgt tcagatatag tccgcaggct ttaccccaga tcctctgatt gccgatctcg     360
gccatgacct ctggttgttt cacaagcaca cagggtcagt cgcccccgtt gcgcctctgt     420
acagtctgta cagaccttct cagctgaatg tttccgagac tagagactaa aatctgaatc     480
actttggccc agagagaggg ttcgcgaagt cccacacacc cttctagaag gagagaccag     540
agccacgaaa catgaagcct gatcgcttat ttttttttt tttttggcc ccggagtgcc      600 cgcggtcacg gtactttggg gttatgacag gctgtttgac ttccatggat aatcccttt      660 aattattag gctgaccact caccggacct gtttcgcctg tgcaacttca ccagtcggag      720
gtcatgctca aattgtcagt cagatacttt atacatactc tgtgtacaac ataccacaac     780
acacacgcac acacatagaa agtacataca tgctggatcg gaacccacca cgccttgtac     840
atacacccac acacccctcc ccacaccct cttccggca ttttcgcgc cagagatcgt       900 cgcctttgcc ccttaggcaa gttcaccgt tatgttaggt aaccctctcg acggggccgc     960
ctgcggatgt tggcgcatgc ttgacacgcc cggtcgtgcg gcgttgctag tcctcgaaag    1020
tcaggtattg caccggaac ccctgatcac aagcacttga tcacggcggg agcaccgcg    1080 cgcctgaacg ggaccccagc caatgccgga ccagaggccg aagcgggaag gtgtcttgct    1140
ttctggcctg cccttttctt tcaacaatgg gcaatacggg tcagcgaaac ccttcctagt    1200
cctcgcagca aactcgagct gctatcagat tcccgggaag cggcctgcca cagccgctca    1260
acccggcctt ggcatggcca ggcggccctt tcatgtgtcg aaagcggcag gtcatcagca    1320
cagatctcga gggtgggaaa gagaggggg ggagggcga tgctggggcg atgctgctag    1380
gagccgcatt cggggagggg gccctgctgt tcatccatat cccaggatga tgcgagattg    1440
aagcaagata aataacacgg cttcccctc cctttcgat ccggaccaga ccatcgtctc     1500
caacacccca agtcgatcc gacaagtccc aatccacccc gccgcccct cctccgtcg      1560 ccgtcccggt cttccgattt cgtcaag atg cac ttc tcc acc gct ctc ctg gcc   1614
                               Met His Phe Ser Thr Ala Leu Leu Ala
                                 1               5 ttc ctg ccc gcc gcc ctc gcg gcc cct act gcc gag acc ctc gac aag    1662
Phe Leu Pro Ala Ala Leu Ala Ala Pro Thr Ala Glu Thr Leu Asp Lys
 10              15                  20                  25 cgc gcc ccg atc ctg act gct cgc gct ggc cag gtc gtc ccg ggc aag    1710
Arg Ala Pro Ile Leu Thr Ala Arg Ala Gly Gln Val Val Pro Gly Lys
             30                  35                  40 tac atc atc aag ctc cgc gac gga gcc agc gac gat gtc ctt gag gcc    1758
Tyr Ile Ile Lys Leu Arg Asp Gly Ala Ser Asp Asp Val Leu Glu Ala
         45                  50                  55 gcc atc ggc aag ctc cgc tcc aag gcc gac cac gtc tac cgc ggc aag    1806
Ala Ile Gly Lys Leu Arg Ser Lys Ala Asp His Val Tyr Arg Gly Lys
     60                  65                  70
```

-continued

| | |
|---|---|
| ttc agg ggc ttt gcc ggc aag ctc gag gat gac gtc ctt gac gcc atc<br>Phe Arg Gly Phe Ala Gly Lys Leu Glu Asp Asp Val Leu Asp Ala Ile<br>   75                         80                   85 | 1854 |
| cgt ctt ctc ccc gaa gtgagtccgc gtcccggaaa gaaatagagc gagcggggga<br>Arg Leu Leu Pro Glu<br>90 | 1909 |
| gagagtgaag ggcgaaaaga gccgtgtttt gttaaccgct tgtcttttct ttctctcttg | 1969 |
| caatag gtc gag tac gtc gag gag gag gcc atc ttc acc atc aac gcg<br>       Val Glu Tyr Val Glu Glu Glu Ala Ile Phe Thr Ile Asn Ala<br>           95                   100               105 | 2017 |
| tac acc tcg cag tcc aac gcc ccc tgg ggc ctt gcg cgc ctc tcg tcc<br>Tyr Thr Ser Gln Ser Asn Ala Pro Trp Gly Leu Ala Arg Leu Ser Ser<br>  110                       115                    120 | 2065 |
| aag acc gcg ggc tcc acc acc tac acc tac gac acc agc gcc ggc gag<br>Lys Thr Ala Gly Ser Thr Thr Tyr Thr Tyr Asp Thr Ser Ala Gly Glu<br>125                    130                  135                140 | 2113 |
| ggc acc tgt gcc tat gtg atc gac acg ggc atc tac act agc cac tcc<br>Gly Thr Cys Ala Tyr Val Ile Asp Thr Gly Ile Tyr Thr Ser His Ser<br>                 145                    150                  155 | 2161 |
| gtatgtctcg cggttacctc cccttcgga agaaggggca tccatatgct gacccctcct | 2221 |
| gatcacag gac ttc ggc ggc cgt gcc act ttc gcc gcc aac ttc gtc gac<br>         Asp Phe Gly Gly Arg Ala Thr Phe Ala Ala Asn Phe Val Asp<br>                     160                    165                    170 | 2271 |
| agc tct aac acc gat ggc aac ggc cac ggc acc cac gtc gcc ggc acc<br>Ser Ser Asn Thr Asp Gly Asn Gly His Gly Thr His Val Ala Gly Thr<br>               175                    180                  185 | 2319 |
| atc ggc ggc acc acg tac ggt gtt gcc aag aag acc aag ctc tac gcc<br>Ile Gly Gly Thr Thr Tyr Gly Val Ala Lys Lys Thr Lys Leu Tyr Ala<br>        190                    195                  200 | 2367 |
| gtc aag gtt ctc ggc tcc gac ggc tct ggc acc ac gtatgcctcg<br>Val Lys Val Leu Gly Ser Asp Gly Ser Gly Thr Thr<br>    205                     210 | 2412 |
| cacccgcgca cccgcacacc cgcccggccg ttatcttctg actgacattc ctctttctcc | 2472 |
| tctctag t tct ggt gtc att gct ggc atc aac ttc gtc gct gac gac gcg<br>          Ser Gly Val Ile Ala Gly Ile Asn Phe Val Ala Asp Asp Ala<br>               215                    220                  225 | 2522 |
| ccc aag cgc agc tgc ccc aag ggc gtc gtc gcc aac atg tcg ctc ggc<br>Pro Lys Arg Ser Cys Pro Lys Gly Val Val Ala Asn Met Ser Leu Gly<br>        230                    235                  240 | 2570 |
| ggt agc tac tcg gcc tcc atc aac aac gcc gcc gcc gcc ctc gtc agg<br>Gly Ser Tyr Ser Ala Ser Ile Asn Asn Ala Ala Ala Ala Leu Val Arg<br>245                   250                  255                260 | 2618 |
| tcg ggc gtc ttc ctg gcc gtc gcc gcc ggc aac gag aac cag aac gcc<br>Ser Gly Val Phe Leu Ala Val Ala Ala Gly Asn Glu Asn Gln Asn Ala<br>               265                    270                  275 | 2666 |
| gcc aac tcg tcg ccc gcc tcc gag gcg tcc gcc tgc acc gtc ggc gcc<br>Ala Asn Ser Ser Pro Ala Ser Glu Ala Ser Ala Cys Thr Val Gly Ala<br>        280                    285                  290 | 2714 |
| acc gac agg aac gac gcc aag gcc agc tac tcc aac tac ggc agc gtc<br>Thr Asp Arg Asn Asp Ala Lys Ala Ser Tyr Ser Asn Tyr Gly Ser Val<br>               295                    300                  305 | 2762 |
| gtc gat atc cag gcc ccc ggc tcc aac atc ctg agc acc tgg atc ggc<br>Val Asp Ile Gln Ala Pro Gly Ser Asn Ile Leu Ser Thr Trp Ile Gly<br>        310                    315                  320 | 2810 |
| agc acc tct gct acc gtaagccccc cctcccccca cccaccccca gcctttggcg<br>Ser Thr Ser Ala Thr<br>325 | 2865 |
| acattcccgc cccgtattta tttctccggg gtgggggaga aacaaaacaa aatagctaac | 2925 |

-continued

```
atgagatgca ctctcag aac acc atc tcg ggt acc tcg atg gcc tcc ccc      2975
                   Asn Thr Ile Ser Gly Thr Ser Met Ala Ser Pro
                   330                 335                 340
cac att gcc ggc ctc ggt gcc tac ctc ctg gcc ctc gag ggc tcc aag     3023
His Ile Ala Gly Leu Gly Ala Tyr Leu Leu Ala Leu Glu Gly Ser Lys
                345                 350                 355
acc cct gcc gag ctc tgc aac tac atc aag tcg acc ggc aac gcc gcc     3071
Thr Pro Ala Glu Leu Cys Asn Tyr Ile Lys Ser Thr Gly Asn Ala Ala
            360                 365                 370
atc act ggc gtt ccc agc ggc acc acc aac cgc atc gcc ttc aac ggc     3119
Ile Thr Gly Val Pro Ser Gly Thr Thr Asn Arg Ile Ala Phe Asn Gly
        375                 380                 385
aac ccc tct gcc tgaattgttt cccgcgatcc gggacaaaat ggggcatgag         3171
Asn Pro Ser Ala
    390
cacttcctgc acctcttctt attctagagg attcgggagt ggggagccgg caaaaaaagg   3231
aggtggtgga ggaggaggag gaggagataa cggccggggt cttctccgag cgaatgaggg   3291
ctgcatattc tcttgttcat ttttttggtt catgtctatt atggttttac gcattttatt   3351
ctagttggga cagagtcacg atgcgggtcc gaggggcgcc gatcggggtt cctgccccacc  3411
tccccagcgt ctaaataact ttcatagacg aggaaatgat gagatctcat gagcggaccg   3471
cgaaggcctg gactgacttc tatcgtgact aattatgtga atcatgaggg cggaatgaga   3531
gagatgatat gtcagaatac gcatacttaa ggtgcaattg ctggcgggca attgcggcgt   3591
cacttttgct tttcgacatg atatcatgtc tccttaatcc aagtagttaa taattagtct   3651
ataaataatt tgtctataat tttgtctatt gcctgaagaa ataagcgatt ttgcaaattc   3711
tggtatgtag agtacaggtc aagtattgga gaggaaggaa ggaagcggta tgtttctcat   3771
attgacaagt gacaggagca agcttcttcc tagaatctta gcaaggaaat gttgaaaatt   3831
aagaaagcag aatagaaaca aggactaata gagcaattga ttgactcaat caatcgttaa   3891
ttatgagtcg aagataggtt ctcaaaactt tttcaaatta gttttgggag gacatgcccg   3951
agccatgtaa aacgggcgag gtacctcggt atgttaatgg ggttgcgtaa tgcttggctg   4011
tcgaggatac tagtaattgt atcgtgtttg tcagaatacc tacttaggtg caattgctgg   4071
aagcagcaat tgcggcgtcg cttttgcagt ttcacagtgt tgaagaggtg agggcaaaca   4131
tgtatcgcat atcttggggg tcggtttacc aagagagata tcatatctaa cccctaagag   4191
atgtgtatt                                                           4200

<210> SEQ ID NO 2
<211> LENGTH: 392
<212> TYPE: PRT
<213> ORGANISM: Chrysosporium lucknowense

<400> SEQUENCE: 2

Met His Phe Ser Thr Ala Leu Leu Ala Phe Leu Pro Ala Ala Leu Ala
1               5                   10                  15

Ala Pro Thr Ala Glu Thr Leu Asp Lys Arg Ala Pro Ile Leu Thr Ala
            20                  25                  30

Arg Ala Gly Gln Val Val Pro Gly Lys Tyr Ile Ile Lys Leu Arg Asp
        35                  40                  45

Gly Ala Ser Asp Asp Val Leu Glu Ala Ala Ile Gly Lys Leu Arg Ser
    50                  55                  60

Lys Ala Asp His Val Tyr Arg Gly Lys Phe Arg Gly Phe Ala Gly Lys
65                  70                  75                  80

Leu Glu Asp Asp Val Leu Asp Ala Ile Arg Leu Leu Pro Glu Val Glu
```

```
            85                  90                  95
Tyr Val Glu Glu Glu Ala Ile Phe Thr Ile Asn Ala Tyr Thr Ser Gln
            100                 105                 110

Ser Asn Ala Pro Trp Gly Leu Ala Arg Leu Ser Ser Lys Thr Ala Gly
            115                 120                 125

Ser Thr Thr Tyr Thr Tyr Asp Thr Ser Ala Gly Glu Gly Thr Cys Ala
            130                 135                 140

Tyr Val Ile Asp Thr Gly Ile Tyr Thr Ser His Ser Asp Phe Gly Gly
145                 150                 155                 160

Arg Ala Thr Phe Ala Ala Asn Phe Val Asp Ser Ser Asn Thr Asp Gly
                165                 170                 175

Asn Gly His Gly Thr His Val Ala Gly Thr Ile Gly Gly Thr Thr Tyr
            180                 185                 190

Gly Val Ala Lys Lys Thr Lys Leu Tyr Ala Val Lys Val Leu Gly Ser
            195                 200                 205

Asp Gly Ser Gly Thr Thr Ser Gly Val Ile Ala Gly Ile Asn Phe Val
            210                 215                 220

Ala Asp Asp Ala Pro Lys Arg Ser Cys Pro Lys Gly Val Val Ala Asn
225                 230                 235                 240

Met Ser Leu Gly Gly Ser Tyr Ser Ala Ser Ile Asn Asn Ala Ala Ala
                245                 250                 255

Ala Leu Val Arg Ser Gly Val Phe Leu Ala Val Ala Ala Gly Asn Glu
            260                 265                 270

Asn Gln Asn Ala Ala Asn Ser Ser Pro Ala Ser Glu Ala Ser Ala Cys
            275                 280                 285

Thr Val Gly Ala Thr Asp Arg Asn Asp Ala Lys Ala Ser Tyr Ser Asn
            290                 295                 300

Tyr Gly Ser Val Val Asp Ile Gln Ala Pro Gly Ser Asn Ile Leu Ser
305                 310                 315                 320

Thr Trp Ile Gly Ser Thr Ser Ala Thr Asn Thr Ile Ser Gly Thr Ser
                325                 330                 335

Met Ala Ser Pro His Ile Ala Gly Leu Gly Ala Tyr Leu Leu Ala Leu
            340                 345                 350

Glu Gly Ser Lys Thr Pro Ala Glu Leu Cys Asn Tyr Ile Lys Ser Thr
            355                 360                 365

Gly Asn Ala Ala Ile Thr Gly Val Pro Ser Gly Thr Thr Asn Arg Ile
            370                 375                 380

Ala Phe Asn Gly Asn Pro Ser Ala
385                 390

<210> SEQ ID NO 3
<211> LENGTH: 1159
<212> TYPE: DNA
<213> ORGANISM: Chrysosporium lucknowense

<400> SEQUENCE: 3
atgcacttct ccaccgctct cctggccttc ctgcccgccg ccctcgcggc ccctactgcc      60
gagaccctcg acaagcgcgc cccgatcctg actgctcgcg ctggccaggt cgtcccgggc     120
aagtacatca tcaagctccg cgacggagcc agcgacgatg tccttgaggc cgccatcggc     180
aagctccgct ccaaggccga ccacgtctac cgcggcaagt tcaggggctt tgccggcaag     240
ctcgaggatg acgtccttga cgccatccgt cttgtcgagt acgtcgagga ggaggccatc     300
ttcaccatca acgcgtacac ctcgcagtcc aacgcccctt ggggccttgc cgcgctctcg     360
tccaagaccg cgggctccac cacctacacc tacgacacca gcgccggcga gggcacctgt     420
```

```
gcctatgtga tcgacacggg catctacact agccactcga cttcggcggc cgtgccactt      480
tcgccgccaa cttcgtcgac agctctaaca ccgatggcaa cggccacggc acccacgtcg      540
ccggcaccat cggcggcacc acgtacggtg ttgccaagaa gaccaagctc tacgccgtca      600
aggttctcgg ctccgacggc tctggcacct tctggtgtca ttgctggcat caacttcgtc      660
gctgacgacg cgcccaagcg cagctgcccc aagggcgtcg tcgccaacat gtcgctcggc      720
ggtagctact cggcctccat caacaacgcc gccgccgccc tcgtcaggtc gggcgtcttc      780
ctggccgtcg ccgccggcaa cgagaaccag aacgccgcca ctcgtcgcc cgcctccgag       840 gcgtccgcct gcaccgtcgg cgccaccgac aggaacgacg ccaaggccag ctactccaac     900
tacggcagcg tcgtcgatat ccaggccccc ggctccaaca tcctgagcac ctggatcggc     960
agcacctctg aacaccatct cgggtacctc gatggcctcc ccccacattg ccggcctcgg    1020
tgcctacctc ctggccctcg agggctccaa gaccctgcc gagctctgca actacatcaa     1080
gtcgaccggc aacgccgcca tcactggcgt tcccagcggc accaccaacc gcatcgcctt    1140
caacggcaac ccctctgcc                                                 1159

<210> SEQ ID NO 4
<211> LENGTH: 4325
<212> TYPE: DNA
<213> ORGANISM: Chrysosporium lucknowense
<220> FEATURE:
<221> NAME/KEY: CDS
<222> LOCATION: (1759)..(2130)
<220> FEATURE:
<221> NAME/KEY: CDS
<222> LOCATION: (2189)..(3418)

<400> SEQUENCE: 4
gcccttacgc gtaagtatta cagatcgcgt tcgggcaact ccctagaatc atggagcaca      60
gcatcggctc gatcgcccaa caacttccta gcattgactt caaaaaggag acatgttggt     120
tacaacgatc gatgtttaca aaactcgacc attcctattt cctcgtatgc tcccaacgct     180
cttcgaacct gacacactac cacgcattgt ccccagcata tctaccaaca tcattgaaaa     240
tgctgcggca ttgttattgt ctaggctttt ttcttttaag caaacgtcgt ggatacccta     300
gatagagaat acgacggata atgttttcac aagatctgtg gcatcaagga tatgctccac     360
gaacctgacc tggcaacttg gttacagtcc gcgggttatt aaagtagtct cgacttttgc     420
gcccgagact aaggtgggca ccaaagggg gctggtttcg catagccgaa tgaatcatct      480
ctcagtcgat cgatttggag cgagtgttgc tccggaggtc cagtatgacc tataatattg     540
caacagctga cagctgatat tccgcctggt gaatatgaca ccgataggct gttcaacgaa     600
tcaccttttg cccgatggag gaactactac gctgtgcaat aattatttat gcacaaagtg     660
cagtgcgcaa tgttttgac ggatactcgc actggtactc cgtccactcg cggaatccag      720
ggtctgctgg gatcacggtc gagtcagacg gacaatgcga tgcgaccct gcacagctt       780 cgtcgctcgt gacccatcat ccgtccctga cagggagcgg cgggttggca gggtggaga     840 tgacgccccg cccttgcact acttggcttg gcggtgacgt gccggaatc agatctgacc     900 tcaacgtgca agcagtcaac agcggacagc gggtcaagat gtttgacagc ttatcaagtt     960
ccggctgcat tgagccaaca gaggaaatcg ctgcctcgct ccccggaac tgcacctcca      1020 accgagcttt tacgacctgg tctgccagtg caagccagtg gagaatgcag gcagccgag     1080 cccagggcaa gccaaggcag ccaaccgtct ggtacgcgt gtggacggga ccaagtcatg      1140
tacccagtaa ctcccagtag gtaacagccg ggggtccgaa agcggtggga gctcaactgg    1200
```

-continued

```
ccgcagatcc cggacagtca gcctcgccgc ggcatctgcg tgcgacgcct ttgtttcacc    1260
gtacaataga cgctttggtg cgcaacttct gccggaaata agaatcgttt acgtatgctg    1320
cacgctgcct gcctacctat cttatggagc ttcgcaactg aggagtcttg cacttcgccc    1380
actgcacttg gtgatggcgg tatcaggcta tcagcggcct ggtgactgtc cgataagcgc    1440
tggtccaccc gttatctccc ttccccagag acaacacgcc cggagcaggc tcatacgtga    1500
ttggatgccc cgccttgact agtccgcatt aggtgaaagc gggccaaacc agcattggtc    1560
tgaggcaact gccagctgcg ccttccgtta aagcagctcc ggtcctctcc cacgctcgct    1620
gctcctctct tcttccttca tcaaaccatc ttcctcttcc tgttcgccga atcaagggaa    1680
gaggtgacag acttgctttt tatccccga gtttctcgaa gtcgcaattt ttacggcttc     1740
```

```
gcctctcttt cgttcacc atg aga ggc ctc gtc gca ttc tcg ctc gca gcc    1791
                    Met Arg Gly Leu Val Ala Phe Ser Leu Ala Ala
                     1               5                  10 tgc gtt tcg gca gcg ccg agc ttc aag acc gag acc atc aac ggc gag    1839
Cys Val Ser Ala Ala Pro Ser Phe Lys Thr Glu Thr Ile Asn Gly Glu
         15                  20                  25 cat gcc ccc att ctc tcc tcg tcg aat gcc gag gtc gtc ccc aac tcg    1887
His Ala Pro Ile Leu Ser Ser Ser Asn Ala Glu Val Val Pro Asn Ser
         30                  35                  40 tat atc atc aag ttc aag aag cat gtg gat gag agc tcg gcc tcc gcc    1935
Tyr Ile Ile Lys Phe Lys Lys His Val Asp Glu Ser Ser Ala Ser Ala
 45                  50                  55 cac cat gcc tgg atc caa gac atc cat acc tcg cgc gag aaa gtt cgt    1983
His His Ala Trp Ile Gln Asp Ile His Thr Ser Arg Glu Lys Val Arg
 60                  65                  70                  75 caa gac ttg aag aag cgc ggc cag gtg ccg ctg ctt gac gac gtc ttc    2031
Gln Asp Leu Lys Lys Arg Gly Gln Val Pro Leu Leu Asp Asp Val Phe
                 80                  85                  90 cat ggc ctc aag cac acc tac aag att ggc caa gag ttc ctt ggc tac    2079
His Gly Leu Lys His Thr Tyr Lys Ile Gly Gln Glu Phe Leu Gly Tyr
                 95                 100                 105 tct ggc cat ttt gat gac gaa acc atc gag caa gtc cgg agg cac ccc    2127
Ser Gly His Phe Asp Asp Glu Thr Ile Glu Gln Val Arg Arg His Pro
            110                 115                 120 gat gtaagttgac tccagggcga ttgggctctt tccacatgct gatccacacg          2180
Asp ggcgacag gtg gag tac att gag cgc gac agc att gtc cac acg atg cgt   2230
         Val Glu Tyr Ile Glu Arg Asp Ser Ile Val His Thr Met Arg
             125                 130                 135 gtc acc gag gaa aca tgc gat ggc gag ctt gag aag gcc gct cct tgg    2278
Val Thr Glu Glu Thr Cys Asp Gly Glu Leu Glu Lys Ala Ala Pro Trp
 140                 145                 150 ggc ttg gcc cgt atc tcg cac cga gat acg ctc ggc ttc tcg acg ttc    2326
Gly Leu Ala Arg Ile Ser His Arg Asp Thr Leu Gly Phe Ser Thr Phe
155                 160                 165                 170 aac aag tat ctg tat gcc gcc gag ggc agt gag ggc gtt gac gcg tac    2374
Asn Lys Tyr Leu Tyr Ala Ala Glu Gly Ser Glu Gly Val Asp Ala Tyr
                 175                 180                 185 gtc atc gac acc ggt acc aac att gag cac gtc gac ttc gag ggt cgc    2422
Val Ile Asp Thr Gly Thr Asn Ile Glu His Val Asp Phe Glu Gly Arg
             190                 195                 200 gcc aaa tgg ggc aag acc atc ccc gca ggc gat gct gat gtt gac ggc    2470
Ala Lys Trp Gly Lys Thr Ile Pro Ala Gly Asp Ala Asp Val Asp Gly
         205                 210                 215 aac ggc cac gga acc aac tgc tcc ggc acc atc gct ggc aag aag tac    2518
Asn Gly His Gly Thr Asn Cys Ser Gly Thr Ile Ala Gly Lys Lys Tyr
```

```
                  220                 225                 230
ggc gtc gcc aag aag gcg aat gtc tat gcc gtc aag gtt ctg cgc tcc         2566
Gly Val Ala Lys Lys Ala Asn Val Tyr Ala Val Lys Val Leu Arg Ser
235                 240                 245                 250 aac ggc tcc ggc acc atg gct gat gtc gtt gcc ggt gtc gaa tgg gct         2614
Asn Gly Ser Gly Thr Met Ala Asp Val Val Ala Gly Val Glu Trp Ala
                    255                 260                 265 gcc aag tcc cat ctg gag cag gtg cag gct gcc aag gat ggc aag cgc         2662
Ala Lys Ser His Leu Glu Gln Val Gln Ala Ala Lys Asp Gly Lys Arg
                270                 275                 280 aag ggc ttc aag ggt tcc gtc gcc aac atg tcg ctt gga ggc ggc aag         2710
Lys Gly Phe Lys Gly Ser Val Ala Asn Met Ser Leu Gly Gly Gly Lys
285                 290                 295 acc agg gcc ctc gat gac act gtg aac gct gct gtc tct gtc ggt atc         2758
Thr Arg Ala Leu Asp Asp Thr Val Asn Ala Ala Val Ser Val Gly Ile
300                 305                 310 cac ttc gcc gtc gcc gcc ggc aac gac aac gcc gat gcc tgc aac tac         2806
His Phe Ala Val Ala Ala Gly Asn Asp Asn Ala Asp Ala Cys Asn Tyr
315                 320                 325                 330 tcg cct gct gcg gcc gag aag gct gtc acg gtt ggt gcc tcg gct att         2854
Ser Pro Ala Ala Ala Glu Lys Ala Val Thr Val Gly Ala Ser Ala Ile
                    335                 340                 345 gac gac agc cgt gcc tac ttc tcc aac tac ggc aag tgc acc gac atc         2902
Asp Asp Ser Arg Ala Tyr Phe Ser Asn Tyr Gly Lys Cys Thr Asp Ile
                350                 355                 360 ttc gcc ccc ggc ctg agc atc ctc tcc acc tgg atc ggc agc aag tat         2950
Phe Ala Pro Gly Leu Ser Ile Leu Ser Thr Trp Ile Gly Ser Lys Tyr
            365                 370                 375 gcc acc aac acc atc tct ggc acc tcg atg gcc tcc ccc cat att gct         2998
Ala Thr Asn Thr Ile Ser Gly Thr Ser Met Ala Ser Pro His Ile Ala
380                 385                 390 ggt ctg ctg gcc tac tat ctc tcg ctc cag ccc gcc acc gat tcg gag         3046
Gly Leu Leu Ala Tyr Tyr Leu Ser Leu Gln Pro Ala Thr Asp Ser Glu
395                 400                 405                 410 tac tcg gtc gct ccc atc acc cct gag aag atg aag tcg aac ttg ctc         3094
Tyr Ser Val Ala Pro Ile Thr Pro Glu Lys Met Lys Ser Asn Leu Leu
                    415                 420                 425 aag atc gcc acc cag gat gcc ctt act gac atc ccc gac gag acg ccc         3142
Lys Ile Ala Thr Gln Asp Ala Leu Thr Asp Ile Pro Asp Glu Thr Pro
                430                 435                 440 aat ctg ctc gcc tgg aac ggc ggt ggc tgc aac aac tat acc gcc atc         3190
Asn Leu Leu Ala Trp Asn Gly Gly Gly Cys Asn Asn Tyr Thr Ala Ile
            445                 450                 455 gtc gag gct ggc ggc tac aag gcc aag aag aag acc acg act gac aag         3238
Val Glu Ala Gly Gly Tyr Lys Ala Lys Lys Lys Thr Thr Thr Asp Lys
460                 465                 470 gtt gac att ggc gcc tcg gtc tct gag ctt gag aag ctt atc gag cac         3286
Val Asp Ile Gly Ala Ser Val Ser Glu Leu Glu Lys Leu Ile Glu His
475                 480                 485                 490 gat ttt gag gtc atc tct ggc aag gtt gtc aag ggc gtc tcg tcg ttt         3334
Asp Phe Glu Val Ile Ser Gly Lys Val Val Lys Gly Val Ser Ser Phe
                    495                 500                 505 gcg gac aag gcc gag aag ttc tct gag aag att cac gag ctg gtc gat         3382
Ala Asp Lys Ala Glu Lys Phe Ser Glu Lys Ile His Glu Leu Val Asp
                510                 515                 520 gag gaa ctc aag gag ttt ctt gag gac atc gct gcc taagccttag              3428
Glu Glu Leu Lys Glu Phe Leu Glu Asp Ile Ala Ala
                525                 530 acatgccatc ggcgttgtga gcgtgcagcc tgagatgcgt attttggtct gggattaggg       3488
```

```
gatagggatt gttttttttt tcgtctctgc ttttcttggt ctattggacg ggcatacatc     3548
gacacggtgg gtgttccttg tactggatgg gtaacatggg attcggacgg acgcaagatt     3608
gtctggcttg gtttgcattt gagggtagtc gcgttcgttc agctccatca ttgatcagtt     3668
ctcattcgtc cactgacggc ctcgcatcaa tcaggccgtc cactctgccc gtctctcgaa     3728
atgcggctgg ccgtggtcca ttctgctcct tccgctcgtg ttctccgcgg cagctctgat     3788
ccagttgtgc tttccctagg aacccgcggg cccctcccc ctcccttcc cttcccttcc     3848 cttcccttcc ctctctcgcc cccggtcccc ctgtgtactc ggcccttgtt tctccatgat     3908
ggcttccatc tatctcgctc tcctctcccc cgctcccgtt tggcctaggg tctttcgtcc     3968
tctgtcgtat ccgcggaacc cacattgtgc cacgaacctg tgcatctcat ctctcttggc     4028
ataggtttag ctacacagtt ttactgttga ttagtctcct ctccctgaca aactgttacc     4088
gcgtcgctgt ttcggtgcga ctgcaccgtt acgcgggcac cgccttgttc caccgtttca     4148
atgctgcgtc ggcccagcct caagtcgagg acaaacctca aacgccgcaa gtccaccttg     4208
tcaacgcagg gggttgtcct tgagcatcac gacccggcgc tgggcacaac gggatgctca     4268
tattgcggct taggaggcct acgtcagagc ccagagccgt atcatggcag aacccgc     4325
```

```
<210> SEQ ID NO 5
<211> LENGTH: 534
<212> TYPE: PRT
<213> ORGANISM: Chrysosporium lucknowense

<400> SEQUENCE: 5

Met Arg Gly Leu Val Ala Phe Ser Leu Ala Ala Cys Val Ser Ala Ala
1               5                   10                  15

Pro Ser Phe Lys Thr Glu Thr Ile Asn Gly Glu His Ala Pro Ile Leu
            20                  25                  30

Ser Ser Ser Asn Ala Glu Val Val Pro Asn Ser Tyr Ile Ile Lys Phe
        35                  40                  45

Lys Lys His Val Asp Glu Ser Ser Ala Ser Ala His His Ala Trp Ile
    50                  55                  60

Gln Asp Ile His Thr Ser Arg Glu Lys Val Arg Gln Asp Leu Lys Lys
65                  70                  75                  80

Arg Gly Gln Val Pro Leu Leu Asp Asp Val Phe His Gly Leu Lys His
                85                  90                  95

Thr Tyr Lys Ile Gly Gln Glu Phe Leu Gly Tyr Ser Gly His Phe Asp
            100                 105                 110

Asp Glu Thr Ile Glu Gln Val Arg Arg His Pro Asp Val Glu Tyr Ile
        115                 120                 125

Glu Arg Asp Ser Ile Val His Thr Met Arg Val Thr Glu Glu Thr Cys
    130                 135                 140

Asp Gly Glu Leu Glu Lys Ala Ala Pro Trp Gly Leu Ala Arg Ile Ser
145                 150                 155                 160

His Arg Asp Thr Leu Gly Phe Ser Thr Phe Asn Lys Tyr Leu Tyr Ala
                165                 170                 175

Ala Glu Gly Ser Glu Gly Val Asp Ala Tyr Val Ile Asp Thr Gly Thr
            180                 185                 190

Asn Ile Glu His Val Asp Phe Glu Gly Arg Ala Lys Trp Gly Lys Thr
        195                 200                 205

Ile Pro Ala Gly Asp Ala Asp Val Asp Gly Asn Gly His Gly Thr Asn
    210                 215                 220

Cys Ser Gly Thr Ile Ala Gly Lys Lys Tyr Gly Val Ala Lys Lys Ala
225                 230                 235                 240
```

```
Asn Val Tyr Ala Val Lys Val Leu Arg Ser Asn Gly Ser Gly Thr Met
                245                 250                 255
Ala Asp Val Val Ala Gly Val Glu Trp Ala Ala Lys Ser His Leu Glu
            260                 265                 270
Gln Val Gln Ala Ala Lys Asp Gly Lys Arg Lys Gly Phe Lys Gly Ser
        275                 280                 285
Val Ala Asn Met Ser Leu Gly Gly Gly Lys Thr Arg Ala Leu Asp Asp
    290                 295                 300
Thr Val Asn Ala Ala Val Ser Val Gly Ile His Phe Ala Val Ala Ala
305                 310                 315                 320
Gly Asn Asp Asn Ala Asp Ala Cys Asn Tyr Ser Pro Ala Ala Ala Glu
                325                 330                 335
Lys Ala Val Thr Val Gly Ala Ser Ala Ile Asp Asp Ser Arg Ala Tyr
            340                 345                 350
Phe Ser Asn Tyr Gly Lys Cys Thr Asp Ile Phe Ala Pro Gly Leu Ser
        355                 360                 365
Ile Leu Ser Thr Trp Ile Gly Ser Lys Tyr Ala Thr Asn Thr Ile Ser
    370                 375                 380
Gly Thr Ser Met Ala Ser Pro His Ile Ala Gly Leu Leu Ala Tyr Tyr
385                 390                 395                 400
Leu Ser Leu Gln Pro Ala Thr Asp Ser Glu Tyr Ser Val Ala Pro Ile
                405                 410                 415
Thr Pro Glu Lys Met Lys Ser Asn Leu Leu Lys Ile Ala Thr Gln Asp
            420                 425                 430
Ala Leu Thr Asp Ile Pro Asp Glu Thr Pro Asn Leu Leu Ala Trp Asn
        435                 440                 445
Gly Gly Gly Cys Asn Asn Tyr Thr Ala Ile Val Glu Ala Gly Gly Tyr
    450                 455                 460
Lys Ala Lys Lys Lys Thr Thr Thr Asp Lys Val Asp Ile Gly Ala Ser
465                 470                 475                 480
Val Ser Glu Leu Glu Lys Leu Ile Glu His Asp Phe Glu Val Ile Ser
                485                 490                 495
Gly Lys Val Val Lys Gly Val Ser Ser Phe Ala Asp Lys Ala Glu Lys
            500                 505                 510
Phe Ser Glu Lys Ile His Glu Leu Val Asp Glu Leu Lys Glu Phe
        515                 520                 525
Leu Glu Asp Ile Ala Ala
    530

<210> SEQ ID NO 6
<211> LENGTH: 1602
<212> TYPE: DNA
<213> ORGANISM: Chrysosporium lucknowense

<400> SEQUENCE: 6
atgagaggcc tcgtcgcatt ctcgctcgca gcctgcgttt cggcagcgcc gagcttcaag      60
accgagacca tcaacggcga gcatgccccc attctctcct cgtcgaatgc cgaggtcgtc     120
cccaactcgt atatcatcaa gttcaagaag catgtggatg agagctcggc tccgcccac      180 catgcctgga tccaagacat ccatacctcg cgcgagaaag ttcgtcaaga cttgaagaag     240
cgcggccagg tgccgctgct tgacgacgtc ttccatggcc tcaagcacac ctacaagatt     300
ggccaagagt tccttggcta ctctggccat tttgatgacg aaaccatcga gcaagtccgg     360
aggcaccccg atgtggagta cattgagcgc gacagcattg tccacacgat gcgtgtcacc     420
```

-continued

```
gaggaaacat gcgatggcga gcttgagaag gccgctcctt ggggcttggc ccgtatctcg      480
caccgagata cgctcggctt ctcgacgttc aacaagtatc tgtatgccgc cgagggcagt      540
gagggcgttg acgcgtacgt catcgacacc ggtaccaaca ttgagcacgt cgacttcgag      600
ggtcgcgcca aatggggcaa gaccatcccc gcaggcgatg ctgatgttga cggcaacggc      660
cacggaacca actgctccgg caccatcgct ggcaagaagt acggcgtcgc caagaaggcg      720
aatgtctatg ccgtcaaggt tctgcgctcc aacggctccg gcaccatggc tgatgtcgtt      780
gccggtgtcg aatgggctgc caagtcccat ctggagcagg tgcaggctgc caaggatggc      840
aagcgcaagg gcttcaaggg ttccgtcgcc aacatgtcgc ttggaggcgg caagaccagg      900
gccctcgatg acactgtgaa cgctgctgtc tctgtcggta tccacttcgc cgtcgccgcc      960
ggcaacgaca cgccgatgc ctgcaactac tcgcctgctg cggccgagaa ggctgtcacg     1020
gttggtgcct cggctattga cgacagccgt gcctacttct ccaactacgg caagtgcacc     1080
gacatcttcg ccccccggcct gagcatcctc tccacctgga tcggcagcaa gtatgccacc     1140
aacaccatct ctggcaccct cgatggcctcc ccccatattg ctggtctgct ggcctactat     1200
ctctcgctcc agcccgccac cgattcggag tactcggtcg ctcccatcac ccctgagaag     1260
atgaagtcga acttgctcaa gatcgccacc caggatgccc ttactgacat ccccgacgag     1320
acgcccaatc tgctcgcctg gaacggcggt ggctgcaaca actataccgc catcgtcgag     1380
gctggcggct acaaggccaa gaagaagacc acgactgaca aggttgacat tggcgcctcg     1440
gtctctgagc ttgagaagct tatcgagcac gattttgagg tcatctctgg caaggttgtc     1500
aagggcgtct cgtcgtttgc ggacaaggcc gagaagttct ctgagaagat tcacgagctg     1560
gtcgatgagg aactcaagga gtttcttgag gacatcgctg cc                        1602
```

<210> SEQ ID NO 7
<211> LENGTH: 5871
<212> TYPE: DNA
<213> ORGANISM: Chrysosporium lucknowense
<220> FEATURE:
<221> NAME/KEY: CDS
<222> LOCATION: (2211)..(2312)
<220> FEATURE:
<221> NAME/KEY: CDS
<222> LOCATION: (2369)..(2525)
<220> FEATURE:
<221> NAME/KEY: CDS
<222> LOCATION: (2596)..(3527)

<400> SEQUENCE: 7

```
gctggctcac cgttatttgc tcccgcagga agtccaggtc ctcctcgcag ttggacaaac       60
tctgcttcgc agcctgcaac tttgactcaa ggagcgcctc ggcctcgtcg attgggtaag      120
acagcatgac gttggcctgc caaatgtcag cctctagaag cacactccca ctctcgttgg      180
aaaggttcct accccaagcc acaagtaaac ctcgtccgtc ggcggtatct cggccttcgc      240
atagagagtg tcgttcaatt cgaatgttgt ctctatcgga tcagattcgc cctgccacaa      300
tcaaccgccg atcagcacca tggccgctca tcgagagtgg caacgcctcg ccctaccgtc      360
ctcagcttca aaaagcggac agcctccagc gttttccgaa tgtcgggcat tttgtccttt      420
agtcccgcta ccctccgctg caggttctgc tccatgaact ggtatttcct gcacgccgac      480
cacgtatcag ccgaacgccg tccgtcaagg ctggatttca atcttaaccg ggagagctca      540
cgcaatcatc tcttggaacc gacgcagcgt cggctcaaca tctgctcgtg acgtgacata      600
gtcctcgacc ttgtcgacga atggcgcata cggaatgcca cgaggattgg agggtgtggc      660
gtccctgtct cgtgcaggtg gtcagtcagc aataacagcc agagtgcata tgctagaatg      720
```

```
gcgcccgcgg gggagggaaa gtttggttac cttgctgctg cttccttgtc tgtgctcgcc      780
atcttggaca aattctcaca tgttgcagtg gaaggatact gcaagcgact gttaacccga      840
gccaacggag tgacgtcggg tttggtacct agtttaggtc aagccgttct caagctgctg      900
gccaaaaatt catggcgggg tcgagtgggc agcgaggtac tcctcgtagg gagcaaggtg      960
aagatgtggg gtagcagggg tcgacgctac aaagtacttt gtatccggat tgctgtgtgg     1020
tacgaagcgc ccgtgtgttg gatgctctct gtatgtacgg agtactgtac ctttctccat     1080
gcgctgcccc attctctatt tggttgcacc tgcttcgttc gtagtgtatg tacagcagta     1140
caactatcta cgacacctgc actgactagt gcgtagaatt ctttagtttc tcgagtacgg     1200
cgctaacgct tcgcgcagca agcaccttct tctgattgtg ttactgtgct caaacctcgc     1260
cagccagctg cggtgctcca caagcccggc cgtgcccaac cgccatttgc atcccggtcc     1320
catgaatctg tggacgaccc atccctctct gtaccgcgtc gcggtatcag cccagaatga     1380
tagcgggaag acaaacgcag tgattcggat tacgctcgca ggaaatgggg ggagtagctt     1440
gatagctctc cacggcgagg gtgtctcagg ctgaggtgtc aactagttgt atgtacactc     1500
aggacgaggc attctgcgtt ttgaaacacc aatcttccaa taccggaggt gttgtatgca     1560
ggatcacttg aatatgtttg cacccattat tactgtacct ggatgattcg acagggcga     1620 gcatgattgg tcgccccgtt ttgtcaccgc attcgcagcg tcggcgggaa gcagccacgt     1680
agagcactgc caaacgtttc aagagacacc ccatatggag taaattggag taatctgtat     1740
ccttcagagc cgtcaatcaa actattgttt ctcagcagga tggcccgttg ctcatggggg     1800
atgtaccctg gtaggtagtt cgttgttgat gacttccttg gatgagcctg ctgcgcatga     1860
aggtgccggg gccccaggtt gggtgcctaa aactaactgt aaacagacgc acggtggcga     1920
cgacgtagcc gaaccggtgt agcgagcttt ccccggccac tacgtaatcg ggcgatgca     1980 ctgcaggaac acctcacacc tgacctaccc ccttcgcctc cgcatccgtc ccaacccgct     2040
tccccaacct ttccatcaac tacttccgag actcgacatc ccttttcgc gtcgtgtctc      2100 atcgtcgtta tcatcaccat cggcgataga tttgttcgct tcgatcgtcg catcgccttg     2160
acttccattc gtccttcacg ccgaccgacc ggaccagaca gtcgcccaaa atg aag       2216
                                                          Met Lys
                                                           1 gat gct ttt ttg ctg acc gca gct gtg ctg ctc ggc tcc gcc cag gga      2264
Asp Ala Phe Leu Leu Thr Ala Ala Val Leu Leu Gly Ser Ala Gln Gly
        5                  10                 15 gca gtt cac aaa atg aag ctg cag aag atc cct ctc tct gag cag ctt     2312
Ala Val His Lys Met Lys Leu Gln Lys Ile Pro Leu Ser Glu Gln Leu
    20                  25                  30 gtacgtctga ccccgttcaa gcacgcgtca gcggctactg accttatcgc gtccag gag    2371
                                                                Glu
                                                                 35 gcg gtt ccc atc aac acc cag ctc gag cat ctc ggc caa aaa tac atg     2419
Ala Val Pro Ile Asn Thr Gln Leu Glu His Leu Gly Gln Lys Tyr Met
            40                  45                  50 ggg ttg cgc cca cgt gaa tct caa gcc gat gcc atc ttt aag ggc atg     2467
Gly Leu Arg Pro Arg Glu Ser Gln Ala Asp Ala Ile Phe Lys Gly Met
        55                  60                  65 gtt gcc gac gtc aag ggc aac cat cct att ccc atc tcc aac ttc atg     2515
Val Ala Asp Val Lys Gly Asn His Pro Ile Pro Ile Ser Asn Phe Met
    70                  75                  80 aac gca cag t gtatgtgacg ccactgtggt ggcatggatg gctcgtcctc             2565
Asn Ala Gln
    85
```

```
aattcggaga ctgacactgg agcaccctag ac ttc tcc gag atc acg att gga         2618
                                    Tyr Phe Ser Glu Ile Thr Ile Gly
                                                             90 aca ccc cct cag tca ttc aag gtg gtc ctc gat acc ggt agc tcc aac         2666
Thr Pro Pro Gln Ser Phe Lys Val Val Leu Asp Thr Gly Ser Ser Asn
95          100                 105                 110 ctg tgg gtt cca tca gtc gag tgc ggc tcg att gct tgt tac ctg cac         2714
Leu Trp Val Pro Ser Val Glu Cys Gly Ser Ile Ala Cys Tyr Leu His
                115                 120                 125 tcg aag tat gac tca tct gcc tcg tcc acc tac aag aag aac gga acc         2762
Ser Lys Tyr Asp Ser Ser Ala Ser Ser Thr Tyr Lys Lys Asn Gly Thr
        130                 135                 140 tcg ttc gag atc cgc tac ggg tca ggc agc ctg agc ggg ttt gtc tct         2810
Ser Phe Glu Ile Arg Tyr Gly Ser Gly Ser Leu Ser Gly Phe Val Ser
145                 150                 155 cag gac aca gtg tcc atc ggc gat atc act atc cag ggc cag gac ttt         2858
Gln Asp Thr Val Ser Ile Gly Asp Ile Thr Ile Gln Gly Gln Asp Phe
    160                 165                 170 gcc gag gcg acc agc gag ccc ggt ctt gcc ttt gcc ttt ggc cgt ttc         2906
Ala Glu Ala Thr Ser Glu Pro Gly Leu Ala Phe Ala Phe Gly Arg Phe
175             180                 185                 190 gac ggt atc ctt ggc ctt ggc tac gac cgg atc tca gtc aac ggc atc         2954
Asp Gly Ile Leu Gly Leu Gly Tyr Asp Arg Ile Ser Val Asn Gly Ile
                195                 200                 205 gtc ccg cct ttt tac aag atg gtc gag cag aag ctc atc gat gag ccc         3002
Val Pro Pro Phe Tyr Lys Met Val Glu Gln Lys Leu Ile Asp Glu Pro
            210                 215                 220 gtc ttc gcc ttc tac ctg gcc gat acc aat ggc cag tct gag gtt gtc         3050
Val Phe Ala Phe Tyr Leu Ala Asp Thr Asn Gly Gln Ser Glu Val Val
        225                 230                 235 ttt ggc ggt gtt gac cac gac aag tac aag ggc aag atc acc acc att         3098
Phe Gly Gly Val Asp His Asp Lys Tyr Lys Gly Lys Ile Thr Thr Ile
240                 245                 250 ccg ttg agg cgc aag gcc tac tgg gag gtt gac ttc gat gcc att tct         3146
Pro Leu Arg Arg Lys Ala Tyr Trp Glu Val Asp Phe Asp Ala Ile Ser
255                 260                 265                 270 tac ggc gac gac act gcc gag ctt gag aac act ggc atc atc ctg gac         3194
Tyr Gly Asp Asp Thr Ala Glu Leu Glu Asn Thr Gly Ile Ile Leu Asp
                275                 280                 285 acc ggt act tct ctg atc gct ctg ccc agc cag ctc gcc gag atg ctc         3242
Thr Gly Thr Ser Leu Ile Ala Leu Pro Ser Gln Leu Ala Glu Met Leu
            290                 295                 300 aac gct cag atc ggc gct aag aag agc tac act ggc cag tac acc atc         3290
Asn Ala Gln Ile Gly Ala Lys Lys Ser Tyr Thr Gly Gln Tyr Thr Ile
        305                 310                 315 gac tgc aac aag cgc gac tcc ctc aag gat gtc acg ttc aac ctg gct         3338
Asp Cys Asn Lys Arg Asp Ser Leu Lys Asp Val Thr Phe Asn Leu Ala
    320                 325                 330 ggc tac aat ttc acg ctc ggc ccc tac gac tac gtt ctc gag gtc cag         3386
Gly Tyr Asn Phe Thr Leu Gly Pro Tyr Asp Tyr Val Leu Glu Val Gln
335             340                 345                 350 ggc agc tgc att tct acc ttt atg ggc atg gat ttc ccg gct cct act         3434
Gly Ser Cys Ile Ser Thr Phe Met Gly Met Asp Phe Pro Ala Pro Thr
                355                 360                 365 ggg cca ctt gcg atc ctg ggc gat gcc ttc ctc cgg agg tat tac tcc         3482
Gly Pro Leu Ala Ile Leu Gly Asp Ala Phe Leu Arg Arg Tyr Tyr Ser
            370                 375                 380 att tat gac ctt ggc gcc gac acc gtc ggt ctg gct gag gcc aag             3527
Ile Tyr Asp Leu Gly Ala Asp Thr Val Gly Leu Ala Glu Ala Lys
        385                 390                 395
```

```
tgattgaagg atgggcggca gggaaagacg atgggtaata cggggagtct gggaatcggg    3587
ctttggactg tggtctgtat ctagttgctc aagagagttg tcgtttgatt ttgttatagg    3647
atctgtctag gaaccttagc aggagtgaaa ttttttcgtg tacgagcatc ggcgggctga    3707
agtggtttga taacaagtct ggacttgagt acgcaggcag ttgcacaatc tgcttcgccg    3767
aggagagcaa aggcgtcctc tttgaaaaag cctacctacg cgtcacaggg gtataatttt    3827
ttgagtttga cctacgccct gtcccatacc aaccgcgtcc caatcccgt caacccttgc     3887 aatgtcatta cccgtggatg tatcacgtag cagaagccga catcccacac gcttcaacct    3947
tcctatccag acaatgacat ggtaagctca ttttttaaag gtcgccgtcc tccctccctt    4007
cacgtgattc attttccttg cgccttgtgg cgcatcccct gacttcatgc cgtacggatc    4067
aaagggtgca aacttgcccc gcacctcttt tctgccgcca tcatcatcac catcatcgcc    4127
gtttgtcgcc tgcgcagcat gtagcacgga cgacgccttg ctgtagtcaa acggctcctg    4187
ctcggcatcg tcatcatggc cttcctcctg ttcgcccgag gtctgttcgt cggctgccga    4247
ggtcgcggcg gaggcagatg tctgctgctg ctgctgctgc tgctgcttct gggctttctt    4307
ggcggctcga agtgccttcc tggcttgagc cttgagttcc tttgctccct ttatgtctcc    4367
gttttgagcc agttgctctg ccaagagctg agcacgcttg aactcttctc gagcagcctt    4427
cttggcttgt ttctttgcct gctgtggcgg cttgtcatca ccaccctcaa cttcctgctc    4487
gacactagga gacttcgggt ggtctttgcc tgcgaactaa tctccaccca tctcgatgtc    4547
ggaaactgct tcggcttcgg atgctgactc aacatcaaca tccctagact tccgcttttcg   4607 accagccttc agagtgaaac cttcttcttc gagaacaggg agaccccttgg tgtcttgttc   4667 agcgacacgc ctgatgaagg atgctttttt gctgaccgca gctgtgctgc tcggctccgc    4727
ccagggagca gttcacaaaa tgaagctgca gaagatccct ctctctgagc agcttgaggc    4787
ggttcccatc aacacccagc tcgagcatct cggccaaaaa tacatggggt gcgcccacg     4847 tgaatctcaa gccgatgcca tctttaaggg catggttgcc gacgtcaagg gcaaccatcc    4907
tattcccatc tccaacttca tgaacgcaca gtacttctcc gagatcacga ttggaacacc    4967
ccctcagtca ttcaaggtgg tcctcgatac cggtagctcc aacctgtggg ttccatcagt    5027
cgagtgcggc tcgattgctt gttacctgca ctcgaagtat gactcatctg cctcgtccac    5087
ctacaagaag aacggaacct cgttcgagat ccgctacggg tcaggcagcc tgagcgggtt    5147
tgtctctcag gacacagtgt ccatcggcga tatcactatc cagggccagg actttgccga    5207
ggcgaccagc gagcccggtc ttgcctttgc ctttggccgt ttcgacggta tccttggcct    5267
tggctacgac cggatctcag tcaacggcat cgtcccgcct ttttacaaga tggtcgagca    5327
gaagctcatc gatgagcccg tcttcgcctt ctacctggcc gataccaatg ccagtctga    5387 ggttgtcttt ggcggtgttg accacgacaa gtacaagggc aagatcacca ccattccgtt    5447
gaggcgcaag gcctactggg aggttgactt cgatgccatt tcttacggcg acgacactgc    5507
cgagcttgag aacactggca tcatcctgga caccggtact tctctgatcg ctctgcccag    5567
ccagctcgcc gagatgctca acgctcagat cggcgctaag aagagctaca ctggccagta    5627
caccatcgac tgcaacaagc gcgactccct caaggatgtc acgttcaacc tggctggcta    5687
caatttcacg ctcggcccct acgactacgt tctcgaggtc cagggcagct gcatttctac    5747
ctttatgggc atggatttcc cggctcctac tgggccactt gcgatcctgg gcgatgcctt    5807
cctccggagg tattactcca tttatgacct tggcgccgac accgtcggtc tggctgaggc    5867
caag                                                                 5871
```

<210> SEQ ID NO 8
<211> LENGTH: 397
<212> TYPE: PRT
<213> ORGANISM: Chrysosporium lucknowense

<400> SEQUENCE: 8

```
Met Lys Asp Ala Phe Leu Leu Thr Ala Ala Val Leu Leu Gly Ser Ala
1               5                   10                  15

Gln Gly Ala Val His Lys Met Lys Leu Gln Lys Ile Pro Leu Ser Glu
            20                  25                  30

Gln Leu Glu Ala Val Pro Ile Asn Thr Gln Leu Glu His Leu Gly Gln
        35                  40                  45

Lys Tyr Met Gly Leu Arg Pro Arg Glu Ser Gln Ala Asp Ala Ile Phe
    50                  55                  60

Lys Gly Met Val Ala Asp Val Lys Gly Asn His Pro Ile Pro Ile Ser
65                  70                  75                  80

Asn Phe Met Asn Ala Gln Tyr Phe Ser Glu Ile Thr Ile Gly Thr Pro
                85                  90                  95

Pro Gln Ser Phe Lys Val Val Leu Asp Thr Gly Ser Ser Asn Leu Trp
            100                 105                 110

Val Pro Ser Val Glu Cys Gly Ser Ile Ala Cys Tyr Leu His Ser Lys
        115                 120                 125

Tyr Asp Ser Ser Ala Ser Ser Thr Tyr Lys Lys Asn Gly Thr Ser Phe
    130                 135                 140

Glu Ile Arg Tyr Gly Ser Gly Ser Leu Ser Gly Phe Val Ser Gln Asp
145                 150                 155                 160

Thr Val Ser Ile Gly Asp Ile Thr Ile Gln Gly Gln Asp Phe Ala Glu
                165                 170                 175

Ala Thr Ser Glu Pro Gly Leu Ala Phe Ala Phe Gly Arg Phe Asp Gly
            180                 185                 190

Ile Leu Gly Leu Gly Tyr Asp Arg Ile Ser Val Asn Gly Ile Val Pro
        195                 200                 205

Pro Phe Tyr Lys Met Val Glu Gln Lys Leu Ile Asp Glu Pro Val Phe
    210                 215                 220

Ala Phe Tyr Leu Ala Asp Thr Asn Gly Gln Ser Glu Val Val Phe Gly
225                 230                 235                 240

Gly Val Asp His Asp Lys Tyr Lys Gly Lys Ile Thr Thr Ile Pro Leu
                245                 250                 255

Arg Arg Lys Ala Tyr Trp Glu Val Asp Phe Asp Ala Ile Ser Tyr Gly
            260                 265                 270

Asp Asp Thr Ala Glu Leu Glu Asn Thr Gly Ile Ile Leu Asp Thr Gly
        275                 280                 285

Thr Ser Leu Ile Ala Leu Pro Ser Gln Leu Ala Glu Met Leu Asn Ala
    290                 295                 300

Gln Ile Gly Ala Lys Lys Ser Tyr Thr Gly Gln Tyr Thr Ile Asp Cys
305                 310                 315                 320

Asn Lys Arg Asp Ser Leu Lys Asp Val Thr Phe Asn Leu Ala Gly Tyr
                325                 330                 335

Asn Phe Thr Leu Gly Pro Tyr Asp Tyr Val Leu Glu Val Gln Gly Ser
            340                 345                 350

Cys Ile Ser Thr Phe Met Gly Met Asp Phe Pro Ala Pro Thr Gly Pro
        355                 360                 365

Leu Ala Ile Leu Gly Asp Ala Phe Leu Arg Arg Tyr Tyr Ser Ile Tyr
    370                 375                 380
```

Asp Leu Gly Ala Asp Thr Val Gly Leu Ala Glu Ala Lys
385                 390                 395

<210> SEQ ID NO 9
<211> LENGTH: 1191
<212> TYPE: DNA
<213> ORGANISM: Chrysosporium lucknowense

<400> SEQUENCE: 9

```
atgaaggatg cttttttgct gaccgcagct gtgctgctcg gctccgccca gggagcagtt    60
cacaaaatga agctgcagaa gatccctctc tctgagcagc ttgaggcggt tcccatcaac   120
acccagctcg agcatctcgg ccaaaaatac atggggttgc gcccacgtga atctcaagcc   180
gatgccatct taagggcat ggttgccgac gtcaagggca accatcctat tcccatctcc   240
aacttcatga acgcacagta cttctccgag atcacgattg aacacccccc tcagtcattc   300
aaggtggtcc tcgataccgg tagctccaac ctgtgggttc catcagtcga gtgcggctcg   360
attgcttgtt acctgcactc gaagtatgac tcatctgcct cgtccaccta caagaagaac   420
ggaacctcgt tcgagatccg ctacgggtca ggcagcctga gcgggtttgt ctctcaggac   480
acagtgtcca tcggcgatat cactatccag ggccaggact ttgccgaggc gaccagcgag   540
cccggtcttg cctttgcctt tggccgtttc gacggtatcc ttggccttgg ctacgaccgg   600
atctcagtca acggcatcgt cccgcctttt tacaagatgg tcgagcagaa gctcatcgat   660
gagcccgtct tcgccttcta cctggccgat accaatggcc agtctgaggt tgtctttggc   720
ggtgttgacc acgacaagta caagggcaag atcaccacca ttccgttgag cgcaaggcc   780
tactgggagg ttgacttcga tgccatttct tacggcgacg cactgccga gcttgagaac   840
actggcatca tcctggacac cggtacttct ctgatcgctc tgcccagcca gctcgccgag   900
atgctcaacg ctcagatcgg cgctaagaag agctacactg gccagtacac catcgactgc   960
aacaagcgcg actccctcaa ggatgtcacg ttcaacctgg ctggctacaa tttcacgctc  1020
ggcccctacg actacgttct cgaggtccag ggcagctgca tttctacctt tatgggcatg  1080
gatttcccgg ctcctactgg gccacttgcg atcctgggcg atgccttcct ccggaggtat  1140
tactccattt atgaccttgg cgccgacacc gtcggtctgg ctgaggccaa g           1191
```

<210> SEQ ID NO 10
<211> LENGTH: 23188
<212> TYPE: DNA
<213> ORGANISM: Artifical Sequence
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (1324)..(2171)
<223> OTHER INFORMATION: pyrE coding sequence
<220> FEATURE:
<221> NAME/KEY: misc_feature
<222> LOCATION: (2680)..(2680)
<223> OTHER INFORMATION: n is a, c, g, or t
<220> FEATURE:
<221> NAME/KEY: misc_feature
<222> LOCATION: (4236)..(4811)
<223> OTHER INFORMATION: hTel
<220> FEATURE:
<221> NAME/KEY: misc_feature
<222> LOCATION: (4236)..(5432)

```
<223> OTHER INFORMATION: hTel
<220> FEATURE:
<221> NAME/KEY: misc_feature
<222> LOCATION: (7031)..(7932)
<223> OTHER INFORMATION: Complement of pyrG coding sequence
<220> FEATURE:
<221> NAME/KEY: misc_feature
<222> LOCATION: (11601)..(13397)
<223> OTHER INFORMATION: Pcbh
<220> FEATURE:
<221> NAME/KEY: misc_feature
<222> LOCATION: (16731)..(17746)
<223> OTHER INFORMATION: Tcbh
<220> FEATURE:
<221> NAME/KEY: misc_feature
<222> LOCATION: (17757)..(19553)
<223> OTHER INFORMATION: Pcbh
<220> FEATURE:
<221> NAME/KEY: misc_feature
<222> LOCATION: (22173)..(23188)
<223> OTHER INFORMATION: Tcbh1

<400> SEQUENCE: 10
```

| | | | | |
|---|---|---|---|---|
| gcggccgcca | ccgcgggaac | aatcttctct | catgctccgg | atatgggcaa | ggccaagaac | 60 |
| gcggctgtgg | agttcaagaa | actcttccgc | aacaacaacc | ccactacatc | tgcaatcaat | 120 |
| agctatcggt | acggaccccc | cgtccacgtt | gcctccatgc | aaggggaggt | tgaatttcgt | 180 |
| gacgtgtcgt | tccggtatcc | cacacgtctg | gaacagcctg | ttctacgcca | cttgaacctc | 240 |
| accgtcaagc | caggactaat | atgtcgctct | ggtggggtcg | agtggtagtg | gcaagagtac | 300 |
| gattgttgcc | ctgttggaac | ggttttatga | agcgcaggtg | ggcgagattt | atattgacgg | 360 |
| acgcaacatc | aaagcgttgg | acaagaagtc | gtatcgcagt | catttggcgc | tggtcagtca | 420 |
| ggaaccatcg | ctgttccatg | gcactatccg | ggagaacatt | ctcctgggtt | gtacggataa | 480 |
| ggaacatgtg | tcggaggata | tggtggtcag | agcgtgcaga | gatgcgaata | tttatgattt | 540 |
| catcatgtcg | ttgccgtgag | tcctccctgt | ccctttcctc | tttgtggtat | atatgcggtt | 600 |
| actgatagag | aaacagacaa | ggctttgaca | ccctcgttgg | taacaagggt | ggcatgttgt | 660 |
| caggtggaca | gaaacagcgt | atcgcgattg | cgcgtgcgtt | gattcggaac | ccgcgcattt | 720 |
| tgttgttgga | cgaggcgact | tccgcgctgg | attctgagtc | ggagaaggtg | gtgcaggctg | 780 |
| cgctggacgc | ggctgccaag | gggaggacca | ctattgcggt | ggcgcatcgg | ctaagtacga | 840 |
| ttcaacgggc | ggatatgatc | tatttcttag | agcaggagga | ggtgattgag | tgtgggacac | 900 |
| ataaggagct | gttgaggagg | aggggacggt | attatgagat | ggtgaatttg | cagactttga | 960 |
| ggtgatgana | ccattgactt | ggtggtggt | ncatgggtta | atgtgaaggc | gttagtggta | 1020 |
| atgtatatta | atggtgagat | gggctttgat | tgggtttaat | tggaatctgt | atattttcag | 1080 |
| atggagtcaa | cttttgaatg | gccaatatat | cctcggcgat | accgtcggag | ataagataag | 1140 |
| aataatcgca | cactattccc | aaagcatact | ggtacatact | gcattcggct | agtgcggggt | 1200 |
| gcttacctca | tccacccgaa | tgagcccaac | tttttttgtct | caatcaataa | ttgcatccaa | 1260 |
| attccccgc | aacttccccc | tccaaccccg | tgtctatacc | actccctcca | cacccacaca | 1320 |
| atcacaatgg | ctctccctgc | ctacaagacc | gccttcctgg | agtctctcgt | cggccaacgt | 1380 |
| gctgactttc | ggcaccttca | ccctgaagtc | gggtcgccgt | gcgtcacccc | tccaacaccg | 1440 |
| gcattatcgc | aatcggaaga | cttaccactg | tatacagact | cccctactt | cttcaacgcc | 1500 |
| ggcatcttca | acaccgcctc | tctcctctcc | gccctctcca | ccatggccca | caccatcatc | 1560 |
| accttcctcg | ctgagaaccc | ttccatcccc | aagcccgacg | tcatgcttcg | ggtaaaaaac | 1620 |
| cccctctttc | cccaataccc | cacttccact | caacaaccca | taaataacta | acaaaaaccc | 1680 |

-continued

```
cctaaacagc cccgcataca aaggcatccc cctcgcgtgc gccaccctcc ttgaactcaa    1740
ccgcatcgac cccgccacct ggggcagcgt gtcctacagc tacaaccgca agaagccaa     1800 ggatcacggc gaaggcggca acattgtcgg cgccgctctg aagggcaaga ccgtgcttgt    1860
gatcgacgat gtcatcacgg ccggtaccgc catgcgtgag accctcaacc tggtcgccaa    1920
ggagggcggc aaggtcgtcg gattcactgt tgctctggac cgcttggaga agatgcccgg    1980
acccaaggac gagaacggtg tcgaggacga taagcccaga atgagtgcta tgggtcagat    2040
ccgtaaggag tatggtgtgc ccacgacgag tattgttact ctggatgatt tgatcaagtt    2100
gatgcaggcg aagggcaatg aggccgatat gaagcggttg gaggagtata gggctaagta    2160
tcaggctagt gattagtcgg tttcattgac cgattgtttg ggtgggtgtg agaggttagg    2220
ttaggttgtg ggcgtaggaa tgaaaagctg tatacatagg ggcctgaaga ggtgcgtaga    2280
gacggtcgtg agatgtttta tgtcaaaatc ttgaacaaat gacaccttaa aaagacccc     2340 ttggtttcag ctgaattagc ccggaaagat gctcggcacg ccatgagtct agcccactca    2400
gtgggcaccc gtttcccaca tttgaagtgg ccgacgctta tttggctgag gctgtggcct    2460
ggaaaggcac tatggcgtgc tgcggtacaa ggccggggct ggcgtacgaa ccacgacgcc    2520
cgaagggaac tcttcggtct tactactact atgtcccccag ttgaccccccc gaggagagtg   2580 cgtgattgat tggttgtaga tgccgagctc tgggcatctt atgaatccat ggttggcgg    2640 ctcattaccg ctgtatatcg tctggatcgc gcggttactn tgaaaatgga tcgttataag    2700
cagtagtaac taacaatctc gcacggatca tgtccttgcc gctaaacccc caagtacat     2760 cggaaatcgg ccccagctca ggcacatgct atgatgcttt tttattttga aagtcagcta    2820
gtctggatgg catttctttt gctccccaag cgtggatttt cctggacaaa tagtccgcta    2880
atcaaaattc actactcagt ctcacacaag acatcttaga ccattatatt tgggatgcgg    2940
cacagttgca tgcagctaga ctggataatt tataagcaac cattcgttat gatacatgga    3000
gtgacttcaa ataataaatt cgccctgctg ctatgttctc gttcctagcc actactccat    3060
tctactgaat tgtactattt tcttttttaac gcatactcca tgttcgtttc taaaactaga    3120
acagaatcta aaacactcaa taaatgtcca ccgctggcac actcccaccc cctcccgacg    3180
gtggatttca cgcctgggcc caagtagtct ccggccactt agtggttgcg gtaacatggg    3240
gctatgcagc cagcttcggc gtcttccaag accattatga agtcactcta ccgcaaccct    3300
cgtccgatat ttcgtggatc ggtggcttcc aggtcttctg tctcctattc atgtcccctc    3360
tctccgggcg cgcgacggat gccggacaag ctcggcttgt cgtcggcatt ggcgcatttt    3420
tgttgttact tggaaccttc atgaccagcc tagcaagggt ctattggcaa ctatttctct    3480
cccaggggct ctgcattggt atcggccagg gacttatgtg gttgcctagt gtgactctcg    3540
tttccacgta ctttgtccga cgccgtgtgt tcgccgtcac ggctgctgcc accggaacca    3600
gcacaggggg gattatcttt ccagctatga tctcaataca ctcgactcgg cttcaccttt    3660
cgtgaaagaa tcgccgtctg cagagggtaa gaggcggagt agctttatcg cttctgttct    3720
ttatgaaaga cataggtgga cgattcatga ccttctgctg atgcagcaga tactttcctc    3780
ccttcacgaa gctcttctac gggagttgta tgatgtgatg atggattgct acgaaggaaa    3840
acctcggccc atcggtccgt gatgtacgta ctggagaatc atatcgaaat ggatctttcg    3900
acactgaaat acgtcgagcc tgctccgctt ggaagcggcg aggagcctcg tcctgtcaca    3960
actaccaaca tggagtacga taagggccag ttcgccagc tcattaagag ccagttcatg     4020
ggcgttggca tgatggccgt catgcatctg tacttcaagt acaccaacgc tcttctgatc    4080
```

```
cagtcgatca tccgctgaag gcgctttcga atctggttaa gatccacgtc ttcgggaagc    4140
cagcgactgg tgacctccag cgtccctta aggcttgcca acagctttct cagccagggc     4200
cagcccaaga ccgacaagga gcttatcgat ttcgaacccc cgcgccgcct ttgcgagggt    4260
ggagttgcct tagggttagg gttagggtta gggttagggt tagggttagg gttagggtta    4320
gggttagggt tagggttagg gttagggtta gggttagggt tagggttagg gttagggtca    4380
gggtcagggt agggtcaggg gtagggtcag ggtaggggg agggtcaggg ttagggttag     4440
ggttagggtt agggttaggg ttagggttag ggtcagggtt agggttaggg ttaggggtag    4500 gggtagggg agggttaggg ttagggttag ggttaggggtt agggttaggg ttagggtcag    4560
ggtcagggtc aggggtaggg tagggtaggg ttaggggtta gggttagggt tagggttagg    4620
gttagggtta gggttaaggg ttaagggtta agggnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800 nnnnnntgg gaattcgcgg cctaactata acggtcctaa ggtagcgagg ccgcgaattc     4860
ccannnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnccct taacccttaa cccttaaccc     5040
taaccctaac cctaacccta accctaaccc taaccctaa ccctaccta ccctaccct       5100 gaccctgacc ctgaccctaa ccctaaccct aaccctaacc ctaaccctaa ccctaaccct    5160 accctaccc ctaccctaa ccctaaccct aaccctgacc ctaaccctaa ccctaaccct      5220
aaccctaacc ctaaccctaa ccctgaccct accctaccc ctgaccctac ccctgacccct    5280 accctgaccc tgaccctaac cctaacccta accctaaccc taaccctaac cctaaccta     5340 accctaaccc taaccctaac cctaacccta accctaaccc taaccctaac cctaaccta     5400 aggcaactcc accctcgcaa aggcggcgcg ggggttcgaa atcgataagc tcctccctcc    5460
agaacgccga gaagaactgg aggggtggtg tcaaggagga gtaagctcct tattgaagtc    5520
ggaggacgga gcggtgtcaa gaggatattc ttcgactctg tattatagat aagatgatga    5580
ggaattggag gtagcatagc ttcatttgga tttgctttcc aggctgagac tctagcttgg    5640
agcatagagg gtccttttggc tttcaatatt ctcaagtatc tcgagatctt attcacatat    5700
cccttagata cgatcaaaac ccgcattcag tctcgcgaat attcgcagtt cctgagaacc    5760
aacacaggaa ccagcatatg gagacaccca gggatattcc gcggccttta ccaaggtatc    5820
gcgagcgtaa ccgctgcctc atttcccaca ggttggtgat acccaacatt atccttaccc    5880
aactcatatt cattgagcaa aaaataacg gtcaaagcgg gcgcattctt catcacatac    5940
gagtatgcac agtcaggact ccaagtcata catcaaaaac ttggaacgca tgagtctagc    6000
tcagctcggc tcttttccga ttttttgcgca gcctccgttg cggatcttgc tgcttgcgga    6060
gtctttgctc cggctgatgc attaaaacac aacgcgcaga tgatccaatc acaccatcca    6120
gacgcatcag cacctgtagc tgggggaagg gtaggtggtg tagcccagaa agcgacacgg    6180
ctagctttca agaagtttat caaccctaga cagctttgga gcggataccc ggctcttgtg    6240
gcgcatagct tgccagtgtc ggcgattcag atgcctctgt acgagtcttt tcggtatcga    6300 attttttgaat atagattcgg agatcgagag aaggtgctag aaagaccaag agagtatgga    6360
aagaaagagg cccattcgac aatcggagag gctgcagcga cagccgcaat aagtgctgcg    6420
gtctcgggcg gtatagctag tgtcttgaca gcacccatgg atatggtccg gacacgaatc    6480
```

```
atgctcgatg ctgcagatac aactgcacct cagaagaaaa ggatgatcaa taccgtacgg   6540
gagattgtac gaacagatgg cccgagagga ctattccgag ggtgtgctat caacacgttt   6600
atggccgctg tcggatcagg attatacttt ggtctctacg agagcaccaa atggtggcta   6660
ggctctgact cgatggataa ttgtgccgtg ttagagtagg gggtggtggg aaatcttgta   6720
tataattgtg attgtttgta cgatagtgac cgactgtaca ttagtgatac cccactctaa   6780
gaaaatagac caatctccag ctgcaccttc agacactccg gtacaaattc tcgtctatgt   6840
tggagattgt tgtgactttg aaacatgacc cttgaccctg attttgaatt tgtccatata   6900
tcgaggcagg tgtcttattc gtacggagag ggtatctgtc gtagacacat agtagtagtc   6960
atttcgagtg ctgaatttat aaatcgcatc atacttgcga catactgcca taaaaggagt   7020
acgtatccac cactacttat tgcgcaccaa cacgcttcag gtatgcatcc catccctcct   7080
tctggtactg cttcgccgcc tccacgggat caggagcagc ataaattcca cggccagcaa   7140
taataaagtc ggcaccgcgt ccaacagccg actcaggagt ttggtactgc tgtcccagct   7200
tgtcacccct cgaggagagg ttgacacctg tcgtgaagac gacaaaatct tcctcctccg   7260
aaggcgagct aacttcagac tgaacctcgc caaggtgacg tgtcgagacg aatcccatca   7320
caaacttctt atacttccga gcatagtcaa cagaagaagt agtatattga ccggtagcca   7380
aagatccctt ggaggtcatc tccgcaagga tcaaaaggcc cctctcggag ccgtaggga   7440 agtcctcggc cgaagcagtc tgggccagag cctcgacgat accctcaccg ggcagaatac   7500
tgcagttgat gatgtgggcc cactcagaga tacgcagagt gccgccatgg tactgctttt   7560
ggactgtgtt tccgatatcg atgaacttgc gatcttcgaa gatgaggaaa ttgtgcttct   7620
ctgcaagggc cttcagaccg gtgatggttt cttcgctgaa atcggagagg atatcgatgt   7680
gagttttgat cacggcaatg tacgaccga gtcctgttat ataatccacc attaaccatt   7740
actagatcac atgtaagtgg catccccggt gcgcatacgg tcagccaaat ccagcagctc   7800
tttggtggtt gtcacgtcgg cggaaacggt gacattggtt ttcttggcct cggcaacctc   7860
gaagagcttc tttacgagcg cattggggtg cttgctagcg cgtgcgctgt aggtcaattg   7920
cgacttggaa gacatgttgg cgatggaggg gtagcgcggg gttctgcaaa tattgtataa   7980
atgagcactt agtggttgaa actggcttat tagtaggtta gtacttcgag ttttcagtaa   8040
ttagacaaaa taatcaggat gtccaactac taactcttga tatatggaat gaaatgtaga   8100
tacaaactgc acgacaattg ccgcgaaaaa ttaaattgaa tctatggagg ggactgtcat   8160
gcactagcca cacgtttctc cgcctgtggg gtgagccaca tgcctcattt tgaccaaaca   8220
catcgatgca gtcacatgta gataagatta gggcctatcc ttagggtacc gtccacgcgg   8280
ggattatgcc tggcttttg cctgcttttg atatcctttc agggacatag caataagccc   8340
aaccctatcg gccataataa tgtcaattcc agcagcggct gggtctaga atatttaatc   8400 agctaccgag caacttctac atcacagttt gaaagcacta aggatcaata tagaagcact   8460
taccttcgca ttttctggta tattgttctg agatccatag gatctccatg gacgcgtgac   8520
gtcgagtacc atttaattct atttgtgttt gatcgagacc taatacagcc cctacaacga   8580
ccatcaaagt cgtatagcta ccagtgagga agtggactca aatcgacttc agcaacatct   8640
cctggataaa ctttaagcct aaactataca gaataagata ggtggagagc ttataccgag   8700
ctcgcggccg caggtaccag gcaattcgcc ctatagtgag tcgtattacg cgcgctcact   8760
ggccgtcgtt ttacaacgtc gtgactggga aaccctggc gttacccaac ttaatcgcct   8820
tgcagcacat cccccttcg ccagctggcg taatagcgaa gaggcccgca ccgatcgccc   8880
```

```
ttcccaacag ttgcgcagcc tgaatggcga atgggacgcg ccctgtagcg gcgcattaag    8940
cgcggcgggt gtggtggtta cgcgcagcgt gaccgctaca cttgccagcg ccctagcgcc    9000
cgctcctttc gctttcttcc cttcctttct cgccacgttc gccggctttc cccgtcaagc    9060
tctaaatcgg gggctccctt tagggttccg atttagtgct ttacggcacc tcgaccccaa    9120
aaaacttgat tagggtgatg gttcacgtag tgggccatcg ccctgataga cggttttcg     9180 cccttttgacg ttggagtcca cgttctttaa tagtggactc ttgttccaaa ctggaacaac    9240
actcaaccct atctcggtct attcttttga tttataaggg attttgccga tttcggccta    9300
ttggttaaaa aatgagctga tttaacaaaa attttaacgcg aattttaaca aaatattaac    9360
gcttacaatt taggtggcac ttttcgggga aatgtgcgcg gaacccctat tgtttatttt    9420
ttctaaatac attcaaatat gtatccgctc atgagacaat aaccctgata aatgcttcaa    9480
taatattgaa aaaggaagag tatgagtatt caacatttcc gtgtcgccct tattcccttt    9540
tttgcggcat tttgccttcc tgttttttgct cacccagaaa cgctggtgaa agtaaaagat    9600
gctgaagatc agttgggtgc acgagtgggt tacatcgaac tggatctcaa cagcggtaag    9660
atccttgaga gttttcgccc cgaagaacgt tttccaatga tgagcacttt taaagttctg    9720
ctatgtggcg cggtattatc ccgtattgac gccgggcaag agcaactcgg tcgccgcata    9780
cactattctc agaatgactt ggttgagtac tcaccagtca cagaaaagca tcttacggat    9840
ggcatgacag taagagaatt atgcagtgct gccataacca tgagtgataa cactgcggcc    9900
aacttacttc tgacaacgat cggaggaccg aaggagctaa ccgcttttttt gcacaacatg    9960 ggggatcatg taactcgcct tgatcgttgg gaaccggagc tgaatgaagc cataccaaac    10020
gacgagcgtg acaccacgat gcctgtagca atggcaacaa cgttgcgcaa actattaact    10080
ggcgaactac ttactctagc ttcccggcaa caattaatag actggatgga ggcggataaa    10140
gttgcaggac cacttctgcg ctcggccctt ccggctggct ggtttattgc tgataaatct    10200
ggagccggtg agcgtgggtc tcgcggtatc attgcagcac tggggccaga tggtaagccc    10260
tcccgtatcg tagttatcta cacgacgggg agtcaggcaa ctatggatga acgaaataga    10320
cagatcgctg agataggtgc ctcactgatt aagcattggt aactgtcaga ccaagtttac    10380
tcatatatac tttagattga tttaaaactt cattttttaat ttaaaaggat ctaggtgaag    10440
atcctttttg ataatctcat gaccaaaatc ccttaacgtg agttttcgtt ccactgagcg    10500
tcagaccccg tagaaaagat caaaggatct tcttgagatc ctttttttct gcgcgtaatc    10560
tgctgcttgc aaacaaaaaa accaccgcta ccagcggtgg tttgtttgcc ggatcaagag    10620
ctaccaactc tttttccgaa ggtaactggc ttcagcagag cgcagatacc aaatactgtc    10680
cttctagtgt agccgtagtt aggccaccac ttcaagaact ctgtagcacc gcctacatac    10740
ctcgctctgc taatcctgtt accagtggct gctgccagtg gcgataagtc gtgtcttacc    10800
gggttggact caagacgata gttaccggat aaggcgcagc ggtcgggctg aacggggggt    10860
tcgtgcacac agcccagctt ggagcgaacg acctacaccg aactgagata cctacagcgt    10920
gagctatgag aaagcgccac gcttcccgaa gggagaaagg cggacaggta tccggtaagc    10980
ggcagggtcg gaacaggaga gcgcacgagg gagcttccag ggggaaacgc ctggtatctt    11040
tatagtcctg tcgggtttcg ccacctctga cttgagcgtc gatttttgtg atgctcgtca    11100
ggggggcgga gcctatggaa aaacgccagc aacgcggcct ttttacggtt cctggccttt    11160
tgctggcctt ttgctcacat gttctttcct gcgttatccc ctgattctgt ggataaccgt    11220
attaccgcct ttgagtgagc tgataccgct cgccgcagcc gaacgaccga gcgcagcgag    11280
```

```
tcagtgagcg aggaagcgga agagcgccca atacgcaaac cgcctctccc cgcgcgttgg    11340
ccgattcatt aatgcagctg gcacgacagg tttcccgact ggaaagcggg cagtgagcgc    11400
aacgcaatta atgtgagtta gctcactcat taggcacccc aggctttaca ctttatgctt    11460
ccggctcgta tgttgtgtgg aattgtgagc ggataacaat ttcacacagg aaacagctat    11520
gaccatgatt acgccaagcg cgcaattaac cctcactaaa gggaacaaaa gctggagctc    11580
caccgcggtg gcggccggcc gcggatcnnn nnnnnnnnnn nnnnnaaggt atccgatttg    11640
gggaacgtcg atgaaagtat tgcaaaagtg acgagagttg cgcaactaac tcgctgccga    11700
agaagctgcg gaagaaagag aacaccgaaa gtggaataac gttacggatg tcctgacctc    11760
aaagttgaaa ccagcccttc ctgctctatt tgggaaagcg gcttgccctt gaatgcgctg    11820
cactgtggca cgactaccag tgatcgggag gagcaaacta ccctggtccg ttccttggtg    11880
gggcggcact aggcccaact tagggtgatc ggaggtcgat gccgcggtcc tcgttggtct    11940
gggctcttct catttcccgg tttgcacccc ccgttgcacc tgctgatcgc ccgccaacgc    12000
cgatgaggtt gcgcccagac cgacaatcac cgcggctgca ttcccaagta tattgaagat    12060
ggcaccaggt acccggtttt gcgtcccagt cgtttggtgc caaatttggg agttttgag    12120 cctcaagatc tggggaaatc gacctcaact tccatacaag ttaaagtcgc acacacggcg    12180
agttccacga agagacacat ttttttctga aggcctctct ccccgcacat cagaaaccac    12240
caaataccaa gactgcagaa gccggggtaa gtgggccacc gggactacac taaaatgcgg    12300
ggagaagcga gatccgttgc gaagggaagg gatgggtgt gctgcggctt tctccgctct    12360
cgtgcgcctt ttgcttgaat ctagtgtaca ccagggtagg ctccgaagga gtatctacgg    12420
cagcgctgtt cgtgctgcgt tgagagtcag ggcggagacg agcaggcgac aggagcctcg    12480
caccggcact tcggatcgca tttgcgcgga gcgtcaaata cgctcttctg cggtcatcag    12540
agagcatcgt gaaccaaggt tcttccgcag ggcggcctgg gcttgcagag tcgcactcg    12600 gcggacgcct tccgtgtcac ccctgataac ctggctgccg cgcccagact cctccaatga    12660
ggtgtgtggt tgccctcgcc gacccttcag caaccttaat cgcttccatc gcacggctcc    12720
acgtcctcga acgatgccct cagtccgtgc ccggccgtgg caaccataac gtgacatcgc    12780
cgcccagcct actagccgct atcgaccggt taggcttgtc accgcagcgc ccattctcca    12840
tcgggcctct actctgatcc acctcaccca ccgcaagcac tagcgagcct caccagagtg    12900
caagcgacac gacccgcttg gcccttcgtc cttgactatc tcccagacct cttgccatct    12960
tgccgacgcc gccccctttt ttttctcctc ccctgccgg caggtcggtg gccccagtcc    13020
cgagatggca ttgctccgtt gtccatgacg accatcatt cgatggctga ctggcacact    13080
cgtcttgttt gagcatcgac ggcccgcggc ccgtctccca cggtacggaa cctcgttgta    13140
cagtacctct cgtaatgata cccaacaccg gggccgagcg ctgggagggc ggcgttcccg    13200
agaagccggg aaggcggctg gccggctgac ctttgtgact tggcgatgga tgcggccatg    13260
gagaatgtcc gtccgaagcg acgcgacaat tagcctggct accatcgata taaattgggt    13320
gattcccagc tcttgatggg cgtgtcttct gcctggcagc cctcgtcttc agatcaagca    13380
actgtgtgct gatcctcttc cgtcatgggc ttccgatctc tactcgccct gagcggcctc    13440
gtctgcacag ggttggcaaa tgtgatttcc aagcgcgcga ccttggattc atggttgagc    13500
aacgaagcga ccgtggctcg tactgccatc ctgaataaca tcggggcgga cggtgcttgg    13560
gtgtcgggcg cggactctgg cattgtcgtt gctagtccca gcacggataa cccggactgt    13620
atgtttcgag ctcagattta gtatgagtgt gtcattgatt gattgatgct gactggcgtg    13680
```

```
tcgtttgttg tagacttcta cacctggact cgcgactctg gtctcgtcct caagaccctc   13740
gtcgatctct tccgaaatgg agataccagt ctcctctcca ccattgagaa ctacatctcc   13800
gcccaggcaa ttgtccaggg tatcagtaac ccctctggtg atctgtccag cggcgctggt   13860
ctcggtgaac ccaagttcaa tgtcgatgag actgcctaca ctggttcttg gggacggccg   13920
cagcgagatg gtccggctct gagagcaact gctatgatcg gcttcgggca gtggctgctt   13980
gtatgttctc cacccccttg cgtctgatct gtgacatatg tagctgactg gtcaggacaa   14040
tggctacacc agcaccgcaa cggacattgt ttggcccctc gttaggaacg acctgtcgta   14100
tgtggctcaa tactgaacc agacaggata tggtgtgttt gttttatttt aaatttccaa    14160
agatgcgcca gcagagctaa cccgcgatcg cagatctctg ggaagaagtc aatggctcgt   14220
cttttcttta cgattgctgtg caacaccgcg cccttgtcga aggtagtgcc ttcgcgacgg   14280
ccgtcggctc gtcctgctcc tggtgtgatt ctcaggcacc cgaaattctc tgctacctgc   14340
agtccttctg gaccggcagc ttcattctgg ccaacttcga tagcagccgt tccggcaagg   14400
acgcaaacac cctcctggga agcatccaca cctttgatcc tgaggccgca tgcgacgact   14460
ccaccttcca gccctgctcc ccgcgcgcgc tcgccaacca aaggaggtt gtagactctt     14520 tccgctcaat ctataccctc aacgatggtc tcagtgacag cgaggctgtt gcggtgggtc   14580
ggtaccctga ggacacgtac tacaacggca acccgtggtt cctgtgcacc ttggctgccg   14640
cagagcagtt gtacgatgct ctataccagt gggacaagca ggggtcgttg gaggtcacag   14700
atgtgtcgct ggacttcttc aaggcactgt acagcgatgc tgctactggc acctactctt   14760
cgtccagttc gacttatagt agcattgtag atgccgtgaa gactttcgcc gatggcttcg   14820
tctctattgt ggtaagtcta cgctagacaa gcgctcatgt tgacagaggg tgcgtactaa   14880
cagaagtagg aaactcacgc cgcaagcaac ggctccatgt ccgagcaata cgacaagtct   14940
gatggcgagc agctttccgc tcgcgacctg acctggtctt atgctgctct gctgaccgcc   15000
aacaaccgtc gtaactccgt cgtgcctgct tcttggggcg agacctctgc cagcagcgtg   15060
cccggcacct gtgcggccac atctgccatt ggtacctaca gcagtgtgac tgtcacctcg   15120
tggccgagta tcgtggctac tggcggcacc actacgacgg ctaccccac tggatctggc     15180 agcgtgacct cgaccagcaa gaccaccgcg actgctagca agaccagcac cagtacgtca   15240
tcaacctcct gtaccactcc cacggcgaat gtgatatcca agcgcgcgcc agtaccccca   15300
ggagaagatt ccaaagatgt agccgcccca cacagacagc cactcacctc ttcagaacga   15360
tccaagcgcg aggtccagct cgtcgagagc ggcggtggcc tcgtccagcc cggtcgcagc   15420
ctccgcctca gctgcgccgc cagcggcttc accttcgacg actacgccat gcactgggtc   15480
cgtcaagccc ctggcaaggg cctggagtgg gtctccgcca tcacctggaa cagcggccac   15540
atcgactacg ccgacagcgt cgagggccgc ttcaccatca gccgcgacaa cgccaagaac   15600
agcctctacc tccagatgaa cagcctccgc gccgaggaca ccgccgtcta ctactgcgcc   15660
aaggtctcct acctcagcac cgccagcagc ctcgactact ggggccaggg caccctcgtc   15720
accgtgtcca gcgccagcac caagggtccc agcgtcttcc cctcgccccc cagcagcaag   15780
agcaccagcg gcggcactgc cgccctcggc tgcctcgtca aggactactt ccccgagccc   15840
gtcacggtct cctggaattc cggtgccctc acctccggcg tccacacctt ccccgccgtc   15900
ctccagagca gcggcctcta cagcctcagc agcgtcgtca ccgtccccag cagctccctc   15960
ggcacccaga cctacatctg caacgtcaac cacaagccca gcaacaccaa ggtcgacaaa   16020
accgtcgagc ccaagagctg cgacaagacc cacacctgcc cccctgccc tgcccccgag    16080
```

```
ctgctcggcg gtccctccgt cttcctcttc cccccccaagc ccaaggacac cctcatgatc   16140
agccgcaccc ccgaggtcac ctgcgtcgtc gtcgacgtgt cccacgagga cccggaggtc   16200
aagttcaact ggtacgtcga cggtgtcgag gtccacaacg ctaagaccaa gccccgcgag   16260
gagcagtaca acagcaccta ccgcgtcgtg tccgtcctca ccgtcctcca ccaggactgg   16320
ctcaacggca aggaatacaa gtgcaaggtc tccaacaagg ccctcccccgc tcccatcgag   16380 aagaccatca gcaaggccaa gggccagccc cgggagcccc aggtctacac cctccccccc   16440
tcgcgggagg agatgaccaa gaaccaggtc tccctcacct gcctggtcaa gggcttctac   16500
cccagcgaca tcgccgtcga gtgggagagc aacggccagc ccgagaacaa ctacaagacc   16560
actccccccg tcctcgacag cgacggcagc ttcttcctct acagcaagct caccgtcgac   16620
aagagccgct ggcagcaggg caacgtcttc agctgcagcg tcatgcacga ggccctccac   16680
aaccactaca cccagaagag cctcagcctc tcccccggca gtaagggcc cagatcctaa    16740 gtaagtaaac gaacctctct gaaggaggtt ctgagacacg cgcgattctt ctgtatatag   16800
tttatttttt cactctggag tgcttcgctc caccagtaca taaacctttt ttttcacgta   16860
acaaaatggc ttcttttcag accatgtgaa ccatcttgat gccttgacct cttcagttct   16920
cactttaacg tanttcgcgt tagtctgtat gtcccagttg catgtagttg agataaatac   16980
ccctggaagt gggtctgggc ctttgtggga cggagccctc tttctgtggt ctggagagcc   17040
cgctctctac cgcctacctt cttaccacag tacactactc acacattgct gaactgaccc   17100
atcataccgt actttatcct gttaattcgt ggtgctgtcg actattctat ttgctcaaat   17160
ggagagcaca ttcatcggcg cagggataca cggtttatgg accccaagag tgtaaggact   17220
attattagta atattatatg cctctaggcg ccttaacttc aacaggcgag cactactaat   17280
caacttttgg tagacccaat tacaaacgac catacgtgcc ggaaattttg ggattccgtc   17340
cgctctcccc aaccaagcta gaagaggcaa cgaacagcca atcccggtgc taattaaatt   17400
atatggttca ttttttttaa aaaaattttt tcttcccatt ttcctctcgc ttttcttttt   17460
cgcatcgtag ttgatcaaag tccaagtcaa gcgagctatt tgtgctatag ctcggtggct   17520
ataatcagta cagcttagag aggctgtaaa ggtatgatac cacagcagta ttcgcgctat   17580
aagcggcact cctagactaa ttgttacggt ctacagaagt aggtaataaa agcgttaatt   17640
gttctaaata ctagaggcac ttagagaagc tatctaaata tatattgacc ctagcttatt   17700
atccctatta gtaagttagt tagctctaac ctatagatag ccaaatgcgg ccggccgcgg   17760
atcnnnnnnn nnnnnnnnnn naaggtatcc gatttgggga acgtcgatga agtattgca    17820 aaagtgacga gagttgcgca actaactcgc tgccgaagaa gctgcggaag aaagagaaca   17880
ccgaaagtgg aataacgtta cggatgtcct gacctcaaag ttgaaaccag ccttcctgc   17940 tctatttggg aaagcggctt gcccttgaat gcgctgcact gtggcacgac taccagtgat   18000
cgggaggagc aaaactaccct ggtccgttcc ttggtggggc ggcactaggc ccaacttagg   18060
gtgatcggag gtcgatgccg cggtcctcgt tggtctgggc tcttctcatt tcccggtttg   18120 cacccccgt tgcacctgct gatcgcccgc caacgccgat gaggttgcgc ccagaccgac    18180
aatcaccgcg gctgcattcc caagtatatt gaagatggca ccaggtaccc ggttttgcgt   18240
cccagtcgtt tggtgccaaa tttgggagtt tttgagcctc aagatctggg gaaatcgacc   18300
tcaacttcca tacaagttaa agtcgcacac acggcgagtt ccacgaagag acacatttt    18360 ttctgaaggc ctctctcccc gcacatcaga aaccaccaaa taccaagact gcagaagccg   18420
gggtaagtgg gccaccggga ctacactaaa atgcggggag aagcgagatc cgttgcgaag   18480
```

```
ggaagggatg gggtgtgctg cggctttctc cgctctcgtg cgccttttgc ttgaatctag   18540
tgtacaccag ggtaggctcc gaaggagtat ctacggcagc gctgttcgtg ctgcgttgag   18600
agtcagggcg gagacgagca ggcgacagga gcctcgcacc ggcacttcgg atcgcatttg   18660
cgcggagcgt caaatacgct cttctgcggt catcagagag catcgtgaac caaggttctt   18720
ccgcagggcg gcctgggctt cgcagagtcg cactcggcgg acgccttccg tgtcacccct   18780
gataacctgg ctgccgcgcc cagactcctc caatgaggtg tgtggttgcc ctcgccgacc   18840
cttcagcaac cttaatcgct tccatcgcac ggctccacgt cctcgaacga tgccctcagt   18900
ccgtgcccgg ccgtggcaac cataacgtga catcgccgcc cagcctacta gccgctatcg   18960
accggttagg cttgtcaccg cagcgcccat tctccatcgg gcctctactc tgatccacct   19020
cacccaccgc aagcactagc gagcctcacc agagtgcaag cgacgacc cgcttggccc    19080
ttcgtccttg actatctccc agacctcttg ccatcttgcc gacgccgccc ccttttttt   19140
ctcctccccc tgccggcagg tcggtggccc cagtcccgag atggcattgc tccgttgtcc   19200
atgacgaccc atcattcgat ggctgactgg cacactcgtc ttgtttgagc atcgacggcc   19260
cgcggcccgt ctcccacggt acggaacctc gttgtacagt acctctcgta atgataccca   19320
acaccggggc cgagcgctgg gagggcggcg ttcccgagaa gccgggaagg cggctggccg   19380
gctgaccttt gtgacttggc gatggatgcg gccatggaga atgtccgtcc gaagcgacgc   19440
gacaattagc ctggctacca tcgatataaa ttgggtgatt cccagctctt gatgggcgtg   19500
tcttctgcct ggcagccctc gtcttcagat caagcaactg tgtgctgatc ctcttccgtc   19560
atgggcttcc gatctctact cgccctgagc ggcctcgtct gcacagggtt ggcaaatgtg   19620
atttccaagc gcgcgacctt ggattcatgg ttgagcaacg aagcgaccgt ggctcgtact   19680
gccatcctga ataacatcgg ggcggacggt gcttgggtgt cgggcgcgga ctctggcatt   19740
gtcgttgcta gtcccagcac ggataacccg gactgtatgt ttcgagctca gatttagtat   19800
gagtgtgtca ttgattgatt gatgctgact ggcgtgtcgt ttgttgtaga cttctacacc   19860
tggactcgcg actctggtct cgtcctcaag accctcgtcg atctcttccg aaatggagat   19920
accagtctcc tctccaccat tgagaactac atctccgccc aggcaattgt ccagggtatc   19980
agtaacccct ctggtgatct gtccagcggc gctggtctcg gtgaacccaa gttcaatgtc   20040
gatgagactg cctacactgg ttcttgggga cggccgcagc gagatggtcc ggctctgaga   20100
gcaactgcta tgatcggctt cgggcagtgg ctgcttgtat gttctccacc cccttgcgtc   20160
tgatctgtga catatgtagc tgactggtca ggacaatggc tacaccagca ccgcaacgga   20220
cattgttggg cccctcgtta ggaacgacct gtcgtatgtg gctcaatact ggaaccagac   20280
aggatatggt gtgtttgttt tattttaaat ttccaaagat gcgccagcag agctaacccg   20340
cgatcgcaga tctctgggaa gaagtcaatg gctcgtcttt ctttacgatt gctgtgcaac   20400
accgcgccct tgtcgaaggt agtgccttcg cgacggccgt cggctcgtcc tgctcctggt   20460
gtgattctca ggcacccgaa attctctgct acctgcagtc cttctggacc ggcagcttca   20520
ttctggccaa cttcgatagc agccgttccg gcaaggacgc aaacaccctc ctgggaagca   20580
tccacacctt tgatcctgag gccgcatgcg acgactccac cttccagccc tgctccccgc   20640
gcgcgctcgc caaccacaag gaggttgtag actctttccg ctcaatctat accctcaacg   20700
atggtctcag tgacagcgag gctgttgcgg tgggtcggta ccctgaggac acgtactaca   20760
acggcaaccc gtggttcctg tgcaccttgg ctgccgcaga gcagttgtac gatgctctat   20820
accagtggga caagcagggg tcgttggagg tcacagatgt gtcgctggac ttcttcaagg   20880
```

```
cactgtacag cgatgctgct actggcacct actcttcgtc cagttcgact tatagtagca   20940
ttgtagatgc cgtgaagact ttcgccgatg gcttcgtctc tattgtggta agtctacgct   21000
agacaagcgc tcatgttgac agagggtgcg tactaacaga agtaggaaac tcacgccgca   21060
agcaacggct ccatgtccga gcaatacgac aagtctgatg gcgagcagct ttccgctcgc   21120
gacctgacct ggtcttatgc tgctctgctg accgccaaca accgtcgtaa ctccgtcgtg   21180
cctgcttctt ggggcgagac ctctgccagc agcgtgcccg gcacctgtgc ggccacatct   21240
gccattggta cctacagcag tgtgactgtc acctcgtggc cgagtatcgt ggctactggc   21300
ggcaccacta cgacggctac ccccactgga tctggcagcg tgacctcgac cagcaagacc   21360
accgcgactg ctagcaagac cagcaccagt acgtcatcaa cctcctgtac cactcccacg   21420
gcgaatgtga tatccaagcg cgcgccagta cccccaggag aagattccaa agatgtagcc   21480
gccccacaca gacagccact cacctcttca gaacgatcca agcgcgacat ccagatgacc   21540
cagagcccca gcagcctcag cgccagcgtc ggtgaccgcg tcaccatcac ctgccgcgcc   21600
agccagggca tccgcaacta cctcgcctgg tatcagcaga agcccggcaa ggcccccaag   21660
ctcctcatct acgccgccag caccctccag agcggcgtcc ccagccgctt cagcggctcc   21720
ggcagcggca ccgacttcac cctcaccatc agcagcctcc agcccgagga cgtcgccacc   21780
tactactgcc agcgctacaa ccgtgccccc tacaccttcg gccagggcac caaggtcgag   21840
atcaagggcc agcccaaggc cgctcccagc gtcaccctct ccccccctc gagcgaggag   21900
ctgcaggcca acaaggccac cctcgtctgc ctcatcagcg acttctaccc cggtgccgtc   21960
accgtcgcct ggaaggccga cagcagcccc gtcaaggctg gcgtcgagac caccaccccc   22020
agcaagcaga gcaacaacaa gtacgccgcc tccagctacc tcagcctcac ccccgagcag   22080
tggaagagcc acaagagcta cagctgccag gtcacccacg agggcagcac cgtcgagaag   22140
accgtcgccc ccaccgagtg cagctaaggg cccagatcct aagtaagtaa acgaacctct   22200
ctgaaggagg ttctgagaca cgcgcgattc ttctgtatat agttttattt ttcactctgg   22260
agtgcttcgc tccaccagta cataaacctt ttttttcacg taacaaaatg gcttcttttc   22320
agaccatgtg aaccatcttg atgccttgac ctcttcagtt ctcactttaa cgtanttcgc   22380
gttagtctgt atgtcccagt tgcatgtagt tgagataaat accctggaa gtgggtctgg   22440
gcctttgtgg gacggagccc tcttctgtg tctggagag cccgctctct accgcctacc   22500
ttcttaccac agtacactac tcacacattg ctgaactgac ccatcatacc gtactttatc   22560
ctgttaattc gtggtgctgt cgactattct atttgctcaa atggagagca cattcatcgg   22620
cgcagggata cacggtttat ggaccccaag agtgtaagga ctattattag taatatata   22680
tgcctctagg cgccttaact tcaacaggcg agcactacta atcaactttt ggtagaccca   22740
attacaaacg accatacgtg ccggaaattt tgggattccg tccgctctcc ccaaccaagc   22800
tagaagaggc aacgaacagc caatcccggt gctaattaaa ttatatggtt catttttttt   22860
aaaaaaattt tttcttccca ttttcctctc gcttttcttt ttcgcatcgt agttgatcaa   22920
agtccaagtc aagcgagcta tttgtgctat agctcggtgg ctataatcag tacagcttag   22980
agaggctgta aaggtatgat accacagcag tattcgcgct ataagcggca ctcctagact   23040
aattgttacg gtctacagaa gtaggtaata aaagcgttaa ttgttctaaa tactagaggc   23100
acttagagaa gctatctaaa tatatattga ccctagctta ttatccctat tagtaagtta   23160
gttagctcta acctatagat agccaaat                                      23188
```

<210> SEQ ID NO 11

```
<211> LENGTH: 1012
<212> TYPE: DNA
<213> ORGANISM: Chrysosporium lucknowense
<220> FEATURE:
<221> NAME/KEY: misc_feature
<222> LOCATION: (191)..(191)
<223> OTHER INFORMATION: n is a, c, g, or t

<400> SEQUENCE: 11
aagtaaacga acctctctga aggaggttct gagacacgcg cgattcttct gtatatagtt      60
ttattttca ctctggagtg cttcgctcca ccagtacata aaccttttt ttcacgtaac      120
aaaatggctt cttttcagac catgtgaacc atcttgatgc cttgacctct tcagttctca    180
ctttaacgta nttcgcgtta gtctgtatgt cccagttgca tgtagttgag ataaataccc     240
ctggaagtgg gtctgggcct tgtgggacg gagccctctt tctgtggtct ggagagcccg      300
ctctctaccg cctaccttct taccacagta cactactcac acattgctga actgacccat    360
cataccgtac tttatcctgt taattcgtgg tgctgtcgac tattctattt gctcaaatgg     420
agagcacatt catcggcgca gggatacacg gtttatggac cccaagagtg taaggactat    480
tattagtaat attatatgcc tctaggcgcc ttaacttcaa caggcgagca ctactaatca    540
acttttggta gacccaatta caaacgacca tacgtgccgg aaattttggg attccgtccg   600
ctctccccaa ccaagctaga agaggcaacg aacagccaat cccggtgcta attaaattat   660
atggttcatt ttttttaaaa aaattttttc ttcccatttt cctctcgctt ttcttttcg      720
catcgtagtt gatcaaagtc caagtcaagc gagctatttg tgctatagct cggtggctat    780
aatcagtaca gcttagagag gctgtaaagg tatgatacca cagcagtatt cgcgctataa   840
gcggcactcc tagactaatt gttacggtct acagaagtag gtaataaaag cgttaattgt    900
tctaaatact agaggcactt agagaagcta tctaaatata tattgacccct agcttattat   960
ccctattagt aagttagtta gctctaacct atagatagcc aaatgcggcc gg            1012

<210> SEQ ID NO 12
<211> LENGTH: 352
<212> TYPE: DNA
<213> ORGANISM: Chrysosporium lucknowense

<400> SEQUENCE: 12
atggttcatt ttttttaaaa aaattttttc ttcccatttt cctctcgctt ttcttttcg      60
catcgtagtt gatcaaagtc caagtcaagc gagctatttg tgctatagct cggtggctat    120
aatcagtaca gcttagagag gctgtaaagg tatgatacca cagcagtatt cgcgctataa   180
gcggcactcc tagactaatt gttacggtct acagaagtag gtaataaaag cgttaattgt    240
tctaaatact agaggcactt agagaagcta tctaaatata tattgacccct agcttattat   300
ccctattagt aagttagtta gctctaacct atagatagat gcatgcggcc gc            352

<210> SEQ ID NO 13
<211> LENGTH: 714
<212> TYPE: DNA
<213> ORGANISM: Aspergillus niger
<220> FEATURE:
<221> NAME/KEY: CDS
<222> LOCATION: (1)..(714)

<400> SEQUENCE: 13 atg gct ctc cct gcc tac aag acc gcc ttc ctg gag tct ctc gtc ggc      48
Met Ala Leu Pro Ala Tyr Lys Thr Ala Phe Leu Glu Ser Leu Val Gly
1               5                   10                  15 caa cgt gct gac ttt cgg cac ctt cac cct gaa gtc ggg tcg ccg tac      96
```

```
Gln Arg Ala Asp Phe Arg His Leu His Pro Glu Val Gly Ser Pro Tyr
            20                  25                  30 tcc ccc tac ttc ttc aac gcc ggc atc ttc aac acc gcc tct ctc ctc      144
Ser Pro Tyr Phe Phe Asn Ala Gly Ile Phe Asn Thr Ala Ser Leu Leu
        35                  40                  45 tcc gcc ctc tcc acc gca tac gcc cac acc atc atc acc ttc ctc gct      192
Ser Ala Leu Ser Thr Ala Tyr Ala His Thr Ile Ile Thr Phe Leu Ala
 50                  55                  60 gag aac cct tcc atc ccc aag ccc gac gtc atc ttc ggc ccc gca tac      240
Glu Asn Pro Ser Ile Pro Lys Pro Asp Val Ile Phe Gly Pro Ala Tyr
 65                  70                  75                  80 aaa ggc atc ccc ctc gcg tgc gcc acc ctc ctt gaa ctc aac cgc atc      288
Lys Gly Ile Pro Leu Ala Cys Ala Thr Leu Leu Glu Leu Asn Arg Ile
                 85                  90                  95 gac ccc gcc acc tgg ggc agc gtg tcc tac agc tac aac cgc aaa gaa      336
Asp Pro Ala Thr Trp Gly Ser Val Ser Tyr Ser Tyr Asn Arg Lys Glu
            100                 105                 110 gcc aag gat cac ggc gaa ggc ggc aac att gtc ggc gcc gct ctg aag      384
Ala Lys Asp His Gly Glu Gly Gly Asn Ile Val Gly Ala Ala Leu Lys
        115                 120                 125 ggc aag acc gtg ctt gtg atc gac gat gtc atc acg gcc ggt acc gcc      432
Gly Lys Thr Val Leu Val Ile Asp Asp Val Ile Thr Ala Gly Thr Ala
130                 135                 140 atg cgt gag acc ctc aac ctg gtc gcc aag gag ggc ggc aag gtc gtc      480
Met Arg Glu Thr Leu Asn Leu Val Ala Lys Glu Gly Gly Lys Val Val
145                 150                 155                 160 gga ttc act gtt gct ctg gac cgc ttg gag aag atg ccc gga ccc aag      528
Gly Phe Thr Val Ala Leu Asp Arg Leu Glu Lys Met Pro Gly Pro Lys
                165                 170                 175 gac gag aac ggt gtc gag gac gat aag ccc aga atg agt gct atg ggt      576
Asp Glu Asn Gly Val Glu Asp Asp Lys Pro Arg Met Ser Ala Met Gly
            180                 185                 190 cag atc cgt aag gag tat ggt gtg ccc acg acg agt att gtt act ctg      624
Gln Ile Arg Lys Glu Tyr Gly Val Pro Thr Thr Ser Ile Val Thr Leu
        195                 200                 205 gat gat ttg atc aag ttg atg cag gcg aag ggc aat gag gcc gat atg      672
Asp Asp Leu Ile Lys Leu Met Gln Ala Lys Gly Asn Glu Ala Asp Met
210                 215                 220 aag cgg ttg gag gag tat agg gct aag tat cag gct agt gat              714
Lys Arg Leu Glu Glu Tyr Arg Ala Lys Tyr Gln Ala Ser Asp
225                 230                 235

<210> SEQ ID NO 14
<211> LENGTH: 238
<212> TYPE: PRT
<213> ORGANISM: Aspergillus niger

<400> SEQUENCE: 14

Met Ala Leu Pro Ala Tyr Lys Thr Ala Phe Leu Glu Ser Leu Val Gly
1               5                   10                  15

Gln Arg Ala Asp Phe Arg His Leu His Pro Glu Val Gly Ser Pro Tyr
            20                  25                  30

Ser Pro Tyr Phe Phe Asn Ala Gly Ile Phe Asn Thr Ala Ser Leu Leu
        35                  40                  45

Ser Ala Leu Ser Thr Ala Tyr Ala His Thr Ile Ile Thr Phe Leu Ala
 50                  55                  60

Glu Asn Pro Ser Ile Pro Lys Pro Asp Val Ile Phe Gly Pro Ala Tyr
 65                  70                  75                  80

Lys Gly Ile Pro Leu Ala Cys Ala Thr Leu Leu Glu Leu Asn Arg Ile
                 85                  90                  95
```

```
Asp Pro Ala Thr Trp Gly Ser Val Ser Tyr Ser Tyr Asn Arg Lys Glu
            100                 105                 110

Ala Lys Asp His Gly Glu Gly Asn Ile Val Gly Ala Ala Leu Lys
        115                 120                 125

Gly Lys Thr Val Leu Val Ile Asp Asp Val Ile Thr Ala Gly Thr Ala
130                 135                 140

Met Arg Glu Thr Leu Asn Leu Val Ala Lys Glu Gly Lys Val Val
145                 150                 155                 160

Gly Phe Thr Val Ala Leu Asp Arg Leu Glu Lys Met Pro Gly Pro Lys
                165                 170                 175

Asp Glu Asn Gly Val Glu Asp Lys Pro Arg Met Ser Ala Met Gly
            180                 185                 190

Gln Ile Arg Lys Glu Tyr Gly Val Pro Thr Thr Ser Ile Val Thr Leu
            195                 200                 205

Asp Asp Leu Ile Lys Leu Met Gln Ala Lys Gly Asn Glu Ala Asp Met
    210                 215                 220

Lys Arg Leu Glu Glu Tyr Arg Ala Lys Tyr Gln Ala Ser Asp
225                 230                 235

<210> SEQ ID NO 15
<211> LENGTH: 831
<212> TYPE: DNA
<213> ORGANISM: Aspergillus oryzae
<220> FEATURE:
<221> NAME/KEY: CDS
<222> LOCATION: (1)..(831)

<400> SEQUENCE: 15 atg tct tcc aag tcg caa ttg acc tac agc gca cgc gct agc aag cac      48
Met Ser Ser Lys Ser Gln Leu Thr Tyr Ser Ala Arg Ala Ser Lys His
1               5                   10                  15 ccc aat gcg ctc gta aag aag ctc ttc gag gtt gcc gag gcc aag aaa      96
Pro Asn Ala Leu Val Lys Lys Leu Phe Glu Val Ala Glu Ala Lys Lys
            20                  25                  30 acc aat gtc acc gtt tcc gcc gac gtg aca acc acc aaa gag ctg ctg     144
Thr Asn Val Thr Val Ser Ala Asp Val Thr Thr Thr Lys Glu Leu Leu
        35                  40                  45 gat ttg gct gac cgg ctc ggt ccg tac att gcc gtg atc aaa act cac     192
Asp Leu Ala Asp Arg Leu Gly Pro Tyr Ile Ala Val Ile Lys Thr His
    50                  55                  60 atc gat atc ctc tcc gat ttc agc gaa gaa acc atc acc ggt ctg aag     240
Ile Asp Ile Leu Ser Asp Phe Ser Glu Glu Thr Ile Thr Gly Leu Lys
65                  70                  75                  80 gcc ctt gca gag aag cac aat ttc ctc atc ttc gaa gat cgc aag ttc     288
Ala Leu Ala Glu Lys His Asn Phe Leu Ile Phe Glu Asp Arg Lys Phe
                85                  90                  95 atc gat atc gga aac aca gtc caa aag cag tac cat ggc ggc act ctg     336
Ile Asp Ile Gly Asn Thr Val Gln Lys Gln Tyr His Gly Gly Thr Leu
            100                 105                 110 cgt atc tct gag tgg gcc cac atc atc aac tgc agt att ctg ccc ggt     384
Arg Ile Ser Glu Trp Ala His Ile Ile Asn Cys Ser Ile Leu Pro Gly
        115                 120                 125 gag ggt atc gtc gag gct ctg gcc cag act gct tcg gcc gag gac ttc     432
Glu Gly Ile Val Glu Ala Leu Ala Gln Thr Ala Ser Ala Glu Asp Phe
    130                 135                 140 ccc tac ggc tcc gag agg ggc ctt ttg atc ctt gcg gag atg acc tcc     480
Pro Tyr Gly Ser Glu Arg Gly Leu Leu Ile Leu Ala Glu Met Thr Ser
145                 150                 155                 160 aag gga tct ttg gct acc ggt cag tat act act tct tct gtt gac tat     528
```

```
Lys Gly Ser Leu Ala Thr Gly Gln Tyr Thr Thr Ser Ser Val Asp Tyr
                165                 170                 175 gct cgg aag tat aag aag ttt gtg atg gga ttc gtc tcg aca cgt cac      576
Ala Arg Lys Tyr Lys Lys Phe Val Met Gly Phe Val Ser Thr Arg His
            180                 185                 190 ctt ggc gag gtt cag tct gaa gtt agc tcg cct tcg gag gag gaa gat      624
Leu Gly Glu Val Gln Ser Glu Val Ser Ser Pro Ser Glu Glu Glu Asp
        195                 200                 205 ttt gtc gtc ttc acg aca ggt gtc aac ctc tcc tcg aag ggt gac aag      672
Phe Val Val Phe Thr Thr Gly Val Asn Leu Ser Ser Lys Gly Asp Lys
    210                 215                 220 ctg gga cag cag tac caa act cct gag tcg gct gtt gga cgc ggt gcc      720
Leu Gly Gln Gln Tyr Gln Thr Pro Glu Ser Ala Val Gly Arg Gly Ala
225                 230                 235                 240 gac ttt att att gct ggc cgt gga att tat gct gct cct gat ccc gtg      768
Asp Phe Ile Ile Ala Gly Arg Gly Ile Tyr Ala Ala Pro Asp Pro Val
                245                 250                 255 gag gcg gcg aac cag tac cag aag gag gga tgg gat gca tac ctg aag      816
Glu Ala Ala Asn Gln Tyr Gln Lys Glu Gly Trp Asp Ala Tyr Leu Lys
            260                 265                 270 cgt gtt ggt gcg caa                                                  831
Arg Val Gly Ala Gln
        275

<210> SEQ ID NO 16
<211> LENGTH: 277
<212> TYPE: PRT
<213> ORGANISM: Aspergillus oryzae

<400> SEQUENCE: 16

Met Ser Ser Lys Ser Gln Leu Thr Tyr Ser Ala Arg Ala Ser Lys His
1               5                   10                  15

Pro Asn Ala Leu Val Lys Lys Leu Phe Glu Val Ala Glu Ala Lys Lys
            20                  25                  30

Thr Asn Val Thr Val Ser Ala Asp Val Thr Thr Lys Glu Leu Leu
        35                  40                  45

Asp Leu Ala Asp Arg Leu Gly Pro Tyr Ile Ala Val Ile Lys Thr His
    50                  55                  60

Ile Asp Ile Leu Ser Asp Phe Ser Glu Glu Thr Ile Thr Gly Leu Lys
65                  70                  75                  80

Ala Leu Ala Glu Lys His Asn Phe Leu Ile Phe Glu Asp Arg Lys Phe
                85                  90                  95

Ile Asp Ile Gly Asn Thr Val Gln Lys Gln Tyr His Gly Gly Thr Leu
            100                 105                 110

Arg Ile Ser Glu Trp Ala His Ile Ile Asn Cys Ser Ile Leu Pro Gly
        115                 120                 125

Glu Gly Ile Val Glu Ala Leu Ala Gln Thr Ala Ser Ala Glu Asp Phe
    130                 135                 140

Pro Tyr Gly Ser Glu Arg Gly Leu Leu Ile Leu Ala Glu Met Thr Ser
145                 150                 155                 160

Lys Gly Ser Leu Ala Thr Gly Gln Tyr Thr Thr Ser Ser Val Asp Tyr
                165                 170                 175

Ala Arg Lys Tyr Lys Lys Phe Val Met Gly Phe Val Ser Thr Arg His
            180                 185                 190

Leu Gly Glu Val Gln Ser Glu Val Ser Ser Pro Ser Glu Glu Glu Asp
        195                 200                 205

Phe Val Val Phe Thr Thr Gly Val Asn Leu Ser Ser Lys Gly Asp Lys
    210                 215                 220
```

```
Leu Gly Gln Gln Tyr Gln Thr Pro Glu Ser Ala Val Gly Arg Gly Ala
225                 230                 235                 240

Asp Phe Ile Ile Ala Gly Arg Gly Ile Tyr Ala Ala Pro Asp Pro Val
                245                 250                 255

Glu Ala Ala Asn Gln Tyr Gln Lys Glu Gly Trp Asp Ala Tyr Leu Lys
            260                 265                 270

Arg Val Gly Ala Gln
        275

<210> SEQ ID NO 17
<211> LENGTH: 580
<212> TYPE: DNA
<213> ORGANISM: human
<220> FEATURE:
<221> NAME/KEY: misc_feature
<222> LOCATION: (423)..(574)
<223> OTHER INFORMATION: n is a, c, g, or t

<400> SEQUENCE: 17 cgaaccccg cgccgccttt gcgagggtgg agttgcctta gggttagggt tagggttagg      60
gttagggtta gggttagggt tagggttagg gttagggtta gggttagggt tagggttagg    120
gttagggtta gggttagggt tagggtcagg gtcagggtag ggtcaggggt agggtcaggg    180
gtaggggtag ggtcagggtt agggttaggg ttagggttag ggttagggtt agggttaggg    240
tcagggttag ggttagggtt aggggtaggg gtaggggtag ggttagggtt agggttaggg    300
ttagggttag ggttagggtt agggtcaggg tcagggtcag gggtagggta gggtagggtt    360
aggggttagg gttagggtta gggttagggt tagggttagg gttaagggtt aagggttaag    420
ggnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnntgggaa                          580
```

EXPRESSION AND HIGH-THROUGHPUT SCREENING OF COMPLEX EXPRESSED DNA LIBRARIES IN FILAMENTOUS FUNGI

CROSS REFERENCE TO RELATED APPLICATION

This application is a national stage application under 35 U.S.C. 371 of PCT Application No. PCT/US2007/087020, having an international filing date of Dec. 10, 2007, which designated the United States, which PCT application claimed the benefit of U.S. Application Ser. No. 60/869,341, filed Dec. 10, 2006, the entire disclosure of each of which is hereby incorporated by reference.

REFERENCE TO SEQUENCE LISTING

This application contains a Sequence Listing submitted as an electronic text file named "5671-2_ST25.txt", having a size in bytes of 95 KB, and created on Dec. 10, 2007. The information contained in this electronic file is hereby incorporated by reference in its entirety pursuant to 37 CFR §1.52 (e)(5).

FIELD OF THE INVENTION

The invention provides a method for the expression and subsequent screening of DNA libraries, particularly synthetic, genomic, and cDNA libraries, in filamentous fungal hosts. In particular, the invention provides vectors, host strains, and a method for the expression and screening of complex DNA libraries, including, but not limited to, combinatory (combinatorial) libraries expressing one, two or more variable constituents and/or prepared from two or more sub-libraries (e.g., for the expression and screening of immunoglobulin (including fragments and derivatives of whole immunoglobulin proteins) and other receptor or complex DNA libraries or libraries of libraries). The invention is useful for the expression and screening for a large variety of proteins and protein complexes, including human proteins. The system employs transformed or transfected filamentous fungal strains that generate transferable reproductive elements, for example by efficient sporulation, in submerged culture. The fungi preferably exhibit a morphology that minimizes or eliminates the formation of entangled mycelia. Particularly preferred fungal strains are also capable of expressing isolatable quantities of exogenous proteins, including, but not limited to, large proteins having two or more heterogeneous domains, subunits, or constituents as well as protein complexes, for evaluation. The mutant fungal strains of the invention are particularly well-suited for high-throughput screening techniques, due to their production of transferable reproductive elements, high levels of expression, low protease activity, and very low culture viscosity and improved recombination characteristics for both integrative and replicating vector molecules. In addition, the mutant fungal strains and the methods of the invention are well suited for the efficient selection of proteins expressed by large libraries or libraries of libraries. They are also suitable for the large-scale, economical production of such proteins, providing a platform in which expression, screening and production of the proteins all take place in a single host species.

BACKGROUND OF THE INVENTION

There is a need in the art for improved systems for the expression and screening of a variety of peptides and proteins, including proteins and protein complexes that are heterologous to the host in which they are expressed, and particularly including proteins with two or more heterogeneous or heteromeric domains, subunits and/or constituents. There is a need in the art for improved systems for the expression and screening of mammalian proteins and even more particularly, human proteins, in order to elucidate protein-protein interactions or interactions of proteins with other molecules, for directed molecular evolution strategies, and/or for the production and selection of recombinant complex proteins and/or engineered proteins for research, diagnostic and/or therapeutic applications. To name just a few non-limiting examples, there is a continued need in the art for improved systems for the expression and screening of complex proteins including, but not limited to, immunoglobulins (antibodies, including fragments and/or domains and/or derivatives thereof), other receptors, enzymes, hormones, lymphokines and DNA binding proteins. For example, the ability to engineer and rapidly identify useful therapeutic and/or diagnostic antibodies (or fragments and/or domains and/or derivatives thereof) or to provide an affinity-based screen for the selection of a variety of receptors and/or ligands is highly desirable. Proteins having two or more heterogeneous or variable domains, subunits, or constituents are particularly challenging to engineer and efficiently screen. Having a rapid method to identify proteins, including complex proteins, that are useful as therapeutic, diagnostic and/or research tools for use in mammalian, and particularly, human, applications, is therefore invaluable.

Moreover, in order to effectively screen for certain proteins, especially those with highly variable domains (e.g., immunoglobulins, T cell receptors, MHC-peptide complexes), the expression and screening of very large libraries, including libraries of libraries, may be desirable, if not necessary, in order to be able to select the best candidates for further development or to cover all of the possible permutations of protein structures encompassed by the variability in the proteins. With large libraries, it can be especially difficult and/or prohibitively time-consuming and/or costly to produce sufficient quantities of proteins to effectively screen and select candidates from the large pool of candidates, and then perform additional evaluation as needed to identify the best candidates, and/or perform further screening and selection to ensure that all of the best candidates are identified from the original pool. Accordingly, being able to efficiently and effectively express and select a desired protein from a large pool of proteins (and further evolve such proteins to a preferred candidate, if desired) in a system that is economical (cost-effective) and provides results in a relatively short time frame, and then readily produce such proteins on an economical, large-scale production basis, is highly desirable. If most or all of these goals could all be achieved in a single host organism or cell, the advantages would be great. Accordingly, there remains a pressing need for new approaches to the characterization of proteins and polypeptides (the term "protein" as used hereinafter should be understood to encompass peptides and polypeptides as well.), and to the design, identification, and/or modification, and isolation of the genes encoding these proteins, so as to enable the modification and/or production of the proteins.

One approach to the problem of expressing proteins or polypeptides is through the expression of a genomic DNA library in a bacterium such as *E. coli*, where the expressed proteins are screened for a property or activity of interest. This approach suffers from several serious disadvantages, one of which is that bacteria typically do not effectively express genes having introns. Eukaryotic genomes of higher organisms are generally too complex for comprehensive expression of DNA libraries in bacteria. When all eukaryotic species are considered, bacteria represent only about 0.3% of all known species (E. O. Wilson, "The Current State of Biological Diversity", in *Biodiversity*, National Academy Press, Washington D.C., 1988, Chapter 1); thus the fraction of the world's genetic diversity accessible to bacterial expression systems is extremely limited.

To avoid problems with introns, it is possible to prepare a cDNA library and express it in bacteria. However, this approach relies upon the presence of RNA transcripts, and any genes not actively being transcribed will not be represented in the library. Many desirable proteins are expressed only under specific conditions (e.g., virulence factors in pathogenic fungi) and these conditions may not exist at the time the mRNA is harvested. In order to obtain sufficient RNA to prepare a cDNA library, it is necessary to culture suitable quantities of the organism or host cell of interest. In contrast, sufficient genomic DNA can be obtained from a very small number of individual cells by PCR amplification, using either random primers or primers designed to favor certain classes of genes. Finally, genes that are highly expressed in an organism or host cell will tend to be over-represented in the mRNA, and thus over-represented at the expense of minimally-expressed genes, which are often some of the more interesting genes, in a cDNA library. In order to have a high level of coverage of the mRNA species present, a much larger number of clones must be screened if a cDNA library is employed instead of a genomic library, since the latter will have a more nearly equal representation of the variety of genes present. Clearly it is more desirable to screen a genomic DNA library if at all possible.

Also, most bacteria, including *E. coli*, are incapable of secretion of many proteins, and thus are undesirable as a host cell for screening purposes where the screening relies upon secretion of the gene product. An additional disadvantage for *E. coli*, and for bacterial hosts in general, is that prokaryotes cannot provide many of the post-translational modifications required for the activity of numerous eukaryotic proteins. Moreover, expression of complex multi-domain or multi-subunit proteins (e.g., immunoglobulin) is not readily feasible in *E. coli*. In addition to glycosylation, subunit cleavage, disulfide bond formation, and proper folding of proteins are examples of the post-translational processing often required to produce an active protein.

To ensure such processing one can sometimes use mammalian cells, but mammalian cells are difficult to maintain, require expensive media, and are not generally transformed with high efficiency, and development of stable production cell lines requires long timeframes. Such transformation systems are therefore not convenient for high-throughput screening of proteins, although efforts have been made to employ mammalian cells as hosts for cDNA library screening (Schouten et al., WO 99/64582). An approach involving fusion of transformed protoplasts with mammalian cells prior to library screening has been described (U.S. Pat. No. 5,989, 814), but expression of the protein library occurs in bacteria or yeast prior to cell fusion. There have been efforts to modify glycosylation patterns enzymatically after expression in host cells (Meynial-Salles and Combes, *J. Biotechnol.*, 46:1-14 (1996)), but such methods must be tailored for specific products and are not suitable for expression of proteins from a DNA library. More recently, Maras et al., *Eur. J. Biochem.*, 249:701-707 (1997) (see also U.S. Pat. No. 5,834,251) have described a strain of *Trichoderma reesei* engineered to express human GlcNAc transferase I. The enzyme transfers N-acetylglucosamine to mannose residues on other expressed exogenous proteins, a first step toward more closely approximating natural mammalian products.

The use of yeast as host cells solves some of the above problems, but introduces others. Yeast tend to hyper-glycosylate exogenous proteins (Bretthauer and Castellino, 1999, *Biotechnol. Appl. Biochem.* 30:193-200), and the altered glycosylation patterns often render expressed mammalian proteins highly antigenic (C. Ballou, in *Molecular Biology of the Yeast Sacccharomyces*, J. Strathern et al., eds., Cold Spring Harbor Laboratory Press, NY, 1982, 335-360). Although yeast are capable of coping with a limited number of introns, they are not generally capable of handling complex genes from higher species such as vertebrates. Even genes from filamentous fungi are usually too complex for yeast to transcribe efficiently, and this problem is compounded by differences in expression and splicing sequences between yeast and filamentous fungi (see e.g., M. Innis et al., *Science* 1985 228:21-26). Despite these drawbacks, transformation and expression systems for yeast have been extensively developed, generally for use with cDNA libraries. Yeast expression systems have been developed which are used to screen for naturally secreted and membrane proteins of mammalian origin (Klein, et al., *Proc. Natl. Acad. Sci. USA* 1996 93:7108-7113; Treco, U.S. Pat. No. 5,783,385), and for heterologous fungal proteins (Dalboge and Heldt-Hansen, *Mol. Gen. Genet.* 243:253-260 (1994)) and mammalian proteins (Tekamp-Olson and Meryweather, U.S. Pat. No. 6,017,731).

Proper intron splicing, and glycosylation, folding, and other post-translational modifications of fungal gene products would be most efficiently handled by a fungal host species, making filamentous fungi superior hosts for screening genomic DNA from soil and other samples. It also makes them excellent hosts for the production of fungal enzymes of commercial interest, such as proteases, cellulases, and amylases. It has also been found that filamentous fungi are capable of transcribing, translating, processing, and secreting the products of other eukaryotic genes, including mammalian genes. The latter property makes filamentous fungi attractive hosts for the production of proteins of biomedical interest (e.g., antibodies, other receptors, hormones, etc.). Glycosylation patterns introduced by filamentous fungi more closely resemble those of mammalian proteins than do the patterns introduced by yeast. For these reasons, a great deal of effort has been expended on the development of fungal host systems for expression of heterologous proteins, and a number of fungal expression systems have been developed. For reviews of work in this area, see Maras et al., *Glycoconjugate J.*, 16:99-107 (1999); Peberdy, *Acta Microbiol. Immunol. Hung.* 46:165-174 (1999); Kruszewsa, *Acta Biochim. Pol.* 46:181-195 (1999); Archer et al., *Crit. Rev. Biotechnol.* 17:273-306 (1997); and Jeenes et al., *Biotech. Genet. Eng. Rev.* 9:327-367 (1991).

High-throughput expression and assaying of DNA libraries derived from fungal genomes would also be of use in assigning functions to the many mammalian genes that are currently of unknown function. For example, once a fungal protein having a property of activity of interest is identified, the sequence of the encoding gene may be compared to the human genome sequence to look for homologous genes.

Yelton et al., U.S. Pat. No. 4,816,405, discloses the modification of filamentous Ascomycetes to produce and secrete heterologous proteins. Buxton et al., in U.S. Pat. No. 4,885, 249, and in Buxton and Radford, *Mol. Gen. Genet.* 196:339-344 (1984), discloses the transformation of *Aspergillus niger* by a DNA vector that contains a selectable marker capable of being incorporated into the host cells. McKnight et al., U.S. Pat. No. 4,935,349, and Boel, in U.S. Pat. No. 5,536,661, disclose methods for expressing eukaryotic genes in *Aspergillus* involving promoters capable of directing the expression of heterologous genes in *Aspergillus* and other filamentous fungi. Royer et al., in U.S. Pat. No. 5,837,847, and Berka et al., in WO 00/56900, disclose expression systems for use in *Fusarium venenatum* employing natural and mutant *Fusarium* spp. promoters. Conneely et al., in U.S. Pat. No. 5,955,316, disclose plasmid constructs suitable for the expression and production of lactoferrin in *Aspergillus*. *Cladosporium* glucose oxidase had been expressed in *Aspergillus* (U.S. Pat. No. 5,879,921).

Similar techniques have been used in *Neurospora*. Lambowitz, in U.S. Pat. No. 4,486,533, discloses an autonomously replicating DNA vector for filamentous fungi and its use for the introduction and expression of heterologous genes in *Neurospora*. Stuart et al. describe co-transformation of *Neurospora crassa* spheroplasts with mammalian genes and endogenous transcriptional regulatory elements in U.S. Pat. No. 5,695,965, and an improved strain of *Neurospora* having reduced levels of extracellular protease in U.S. Pat. No. 5,776,730. Vectors for transformation of *Neurospora* are disclosed in U.S. Pat. No. 5,834,191. Takagi et al. describe a transformation system for *Rhizopus* in U.S. Pat. No. 5,436,158. Sisniega-Barroso et al. describe a transformation system for filamentous fungi in WO 99/51756, which employs promoters of the glutamate dehydrogenase genes from *Aspergillus awamori*. Dantas-Barbosa et al., *FEMS Microbiol. Lett.* 1998 169:185-190, describe transformation of *Humicola grisea* var. *thermoidea* to hygromycin B resistance, using either the lithium acetate method or electroporation.

Fungal expression systems in *Aspergillus* and *Trichoderma*, for example, are disclosed by Berka et al. in U.S. Pat. No. 5,578,463; see also Devchand and Gwynne, *J. Biotechnol.* 17:3-9 (1991) and Gouka et al., *Appl. Microbiol. Biotechnol.* 47:1-11 (1997). Examples of transformed strains of *Myceliophthora thermophila, Acremonium alabamense, Thielavia terrestris* and *Sporotrichum cellulophilum* are presented in WO 96/02563 and U.S. Pat. Nos. 5,602,004, 5,604,129 and 5,695,985, which describe certain drawbacks of the *Aspergillus* and *Trichoderma* systems. In addition, the fungal expression system described in U.S. Pat. No. 6,573,086 and PCT Publication No. WO 00/20555 describe a transformation system using filamentous fungal hosts that particularly describe an expression system using *Chyrsosporium* hosts as well as other filamentous fungi.

Methods for the transformation of phyla other than Ascomycetes are known in the art; see for example Munoz-Rivas et al., *Mol. Gen. Genet.* 1986 205:103-106 (*Schizophyllum commune*); van de Rhee et al., *Mol. Gen. Genet.* 1996 250:252-258 (*Agaricus bisporus*); Arnau et al., *Mol. Gen. Genet.* 1991 225:193-198 (*Mucor circinelloides*); Liou et al., *Biosci. Biotechnol. Biochem.* 1992 56:1503-1504 (*Rhizopus niveus*); Judelson et al., *Mol. Plant Microbe Interact.* 1991 4:602-607 (*Phytophthora infestans*); and de Groot et al., *Nature Biotechnol.* 1998 16:839-842 (*Agaricus bisporus*).

In addition to the usual methods of transformation of filamentous fungi, such as for example protoplast fusion, Chakraborty and Kapoor, *Nucleic Acids Res.* 18:6737 (1990) describe the transformation of filamentous fungi by electroporation. De Groot et al., in *Nature Biotechnol.* 16: 839-842 (1998), describe *Agrobacterium tumefaciens*-mediated transformation of several filamentous fungi. Biolistic introduction of DNA into fungi has been carried out; see for example Christiansen et al., *Curr. Genet.* 29:100-102 (1995); Durand et al., *Curr. Genet.* 31:158-161 (1997); and Barcellos et al., *Can. J. Microbiol.* 44:1137-1141 (1998). The use of magnetic particles for "magneto-biolistic" transfection of cells is described in U.S. Pat. Nos. 5,516,670 and 5,753,477, and is expected to be applicable to filamentous fungi.

Most prior efforts in the field of filamentous fungal expression systems have been directed to the identification of strains suitable for industrial production of enzymes, and therefore attention has been focused on culture viscosity, stability of transformation, yield of heterologous protein per unit volume, and yield as a percentage of biomass. DNA libraries have been expressed in fungi; see for example Gems and Clutterbuck, *Curr. Genet.* 1993 24:520-524, where an *Aspergillus nidulans* library was expressed in *A. nidulans* and Gems et al., *Mol. Gen. Genet.* 1994 242:467-471 where a genomic library from *Penicillium* was expressed in *Aspergillus*. The cloning of an *Aspergillus niger* invertase gene by expression in *Trichoderma reesei* was described by Berges et al., *Curr. Genet.* 1993 24:53-59.

U.S. patent application Ser. No. 09/548,938, now U.S. Pat. No. 6,573,086; U.S. patent application Ser. No. 09/834,434, now U.S. Pat. No. 7,122,330; PCT Publication No. WO/0125468; PCT Publication No. WO/0179558; and PCT Publication No. NL/99/00618, described a system for expression of heterologous proteins in fungal host cells, and methods for expressing the gene products of a DNA library, including genomic and/or eukaryotic genomic DNA libraries. These applications also disclose mutant fungal strains that have partially lost their filamentous phenotype and thus provide low-viscosity cultures.

The present invention fulfils a continued need in the art for improved fungal host cell strains, vectors, and methods for the expression and screening of complex DNA libraries, including combinatorial libraries expressing proteins having one, two or more domains, subunits, or constituents, such as immunoglobulins and other receptors or protein complexes.

SUMMARY OF THE INVENTION

The present invention provides expression vectors comprising telomeric sequences and selection markers pyrE and pyrG.

The present invention also provides expression vectors comprising at least one sequence that promotes autonomous replication and enhances transformation in a fungal host, and two selection markers that flank an expression cassette in the vector, wherein the entire expression cassette integrates into the genome of a fungal host transformed with the vector.

In some embodiments, one of the selection markers is pyrE or pyrG. In others, the two selection markers are pyrE and pyrG.

In some embodiments, the selection markers pyrE and pyrG flank the expression cassette in the vector, and the entire expression cassette integrates into the genome of a fungal host transformed with the vector.

In some embodiments, the sequence that promotes autonomous replication and enhances transformation in a fungal host comprises telomeric sequences. In some embodiments, the telomeric sequences are human telomeric sequences, fungal telomeric sequences, or homologues thereof.

In some embodiments, the expression vector further comprises a fungal signal sequence. In some embodiments, the fungal signal sequence is the signal sequence of a fungal gene encoding a protein selected from the group consisting of cellulase, β-galactosidase, xylanase, pectinase, esterase, protease, amylase, chitinase, chitosanase, polygalacturonase and hydrophobin.

In some embodiments, the expression vector further comprises a terminator sequence. In some embodiments, the terminator sequence is TtrpC or Tcbh1. In some embodiments, the terminator sequence comprises SEQ ID NO:11.

In some embodiments, the vector comprises one or more copies of the C1 Repetitive Sequence (CRS). In some embodiments, the vector comprises from one to ten copies of the CRS. In some embodiments, the CRS is located in an upstream region of a promoter within the vector. In some embodiments, the CRS comprises the nucleic acid sequence of SEQ ID NO:12.

In some embodiments, the expression vector further comprises a promoter sequence. In some embodiments, the promoter sequence is Pcbh1 or PgpdA.

In some embodiments, the expression vector further comprises at least one autonomously replicating sequence.

In some embodiments, the expression vector further comprises at least one nucleic acid sequence for replication in a non-fungal host cell.

In some embodiments, the vector is a self-replicating vector.

In some embodiments, the vector is an integrating vector.

In some embodiments, the vector is an autonomous vector when initially transformed into the filamentous fungus, and integrates into the fungus upon extended culture.

In some embodiments, the vector comprises the following elements: Pcbh1, Tcbh1, pyeE, tel, and PyrG.

In some embodiments, the vector comprises a nucleic acid sequence encoding a protein between the elements Pcbh1 and Tcbh1.

In some embodiments, the protein is a fusion protein.

In some embodiments, the protein is an immunoglobulin light chain or a fragment thereof, or an immunoglobulin heavy chain or a fragment thereof.

In some embodiments, the protein comprises both an immunoglobulin light chain or a fragment thereof, and an immunoglobulin heavy chain or a fragment thereof.

In some embodiments, the vector is pPcbh1 glaA(II) heavy (88) Tcbh1 Pcbh1 glaA(II) light(90) Tcbh1 pyeE tel PyrG. In some embodiments, the vector comprises the nucleic acid sequence of SEQ ID NO:10

In some embodiments, the selection markers flank at least one nucleic acid sequence encoding a protein.

In some embodiments, the selection markers flank nucleic acid sequences encoding components of a heterogeneous or heteromultimeric protein.

In some embodiments, the expression vector further comprises an expression-regulating region operably linked to the nucleic acid sequence encoding the protein or components of the heterogeneous or heteromultimeric protein. In some embodiments, the expression regulating region comprises an inducible promoter.

In some embodiments, the nucleic acid sequence encoding each component of the heterogeneous or heteromultimeric protein is operably linked to a different promoter sequence.

In some embodiments, the nucleic acid sequence encoding each component of the heterogeneous or heteromultimeric protein is operably linked to a different terminator sequence.

In some embodiments, the vector comprises nucleic acid sequences for transfer of the nucleic acid sequences encoding the components of the heterogeneous or heteromultimeric protein to or from a non-fungal host cell.

In some embodiments, the non-fungal cell is selected from the group consisting of a bacterium, a yeast, and a mammalian cell.

In some embodiments, the vector comprises nucleic acid sequences for transfer of the nucleic acid sequences encoding the components of the heterogeneous or heteromultimeric protein to or from a bacteriophage. In some embodiments, the nucleic acid sequences for transfer comprise nucleic acid sequences for in vitro homologous recombination.

In some embodiments, the nucleic acid sequences encoding the components of the heterogeneous or heteromultimeric protein are linked to each other.

In some embodiments, the nucleic acid sequences encoding the components of the heterogeneous or heteromultimeric protein are separately linked to different expression-regulating regions.

In some embodiments, the vector comprises at least one nucleic acid sequence encoding a fusion partner, wherein the nucleic acid sequence encoding the fusion partner is operatively linked to a nucleic acid sequence encoding a component of the heterogeneous or heteromultimeric protein.

In some embodiments, the fusion partner is linked to the component with a protein-processing site. In some embodiments, the protein-processing site is a kex2 cleavage site.

In some embodiments, each of the components of the heterogeneous or heteromultimeric protein is linked to a different fusion partner.

In some embodiments, each of the components of the heterogeneous or heteromultimeric fusion protein are linked to each other and to a fusion partner.

In some embodiments, the fusion partner and each of the components is linked by a protease processing site.

In some embodiments, the fusion partner enables secretion of the heterogeneous or heteromultimeric protein from the filamentous fungus.

In some embodiments, each of the nucleic acid sequences encoding a component of the multimeric protein is flanked by restriction enzyme sites.

In some embodiments, the nucleic acid sequence comprising all of the nucleic acid sequences encoding a component of the heterogeneous or heteromultimeric protein is flanked by restriction enzyme sites.

In some embodiments, any one or more of the nucleic acid sequences encoding a component of the heterogeneous or heteromultimeric protein is mutated to reduce the presence of protease processing sites recognized by the fungal proteases, or wherein any one or more of the nucleic acid sequences encoding a component of the heterogeneous or heteromultimeric protein is selected to have reduced presence of protease processing sites recognized by the fungal proteases.

In some embodiments, the nucleic acid sequences encoding the components of the heterogeneous or heteromultimeric protein are optimized to allow efficient transcription, translation, and protein folding in the fungal host.

The present invention also provides an isolated fungus that has been mutated or selected to have low protease activity, wherein the fungus has less than 50% of the protease activity as compared to a non-mutated fungus.

In some embodiments, the fungus has less than 10% of the protease activity of the non-mutated fungus. In some embodiments, the fungus has less than 1% of the protease activity of the non-mutated fungus.

In some embodiments, the fungus is of a genus selected from the group consisting of *Aspergillus, Fusarium, Chrysosporium, Myceliophthora*, and *Trichoderma*.

In some embodiments, the fungus is a strain of *C. lucknowense*. In some embodiments, the fungus is a strain of *C. lucknowense* C1 (VKM F-3500-D).

In some embodiments, the fungus is UV18#100.f having accession number CBS 122188, or a derivative or mutant thereof.

In some embodiments, at least one protease gene selected from alp1, alp2 or pep4 has been disrupted. In some embodiments, each of the protease genes alp1, alp2 or pep4 has been disrupted. In some embodiments, the protease gene comprises a nucleic acid sequence described in this application.

In some embodiments, the fungus is selected from the group consisting of UV18#100f Δalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2.

In some embodiments, the fungus has a phenotype characterized by a culture viscosity, when cultured in suspension, of less than 200 cP at the end of fermentation when grown with adequate nutrients under optimal or near-optimal conditions.

In some embodiments, the fungus has a phenotype characterized by a culture viscosity, when cultured in suspension, of less than 100 cP at the end of fermentation when grown with adequate nutrients under optimal or near-optimal conditions.

In some embodiments, the fungus has a phenotype characterized by culture viscosity, when cultured in suspension, of less than 60 cP at the end of fermentation when grown with adequate nutrients under optimal or near-optimal conditions.

In some embodiments, the fungus has a phenotype characterized by a culture viscosity, when cultured in suspension, of less than 10 cP at the end of fermentation when grown with adequate nutrients under optimal or near-optimal conditions.

In some embodiments, the fungus has or has been mutated to have improved homologous recombination of integrated nucleic acid sequences.

In some embodiments, the fungus has or has been mutated to have reduced non-homologous recombination of integrated nucleic acid sequences.

In some embodiments, the fungus is of the class Euascomycetes.

In some embodiments, the fungus is of the order Onygenales.

In some embodiments, the fungus is of the order Eurotiales.

In some embodiments, the fungus is of the division Ascomycota, with the proviso that it is not of the order Saccharomycetales.

In some embodiments, the fungus is of a genus selected from the group consisting of: *Aspergillus, Trichoderma, Chrysosporium, Myceliophthora, Neurospora, Rhizomucor, Hansenula, Humicola, Mucor, Tolypocladium, Fusarium, Penicillium, Talaromyces, Emericella, Hypocrea, Thielavia, Aureobasidium, Filibasidium, Piromyces, Cryplococcus, Acremonium, Tolypocladium, Scytalidium, Schizophyllum, Sporotrichum, Gibberella, Mucor, Fusarium*, and anamorphs and teleomorphs thereof.

In some embodiments, the fungus is of a genus selected from the group consisting of *Aspergillus, Fusarium, Chrysosporium, Myceliophthora*, and *Trichoderma*.

In some embodiments, the fungus is selected from the group consisting of: *Chrysporium* ATCC 44006 or a derivative or mutant thereof, *Chrysporium* CBS 251.72 or a derivative or mutant thereof, *Chrysporium* CBS143.77 or a derivative or mutant thereof, *Chrysporium* CBS 272.77 or a derivative or mutant thereof, *Chrysporium* VKM F-3500D (C1) or a derivative or mutant thereof, *Chrysporium* UV13-6 (Accession No. VKM F-3632 D) or a derivative or mutant thereof, and *Chrysporium* NG7 C-19 (Accession No. VKM F-3633 D) or a derivative or mutant thereof.

In some embodiments, the fungus is *Chrysosporium* strain UV18-25 having accession number VKM F-3631 D, or a derivative or mutant thereof.

In some embodiments, the fungus is *Trichoderma longibrachiatum* strain X-252, or a derivative or mutant thereof.

In some embodiments, the fungus is *Aspergillus sojae* strain pclA, or a derivative or mutant thereof.

In some embodiments, the fungus is *Aspergillus niger* strain pclA, or a derivative or mutant thereof.

The present invention also provides a method of expressing a plurality of proteins encoded by a combinatorial library of DNA vectors, wherein the combinatorial library of vectors comprises a plurality of different vectors of present invention, each different vector comprising a different protein-encoding nucleic acid sequence, said nucleic acid sequences being operably linked to an expression-regulating region and optionally a secretion signal encoding sequence or a fusion partner, the method comprising the steps of:

stably transforming a filamentous fungus with said library of DNA vectors in order to introduce into each of a plurality of said filamentous fungus at least one of said DNA vectors, wherein said filamentous fungus has a phenotype characterized by growth in suspension and characterized by the production of transferable reproductive elements in suspension;

culturing the transformed filamentous fungus under conditions conducive to formation of transferable reproductive elements in suspension;

separating from one another a plurality of transferable reproductive elements; and culturing into monoclonal cultures or monoclonal colonies the individual transferable reproductive elements, under conditions conducive to expression of the encoded proteins.

The present invention also provides a method of screening a plurality of proteins encoded by a combinatorial library of DNA vectors for an activity or property of interest, comprising the steps of:

expressing the plurality of proteins in monoclonal filamentous fungal cultures or monoclonal filamentous fungal colonies, by a method of the present invention; and screening individual clonal cultures or clonal colonies for the activity or property of interest.

The present invention also provides a method of producing a DNA molecule encoding a protein having an activity or property of interest, comprising the steps of:

expressing a plurality of proteins in monoclonal filamentous fungal cultures or monoclonal filamentous fungal colonies, by a method of the present invention;

screening individual clonal cultures or clonal colonies for the activity or property of interest; and isolating DNA from a clonal culture or clonal colony exhibiting the activity or property of interest.

The present invention also provides a method of producing the nucleotide sequence of a DNA molecule encoding a protein having an activity or property of interest, comprising the steps of:

isolating DNA from a clonal culture or clonal colony exhibiting the activity or property of interest, by a method of the present invention; and sequencing said DNA.

The present invention also provides a method of producing the amino acid sequence of a protein having an activity or property of interest, comprising the steps of:

producing the DNA sequence of the protein having an activity or property of interest, by a method of the present invention; and translating said DNA sequence into an amino acid sequence.

The present invention also provides a method of optimizing a protein's activity or property of interest, comprising the steps of:

stably transforming a filamentous fungus with a combinatorial library of DNA vectors of the present invention comprising mutant forms of the protein, in order to introduce into each of a plurality of said filamentous fungus at least one of said DNA vectors; wherein said filamentous fungus has a phenotype characterized by growth in suspension and by the production of transferable reproductive elements in suspension;

culturing the transformed filamentous fungi under conditions conducive to the formation of transferable reproductive elements;

separating from one another a plurality of transferable reproductive elements;

culturing into clonal cultures or clonal colonies the individual transferable reproductive elements, under conditions conducive to expression of the proteins encoded by the nucleic acid sequences;

screening each individual organism, clonal culture, or clonal colony for an expressed protein having the activity or property of interest;

isolating one or more individual organisms, clonal cultures, or clonal colonies that express said protein exhibiting the activity or property of interest;

isolating nucleic acid sequences from the isolated individual organisms, clonal cultures, or clonal colonies that encode the protein exhibiting the activity or property of interest;

mutating nucleic acid sequences from the isolated individual organisms, clonal cultures, or clonal colonies that encode the protein exhibiting the activity or property of interest;

providing a library of vectors which comprise the mutated nucleic acid sequences obtained in step (h); and repeating steps (b) through (h), until the property or activity of interest either reaches a desirable level or no longer improves.

In some embodiments, the method further comprises, between steps (f) and (g), the steps of: culturing one or more of the individual organisms, clonal cultures, or clonal colonies isolated in step (f); isolating the expressed protein exhibiting the activity or property of interest; and evaluating the isolated protein for the property of interest.

In some embodiments, the filamentous fungus is a fungus according to the present invention.

The present invention also provides a method of expressing a plurality of proteins encoded by a combinatorial library of DNA vectors, wherein the combinatorial library of vectors comprises a plurality of different vectors, each different vector comprising a different protein-encoding nucleic acid sequence, said nucleic acid sequences being operably linked to an expression-regulating region and optionally a secretion signal encoding sequence or a fusion partner, the method comprising the steps of:

stably transforming a filamentous fungus of the present invention with said library of DNA vectors in order to introduce into each of a plurality of said filamentous fungus at least one of said DNA vectors, wherein said filamentous fungus has a phenotype characterized by growth in suspension and characterized by the production of transferable reproductive elements in suspension;

culturing the transformed filamentous fungus under conditions conducive to formation of transferable reproductive elements in suspension;

separating from one another a plurality of transferable reproductive elements; and culturing into monoclonal cultures or monoclonal colonies the individual transferable reproductive elements, under conditions conducive to expression of the encoded proteins.

The present invention also provides a method of screening a plurality of proteins encoded by a combinatorial library of DNA vectors for an activity or property of interest, comprising the steps of:

expressing the plurality of proteins in monoclonal filamentous fungal cultures or monoclonal filamentous fungal colonies, by a method of the present invention; and screening individual clonal cultures or clonal colonies for the activity or property of interest.

The present invention also provides a method of producing a DNA molecule encoding a protein having an activity or property of interest, comprising the steps of:

expressing a plurality of proteins in monoclonal filamentous fungal cultures or monoclonal filamentous fungal colonies, by a method of the present invention;

screening individual clonal cultures or clonal colonies for the activity or property of interest; and isolating DNA from a clonal culture or clonal colony exhibiting the activity or property of interest.

The present invention also provides a method of producing the nucleotide sequence of a DNA molecule encoding a protein having an activity or property of interest, comprising the steps of:

isolating DNA from a clonal culture or clonal colony exhibiting the activity or property of interest, by a method of the present invention; and sequencing said DNA.

The present invention also provides a method of producing the amino acid sequence of a protein having an activity or property of interest, comprising the steps of:

producing the DNA sequence of the protein having an activity or property of interest, by a method of the present invention; and translating said DNA sequence into an amino acid sequence.

The present invention also provides a method of optimizing a protein's activity or property of interest, comprising the steps of:

stably transforming a filamentous fungus of the present invention with a combinatorial library of DNA vectors comprising mutant forms of the protein, in order to introduce into each of a plurality of said filamentous fungus at least one of said DNA vectors; wherein said filamentous fungus has a phenotype characterized by growth in suspension and by the production of transferable reproductive elements in suspension;

culturing the transformed filamentous fungi under conditions conducive to the formation of transferable reproductive elements;

separating from one another a plurality of transferable reproductive elements;

culturing into clonal cultures or clonal colonies the individual transferable reproductive elements, under conditions conducive to expression of the proteins encoded by the nucleic acid sequences;

screening each individual organism, clonal culture, or clonal colony for an expressed protein having the activity or property of interest;

isolating one or more individual organisms, clonal cultures, or clonal colonies that express said protein exhibiting the activity or property of interest;

isolating nucleic acid sequences from the isolated individual organisms, clonal cultures, or clonal colonies that encode the protein exhibiting the activity or property of interest;

mutating nucleic acid sequences from the isolated individual organisms, clonal cultures, or clonal colonies that encode the protein exhibiting the activity or property of interest;

providing a library of vectors which comprise the mutated nucleic acid sequences obtained in step (h); and repeating steps (b) through (h), until the property or activity of interest either reaches a desirable level or no longer improves.

In some embodiments, the method further comprises, between steps (f) and (g), the steps of: culturing one or more of the individual organisms, clonal cultures, or clonal colonies isolated in step (f); isolating the expressed protein exhibiting the activity or property of interest; and evaluating the isolated protein for the property of interest.

In some embodiments, the vectors are expression vectors according to the present invention.

In some embodiments, the screening step is carried out by high-throughput screening.

In some embodiments, the screening step comprises an assay selected from the group consisting of: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, or protein microchip, microarray and cell-based bioassays.

In some embodiments, the protein is a heterogeneous or heteromultimeric protein.

In some embodiments, the heterogeneous or heteromultimeric protein is selected from the group consisting of: a member of the immunoglobulin supergene family, a hormone, a hormone receptor, a cytokine, a cytokine receptor, a growth factor, and a growth factor receptor.

In some embodiments, the member of the immunoglobulin supergene family is selected from the group consisting of: an immunoglobulin, a major histocompatibility complex protein, a major histocompatibility complex linked to a peptide, a T cell receptor, a CD3, and an adhesion molecule.

In some embodiments, the member of the immunoglobulin supergene family is an immunoglobulin.

In some embodiments, the immunoglobulin is selected from the group consisting of: a whole antibody, a fragment of a whole antibody, a single chain antibody, a heavy chain antibody, a bi-specific or multi-specific antibody, and a catalytic antibody.

In some embodiments, the fragment of a whole antibody is selected from the group consisting of: Fv, Fab, Fab', $F(ab')_2$, CH, and Fc.

In some embodiments, the immunoglobulin is selected from the group consisting of: a genetically-engineered antibody or fragment thereof, a humanized antibody or fragment thereof, a catalytic antibody and a neutralizing antibody.

In some embodiments, the expressed protein to biomass ratio is at least 1:1.

In some embodiments, the expressed protein to biomass ratio is at least 2:1.

In some embodiments, the expressed protein to biomass ratio is at least 6:1.

In some embodiments, the expressed protein to biomass ratio is at least 8:1.

In some embodiments, the transferable reproductive elements are individual fungal cells.

In some embodiments, the transferable reproductive elements are spores.

In some embodiments, the transferable reproductive elements are hyphal fragments.

In some embodiments, the transferable reproductive elements are micropellets.

In some embodiments, the transferable reproductive elements are protoplasts.

The present invention also provides a method for obtaining a heterogeneous or heteromultimeric protein having an activity or property of interest, comprising the steps of:

screening a plurality of heterogeneous or heteromultimeric proteins encoded by a combinatorial library of DNA vectors for an activity or property of interest, by a method of the present invention;

culturing on appropriate scale the monoclonal culture or monoclonal colony expressing the activity or property of interest, under conditions conducive to expression of the heterogeneous or heteromultimeric proteins; and isolating the expressed heterogeneous or heteromultimeric protein.

The present invention also provides a method for obtaining a heterogeneous or heteromultimeric protein having an activity or property of interest, comprising optimizing the activity or property of interest by a method of the present invention, culturing on an appropriate scale an individual organism, clonal culture, or clonal colony isolated in the final step (h), and isolating the expressed protein from the culture.

The present invention also provides a method of making a library of transformed filamentous fungi, comprising the steps of:

providing a filamentous fungus having a phenotype characterized by growth in suspension and characterized by the production of transferable reproductive elements in suspension; and stably transforming said filamentous fungus with a combinatorial library comprising a plurality of different vectors of the present invention, each different vector comprising two or more different nucleic acid sequences each encoding a component of the heterogeneous or heteromultimeric protein, said nucleic acid sequences being operably linked to an expression-regulating region and optionally a secretion signal encoding sequence or a fusion partner, in order to introduce into each of a plurality of said filamentous fungus at least one of said DNA vectors.

In some embodiments, the filamentous fungus is a fungus of the present invention.

The present invention also provides a library of transformed filamentous fungi, prepared by a method of the present invention.

In some embodiments, the transformed filamentous fungi express substantially the same level of each of the components of the heteromultimeric protein.

The present invention also provides a method for obtaining a transformed filamentous fungal host expressing a protein having an activity or property of interest, comprising the steps of:

screening a plurality of proteins encoded by a library of DNA vectors for an activity or property of interest, by a method of the present invention; and isolating the monoclonal culture or monoclonal colony expressing the activity or property of interest.

The present invention also provides a method for expression and/or screening for heterogeneous or heteromultimeric proteins, comprising any of the methods as substantially described herein.

The present invention also provides a library of transformed filamentous fungi for the expression and/or screening of heterogeneous or heteromultimeric proteins, as substantially described herein.

The present invention also provides a combinatorial library of vectors comprising a vector of the present invention.

The present invention also provides a vaccine produced from proteins expressed, produced, obtained or optimized by a method of the present invention.

The present invention also provides a method for producing a vaccine, comprising the steps of:

screening by a method of the present invention, a plurality of antigens, or a plurality of immunoglobulins or fragments thereof, for an immunogenic antigen or immunoglobulin or fragment thereof, wherein the plurality is encoded by a library of DNA vectors;

isolating the monoclonal culture or monoclonal colony expressing the immunogenic antigen or immunoglobulin or fragment thereof;

further cultivating the monoclonal culture to express the immunogenic antigen or immunoglobulin or fragment thereof;

isolating the immunogenic antigen or immunoglobulin or fragment thereof for use in a vaccine.

The present invention also provides isolated nucleic acid molecules comprising a nucleic acid sequence selected from the group consisting of:

a nucleic acid sequence encoding a protein comprising an amino acid sequence selected from the group consisting of: SEQ ID NO:2, SEQ ID NO:5, and SEQ ID NO:8;

a nucleic acid sequence encoding a fragment of the protein of (a), wherein the fragment has a biological activity of the protein of (a); and a nucleic acid sequence encoding an amino acid sequence that is at least 70% identical to an amino acid sequence of (a) and has a biological activity of the protein comprising the amino acid sequence.

In some embodiments, the nucleic acid sequence encodes an amino acid sequence that is at least 90% identical to the amino acid sequence of (a) and has a biological activity of the protein comprising the amino acid sequence.

In some embodiments, the nucleic acid sequence encodes an amino acid sequence that is at least 95% identical to the amino acid sequence of (a) and has a biological activity of the protein comprising the amino acid sequence.

In some embodiments, the nucleic acid sequence encodes an amino acid sequence that is at least 97% identical to the amino acid sequence of (a) and has a biological activity of the protein comprising the amino acid sequence.

In some embodiments, the nucleic acid sequence encodes an amino acid sequence that is at least 99% identical to the amino acid sequence of (a) and has a biological activity of the protein comprising the amino acid sequence.

In some embodiments, the nucleic acid sequence encodes a protein comprising an amino acid sequence selected from the group consisting of: SEQ ID NO:2, SEQ ID NO:5, and SEQ ID NO:8.

In some embodiments, the nucleic acid sequence consists of a nucleic acid sequence selected from the group consisting of: SEQ ID NO:1, SEQ ID NO:3, SEQ ID NO:4, SEQ ID NO:6, SEQ ID NO:7, and SEQ ID NO:9.

The present invention also provides isolated nucleic acid molecules comprising a nucleic acid sequence that is fully complementary to a nucleic acid sequence of the present invention.

The present invention also provides isolated proteins comprising an amino acid sequence encoded by the nucleic acid molecule of the present invention.

The present invention also provides isolated fusion proteins comprising an isolated protein of the present invention fused to a protein comprising an amino acid sequence that is heterologous to the isolated protein.

The present invention also provides isolated antibodies or antigen binding fragments thereof that selectively bind to a protein of the present invention.

The present invention also provides a kit for degrading a polypeptide or proteinaceous material comprising at least one isolated protein of the present invention.

The present invention also provides compositions for the degradation of a polypeptide or proteinaceous material comprising at least one isolated protein of the present invention.

The present invention also provides recombinant nucleic acid molecules comprising an isolated nucleic acid molecule of the present invention operatively linked to at least one expression control sequence.

In some embodiments, the recombinant nucleic acid molecule comprises an expression vector.

In some embodiments, the recombinant nucleic acid molecule comprises a targeting vector.

The present invention also provides an isolated host cell transfected with a nucleic acid molecule of the present invention.

In some embodiments, the host cell is a fungus.

In some embodiments, the filamentous fungus is from a genus selected from the group consisting of: *Chrysosporium, Thielavia, Neurospora, Aureobasidium, Filibasidium, Piromyces, Corynascus, Cryplococcus, Acremonium, Tolypocladium, Scytalidium, Schizophyllum, Sporotrichum, Penicillium, Gibberella, Myceliophthora, Mucor, Aspergillus, Fusarium, Humicola,* and *Trichoderma*, and anamorphs and teleomorphs thereof.

In some embodiments, the host cell is a bacterium.

The present invention also provides an oligonucleotide consisting essentially of at least 12 consecutive nucleotides of a nucleic acid sequence selected from the group consisting of: SEQ ID NO:1, SEQ ID NO:3, SEQ ID NO:4, SEQ ID NO:6, SEQ ID NO:7, and SEQ ID NO:9.

The present invention also provides a kit comprising at least one oligonucleotide of the present invention.

The present invention also provides a method for producing a protein of the present invention comprising culturing a cell that has been transfected with a nucleic acid molecule comprising a nucleic acid sequence encoding the protein, and expressing the protein with the transfected cell.

In some embodiments, the method further comprises recovering the protein from the cell or from a culture comprising the cell.

The present invention also provides a genetically modified organism wherein the organism has been genetically modified to express at least one protein of the present invention.

In some embodiments, the genetically modified organism is a microorganism.

In some embodiments, the microorganism is a filamentous fungus.

In some embodiments, the filamentous fungus is from a genus selected from the group consisting of: *Chrysosporium, Thielavia, Neurospora, Aureobasidium, Filibasidium, Piromyces, Corynascus, Cryplococcus, Acremonium, Tolypocladium, Scytalidium, Schizophyllum, Sporotrichum, Penicillium, Talaromyces, Gibberella, Myceliophthora, Mucor, Aspergillus, Fusarium, Humicola,* and *Trichoderma*.

In some embodiments, the filamentous fungus is selected from the group consisting of: *Trichoderma reesei, Chrysosporium lucknowense, Aspergillus japonicus, Penicillium canescens, Penicillium solitum, Penicillium funiculosum*, and *Talaromyces flavus*.

In some embodiments, the genetically modified organism is a plant.

The present invention also provides a recombinant enzyme isolated from a genetically modified microorganism of the present invention.

In some embodiments, the enzyme has been subjected to a purification step.

The present invention also provides a crude fermentation product produced by culturing a genetically modified microorganism of the present invention wherein the crude fermentation product contains at least one protein of the present invention.

The present invention also provides a method for degrading a polypeptide or proteinaceous material, comprising contacting the polypeptide or proteinaceous material with at least one isolated protein of the present invention.

The present invention also provides a method for decreasing the protease activity in a fungus comprising deleting or inactivating a gene that hybridizes to a nucleic acid sequence of the present invention.

BRIEF DESCRIPTION OF THE FIGURES

FIG. 23 shows a partial nucleotide sequence of the terminator region of cbh1 (Tcbh1). The C1 repetitive sequence (CRS) is indicated in gray.

DETAILED DESCRIPTION OF THE INVENTION

Figure 1:
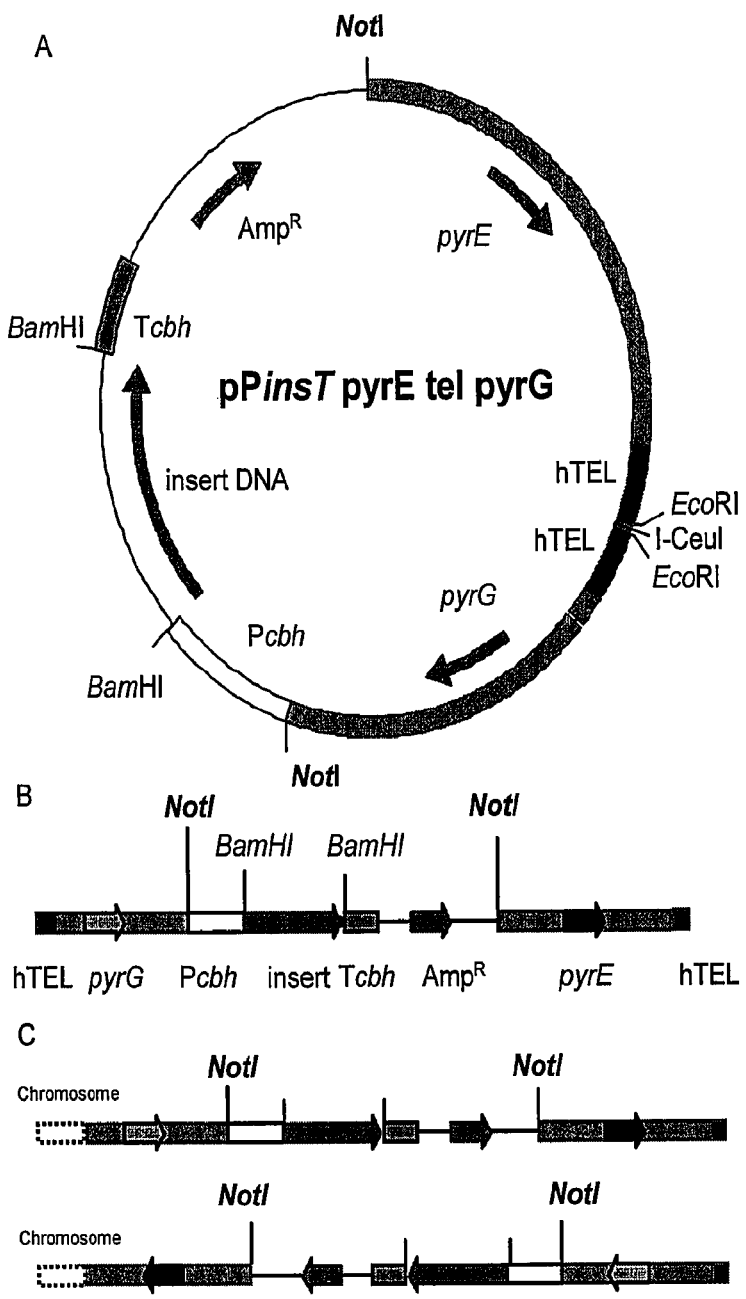
FIGS. 1A-C show: a schematic representation of circular transformation vector pPInsT PyrE tel PyrG (A), the derivative after in vivo linearization (B) and after integration at the telomeric ends of *C. lucknowense* chromosomes (C).

In its broadest aspect, the invention is directed to transformed filamentous fungi that generate transferable reproductive elements in suspension, to libraries of such fungi, and to methods of screening such libraries for biological properties of interest, such as biochemical or biological activity associated with expressed heterogeneous or heteromultimeric complex proteins comprised of two or more domains, subunits or components (multimeric proteins). Combination expression and screening methods useful in the context of expressing and evaluating such complex proteins are particularly described herein. The library of low-viscosity filamentous fungi comprises fungi containing nucleic acid sequences, each nucleic acid sequence encoding a heterologous protein or proteins, which particularly includes heterogeneous or heteromultimeric complex proteins comprised of two or more domains, subunits or components, each of said nucleic acid sequences being operably linked to an expression regulating region and optionally a secretion signal encoding sequence and/or a carrier protein encoding sequence. Preferably a transformed strain according to the invention will secrete the heterologous protein(s).

The present invention combines expression technology with screening technology in filamentous fungal hosts (including, but not limited to, high throughput screening abilities) to produce, express, and/or screen complex libraries (including libraries of libraries) to obtain sufficient quantities of protein to allow for: (i) identification of new or best candidate proteins among a pool, including a very large pool of proteins; (ii) improvement of the new or best candidates or a pool of candidates by directed evolution techniques and/or synthetic DNA modifications to engineer advantageous properties into the proteins; and (iii) manufacturing the proteins produced and selected by these methods in: (a) preclinical quantities, (b) clinical quantities, and/or (c) production quantities for sale. These elements of the invention can all be performed in the same, filamentous fungal system, or alternatively, subsequent to (i) and/or (ii), or possibly (a) and/or (b), the production of the proteins can be readily transferred to a different system (e.g., a mammalian, yeast, bacterial, plant, algae or other filamentous fungal system), for example, a system that may already be approved by the FDA or foreign equivalent and have a proven track record of safety, and production capability. Details of the expression and screening systems encompassed by this invention are described below.

By way of example of expression and screening of complex, heterogenous/heteromultimeric proteins, the present inventors have demonstrated herein that active antibodies can be expressed and screened using the methods of the invention, and in particular, the inventors have demonstrated the combination of: (i) expression technology, (ii) screening technology and (iii) production of active antibodies in a state or form that will allow for the rapid production of sufficient quantities of antibodies (and other proteins), all in a filamentous fungal host system of the invention. The inventors have demonstrated and described the ability to generate and express improved complex libraries (e.g., libraries of libraries) for selecting optimal or preferred candidates, overcoming problems associated with library size versus efficiency of screening and production, and overcoming problems associated with the ability to achieve the end result of producing usable quantitites of selected proteins in a cost-effective and commercially viable manner. The present invention allows for the efficient and rapid production of sufficient quantities of selected proteins to carry on research in a timely manner, which accordingly enables rapid discovery of the best candidates for research, commercial, and clinical applications. Prior to the present invention, because such an efficient and flexible expression and screening system was lacking, the best candidates from complex or large libraries may have been overlooked and inferior candidates brought forth instead as less effective drugs/agents. In addition, drugs with intolerable side effects have been problematic, and new indications for promising drug candidates were missed due to the inefficiencies and economical considerations associated with prior methods. The present invention provides a method that results in more efficient and effective research and development strategies for new drugs/agents, which can lower the cost of healthcare and increase the supply of the drug/agent to more people, more affordably, worldwide.

The characteristics of a fungal host cell suitable for expression of a DNA library are different in many respects from the characteristics of hosts suitable for industrial protein manufacture. In general terms, a suitable fungal host for high-throughput screening should meet numerous criteria; among them are the following:

The host should be transformed with high efficiency.

The host should process intron-containing genes and carry out any necessary splicing.

The host should post-translationally process the expressed protein so that it is produced in an active form.

Where the library is to be assayed for a protein, the host should produce the protein in high enough yield for detection by the assay.

The host should accept a variety of expression regulatory elements, for ease of use and versatility.

The host should permit the use of easily-selectable markers.

The host cell cultures should be of low viscosity.

The host should be deficient in proteases and/or be amenable to suppression of protease expression.

The host should permit screens for a wide variety of exogenous protein activities or properties.

The host should also permit screening of protein activities and/or characteristics from heterogeneous and heteromultimeric protein complexes, such as antibodies and fragments/domains thereof and other heterodimeric or heterogeneous or heteromultimeric receptors.

The host should also allow large-scale fermentation of selected proteins without further modifications or without the requirement to transfer the nucleic acid sequences encoding the proteins into a different host.

The hyphae in a culture of the host fungus should not be so entangled as to prevent the isolation of single clones, and should not be so entangled as to raise the viscosity to the point of preventing efficient transfer and replication in a miniaturized high throughput screening format (e.g. by micropipeting).

The host should not form surface mats, but should preferentially grow as a submerged culture.

The host should allow the efficient production of submerged spores or other propagules under the growth conditions provided in the high throughput screen.

In cases where metabolites are being screened for, it would be advantageous if the host cells secreted the metabolites into the medium, where they could be readily detected and/or assayed. Ideally, the host should secrete only the exogenous protein.

In cases where a protein is being assayed for, it would be particularly advantageous if the host also expressed enough heterologous protein to enable isolation and purification of the protein. A host cell with this characteristic would make it possible to further characterize all heterologous proteins of interest merely by culturing the host cells, without the time-consuming molecular biological manipulations needed to transfer the gene to another organism. Preferably, the host should be capable of secretion of the protein, as this would permit more reliable and more varied assays.

In cases where the protein to be screened is comprised of two or more heterogeneous components (e.g., immunoglobulins), it would be advantageous if the host was versatile enough to efficiently and effectively express large combinatorial libraries.

It would also be advantageous if the host cell were amenable to ready isolation of the heterologous DNA, so that further studies and modifications of the genes themselves may be carried out.

In addition to these qualities of the host, the transformation system should also exhibit certain characteristics. The transformation frequency should be sufficiently high to generate the numbers of transformants required for meaningful screens, and should be highly adaptable to accommodate single, double or multiple expression control regions. The present invention provides novel fungal host cells and vectors for use with such host cells, that meet the criteria above and substantially improve the ability to express and screen for desired products using such fungal host cells. In particular, as discussed above, the present invention provides improved systems for the production and screening of libraries comprising one, two or more variable constituents and/or prepared from two or more sublibraries (e.g., for the expression and screening of immunoglobulin (including fragments and derivatives of whole immunoglobulin proteins) and other receptor or complex DNA libraries or libraries of libraries).

The present invention employs filamentous fungi which produce "transferable reproductive elements" when grown in submerged culture. By "transferable reproductive element" is meant a spore, propagule, hyphal fragment, protoplast, micropellet, or other fungal element that is (1) readily separated from other such elements in the culture medium, and (2) capable of reproducing itself into a monoclonal culture. The fungi preferably also exhibit a less pronounced filamentous phenotype and/or a compact growth morphology, have low protease activity, and/or produce low-viscosity cultures that are suitable for the physical manipulations involved in high-throughput DNA library screening. Particularly preferred are filamentous fungi that, even in the absence of agitation, tend to grow as submerged cultures rather than as surface mats. Other preferred filamentous fungi include those that have improved homologous integration and/or reduced non-homologous integration of exogenously introduced DNA, as compared to a wild-type strain. Any combination of these features is useful in filamentous fungi of the invention, but the invention is not limited to the use of filamentous fungi with these characteristics.

The term "yeast" as used in the context of yeast expression systems generally refers to organisms of the order Saccharomycetales, such as *S. cerevisiae* and *Pichia pastoris*. For the purposes of this disclosure, the terms "fungi" and "fungal" should be understood to refer to Basidiomycetes, Zygomycetes, Oomycetes, and Chythridiomycetes, and Ascomycetes of the class Euascomycetes, which are not of the order Saccharomycetales. Filamentous fungi may be distinguished from yeast by their hyphal elongation during vegetative growth, and obligately aerobic carbon catabolism (vegetative growth in yeast is accomplished by budding from a unicellular thallus, and yeast may employ fermentative catabolism.)

The present invention takes advantage of the properties of the transformation system disclosed in international patent applications PCT/NL99/00618 and PCT/EP99/202516, and further described in U.S. patent application Ser. No. 09/548,938, now U.S. Pat. No. 6,573,086 and in U.S. patent application Ser. No. 09/834,434, now U.S. Pat. No. 7,122,330, and describes significant improvements to these systems. These previous applications describe a transformation system for filamentous fungal hosts including, but not limited to, *Chrysosporium lucknowense, Aspergillus sojae* and *Trichoderma*. These applications also disclose that mutant strains are readily prepared which retain all the advantages of the wild-type host cells, but which have partially lost their filamentous phenotype and thus provide low-viscosity cultures.

While the present invention may, in some embodiments, utilize fungal host strains such as those described above, one aspect of the invention provides improved fungal host strains for use in expression and screening systems. Particularly preferred embodiments of the invention are related to improved fungal host strains with low protease activity, with improved homologous integration of exogenous DNA (improved homologous recombination), and/or with reduced non-homologous integration of exogenous DNA (reduced non-homologous recombination).

The fungi preferred for use in the invention express and secrete large amounts of exogenous protein, producing a high protein/biomass ratio relative to previously known filamentous fungal hosts. The invention provides a transformation system that exhibits high yields of transformants. Improved fungal host strains of the invention are described in more detail below and in the Examples.

The invention also provides libraries of transformant fungi that efficiently express the protein products of heterologous cDNA inserts, and especially genomic DNA inserts. In particular, the invention provides libraries of transformant fungi that efficiently express heterogeneous or heteromultimeric proteins (complex proteins). As used herein, the terms "heterogeneous" and "heteromultimeric" can be used interchangeably to describe proteins that can be produced using the host cells and methods of the invention. Heterogeneous or heteromultimeric proteins are defined as any protein having two or more different or variable domains, subunits, components or constituents (i.e., the domains, subunits, components or constituents are variable, different, or heterogeneous with respect to each other). Heteromultimeric may be more commonly used to describe proteins with two or more different subunits or constituents, while heterogeneous may be more commonly used to describe single proteins with more than one domain or variable region. As such, a heterogeneous protein can include a single protein with more than one domain, and can include a protein with at least one variable domain (the structure of the domain may vary from protein to protein). Heteromultimeric proteins include, but are not limited to, members of the immunoglobulin supergene family (e.g., immunoglobulin, major histocompatibility complex, T cell receptors, CD3, adhesion molecules), hormones and hormone receptors, cytokines and cytokine receptors, other growth factors and growth factor receptors, etc.

Other embodiments of the invention are related to a variety of improved, self-replicating vectors that enable the construction of complex libraries in fungal host strains as described herein. The vectors enable very high transformation frequencies and have allowed the successful integration of library construction and screening in an automated set-up. Moreover, use of the improved vectors of the invention allow for reduced variation in the expression levels between independent or individual transformants, and offer flexibility in transferring the libraries from one organism to another. These vectors are described in detail below and in the Examples.

In another aspect of the invention, the libraries of transformed fungi, and particularly those utilizing the improved fungal host strains and/or vectors described herein, may be used in screening for activities or properties of any heterologous proteins, or in screening for metabolites produced by the transformed fungi as a consequence of exogenous protein activities, or in screening for the heterologous DNA or for RNA transcripts derived therefrom. It will be appreciated that the present invention also enables high-throughput screening for metabolites of non-transformed strains having the phenotypic characteristics described above. It will be further appreciated that the present invention enables the expression and high-throughput screening for a variety of heterologous proteins, including many heterogeneous/heteromultimeric complex proteins comprised of two or more domains, subunits or components (multimeric proteins).

In yet another aspect of the invention, the libraries of transformed fungi may be screened for useful properties of the fungi themselves, such as for example high levels of production of a particular expressed protein, protein complex, or metabolite. This aspect of the invention is illustrated by a quantitative assay for the expressed protein of interest, where the particular transformant having the most favorable combination of protein production, protein processing, and protein secretion would be detected.

In another aspect of the invention, the libraries of transformed fungi may be screened for the presence of DNA sequences capable of hybridizing to a nucleic acid probe of interest.

In a particularly preferred aspect of the invention, transformed fungi as described herein are used to express and screen proteins produced from complex or combinatorial libraries (e.g., libraries of libraries), which include a large variety of heterogeneous or heteromultimeric proteins (e.g., immunoglobulins and fragments thereof, and other receptors, as non-limiting examples).

The expression and screening methods of the invention, and the fungi employed therein, are useful for producing proteins (including mammalian proteins and protein complexes), metabolites, and DNA molecules having utility in a variety of applications, including a variety of diagnostic and therapeutic applications for use in humans. The methods of the invention are also useful for producing nucleic acid and protein sequence information, and this information itself is regarded as a valuable product of the claimed methods.

Another embodiment of the invention relates to the integration of the expression of complex or variable proteins with high-throughput screening of the invention, as exemplified by, but not limited to, immunoglobulin expression, to select improved, targeted, or desired proteins and/or protein complexes having two or more different or variable domains, subunits or constituents (e.g., human monoclonal antibodies) by combining libraries encoding one constituent (e.g., light chain variants) with libraries encoding the other constituent (e.g., heavy chain variants), with individual clones of the resulting combinatorial libraries expressing both constituents (e.g., full-length or single chain antibodies). Since the strain used for screening can also be used to express these complex proteins, positive hits from the screen can be cultivated to produce enough protein for further biochemical and biological investigation. Isolation of the cloned DNA from those strains and subsequent recloning for maximum expression will lead to economical production of such proteins for potential clinical applications, including diagnostic, prognostic, and therapeutic applications. Moreover, the methods of the invention can be used for molecular evolution of such proteins, which can be used to produce highly effective reagents for such applications. These methods of the invention are high throughput expression and screening methods, which are invaluable for the rapid identification of a variety of therapeutically beneficial tools.

Preferred Host Strains for Expression and Screening

The present invention includes fungal strains that either naturally exhibit decreased protease activity or that have been mutated or selected to have low protease activity. In certain embodiments, the invention includes a fungus that has less than 50%, less than 10%, or less than 1% of the protease activity as compared to a non-mutated, non-selected or wild-type fungus. The invention also includes fungal strains in which one or more protease genes have been inactivated or disrupted, as described in greater detail below.

Preferred filamentous fungi of the invention are characterized by the low viscosity of the culture medium. Whereas a typical industrial-grade filamentous fungus will typically produce cultures with viscosities well over 200 centipoise (cP) and usually over 1,000 cP, and can reach over 10,000 cP, the fungi of this invention exhibit a culture viscosity of less than 200 cP, preferably less than 100 cP, more preferably less than 60 cP, and most preferably less than 10 cP after 48 or more hours of culturing in the presence of adequate nutrients under optimal or near-optimal growth conditions. The filamentous fungi of the invention usually exhibit a morphology characterized by short, discrete, non-entangled hyphae, or micropellets. Micropellets are slightly- or non-entangled collections of hyphae arising from a single clone, as distinct from pellets which are much larger and are derived from multiple entangled clones. For example, the mutant UV18-25 *Chrysosporium lucknowense* strain (viscosity<10 cP) and the morphologically similar mutant *Trichoderma longibrachiatum* X-252 strain (viscosity<60 cP) are characterised by the presence of short, distinct, non-entangled hyphae between 100 and 200 microns in length, and the low viscosity engineered mutant *Aspergillus* sojae pclA is characterized by a compact form with considerable branching and short hyphae (see, e.g., FIG. 14 of U.S. Pat. No. 7,122,330). Whereas the low-viscosity fungi described in WO97/26330 are described as having "more extensive hyphal branching," some fungi of the present invention have equivalent or even slightly reduced hyphal branching when compared to the non-mutant strains. It appears that hyphal length plays the dominant role in controlling the viscosity of the culture.

Particularly preferred fungal strains are characterized by having a high exogenous secreted protein/biomass ratio. This ratio is preferably greater than 1:1, more preferably greater than 2:1, more preferably greater than 3:1, more preferably greater than 4:1, more preferably greater than 5:1, and even more preferably 6:1 or greater. Most preferably, the ratio is 8:1 or higher. Such high ratios are advantageous in a high-throughput screening environment, because they result in a higher concentration of exogenous protein, allowing more sensitive and/or more rapid screening assays. This is of particular benefit as the volume of the assay solution decreases, for example upon going from 96-well plates to 384-well plates, and thence to 1536-well plates. The methods of the present invention are suitable for any of these microtiter plate formats, and for most other HTS formats employing liquid samples.

It is contemplated that any filamentous fungus can be converted, by the processes of mutation described herein, into mutant strains suitable for use in the present invention. Among the preferred genera of filamentous fungi are the *Chrysosporium, Thielavia, Neurospora, Aureobasidium, Filibasidium, Piromyces, Cryplococcus, Acremonium, Tolypocladium, Scytalidium, Schizophyllum, Sporotrichum, Penicillium, Gibberella, Myceliophthora, Mucor, Aspergillus, Fusarium, Humicola*, and *Trichoderma*, and anamorphs and teleomorphs thereof. More preferred are *Chrysosporium, Myceliophthora, Trichoderma, Aspergillus*, and *Fusarium*. One preferred genus of fungus is *Chrysosporium*, although the invention is in no way limited to this genus. The genus and species of fungi can be defined by morphology consistent with that disclosed in Barnett and Hunter, *Illustrated Genera of Imperfect Fungi,* 3rd Edition, 1972, Burgess Publishing Company. A source providing details concerning classification of fungi of the genus *Chrysosporium* is Van Oorschot, C.A.N. (1980) "A revision of *Chrysosporium* and allied genera" in *Studies in Mycology No.* 20, Centraal Bureau voor Schimmelcultures (CBS), Baarn, The Netherlands, pp. 1-36. According to these teachings the genus *Chrysosporium* falls within the family Moniliaceae that belongs to the order Hyphomycetales.

Another ready source providing information on fungal nomenclature is the Budapest Treaty depositories, especially those providing online databases (the following internet addresses employ the http protocol). The ATCC (US) provides information at www.atcc.org, the CBS (NE) at www.cbs.knaw.nl, and the VKM (RU) at www.bdt.org.br.bdt.msdn.vkm/general. Another source is NT.ars-grin.gov/fungaldatabases. All these institutions can provide teaching on the distinguishing characteristics of fungal species. An alternate taxonomy of the Ascomycota may be found at www.ncbi.nlm.nih.gov/htbin-post/Taxonomy/wgetorg?mode=Undef&id=4890. According to this alternate taxonomy, the genus *Chrysosporium* belongs to family Onygenaceae, order Onygenales, phylum Ascomycota.

The definition of *Chrysosporium* includes but is not limited to these strains: *C. botryoides, C. carmichaelii, C. crassitunicatum, C. europae, C. evolceannui, C. farinicola, C. fastidium, C. filiforme, C. georgiae, C. globiferum, C. globiferum* var. *articulatum, C. globiferum* var. *niveum, C. hirundo, C. hispanicum, C. holmii, C. indicum, C. inops, C. keratinophilum, C. kreiselii, C. kuzurovianum, C. lignorum, C. lobatum, C. lucknowense, C. lucknowense* Garg 27K, *C. medium, C. medium* var. *spissescens, C. mephiticum, C. merdarium, C. merdarium* var. *roseum, C. minor, C. pannicola, C. parvum, C. parvum* var. *crescens, C. pilosum, C. pseudomerdarium, C. pyriformis, C. queenslandicum, C. sigleri, C. sulfureum, C. synchronum, C. tropicum, C. undulatum, C. vallenarense, C. vespertilium, C. zonatum.*

*C. lucknowense* is a species of *Chrysosporium* that is of particular interest as it has provided a natural high producer of cellulase proteins (international applications WO 98/15633, PCT/NL99/00618, and U.S. Pat. Nos. 5,811,381 and 6,015,707). Strains with international depository accession numbers ATCC 44006, CBS 251.72, CBS 143.77, CBS 272.77, and VKM F-3500D are examples of *Chrysosporium lucknowense* strains. Also included within the definition of *Chrysosporium* are strains derived from *Chrysosporium* predecessors including those that have mutated either naturally or by induced mutagenesis. The methods of the invention, in one embodiment, employ mutants of *Chrysosporium*, obtained by a combination of irradiation and chemically-induced mutagenesis, that tend to produce transferable reproductive elements in suspension, and that exhibit a morphology characterized by short, discrete, non entangled hyphae ("compact growth"), and a phenotype characterized by submerged growth and reduced viscosity of the fermentation medium when cultured in suspension. In another embodiment, the invention employs phenotypically similar mutants of *Trichoderma*. In another embodiment, the invention employs phenotypically similar mutants of *Myceliophthora*. In yet other embodiments the invention employs phenotypically similar mutants of *Aspergillus sojae* or *Aspergillus niger*. The invention also includes any strains derived from predecessors of any fungi described herein including those that have mutated either naturally or by induced mutagenesis, as well as any derivatives or mutants of any of the fungi described herein.

In one aspect, the present invention includes a fungus such as *C. lucknowense* or a mutant or other derivative thereof, and more particularly, from the fungal strain denoted herein as C1 (Accession No. VKM F-3500-D). The invention also includes proteins expressed by the C1 fungus. As described in U.S. Pat. No. 6,015,707 or U.S. Pat. No. 6,573,086, each of which is incorporated herein by reference for all purposes, a strain called C1 (Accession No. VKM F-3500-D), was isolated from samples of forest alkaline soil from Sola Lake, Far East of the Russian Federation. This strain was deposited at the All-Russian Collection of Microorganisms of Russian Academy of Sciences (VKM), Bakhurhina St. 8, Moscow, Russia, 113184, under the terms of the Budapest Treaty on the International Regulation of the Deposit of Microorganisms for the Purposes of Patent Procedure on Aug. 29, 1996, as *Chrysosporium lucknowense* Garg 27K, VKM-F 3500 D. Various mutant strains of *C. lucknowense* C1 have been produced and these strains have also been deposited at the All-Russian Collection of Microorganisms of Russian Academy of Sciences (VKM), Bakhurhina St. 8, Moscow, Russia, 113184, under the terms of the Budapest Treaty on the International Regulation of the Deposit of Microorganisms for the Purposes of Patent Procedure on Sep. 2, 1998. For example, Strain C1 was mutagenised by subjecting it to ultraviolet light to generate strain UV13-6 (Accession No. VKM F-3632 D). This strain was subsequently further mutated with N-methyl-N'-nitro-N-nitrosoguanidine to generate strain NG7C-19 (Accession No. VKM F-3633 D). This latter strain in turn was subjected to mutation by ultraviolet light, resulting in strain UV18-25 (VKM F-3631 D). Strain C1 was classified as a *Chrysosporium lucknowense* based on morphological and growth characteristics of the microorganism, as discussed in detail in U.S. Pat. No. 6,015,707 and U.S. Pat. No. 6,573,086. Additional information concerning the generation of mutant C1 strains and their characteristics can be found in U.S. Pat. No. 7, In particular the anamorph form of *Chrysosporium* has been found to be suited for the screening application according to the invention. The metabolism of the anamorph renders it particularly suitable for a high degree of expression. A teleomorph should also be suitable as the genetic make-up of the anamorphs and teleomorphs is identical. The difference between anamorph and teleomorph is that one is the asexual state and the other is the sexual state; the two states exhibit different morphology under certain conditions.

Another example embodies genetically engineered mutant strains of *Aspergillus sojae*. In one of these mutants a specific endoprotease encoding gene was disrupted. This resulted in a compact growth phenotype exhibiting enhanced branching and short hyphae, and the formation of micropellets in submerged cultivation. Moreover, the *Aspergillus sojae* referred to in this application may be induced to exhibit efficient sporulation under specific submerged cultivation conditions, which renders it especially suitable for use in a high-throughput screening system. In this case, the conditions conducive to formation of the transferable reproductive elements simply consisted of a synthetic medium containing 0.6 g/kg EDTA. The conducive conditions will vary from one host to another, but it is evident that the conditions will already be known if a host has been found to be suitable.

The term "mutant filamentous fungus" as used herein refers simply to fungi not found in nature. The "mutations" that lead to desirable phenotypic characteristics, such as a compact growth form, low viscosity, reduced protease levels, submerged growth, improved homologous integration of DNA, reduced non-homologous integration of DNA, etc., may be introduced randomly by either classical means, such as UV irradiation and chemical mutagenesis, or by molecular biological methods such as cassette mutagenesis, or may be deliberately introduced by genetic engineering methods. Should a naturally occurring fungus be found to possess the necessary properties, it will of course be usable in the methods of the invention.

It is preferable to use non-toxigenic and non-pathogenic fungal strains, of which a number are known in the art, as this will reduce risks to the practitioner and will simplify the overall screening process. In a preferred embodiment the fungi will also be protease deficient, so as to minimize degradation of the exogenous proteins, and/or amenable to suppression of protease production. The use of protease deficient strains as expression hosts is well known; see for example PCT application WO 96/29391. Protease deficient strains may be produced by screening of mutants, or the protease gene(s) may be "knocked out" or otherwise inactivated by methods known in the art, as described for example by Christensen and Hynes in U.S. Pat. No. 6,025,185 (*Aspergillus oryzae* with non-functional areA gene).

It has been found that mutant fungal strains of the invention, including *Chrysoporium* mutant strains, can be made that have reduced expression of protease (e.g., extracellular protease), thus making them even more suitable for the production of proteinaceous products, especially if the proteinaceous product is sensitive to protease activity. Thus the invention may also employ a mutant fungal strain that produces less extracellular protease than the corresponding non-mutant fungal strain, for example less than *C. lucknowense* strain C1 (VKM F-3500 D). An example of such a novel mutant strain is described in detail herein. In particular, the protease activity (other than any selective protease intended to cleave a secreted fusion protein) of such strains is less than half the amount, more preferably less than 30% of the amount, and more preferably less than about 10%, and more preferably less than about 9%, and more preferably less than about 8%, and more preferably less than about 7%, and more preferably less than about 6%, and more preferably less than about 5%, and more preferably less than about 4%, and more preferably less than about 3%, and more preferably less than about 2%, and more preferably less than about 1% of the amount produced by the wild-type, or non-mutant reference strain. The decreased protease activity can be measured by known methods, such as by measuring the halo formed on skim milk plates or by bovine serum albumin (BSA) degradation. Such strains can be produced by selection of natural mutants, by random or directed mutagenesis followed by screening, or by directed genetic modification (genetic engineering), such as by gene deletion or disruption.

By way of example, new mutant fungal strains useful in the present invention are described herein, where the strains were mutated and the selected for the characteristic of low protease activity. In a further example, mutant *Chrysoporium* strains, described below, were produced by the selection process described above, and then further selective disruption of at least one, and up to all three of the protease genes, alp1, pep4, and alp2. Nucleotide and amino acid sequences from each of these genes are provided herein. Random or classical mutagenesis and screening can be used alone or in combination with genetic engineering to readily produce additional low protease mutants. These protease mutants may be obtained not only by disrupting actual protease encoding genes; in addition, strains mutated in genes that regulate protease genes may result in the desired type of strains. These regulatory genes may include those encoding for protease-specific transcription factors as well as broadly acting transcription factors. These low protease strains are highly useful for the production of proteins, and particularly large proteins and protein complexes, and are described in more detail in the Examples section.

Exemplary low protease strains of the present invention, include, but are not limited to, a mutant of strain UV18-25, which has been mutated with ultraviolet light and selected for low protease activity, denoted herein as UV18#100.f (deposited at the Centraalbureau voor Schimmelcultures (CBS) in the Netherlands under the terms of the Budapest Treaty on the International Regulation of the Deposit of Microorganisms for the Purposes of Patent Procedure on Dec. 5, 2007, as *Chrysosporium lucknowense* UV18#100.f, CBS 122188); a strain denoted UV18#100.f $\Delta$pyr5 $\Delta$alp1, a mutant of UV18#100.f in which the protease gene alp1 has been selectively disrupted (and/or $\Delta$alp2 or $\Delta$pep4); and a strain denoted UV18#100.f $\Delta$pyr5 $\Delta$alp1 $\Delta$pep4 $\Delta$alp2, another mutant of UV18#1001 in which three protease genes, alp1, pep4, and alp2 have been disrupted. Production of these mutant strains is described in the Examples section. Each of these strains represents a novel, improved fungal host strain for use with the vectors and in the methods of the present invention.

It may be desirable to inactivate other genes in the host filamentous fungus, such as for example those encoding cellulases and other abundant secreted proteins, in order to minimize interference in the assay by host proteins. The genes encoding secreted proteins may be deleted or mutated, or alternatively genes controlling the induction system or other pathways involved in the expression of unwanted proteins may be modified in such a way as to reduce such expression. Where an endogenous promoter is employed in the vectors of the invention (see below), it may be especially desirable to inactivate genes for other proteins under control by the same inducer. Fungi amenable to suppression of protease secretion are those where protease expression is under the control of a regulatory element that responds to environmental conditions, such that these conditions (e.g., amino acid concentration) can be manipulated to minimize protease production.

In another embodiment of the invention, it is desirable to provide host filamentous fungi with an improved homologous DNA-integration characteristic (e.g., exogenously introduced DNA) and/or with reduced or decreased non-homologous DNA-integration characteristics, as compared to typical or wild-type fungi. Such strains are particularly useful for the expression and screening methods described herein, since such strains can be used to ensure integration of heterologous DNA (e.g., from DNA libraries) at a directed location, and are likely to be more stable transformants in which expression levels of the heterologous proteins can be controlled (e.g., high expression can be achieved, whereby expression levels from transformant to transformant is relatively similar). Moreover, replicating vectors will have improved stability characteristics or improved homologous integration in these strains due to the absence of non-homologous integration. Although these are valuable features in the expression of any heterologous protein, such stable and controlled expression is particularly useful when expressing and screening combinatorial libraries, where two or more protein components must be expressed and associated in order to evaluate a biological activity. Such improvements to the strains may be introduced randomly by either classical means, such as UV irradiation and chemical mutagenesis, or by molecular biological methods such as cassette mutagenesis, or may be deliberately introduced by genetic engineering methods. Should a naturally-occurring fungus be found to possess the necessary properties, it will of course be usable in the methods of the invention.

Proteases

The present invention is also directed to *C. lucknowense* strain C1 (VKM F-3500 D) enzymes with protease activity. For example, the polypeptides denoted herein as Alp1 (SEQ ID NO:2), Alp2 (SEQ ID NO:5), and Pep4 (SEQ ID NO:8) possess protease activity. These enzymes participate in the hydrolysis of peptide bonds that link amino acids together in a polypeptide chain. Example J below demonstrates that cells deficient in each of these enzymes exhibit reduced protease activity.

Proteases may be used in any method where it is desirable to hydrolyze peptide bonds in polypeptides or proteinaceous materials or any other method wherein enzymes of the same or similar function are useful. For example, a protease of the present invention may be incubated with a polypeptide or proteinaceous material to degrade the material. Accordingly, the present invention includes the use of at least one protease of the present invention, compositions comprising at least one protease of the present invention in methods for degrading polypeptides or proteinaceous materials. In one embodiment, the method comprises contacting the polypeptides or protein-containing materials with an effective amount of one or more protease of the present invention.

In one embodiment, the knowledge of the nucleotide sequences encoding the proteases of the invention is used to selectively disrupt or deactivate these genes in the endogenous host. The resulting protease-deficient strains are particularly useful in the expression and screening methods described herein. Exemplary protease deficient strains are discussed in detail above and in the Examples.

Alp1

The enzyme denoted Alp1 is encoded by the genomic nucleic acid sequence represented herein as SEQ ID NO:1 and the cDNA sequence represented herein as SEQ ID NO:3. The Alp1 nucleic acid sequence encodes a 392 amino acid sequence, represented herein as SEQ ID NO:2. The signal peptide for Alp1 is located from positions 1 to about position 16 of SEQ ID NO:2, with the mature protein spanning from about position 17 to position 392 of SEQ ID NO:2. Within Alp1 is a catalytic domain (CD). The amino acid sequence containing the CD of Alp1 spans from a starting point of about position 39 of SEQ ID NO:2 to an ending point of about position 387 of SEQ ID NO:2. As demonstrated below, Alp1 exhibits protease activity on substrates such as casein.

Alp1 has a molecular weight of 31 kDa and an isoelectric point of 9.0. Alp1 exhibits optimal activity at a pH of about 10.5, and exhibits at least 50% of maximum activity with a pH range of 6.5 to 11.7. Alp1 exhibits optimal activity at a temperature of about 60° C., and exhibits at least 50% of maximum activity with a temperature range of 45° C. to 67° C. Substrate specificities of Alp1 are illustrated in Table A below. Enzyme activities and substrate specificities demonstrating enzyme activity for the indicated substrates were determined using standard assays known in the art.

TABLE A

| Substrate | Activity (Units/mg) |
|---|---|
| Casein, pH 7.0, 40° C., 30 min, A275 | 1556 |
| Casein, pH 9.0, 40° C., 30 min, A275 | 1620 |
| Hemoglobin, pH 5.0, 40° C., 30 min, A275 | 140 |
| n-Benzoyl-Phe-Val-Arg-p-Nitroanilide (trypsin-like activity) | 39.3 |
| n-Succinyl-Ala-Ala-Pro-Phe-p-Nitroanilide (chymotrypsin-like activity) | 8.1 |
| n-Succinyl-Ala-Ala-Pro-Leu-p-Nitroanilide (chymotrypsin-like activity) | 1.3 |
| p-Nph-Caproate, pH 7.3 (esterase activity) | 1.5 |

Alp2

The enzyme denoted Alp2 is encoded by the genomic nucleic acid sequence represented herein as SEQ ID NO:4 and the cDNA sequence represented herein as SEQ ID NO:6. The Alp2 nucleic acid sequence encodes a 534 amino acid sequence, represented herein as SEQ ID NO:5. The signal peptide for Alp2 is located from positions 1 to about position 15 of SEQ ID NO:5, with the mature protein spanning from about position 16 to position 534 of SEQ ID NO:5. Alp2 possesses amino acid sequence homology (about 79%) with a protease from Chaetomium thermophilum (GenBank Accession No. ABH07518).

Pep4

The enzyme denoted Pep4 is encoded by the genomic nucleic acid sequence represented herein as SEQ ID NO:7 and the cDNA sequence represented herein as SEQ ID NO:9. The Pep4 nucleic acid sequence encodes a 397 amino acid sequence, represented herein as SEQ ID NO:8. The signal peptide for Pep4 is located from positions 1 to about position 18 of SEQ ID NO:8, with the mature protein spanning from about position 19 to position 397 of SEQ ID NO:8. Pep4 possesses amino acid sequence homology (about 79%) with a protease from *Neurospora crassa* (GenBank Accession No. AAA79878).

The present invention also provides enzyme combinations that break down polypeptides or proteinaceous material. Such enzyme combinations or mixtures can include a multi-enzyme composition that contains at least one protein of the present invention in combination with one or more additional proteins of the present invention or one or more proteases, other enzymes or other proteins from other microorganisms, plants, or similar organisms. Synergistic enzyme combinations and related methods are contemplated. The invention includes methods to identify the optimum ratios and compositions of enzymes with which to degrade each polypeptide or proteinaceous material. These methods entail tests to identify the optimum enzyme composition and ratios.

Another embodiment of the present invention relates to a composition comprising at least about 500 ng, and preferably at least about 1 µg, and more preferably at least about 5 µg, and more preferably at least about 10 µg, and more preferably at least about 25 µg, and more preferably at least about 50 µg, and more preferably at least about 75 µg, and more preferably at least about 100 µg, and more preferably at least about 250 µg, and more preferably at least about 500 µg, and more preferably at least about 750 µg, and more preferably at least about 1 mg, and more preferably at least about 5 mg, of an isolated protein comprising any of the proteins or homologues or fragments thereof discussed herein. Such a composition of the present invention may include any carrier with which the protein is associated by virtue of the protein preparation method, a protein purification method, or a preparation of the protein for use in any method according to the present invention. For example, such a carrier can include any suitable buffer, extract, or medium that is suitable for combining with the protein of the present invention so that the protein can be used in any method described herein according to the present invention.

In one embodiment of the invention, one or more enzymes of the invention is bound to a solid support, i.e., an immobilized enzyme. As used herein, an immobilized enzyme includes immobilized isolated enzymes, immobilized microbial cells which contain one or more enzymes of the invention, other stabilized intact cells that produce one or more enzymes of the invention, and stabilized cell/membrane homogenates. Stabilized intact cells and stabilized cell/membrane homogenates include cells and homogenates from naturally occurring microorganisms expressing the enzymes of the invention and preferably, from genetically modified microorganisms as disclosed elsewhere herein. Thus, although methods for immobilizing enzymes are discussed below, it will be appreciated that such methods are equally applicable to immobilizing microbial cells and in such an embodiment, the cells can be lysed, if desired.

A variety of methods for immobilizing an enzyme are disclosed in Industrial Enzymology 2nd Ed., Godfrey, T. and West, S. Eds., Stockton Press, New York, N.Y., 1996, pp. 267-272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, Calif., 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic, biopolymer or inorganic supports that can form a bond with an enzyme without significantly effecting the activity of the enzyme. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. In one embodiment, the solid support is selected from the group consisting of stabilized intact cells and/or crude cell homogenates (e.g., produced from the microbial host cells expressing recombinant enzymes, alone or in combination with natural enzymes). Preparation of such supports requires a minimum of handling and cost. Additionally, such supports provide excellent stability of the enzyme.

Stabilized intact cells and/or cell/membrane homogenates can be produced, for example, by using bifunctional crosslinkers (e.g., glutaraldehyde) to stabilize cells and cell homogenates. In both the intact cells and the cell membranes, the cell wall and membranes act as immobilizing supports. In such a system, integral membrane proteins are in the "best" lipid membrane environment. Whether starting with intact cells or homogenates, in this system the cells are either no longer "alive" or "metabolizing", or alternatively, are "resting" (i.e., the cells maintain metabolic potential and active enzyme, but under the culture conditions are not growing); in either case, the immobilized cells or membranes serve as biocatalysts.

An enzyme of the invention can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports in a bead form are particularly well-suited. The particle size of an adsorption solid support can be selected such that the immobilized enzyme is retained in the reactor by a mesh filter while the substrate is allowed to flow through the reactor at a desired rate. With porous particulate supports it is possible to control the adsorption process to allow enzymes or cells to be embedded within the cavity of the particle, thus providing protection without an unacceptable loss of activity.

Cross-linking of an enzyme to a solid support involves forming a chemical bond between a solid support and the enzyme. It will be appreciated that although cross-linking generally involves linking the enzyme to a solid support using an intermediary compound, it is also possible to achieve a covalent bonding between the enzyme and the solid support directly without the use of an intermediary compound. Cross-linking commonly uses a bifunctional or multifunctional reagent to activate and attach a carboxyl group, amino group, sulfur group, hydroxy group or other functional group of the enzyme to the solid support. The term "activate" refers to a chemical transformation of a functional group which allows a formation of a bond at the functional group. Exemplary amino group activating reagents include water-soluble carbodiimides, glutaraldehyde, cyanogen bromide, N-hydroxysuccinimide esters, triazines, cyanuric chloride, and carbonyl diimidazole. Exemplary carboxyl group activating reagents include water-soluble carbodiimides, and N-ethyl-5-phenyl-isoxazolium-3-sulfonate. Exemplary tyrosyl group activating reagents include diazonium compounds. And exemplary sulfhydryl group activating reagents include dithiobis-5,5'-(2-nitrobenzoic acid), and glutathione-2-pyridyl disulfide. Systems for covalently linking an enzyme directly to a solid support include Eupergit®, a polymethacrylate bead support available from Rohm Pharma (Darmstadt, Germany), kieselguhl (Macrosorbs), available from Sterling Organics, kaolinite available from English China Clay as "Biofix" supports, silica gels which can be activated by silanization, available from W.R. Grace, and high-density alumina, available from UOP (Des Plains, Ill.).

Entrapment can also be used to immobilize an enzyme. Entrapment of an enzyme involves formation of, inter alia, gels (using organic or biological polymers), vesicles (including microencapsulation), semipermeable membranes or other matrices. Exemplary materials used for entrapment of an enzyme include collagen, gelatin, agar, cellulose triacetate, alginate, polyacrylamide, polystyrene, polyurethane, epoxy resins, carrageenan, and egg albumin. Some of the polymers, in particular cellulose triacetate, can be used to entrap the enzyme as they are spun into a fiber. Other materials such as polyacrylamide gels can be polymerized in solution to entrap the enzyme. Still other materials such as polyglycol oligomers that are functionalized with polymerizable vinyl end groups can entrap enzymes by forming a cross-linked polymer with UV light illumination in the presence of a photosensitizer.

Further embodiments of the present invention include nucleic acid molecules that encode a protein of the present invention, as well as any homologues or fragments of such nucleic acid molecules. A nucleic acid molecule of the present invention includes a nucleic acid molecule comprising, consisting essentially of, or consisting of, a nucleic acid sequence encoding any of the isolated proteins disclosed herein, including a fragment or a homologue of such proteins, described above. Nucleic acid molecules can include a nucleic acid sequence that encodes a fragment of a protein that does not have biological activity, and can also include portions of a gene or polynucleotide encoding the protein that are not part of the coding region for the protein (e.g., introns or regulatory regions of a gene encoding the protein). Nucleic acid molecules can include a nucleic acid sequence that is useful as a probe or primer (oligonucleotide sequences).

Many of the enzymes and proteins of the present invention, including those comprising, consisting essentially of, or consisting of, any of SEQ ID NO:2, SEQ ID NO:5, or SEQ ID NO:8 may be desirable targets for modification and/or used in the products, cells, and processes described herein. These proteins have been described in terms of function and amino acid sequence (and nucleic acid sequence encoding the same) of representative wild-type proteins. In one embodiment of the invention, homologues of a given protein (which can include related proteins from other organisms or modified forms of the given protein) are encompassed for use in the invention. Homologues of a protein are described in detail in the General Definitions below.

In one embodiment, a nucleic molecule of the present invention includes a nucleic acid molecule comprising, consisting essentially of, or consisting of, a nucleic acid sequence represented by SEQ ID NO:1, SEQ ID NO:3, SEQ ID NO:4, SEQ ID NO:6, SEQ ID NO:7, SEQ ID NO:9, or fragments or homologues thereof. Preferably, the nucleic acid sequence encodes a protein (including fragments and homologues thereof) useful in the invention, or encompasses useful oligonucleotides or complementary nucleic acid sequences.

In one embodiment, a nucleic molecule of the present invention includes a nucleic acid molecule comprising, consisting essentially of, or consisting of, a nucleic acid sequence encoding an amino acid sequence represented by SEQ ID NO:2, SEQ ID NO:5, SEQ ID NO:8, or fragments or homologues thereof. Preferably, the nucleic acid sequence encodes a protein (including fragments and homologues thereof) useful in the invention, or encompasses useful oligonucleotides or complementary nucleic acid sequences.

In one embodiment, such nucleic acid molecules include isolated nucleic acid molecules that hybridize under moderate stringency conditions, and more preferably under high stringency conditions, and even more preferably under very high stringency conditions, as described above, with the complement of a nucleic acid sequence encoding a protein of the present invention (i.e., including naturally occurring allelic variants encoding a protein of the present invention). Preferably, an isolated nucleic acid molecule encoding a protein of the present invention comprises a nucleic acid sequence that hybridizes under moderate, high, or very high stringency conditions to the complement of a nucleic acid sequence that encodes a protein comprising an amino acid sequence represented by SEQ ID NO:2, SEQ ID NO:5, SEQ ID NO:8.

One embodiment of the present invention relates to a recombinant nucleic acid molecule which comprises the isolated nucleic acid molecule described above which is operatively linked to at least one expression control sequence. Recombinant nucleic acid molecules are described in detail in the General Definitions below. One or more recombinant molecules of the present invention can be used to produce an encoded product (e.g., a protein) of the present invention. Methods for producing an encoded product and preferred host cells of the invention are described in detail below.

Another aspect of the present invention relates to a genetically modified microorganism that has been transfected with one or more nucleic acid molecules of the present invention. The present invention also encompasses a genetically modified microorganism wherein one or more nucleic acid molecules of the present invention has been disrupted in the organism. In one embodiment, a nucleic acid molecule encoding an endogenous protease may be disrupted. Additional embodiments include fungi in which the alp1, alp2 or pep4 genes, or any combination of the genes, have been disrupted. Genes corresponding to the alp1, alp2 or pep4 genes disclosed herein, or any combination thereof, may also be disrupted in other organisms. Genetically modified microorganisms and methods of producing such organisms are described in detail below.

The invention also contemplates genetically modified plants transformed with one or more nucleic acid molecules of the invention. The plants may be used for production of the enzymes. Methods to generate recombinant plants are known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

Another embodiment of the present invention relates to an isolated binding agent capable of selectively binding to a protein of the present invention. Suitable binding agents may be selected from an antibody, an antigen binding fragment, or a binding partner. The binding agent selectively binds to an amino acid sequence selected from SEQ ID NO:2, SEQ ID NO:5, SEQ ID NO:8, including to any fragment of any of the above sequences comprising at least one antibody binding epitope. Antibodies, antigen binding fragments, and binding partners are described in detail below.

Vectors Useful in the Invention

The present invention includes improved expression/transforming vectors used to express and screen proteins produced from complex or combinatorial libraries (e.g., libraries of libraries), which include a large variety of heterogeneous or heteromultimeric proteins (e.g., immunoglobulins and fragments thereof, and other receptors, as non-limiting examples). The vectors of the present invention allow for very high transformation frequencies and, upon prolonged cultivation, the integration of the linearized vector in the host cell's genome.

In a broad aspect, the vectors include a sequence that promotes autonomous replication and enhances transformation in a fungal host, and two selection markers that flank an expression cassette in the vector, wherein the entire expression cassette integrates into the genome of a fungal host transformed with the vector. As discussed in more detail below, the vectors may include additional elements including, but not limited to, telomeric sequences, fusion partners, promoters, terminators, and other expression regulatory elements.

Preferably a homologous expression-regulating region enabling high expression in the selected host cell of the invention is employed in the transforming vector. High expression-regulating regions derived from a heterologous host, such as from *Trichoderma* or *Aspergillus*, are well known in the art and can also be used. By way of example, and not limitation, examples of proteins known to be expressed in large quantities and thus providing suitable expression regulating sequences for use in the present invention are hydrophobin, protease, amylase, xylanase, pectinase, esterase, beta-galactosidase, cellulase (e.g. endoglucanase, cellobiohydrolase) and polygalacturonase.

An expression-regulating region comprises a promoter sequence operably linked to a nucleic acid sequence encoding the protein to be expressed. The promoter is linked such that the positioning vis-à-vis the initiation codon of the sequence to be expressed allows expression. The promoter sequence can be constitutive but preferably is inducible. Use of an inducible promoter and appropriate induction media favors expression of genes operably linked to the promoter. Any expression regulating sequence from a homologous species, or from a heterologous strain capable of permitting expression of a protein, is envisaged. The expression regulating sequence is suitably a fungal expression-regulating region, e.g. an ascomycete regulating region. Suitably the ascomycete expression regulating region is a regulating region from any of the following genera: *Aspergillus, Trichoderma, Chrysosporium, Myceliophthora, Humicola, Neurospora, Tolypocladium, Fusarium, Penicillium, Talaromyces*, or alternative sexual forms thereof such as *Emericela* and *Hypocrea*. The cellobiohydrolase promoter from *Trichoderma*; alcohol dehydrogenase A, alcohol dehydrogenase R, glutamate dehydrogenase, TAKA amylase, glucoamylase, and glyceraldehyde phosphate dehydrogenase promoters from *Aspergillus*; phosphoglycerate and cross-pathway control promoters of *Neurospora*; lipase and aspartic proteinase promoter of *Rhizomucor miehei*; beta-galactosidase promoter of *Penicillium canescens*; and cellobiohydrolase, endoglucanase, xylanase, glyceraldehyde-3-phosphate dehydrogenase A, and protease promoters from *Chrysosporium* are representative, but not limiting, examples. An expression regulating sequence from the same genus as the host strain is preferable, as it is more likely to be specifically adapted to the host.

Natural expression-regulating sequences from strains of *Chrysosporium* which express proteins in extremely large amounts, are particularly preferred. Examples of such strains have been deposited in accordance with the Budapest Treaty with the All Russian Collection (VKM) depository institute in Moscow. Wild type C1 strain has the number VKM F-3500 D, deposit date Aug. 29, 1996, C1 UV13-6 mutant was deposited with number VKM F-3632 D, and deposit date Sep. 2, 1998, C1 NG7C-19 mutant was deposited with number VKM F-3633 D and deposit date Sep. 2, 1998 and C1 UV18-25 mutant was deposited with number VKM F-3631 D and deposit date Sep. 2, 1998. These strains are also preferred as sources for the generation of low-viscosity mutants; indeed the VKM F-3631 D strain already exhibits the necessary low viscosity phenotype. A low-viscosity mutant *Trichoderma* strain, designated X-252, was obtained after two rounds of irradiation of *Trichoderma longibrachiatum* 18.2KK, which in turn was derived by mutation of the QM 9414 strain of *T. longibrachiatum* (ATCC 26921). In other embodiments the invention employs phenotypically similar mutants of *Aspergillus sojae* and *Aspergillus niger*.

Preferably, where the host is a *Chrysosporium*, a *Chrysosporium* promoter sequence is employed to ensure good recognition thereof by the host. The analogous situation is extended to other fungal genera. Certain heterologous expression-regulating sequences also work as efficiently in *Chrysosporium* as native *Chrysosporium* sequences. This allows well-known constructs and vectors to be used in transformation of *Chrysosporium*, and offers numerous other possibilities for constructing vectors enabling good rates of transformation and expression in this host. For example, standard *Aspergillus* transformation techniques can be used as described for example by Christiansen et al. in *Bio/Technology* 1988 6:1419-1422. Other documents providing details of *Aspergillus* transformation vectors, e.g. U.S. Pat. Nos. 4,816, 405, 5,198,345, 5,503,991, 5,364,770, 5,705,358, 5,728,547, and 5,578,463, EP-B-215.594 (also for *Trichoderma*) and their contents are incorporated by reference. As extremely high expression rates for cellulase have been observed in *Chrysosporium* strains, the expression regulating regions of cellulase genes are particularly preferred.

In one embodiment, the vectors of the invention can comprise a promoter sequence derived from a gene encoding an enzyme, preferably a secreted enzyme. Examples of suitable enzymes from which promoter sequences may be taken are the carbohydrate-degrading enzymes (e.g., cellulases, xylanases, mannanases, mannosidases, pectinases, amylases, e.g., glucoamylases, α-amylases, α- and β-galactosidases, α- and β-glucosidases, β-glucanases, chitinases, chitosanases), proteases (endoproteases, amino-proteases, amino- and carboxy-peptidases), other hydrolases (lipases, esterases, phytases), oxidoreductases (catalases, glucose-oxidases) and transferases (transglycosylases, transglutaminases, isomerases and invertases). Several examples from *Chrysosporium lucknowense* are presented in Table B.

A nucleic acid construct will preferably comprise a nucleic acid expression regulatory region from the host genus, such as *Chrysosporium*, more preferably from the host species, such as *Chrysosporium lucknowense* or a derivative thereof, operably linked to a nucleic acid sequence encoding a protein to be expressed. Particularly preferred nucleic acid constructs will comprise an expression regulatory region from a host, such as *Chrysosporium*, associated with cellulase or xylanase expression, preferably cellobiohydrolase expression, most preferably expression of the 55 kDa cellobiohydrolase (CBH1) described in Table A. As additional examples, the *Chrysosporium* promoter sequences of hydrophobin, protease, amylase, xylanase, esterase, pectinase, beta-galactosidase, cellulase (e.g. endoglucanase, cellobiohydrolase), chitnase, and polygalacturonase are also considered to fall within the scope of the invention.

described in PCT/NL99/00618. The prior art provides a number of expression regulating regions for use in *Aspergillus*, e.g. U.S. Pat. Nos. 4,935,349; 5,198,345; 5,252,726; 5,705,358; and 5,965,384; and PCT application WO 93/07277.

TABLE B

Characteristics of selected enzymes from *Chrysosporium lucknowense*

| Sample | No. of amino acids | Highest pH at which >50% activity is retained | | | Highest pH at which >70% activity is retained | | | Stability 20 h, 50° C. pH 7.5/8 |
|---|---|---|---|---|---|---|---|---|
| | | CMCase | RBB CMCase | Other substrates | CMCase | RBB CMCase | Other substrates | % of max activity remaining |
| 30 kD alkaline protease | | — | — | 12.5 | — | — | 12.0 | — |
| 30 kD Xyl (alkaline) | 333 | — | — | 10.0 | — | — | 8.5 | 80 |
| 51 kD Xyl | | — | — | 8.0 | — | — | 7.5 | — |
| 60 kD Xyl | | — | — | 9.5 | — | — | 9.0 | 85 |
| 30 kD endo (EG3) | 247 | | | | | | | |
| 45 kD endo | | 7.0 | 8.0 | — | 6.5 | 7.0 | — | 75 |
| 55 kD endo | 247 | 8.0 | 8.0 | — | 7.0 | 7.0 | — | 55 |
| 25 kD(21.8 kD)endo (EG5) | 225 | 7.5 | 10.0 | — | 6.5 | 9.0 | — | 80 |
| 43 kD(39.6 kD*)endo (EG6) | 395 | 8.0 | 8.0 | — | 7.2 | 7.2 | — | — |
| 45 kD α,β-Gal/β-Gluc | | — | — | 6.8 | — | — | 5.7 | — |
| 48 kD CBH | | 5.2 | 7.5 | 8.0 | 5.0 | 6.8 | — | — |
| 55 kD CBH1 | 526 | 8.0 | 9.0 | — | 7.4 | 8.5 | — | 70 |
| 65 kD PGU | | — | — | 8.0 | — | — | 7.3 | — |
| 90 kD protease | | — | — | 9.0 | — | — | 9.0 | — |
| 100 kD esterase | | — | — | 9.0 | — | — | 9.0 | — |

Notes:
*molecular weights by MALDI; all others by SDS PAGE
xyl = xylanase
endo = endoglucanase
gal = galactosidase
gluc = glucosidase
CBN = cellbiohydrolase
PGU = polygalacturonase Any of the promoters or regulatory regions of expression of enzymes disclosed in Table B, for example, can be suitably employed, although to be clear, the invention is not limited in any way to the use of these promoters or regulatory regions. The nucleic acid sequences of these promoters and regulatory regions can readily be obtained from a *Chrysosporium* strain. Methods by which promoter sequences can be determined are numerous and well known in the art. Promoter sequences are generally found immediately preceding the ATG start codon at the beginning of the relevant gene. For example, promoter sequences can be identified by deleting sequences upstream of the relevant gene, using recombinant DNA techniques, and examining the effects of these deletions on expression of the gene. Also, for example, promoter sequences can often be inferred by comparing the sequence of regions upstream of the relevant gene with consensus promoter sequences.

For example, the promoter sequences of C1 endoglucanases were identified in this manner (see PCT/NL99/00618) by cloning the corresponding genes. Preferred promoters according to the invention are the 55 kDa cellobiohydrolase (CBH1), glyceraldehyde-3-phosphate dehydrogenase A, and the 30 kDa xylanase (XylF) promoters from *Chrysosporium*, as these enzymes are expressed at high level by their own promoters. The promoters of the carbohydrate-degrading enzymes of *Chrysosporium lucknowense* in particular, especially *C. lucknowense* GARG 27K, can advantageously be used for expressing libraries of proteins in other fungal host organisms.

Particular embodiments of nucleic acid sequences according to the invention are known for *Chrysosporium, Aspergillus* and *Trichoderma*. Promoters for *Chrysosporium* are Expression in *Trichoderma* is disclosed in U.S. Pat. No. 6,022,725. The contents of these patents are hereby incorporated by reference in their entirety.

The hydrophobin gene is a fungal gene that is highly expressed. It is thus suggested that the promoter sequence of a hydrophobin gene, preferably from *Chrysosporium*, may be suitably applied as expression regulating sequence in a suitable embodiment of the invention. *Trichoderma reesei* and *Trichoderma harzianum* gene sequences for hydrophobin have been disclosed for example in the prior art as well as a gene sequence for *Aspergillus fumigatus* and *Aspergillus nidulans* and the relevant sequence information is hereby incorporated by reference (Nakari-Setala et al., *Eur. J. Biochem.* 1996, 235:248-255; Parta et al., *Infect. Immun.* 1994 62:4389-4395; Munoz et al., *Curr. Genet.* 1997, 32:225-230; and Stringer et al., *Mol. Microbiol.* 1995 16:33-44). Using this sequence information a person skilled in the art can obtain the expression regulating sequences of *Chrysosporium* hydrophobin genes without undue experimentation following standard techniques such as those suggested above. A recombinant *Chrysosporium* strain according to the invention can comprise a hydrophobin-regulating region operably linked to the sequence encoding the heterologous protein.

An expression regulating sequence can also additionally comprise an enhancer or silencer. These are also well known in the prior art and are usually located some distance away from the promoter. The expression regulating sequences can also comprise promoters with activator binding sites and repressor binding sites. In some cases such sites may also be modified to eliminate this type of regulation. For example, filamentous fungal promoters in which creA sites are present have been described. The creA sites can be mutated to ensure that the glucose repression normally resulting from the presence of creA is eliminated. Use of such a promoter enables production of the library of proteins encoded by the nucleic acid sequences regulated by the promoter in the presence of glucose. The method is exemplified in WO 94/13820 and WO 97/09438. These promoters can be used either with or without their creA sites. Mutants in which the creA sites have been mutated can be used as expression regulating sequences in a recombinant strain according to the invention and the library of nucleic acid sequences it regulates can then be expressed in the presence of glucose. Such *Chrysosporium* promoters ensure derepression in an analogous manner to that illustrated in WO 97/09438. The identity of creA sites is known from the prior art. Alternatively, it is possible to apply a promoter with CreA binding sites that have not been mutated in a host strain with a mutation elsewhere in the repression system e.g. in the creA gene itself, so that the strain can, notwithstanding the presence of creA binding sites, produce the library of proteins in the presence of glucose.

Terminator sequences are also expression-regulating sequences and these are operably linked to the 3' termini of the sequences to be expressed. A variety of known fungal terminators are likely to be functional in the host strains of the invention. Examples are the *A. nidulans* trpC terminator, *A. niger* alpha-glucosidase terminator, *A. niger* glucoamylase terminator, *Mucor miehei* carboxyl protease terminator (see U.S. Pat. No. 5,578,463), and the *Trichoderma reesei* cellobiohydrolase terminator. *Chrysosporium* terminator sequences, e.g. the EG6 terminator, will of course function well in *Chrysosporium*.

One suitable terminator sequence is the terminator region from the cbh1 gene of *C. lucknowense* (Tcbh1), the sequence of which is represented as SEQ ID NO:11. The Tcbh1 sequence was found to contain an approximately 340 bp repetitive sequence designated the C1 Repetitive Sequence (CRS; represented as SEQ ID NO:12). FIG. 23 illustrates the position of the CRS within the Tcbh1 sequence. The presence of one of more copies of the CRS in an expression vector, either within a larger terminator region or in place of a terminator region, may increase the amount of protein encoded by the expression vector produced by an organism that expresses the vector. The presence of one of more copies of the CRS in an expression vector may also allow an increase in the number of expression cassettes that become integrated in a host cell's genomic DNA when the cell is transfected with the vector. As a result, the CRS may increase the copy number of a gene contained within the expression vector. Example I below provides one non-limiting example of how the presence of the CRS in a vector leads to a 2-fold increase in enzyme activity produced by fungal strains transfected with a vector encoding the enzyme, as compared to those strains transfected with a vector without the CRS.

In certain embodiments of the present invention, an expression vector may contain one or more copies of the CRS. In some embodiments, the expression vector contains 1, 2, 3, 4, 5, 6, 7, 8, 9, 10 or more copies of the CRS. The CRS may be present in the expression vector as part of a terminator sequence or as an independent sequence element within the vector.

A suitable transformation vector for use according to the invention may optionally have the exogenous nucleic acid sequences to be expressed operably linked to a sequence encoding a signal sequence. A signal sequence is an amino acid sequence which, when operably linked to the amino acid sequence of an expressed protein, enables secretion of the protein from the host organism. Such a signal sequence may be one associated with a heterologous protein or it may be one native to the host. The nucleic acid sequence encoding the signal sequence must be positioned in frame to permit translation of the signal sequence and the heterologous proteins. Signal sequences may be particularly preferred where the invention is being used in conjunction with directed molecular evolution, and a single, secreted exogenous protein is being evolved, or for the expression and screening of combinatorial libraries.

It will be understood that it is less advantageous to incorporate a signal sequence in a vector that is to be used to express certain libraries, as this will decrease the probability of expressing the protein of interest. In a genomic library prepared by randomly shearing the DNA and cloning into a vector, the probability that one would obtain an in frame fusion of a gene in the library to the signal sequence is low. Also, even where an in-frame fusion has been obtained, the chosen signal sequence may not work with all genes. For these reasons it may be preferable not to employ a signal sequence when screening a genomic DNA library, but rather to screen for the activity or presence of intracellular exogenous protein. Analysis of the activity or presence of intracellular proteins may be accomplished by pretreating the transformant library with enzymes that convert the fungal cells to protoplasts, followed by lysis. The procedure has been described by van Zeyl et al., *J. Biotechnol.* 59:221-224 (1997). This procedure has been applied to *Chrysosporium* to allow colony PCR from *Chrysosporium* transformants grown in microtiter plates.

Any signal sequence capable of permitting secretion of a protein from a *Chrysosporium* strain is envisaged. Such a signal sequence is preferably a fungal signal sequence, more preferably an Ascomycete signal sequence. Suitable signal sequences can be derived from eukaryotes generally, preferably from yeasts or from any of the following genera of fungi: *Aspergillus, Trichoderma, Chrysosporium, Myceliophthora, Pichia, Neurospora, Rhizomucor, Hansenula, Humicola, Mucor, Tolypocladium, Fusarium, Penicillium, Saccharomyces, Talaromyces* or alternative sexual forms thereof such as *Emericella* and *Hypocrea*. Signal sequences that are particularly useful are those natively associated with cellobiohydrolase, endoglucanase, beta-galactosidase, xylanase, pectinase, esterase, hydrophobin, protease or amylase. Examples include amylase or glucoamylase of *Aspergillus* or *Humicola*, TAKA amylase of *Aspergillus oryzae*, α-amylase of *Aspergillus niger*, carboxyl peptidase of *Mucor* (U.S. Pat. No. 5,578,463), a lipase or proteinase from *Rhizomucor miehei*, cellobiohydrolase of *Trichoderma*, beta-galactosidase of *Penicillium canescens* CBH1 from *Chrysosporium*, and the alpha mating factor of *Saccharomyces*.

Alternatively the signal sequence can be from an amylase or subtilisin gene of a strain of *Bacillus*. A signal sequence from the same genus as the host strain is extremely suitable as it is most likely to be specifically adapted to the specific host; thus when *Chrysosporium lucknowense* is the host, the signal sequence is preferably a signal sequence of *Chrysosporium*. *Chrysosporium* strains C1, UV13-6, NG7C-19 and UV18-25 secrete proteins in extremely large amounts, and signal sequences from these strains are of particular interest. Signal sequences from filamentous fungi and yeast may be useful, as well as signal sequences of non-fungal origin.

As yet another alternative, the exogenous gene in a library to be expressed can be fused to a fusion partner (fusion segment) to produce a fusion protein. Suitable fusion partners for use with the present invention include, but are not limited to, fusion partners that can: enhance a protein's stability; enhance or permit secretion of a protein from the host cell;

provide other enzymatic activity; and/or assist purification of a protein from a host cell (e.g., by affinity chromatography). A suitable fusion partner can be a protein or domain or fragment thereof of any size that has the desired function (e.g., imparts increased stability, solubility, action or activity; provides other enzymatic activity; and/or simplifies purification of a protein). Fusion partners can be joined to amino and/or carboxyl termini of the exogenous protein that is expressed by a DNA library, and can be susceptible to cleavage in order to enable straight-forward recovery of the expressed exogenous protein. The fusion partners are expressed in-frame with the heterologous protein in the expression cassette of the transformation vector. Preferred fusion partners for use in the present invention include any protein that is readily expressed by a fungal host cell of the present invention and which imparts the desired property to the fusion protein, and particularly, which enables or facilitates the secretion, screening and/or recovery of the protein. A variety of suitable proteins will be apparent for use in the present invention and include various fungal proteins, including, but not limited to, cellulases, xylanases, mannanases, mannosidases, pectinases, amylases, (e.g., glucoamylases, α-amylases), α- and β-galactosidases, α- and β-glucosidases, β-glucanases, chitinases, and chitosanases. In one embodiment, preferred fusion partners are small proteins or peptides and/or have high rates of secretion from the fungal host, which make them particularly useful for expression and screening of proteins expressed by complex DNA libraries. The fusion partner need not be a fungal protein, although such proteins may be preferred for stable expression in the host cells.

In the case of expression of multimeric proteins (e.g., proteins having two or more domains, subunits or components), it is not necessary to use the same fusion partner for expression of each domain, subunit or component of the protein. For example, fusion of a carrier with two separable domains can be used to express a multimeric protein such as an immunoglobulin. Alternatively each protein can be expressed fused to a different carrier partner. In yet another embodiment, two components of a multimeric protein expressed according to the invention can be fused to each other both with and without a fusion partner as described above.

The fusion construct as described above is preferably designed to include a protein-processing site (cleavage site), such as (but not limited to) a kex2 cleavage site. The presence of this site results in cleavage of the fusion partner from the protein expressed by the library insert, so that free proteins are produced. Such processing sites are not limited to kex2 cleavage sites, as other sequences can be used that will render the fusion protein susceptible to cleavage. In one embodiment of the invention, it is desirable to construct a DNA library so that the encoded proteins have limited or modified sequences that resemble the processing sites used in the fusion protein, in order to enhance stability and yields of the expressed protein. For example, DNA libraries for immunoglobulins can be modified in regions other than the variable region to be screened, to remove processing sites that might be targets for the fungal host proteases.

A transformed recombinant host fungus according to any of the embodiments of the invention, or particularly the vector used to transform the host fungus, can further comprise a selectable marker. Such a selectable marker permits selection of transformed or transfected cells. A selectable marker often encodes a gene product providing a specific type of resistance foreign to the non-transformed strain. This can be resistance to heavy metals, antibiotics or biocides in general. Prototrophy is also a useful selectable marker of the non-antibiotic variety. Auxotrophic markers generate nutritional deficiencies in the host cells, and genes correcting those deficiencies can be used for selection. Examples of commonly used resistance and auxotrophic selection markers are amdS (acetamidase), hph (hygromycin phosphotransferase), pyrG (orotidine-5'-phosphate decarboxylase), pyr4 (orotidine-5'-phosphate decarboxylase), pyrE (orotate phosphoribosyl transferase), pyr5 (orotate phosphoribosyl transferase), trpC (anthranilate synthase), argB (ornithine carbamoyltransferase), sC (sulphate adenyltransferase), bar (phosphinothricin acetyltransferase), niaD (nitrate reductase), Sh-ble (bleomycin-phleomycin resistance), mutant acetolactate synthase (sulfonylurea resistance), and neomycin phosphotransferase (aminoglycoside resistance). Preferred selection markers in *Chrysosporium* are pyr5 (orotate phosphoribosyl transferase) and pyr4 (orotidine-5'-phosphate decarboxylase). Selection can be carried out by cotransformation where the selection marker is on a separate vector or where the selection marker is on the same nucleic acid fragment as the protein-encoding sequence for the heterologous protein.

In a preferred embodiment, the expression/transformation vector includes at least two selectable markers. In a particularly preferred embodiment, described in more detail below, the transformation vector comprises two selectable markers, located flanking the expression cassette in the vector. The present inventors have found that this vector design is useful to select for transformants in which the entire expression cassette is integrated. During prolonged cultivation, integration of the expression vector into the genome occurs. When a single marker is used, portions of the expression cassette distal to the marker fail to integrate in a significant fraction of transformants. The use of two markers flanking the cassette ensures that the entire cassette integrates in most transformants A further improvement of the transformation frequency may be obtained by the use of the AMA1 replicator sequence (Autonomous Maintenance in *Aspergillus*), which can be useful, for example, in *Aspergillus niger* (Verdoes et al., *Gene* 146:159-165 (1994)). This sequence results in a 10- to 100-fold increase in the transformation frequency in a number of different filamentous fungi. Furthermore, in some embodiments, the introduced DNA can be retained autonomously in the fungal cells, in a multiple-copy fashion, without integration into the fungal genome. In some aspects of the invention, this may be beneficial for a high throughput screening method of the present invention, as the non-integrative state may reduce variations in the level of gene expression between different transformants (however, as described below, the inventors have designed novel vectors for use in the fungal hosts of the invention that allow for integration of vectors while reducing variation in the level of gene expression between different transformants). Moreover, as the introduced DNA is not recombined into the host DNA, no unwanted mutations in the host genome will occur. Uniform levels of exogenous gene expression may be obtained by use of autonomously replicating vectors such as AMA1. The Examples section below and U.S. Pat. No. 7,122,330 describe the production and use of a vector comprising an AMA1 replicator sequence. In the experiments described, this vector was not maintained in *C. lucknowense*. Accordingly, in applications where a non-integrating vector is preferred and *C. lucknowense* is the host cell, alternate strategies for improving transformation efficiency and maintenance of an autologous plasmid may be employed. However, it is anticipated that use of autonomously replicating vectors such as AMA1 will be useful in other fungal hosts.

In a preferred alternative, autonomous replication in fungi can be promoted by telomeric sequences (see e.g. A. Aleksenko and L. Ivanova, *Mol. Gen. Genet.* 1998 260:159-164.), although the invention is not limited to the use of telomeric sequences (other sequences that achieve the goal of autonomous replication may be employed). In particular, human and fungal telomeric sequences have been shown to promote autonomous replication and enhance transformation in various filamentous fungi like *A. nidulans* (Aleksenko and Ivanova, ibid.), *Nectria haematococca* (Kistler H C and Benny U. *Gene* 117, 81-89 (1992)), Podospora anserin (Javerzat J-P, Bhattacherjee V, Barreau C. *Nucleic Acids Research* 21, 497-504 (1993)) and *Fusarium oxysporum* (Powell W A, Kistler H C. *J. Bacteriol.* 172, 3163-3171 (1990).). The present inventors have used human telomeric sequences to develop dedicated exemplary vectors to obtain transformation frequencies that allow complex library construction in fungi. This has enabled the further development and optimization of an efficient DNA transfer protocol and its integration with a robotic handling system for high throughput screening in *C. lucknowense*. The use of telomeric sequences in the vector increased the number of transformants by 50-100-fold. The majority of transformants maintained the vector as a non-integrating linear DNA molecule, although after prolonged cultivation, the vector eventually integrated.

In a further improvement of the telomeric vector described above, the present inventors have designed a vector in which the promoter and terminator sequences are flanked by two selection markers to exclude integration events in which part of the linear vector is lost during integration. Using this vector and the appropriate selective medium, transformants having stable integration of a single copy of the vector within or near the end of the telomeric region of the host chromosomes was achieved with high frequency. These transformants are stable over several generations, even in the absence of selective conditions. Such transformants will result in a more uniform expression pattern of the expressed protein, which is highly desirable in high throughput screening assays. Accordingly, it is a further embodiment of the invention to construct expression vectors wherein the expression cassette is flanked by selectable markers.

Vectors that are particularly suitable for use in the expression and screening methods described herein also contain sequences that allow for replication and efficient transfer and/or selection of the vector to or from another host. In one embodiment, vectors useful in the invention are designed to be efficiently transferred to a bacterial phage or from a bacterial phage (or to and from another organism of interest). For example, in the immunoglobulin screening methods described herein, phage display libraries for immunoglobulins can be constructed using vectors that are readily used to generate derivative vectors used to transform fungal hosts as described herein, wherein the hosts are immediately ready for expression and screening using the methods described herein. Ideally, such vectors can be easily retrieved from the fungal host and used to identify the gene encoding the preferred protein or protein complex, allowing the creation and/or expression of the corresponding gene in the fungal host or in mammalian cells such as CHO cells to offer maximum flexibility for the creation and handling of DNA libraries and particularly, in evolution methods.

Yet another embodiment of the invention relates to vectors that allow specific integration into the fungal DNA of independent vectors expressing the different constituents of the protein complexes desired, using different mutually compatible selection markers for each of the independent vectors. A preferred embodiment in this approach is the use of mutant fungal host strains where the fraction of site-specifically integrated vector copies is improved by either reducing non-homologous recombination, such as by targeted or selected modification of genes involved in recombination processes (e.g., genes homologous to various genes found in *Neurosporra* and other fungi or other organisms e.g., Ku70, KU80 and Lig4; see Ishibashi et al., Proc Natl Acad Sci USA. 2006 Oct. 3; 103(40):14871-6 or Ninomiya et al., Proc Natl Acad Sci USA. 2004 Aug. 17; 101(33):12248-53), or by increasing homologous integration in strains. These integrative vector/strain combinations represent another approach to obtain strains with a more limited variation in expression level within the collection of transformants obtained in the library of libraries designed for multidomain protein expression. In a further embodiment, one can use such mutant strains with modified recombination abilities and produce further improved mutants that also have improved ability to maintain self replicating vectors that are used to transform such strains (e.g., by stabilizing integrative vectors and replicative vectors so that the strains are more stable and can be predictably and reproducibly transformed).

Figure 27:
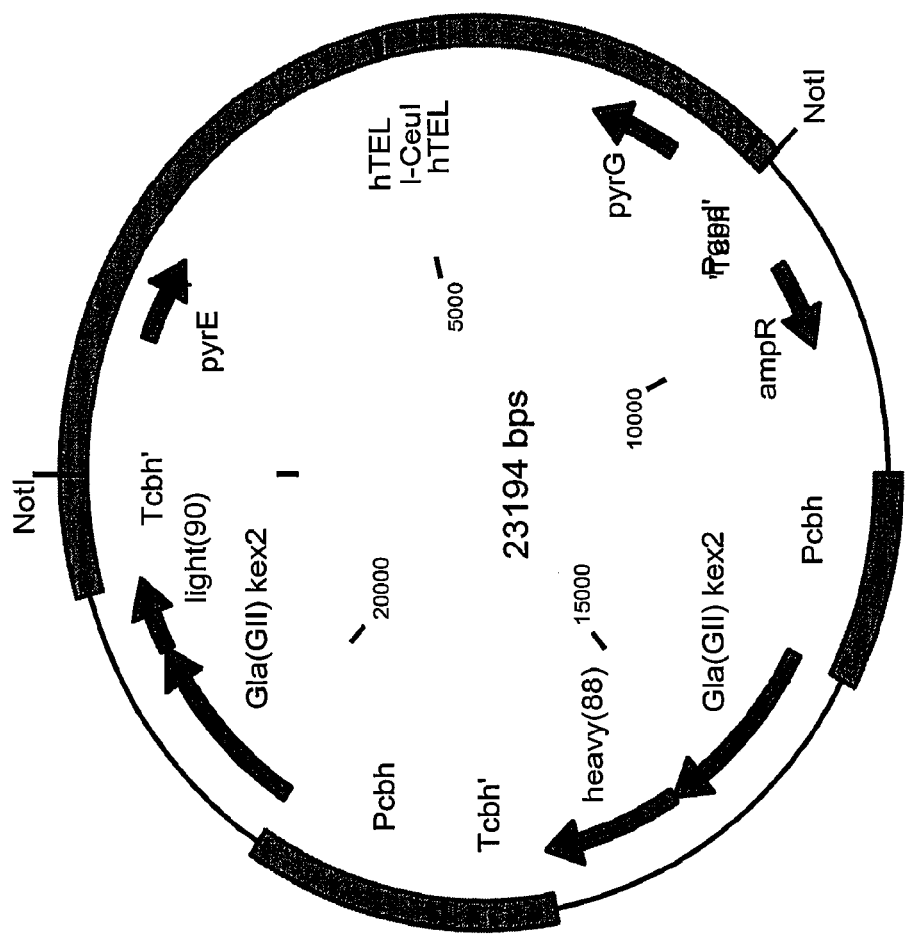
FIG. 27 shows a schematic of the vector Pcbh1 glaA(II) heavy (88) Tcbh1 Pcbh1 glaA(II) light (90) Tcbh1 pyrE tel pyrG. The sequence of the complete vector is represented as SEQ ID NO:10. The vector includes the following features at the indicated sequence locations within SEQ ID NO:10: 1-1324 pyrE flanking region; 1324-2171 pyrE; 3887-4217 pyrE flanking region; 4236-4811 hTEL; 4830-4834 I-CeuI; 4857-5432 hTEL; 5687-7030 pyrG flanking region; 7031-7932 pyrG; 7933-8498 pyrG flanking region; 8520-8703 Pgpd; 8704-8711 Tcbh1; 9500-10360 ampR; 11601-13397 Pcbh1; 13398-15286 Gla(GII) kex2; 15287-16730 heavy (88); 16731-17746 Tcbh1; 17757-19553 Pcbh1; 19554-21442 Gla (GII) kex2; 21443-22173 light (90); and 22173-23188 Tcbh'1.

Improved vectors and strains according to the present invention utilizing many of the approaches described above are described in detail in the Examples and the Figures. One example is the vector pPcbh1 glaA(II) heavy(88) Tcbh1 Pcbh1 glaA(II) light(90) Tcbh1 pyeE tel PyrG, which represents a vector comprising many of the elements described above as well as encoding the heavy and light chains of an immunoglobulin molecule as gla fusion proteins (FIG. 27). This vector was deposited at the Centraalbureau voor Schimmelcultures (CBS) in the Netherlands under the terms of the Budapest Treaty on the International Regulation of the Deposit of Microorganisms for the Purposes of Patent Procedure on Dec. 5, 2007, as *E. coli* JM109 containing the plasmid pPcbh1 glaA(II) heavy(88) Tcbh1 Pcbh1 glaA(II) light(90) Tcbh1 pyeE tel PyrG, Accession # CBS 122187.

This vector includes the heavy and light chain fusion proteins each flanked on one end by the cbh1 promoter and on the end by the cbh1 terminator sequence. Also included in the vector are the pyrE and pyrG selection markers flanking human telomeric sequences (tel). The complete nucleic acid sequence of pPcbh1 glaA(II) heavy(88) Tcbh1 Pcbh1 glaA(II) light(90) Tcbh1 pyeE tel PyrG is represented as SEQ ID NO:10. The coding sequence for the selection marker pyrE is represented as SEQ ID NO:13, and the corresponding pyrE amino acid sequence is represented as SEQ ID NO:14. The coding sequence for the selection marker pyrG is represented as SEQ ID NO:15, and the corresponding pyrG amino acid sequence is represented as SEQ ID NO:16. The vector also contains two copies of a human telomeric sequence (hTel), represented as SEQ ID NO:17. In some embodiments, vectors of the present invention comprise a fragment of hTel, wherein the fragment comprises nucleic acids 1-422 of SEQ ID NO:17. In some embodiments, the sequences encoding the immunoglobulin heavy and light chains (positions 15287 to 16730 and positions 21443 to 22173 of SEQ ID NO:10, respectively) may be removed from the vector and/or replaced with an additional protein-encoding sequence as described elsewhere in this application. The vector also includes two Gla fusion protein encoding sequences with kex2 cleavage sites (positions 13398 to 15286 and positions 19554 to 21442 of SEQ ID NO:10, respectively). Table C below lists the elements present in the vector and the positions of each within SEQ ID NO:10, as depicted in FIG. 27.

TABLE C

Elements of the vector Pcbh1 glaA(II) heavy (88) Tcbh1 Pcbh1 glaA(II) light (90) Tcbh1 pyrE tel pyrG.

| Element or Feature | Position within SEQ ID NO: 10 |
| --- | --- |
| pyrE flanking region | 1-1324 |
| pyrE | 1324-2171 |
| pyrE flanking region | 3887-4217 |
| hTel | 4236-4811 |
| I-CeuI | 4830-4834 |
| hTel | 4857-5432 |
| pyrG flanking region | 5687-7030 |
| pyrG complement | 7031-7932 |
| pyrG flanking region | 7933-8498 |
| Pgpd | 8520-8703 |
| Tcbh1 | 8704-8711 |
| Ampicillin resistance gene | 9500-10360 |
| Pcbh1 | 11601-13397 |
| Gla(GII) kex2 | 13398-15286 |
| Immunoglobulin heavy chain | 15287-16730 |
| Tcbh1 | 16731-17746 |
| Pcbh1 | 17757-19553 |
| Gla(GII) kex2 | 19554-21442 |
| Immunoglobulin light chain | 21443-22173 |
| Tcbh1 | 22173-23188 |

Exemplary vectors that are particularly useful for the expression and screening of complex proteins, such as immunoglobulins, are described herein. Such vectors are generally characterized as being self-replicating vectors (but also include integrating and non-integrating vectors, as well as vectors that are initially maintained as autonomous vectors but will integrate after extended periods of cultivation), comprising promoter and terminator sequences as described above, selectable marker sequences as described above, and other sequences useful for allowing replication in E. coli, yeast, and/or efficient transfer to and/or from a bacterial phage. Particularly preferred vectors for use in the expression and screening of complex libraries as described herein further include telomeric sequences as described above, although any sequence that improves transformation efficiency and stability of a vector can be used. Other particularly preferred vectors include the use of double dominant selection markers flanking the expression cassette, resulting in stable transformants with uniform expression as described above. The vectors preferably contain one or more cloning sites for cloning of the DNA from an expression DNA library which is linked to a sequence encoding a fusion partner for production and appropriate expression (e.g., secretion) of fusion proteins by the vector (described above).

Figure 19:
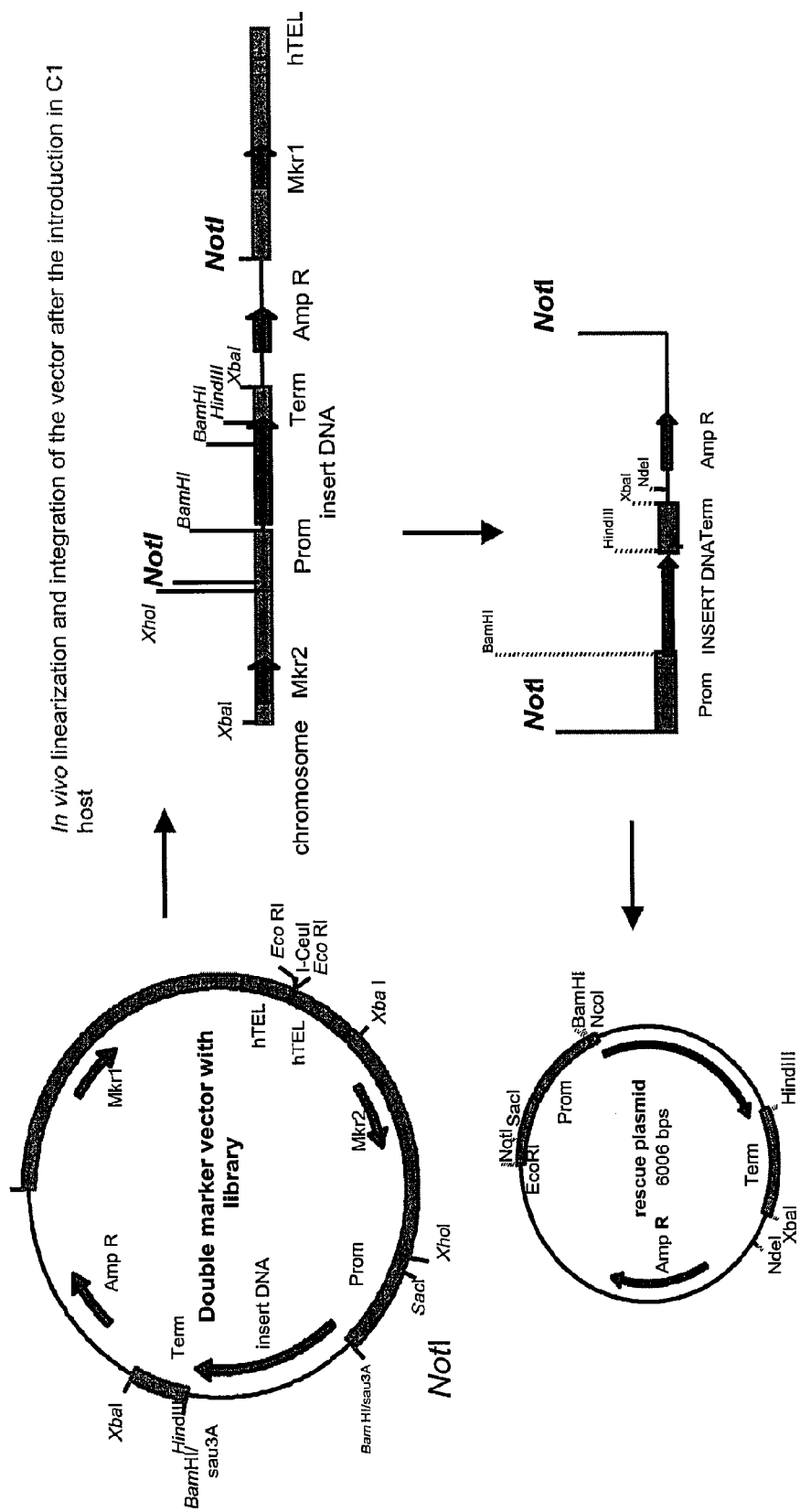

An example of a preferred self-replicating vector for use in the expression and screening of large and/or complex libraries (e.g., combinatorial libraries) is illustrated in FIG. 1 and also in FIG. 19. In one embodiment, such an exemplary vector comprises an expression cassette for expression of the DNA library insert including promoter and terminator sequences (which can optionally include DNA encoding a fusion partner as described above so that the insert is expressed as a fusion protein), selectable markers flanking the expression cassette, restriction enzyme sites to facilitate excision and recovery of the expression cassette, telomeric sequences to enhance transformation efficiency and stability, and optionally, sequences allowing for expression and selection in another host organism, such as E. coli.

Figure 12:
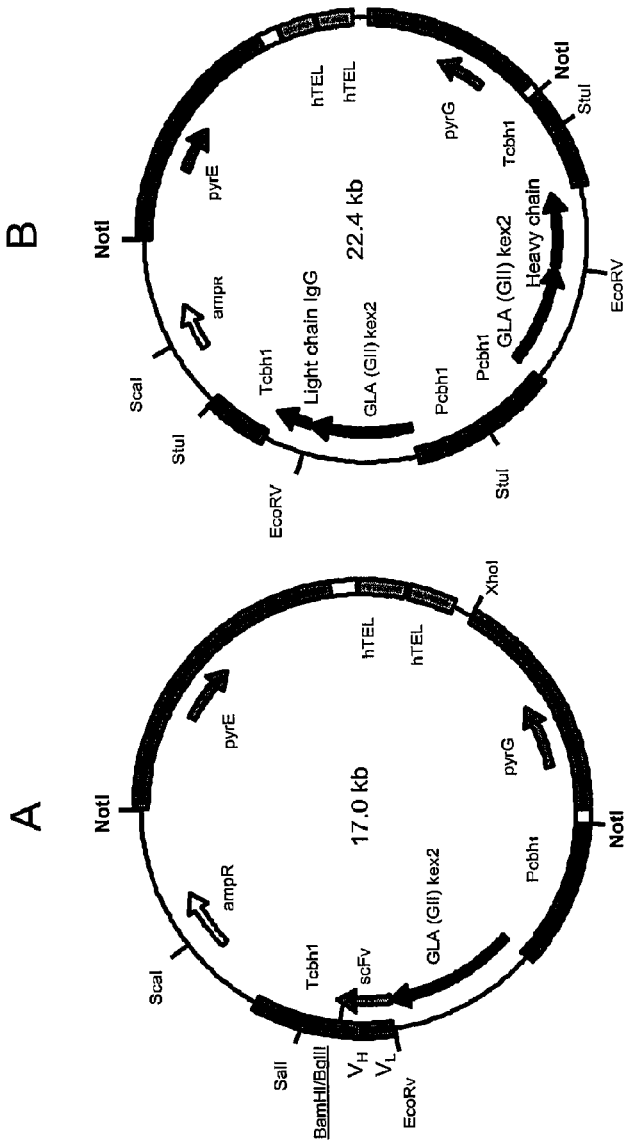

Additional preferred vectors used in the expression and screening for protein complexes containing two or more heterogeneous components, such as immunoglobulins, are illustrated in FIG. 12. While these figures illustrate the use of the vector to express the heavy and light chains of immunoglobulins, it will be apparent that sequences encoding proteins for other complex proteins (e.g., other heteromultimeric receptors) could be used in such vectors and with similar vector designs. FIG. 12A shows a vector in which libraries of immunoglobulin heavy and light chain variable regions ($V_H$ and $V_L$, respectively) are together cloned into a C. lucknowense-specific replicating vector so that glucoamylase fusions to a single-chain Fv are produced. FIG. 12B shows a vector in which full length antibody chains are expressed as glucoamylase fusions, each from their own promoter. Numerous possibilities exist for the latter vector. The light and heavy chains could be placed in either order in either orientation. Additionally, although both chains in this figure are shown utilizing cbh1 promoter and terminator sequences, distinct promoters and terminators could be used to minimize repetitive sequences in the vector. Also, in addition to using individual expression cassettes for the light and heavy chains, the light and heavy chains could be fused at the gene level, introducing processing sites between the carrier and the different chains (e.g., see FIG. 14). In addition, as discussed above, the fusion partner is not limited to glucoamylase, as many other suitable fusion partners could be utilized. In addition, fusion protein processing sites can be introduced to allow for cleavage of the expressed protein from the fusion partner. The vectors use human telomeric sequences (hTel) for replication in C1 and contain two selective markers pyrE and pyrG flanking the expression constructs, and sequences allowing replication in E. coli. Again, the selectable markers and telomeric sequences can be modified based upon vector design and host fungus. In addition, the vector can be designed to include additional elements to facilitate the transfer of the vector from a fungal host to a bacterial phage and/or from a bacterial phage to the fungal host (e.g., using Gateway® technology; see Examples and FIGS. 14-18).

Figure 20:
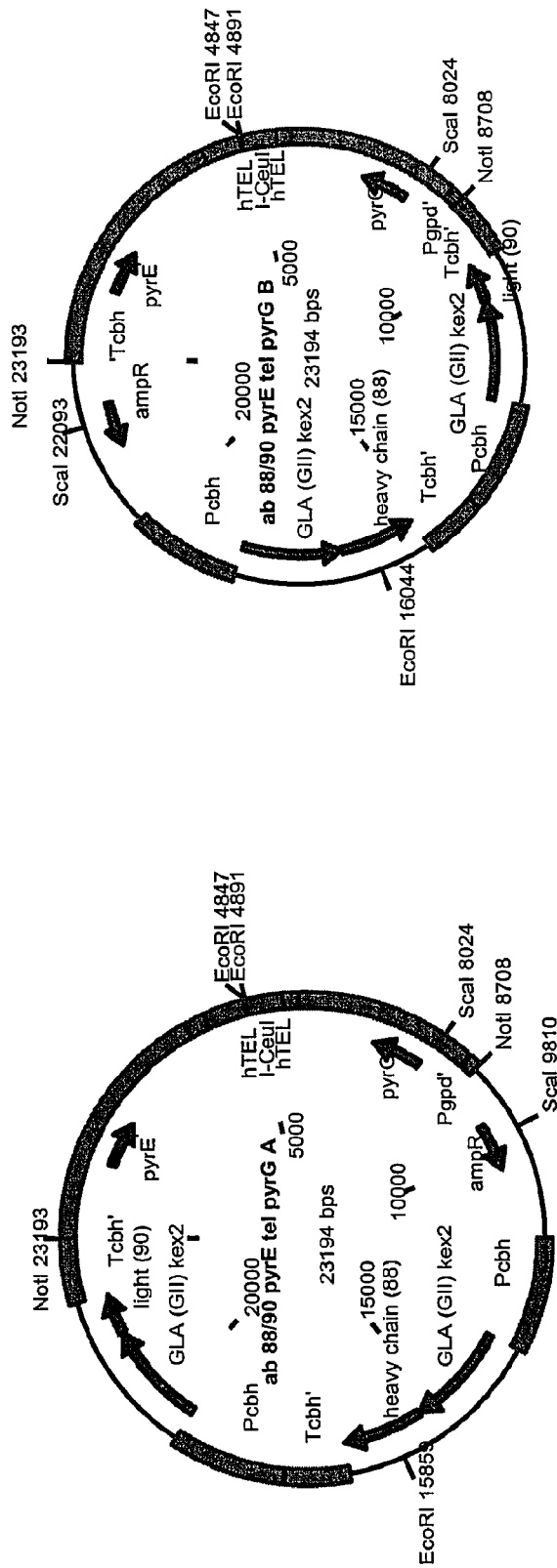
Figure 22:
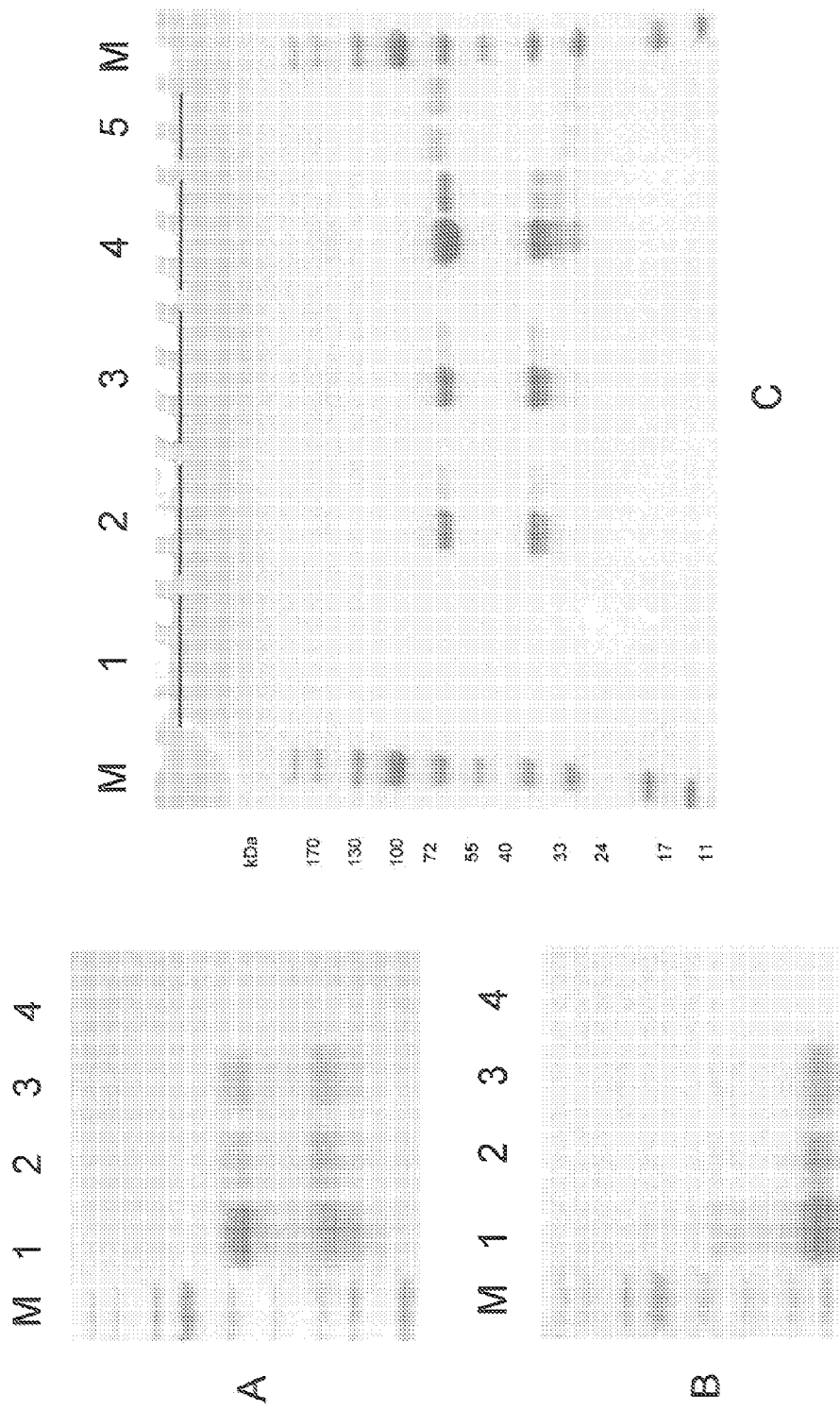
Figure 24:
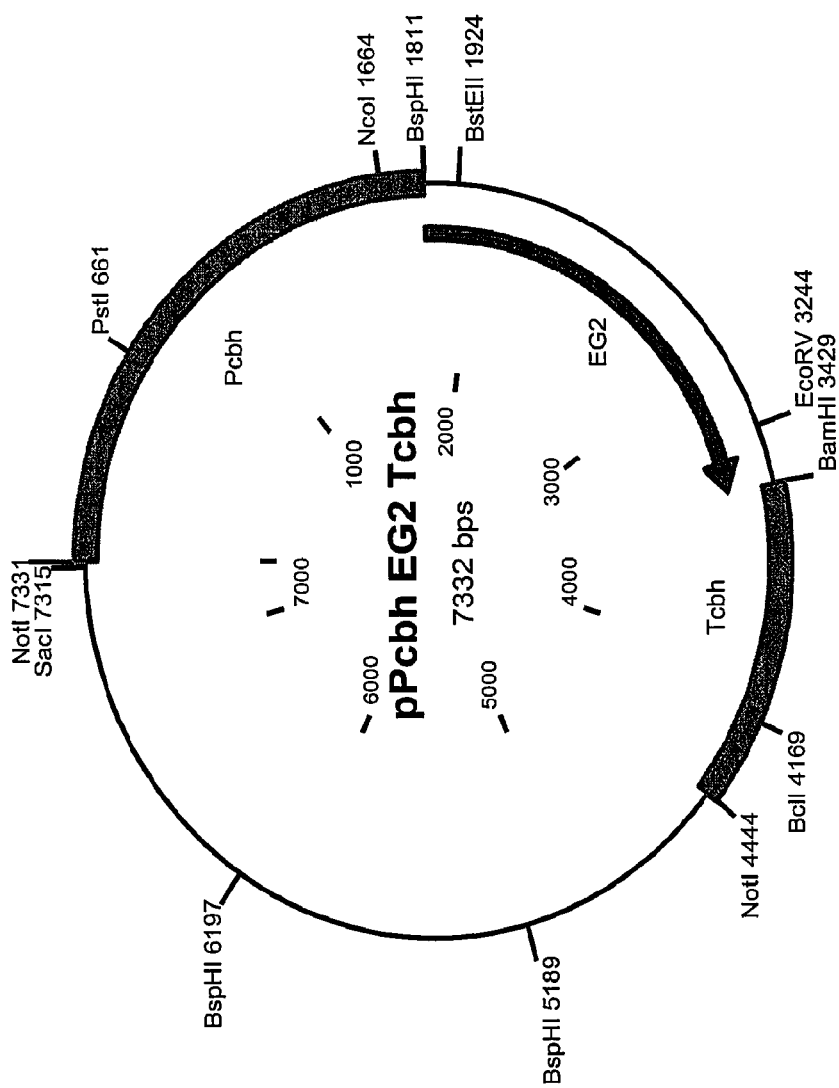
FIG. 24 shows a schematic representation of the eg2 expression vector Pcbh-eg2-Tcbh.

Additional examples of preferred vectors used in the expression and screening for protein complexes containing two or more heterogeneous components, such as immunoglobulins, are illustrated in FIG. 20.

In these examples, upon introduction into C. lucknowense, the vectors spontaneously linearize between the human telomeric sequences (hTel). The use of doubly marked pyr4-pyr5 mutants of C1 ensures that integrants contain the entire expression construct. Individual transformants are then separated and screened for binding in a high-throughput fashion. The expression constructs from transformants of interest can be isolated by purifying genomic DNA from those constructs, digesting with NotI, ligating to recircularize, then transforming E. coli and selecting for ampicillin resistance. The resulting E. coli transformants will contain plasmids carrying the antibody expression construct. In the case where full-length antibodies are screened, the expression constructs can be subcloned directly into expression vectors to allow high-level expression of the antibodies as described herein. When a single-chain Fv is used in the expression screening, the plasmids can be deconstructed and relevant sequences spliced into full-length heavy and light chains for expression as described elsewhere herein.

Libraries and Proteins for Expression and Screening

As used herein the term "heterologous protein" is a protein or polypeptide not normally expressed or secreted by the host strain used for expression and screening according to the invention. A heterologous protein can also include proteins that are native to the host strain, species, or genus, but that are under the control of a promoter other than its own and/or in a different genomic locus. A heterologous protein may be of prokaryotic origin, or it may be derived from a virus, fungus, plant, insect, or higher animal such as a mammal. For pharmaceutical screening purposes, quite often a preference will exist for human proteins, thus a preferred embodiment will be a host wherein the DNA library is of human origin. Such embodiments are therefore also considered suitable examples of the invention.

The present inventors have found that the fungal systems for expression and screening of DNA libraries described herein is useful not only to express and screen simple, monomeric proteins, but also to express and screen more complex proteins and/or protein complexes (heterogeneous or heteromultimeric proteins). For example, a particularly useful embodiment of the present invention is the screening of complex, combinatorial DNA libraries, where the protein expressed by the DNA is composed of two or more domains, constituents or subunits. Exemplary proteins that can be expressed and screened by such combinatorial libraries (libraries of libraries) include, but are not limited to, a variety of heterodimeric or heteromultimeric receptors and proteins, such as members of the immunoglobulin supergene family (e.g., immunoglobulin, major histocompatibility complex, T cell receptors, CD3, adhesion molecules), hormones and hormone receptors, cytokines and cytokine receptors, other growth factors and growth factor receptors, etc. Many of these proteins are involved in the regulation of significant physiological processes, and the ability to study these processes and design or identify diagnostic and therapeutic reagents based on the properties of such proteins has far reaching value, particularly in the area of clinical applications.

In one preferred embodiment of the present invention, the heterologous protein to be expressed and screened for using the fungal system described herein is an immunoglobulin (antibody). According to the present invention, immunoglobulins or antibodies are characterized in that they comprise immunoglobulin domains and as such, they are members of the immunoglobulin superfamily of proteins. Generally speaking, an antibody molecule comprises two types of chains, although heavy chain antibodies as produced in llamas are a different type of antibody molecule consisting of one type of chain. For most antibodies, one type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda (λ) and kappa (κ) chains. In contrast, there are five major H chain classes referred to as isotypes. The five classes include immunoglobulin M (IgM or μ), immunoglobulin D (IgD or δ), immunoglobulin G (IgG or γ), immunoglobulin A (IgA or α), and immunoglobulin E (IgE or ε). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 (γ1), IgG2 (γ2), IgG3 (γ3) and IgG4 (γ4), and two subclasses of IgA including IgA1 (α1) and IgA2 (α2).

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains ($C_H1$, $C_H2$, $C_H3$) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a $C_{H+L}$ region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as an Fab, an Fab', or an F(ab')2 fragment. A fragment lacking the ability to bind to antigen is referred to as an Fc fragment. An Fab fragment comprises one arm of an immunoglobulin molecule containing a L chain ($V_L+C_L$ domains) paired with the $V_H$ region and a portion of the $C_H$ region ($C_H1$ domain). An Fab' fragment corresponds to an Fab fragment with part of the hinge region attached to the $C_H1$ domain. An F(ab')2 fragment corresponds to two Fab' fragments that are normally covalently linked to each other through a di-sulfide bond, typically in the hinge regions.

The $C_H$ domain defines the isotype of an immunoglobulin and confers different functional characteristics depending upon the isotype. For example, μ constant regions enable the formation of pentameric aggregates of IgM molecules and a constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments that somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

In one embodiment, immunoglobulin DNA libraries useful in the present include libraries encoding humanized antibodies. Humanized antibodies are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. Humanized antibodies can be produced, for example, by modeling the antibody variable domains, and producing the antibodies using genetic engineering techniques, such as CDR grafting (described below). A description various techniques for the production of humanized antibodies is found, for example, in Morrison et al. (1984) *Proc. Natl. Acad. Sci. USA* 81:6851-55; Whittle et al. (1987) *Prot. Eng.* 1:499-505; Co et al. (1990) *J. Immunol.* 148:1149-1154; Co et al. (1992) *Proc. Natl. Acad. Sci. USA* 88:2869-2873; Carter et al. (1992) *Proc. Natl. Acad. Sci.* 89:4285-4289; Routledge et al. (1991) *Eur. J. Immunol.* 21:2717-2725 and PCT Patent Publication Nos. WO 91/09967; WO 91/09968 and WO 92/113831. Such techniques may be used in connection with the expression and screening methods described herein to produce and select optimized or evolved humanized antibodies.

The invention is especially useful for the expression and screening of genetically-engineered antibodies or antigen binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies). Genetically engineered antibodies include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source as compared to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

For example it is possible to clone a particular antibody and then identify the variable region genes encoding the desired antibody, including the sequences encoding the CDRs. From here, modified antibodies and antigen binding fragments can be engineered by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell as described herein, in which expression of the antibody will occur and in which the expressed antibodies can be screened for a desirable characteristic, which is typically antigen binding. There are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in the aforementioned European Patent Applications. Methods, employing, for example, phage display technology (see for example U.S. Pat. No. 5,969,108, U.S. Pat. No. 5,565,332, U.S. Pat. No. 5,871,907, U.S. Pat. No. 5,858,657) or the selected lymphocyte antibody method of U.S. Pat. No. 5,627,052 may also be used for the production of antibodies and/or antigen fragments of the invention, as will be readily apparent to the skilled individual. These methods can be used to engineer DNA libraries suitable for expression and screening in conjunction with the fungal systems described herein.

Antibodies to be expressed and screened using the expression and screening systems and methods of the present invention can include whole antibodies (e.g., monoclonal. antibodies), as well as functional equivalents of whole antibodies, such as antigen binding fragments in which one or more antibody domains are truncated or absent (e.g., Fv, Fab, Fab', or F(ab')2 fragments, CH fragments, Fc fragments), as well as genetically-engineered antibodies or antigen binding fragments thereof, including single chain antibodies, heavy chain antibodies, humanized antibodies (discussed above), antibodies that can bind to more than one epitope (e.g., bi-specific antibodies), or antibodies that can bind to one or more different antigens (e.g., bi- or multi-specific antibodies). Antibodies useful in the invention include catalytic antibodies (e.g., antibodies which exhibit catalytic activity; see *Catalytic Antibodies*, Ehud Keinan (Editor), ISBN: 3-527-30688-9, January 2005), neutralizing antibodies, and any antibody type or derivative or fragment thereof that is useful in any research, diagnostic, therapeutic, or other clinical application.

Antibodies and fragments or functional equivalents thereof, as discussed above, may be from any species. Examples include human, mouse, rat, goat, hamster, sheep, horse, monkey, llama and the like. The structure of antibodies and the production thereof in these species are well known in the art.

As another example of the use of the invention to screen for complex proteins, a heterologous protein can include a major histocompatibility protein (MHC), expressed alone or more preferably, in complex with a library of peptides. The identification of peptide epitopes associated with particular T cell receptors is often still a bottle neck in studying T cells and their antigenic targets in, for example, autoimmunity, hypersensitivity, and cancer. In many clinical situations, when pathological T cells are identified, only the major histocompatibility complex (MHC), but not the specific peptide portion of the antigen that is recognized by the T cell, is known. Having a rapid method to identify these peptides would aid in the identification of the protein source of the antigens driving the T cell responses. These peptides would help also in creating tools to monitor the frequency and functional state of the T cells as well as the development of therapeutic reagents to control them.

MHC proteins are generally classified into two categories: class I and class II MHC proteins. An MHC class I protein is an integral membrane protein comprising a glycoprotein heavy chain, also referred to herein as the α chain, which has three extracellular domains (i.e., $\alpha_1$, $\alpha_2$ and $\alpha_3$) and two intracellular domains (i.e., a transmembrane domain (TM) and a cytoplasmic domain (CYT)). The heavy chain is non-covalently associated with a soluble subunit called β2-microglobulin (β2m). An MHC class II protein is a heterodimeric integral membrane protein comprising one α chain and one β chain in noncovalent association. The α chain has two extracellular domains ($\alpha_1$ and $\alpha_2$), and two intracellular domains (a TM domain and a CYT domain). The β chain contains two extracellular domains ($\beta_1$ and $\beta_2$), and two intracellular domains (a TM domain and CYT domain). Many human and other mammalian MHC molecules are well known in the art and any MHC Class I or Class II molecules can be used in the present invention. MHC molecules are cell surface receptors that complex with peptides, the complex of which can be recognized by a T cell receptor. A peptide binding groove of a class I protein can comprise portions of the $\alpha_1$ and $\alpha_2$ domains of the heavy chain capable of forming two β-pleated sheets and two α helices. Inclusion of a portion of the β2-microglobulin chain stabilizes the complex. While for most versions of MHC Class II molecules, interaction of the α and β chains can occur in the absence of a peptide, the two chain complex of MHC Class I is unstable until the binding groove is filled with a peptide. A peptide binding groove of a class II protein can comprise portions of the $\alpha_1$ and $\beta_1$ domains capable of forming two β-pleated sheets and two α helices. A first portion of the $\alpha_1$ domain forms a first β-pleated sheet and a second portion of the $\alpha_1$ domain forms a first α helix. A first portion of the $\beta_1$ domain forms a second β-pleated sheet and a second portion of the $\beta_1$ domain forms a second α helix. The X-ray crystallographic structure of class II protein with a peptide engaged in the binding groove of the protein shows that one or both ends of the engaged peptide can project beyond the MHC protein (Brown et al., pp. 33-39, 1993, Nature, Vol. 364). Thus, the ends of the $\alpha_1$ and $\beta_1$ α helices of class II form an open cavity such that the ends of the peptide bound to the binding groove are not buried in the cavity. Moreover, the X-ray crystallographic structure of class II proteins shows that the N-terminal end of the MHC β chain apparently projects from the side of the MHC protein in an unstructured manner since the first 4 amino acid residues of the β chain could not be assigned by X-ray crystallography. Methods of linking peptides to MHC complexes, which could be developed to create libraries for use in the present invention, is described, for example, in U.S. Pat. No. 5,820,866.

The present invention is useful for effectively and efficiently creating, developing, and selecting reagents useful in vaccines. The vaccines comprise one or more antigens or antibodies or fragments thereof that can be identified, designed and/or developed/evolved using the expression and screening systems described herein. Indeed, the expression and screening system of the invention will allow the identification, creation and production of large quantities of vaccines in a more cost-effective and time-effective (short timeframe) manner than currently available methods for vaccine production. Vaccines to be produced using the methods of the invention include vaccines for any conventional or adapted use, and include both prophylactic and therapeutic vaccines.

When it is desirable to stimulate an immune response, the term "antigen" can be used interchangeably with the term "immunogen", and is used herein to describe a protein, peptide, cellular composition, organism or other molecule which elicits a humoral and/or cellular immune response (i.e., is antigenic), such that administration of the immunogen to an animal (e.g., via a vaccine of the present invention) mounts an antigen-specific immune response against the same or similar antigens that are encountered within the tissues of the animal. Therefore, to vaccinate an animal against a particular antigen means, in one embodiment, that an immune response is elicited against the antigen or immunogenic or toleragenic portion thereof, as a result of administration of the antigen. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a therapeutic composition of the present invention can be any detectable change in any facet of the immune response (e.g., cellular response, humoral response, cytokine production), as compared to in the absence of the administration of the vaccine.

An immunogenic domain (portion, fragment, epitope) of a given antigen can be any portion of the antigen (i.e., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, in the case of a humoral response.

An epitope is defined herein as a single immunogenic site within a given antigen that is sufficient to elicit an immune response, or a single toleragenic site within a given antigen that is sufficient to suppress, delete or render inactive an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions) depending on the type of immune response. An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms).

These are only a few exemplary uses for the expression and screening of DNA libraries for complex proteins described herein. One can readily use the tools and system described herein to screen other libraries for the development and identification of therapeutically and clinically important proteins.

Expression of a library of human genes, derived from a genomic human DNA library, in the filamentous fungi of the invention is expected to be efficient for several reasons. It is now known that the average size of human genes is 3,000-5,000 bp, and that human introns average about 75 to about 150 bp (total range 40→50,000). Filamentous fungi have introns of 40-75 bp, but they can deal with introns up to 500 bp in length. On average, human genes carry 3-5 introns per gene (M. Deutsch, M. Long, Nucl. Acids Res. 1999 27:3219-3228; Table D). Human signal sequences are also known to function in filamentous fungi. For these reasons, it is likely that a large number of human genes can be expressed and secreted at high levels by the methods of this invention.

TABLE D

| Organism | Introns per gene | Average intron size (nt) (range) | Intron structure |
|---|---|---|---|
| Animal/Plant | 3-5 | 75-150 (40->50000) 80% under 150 nt | GTnnGt . . . CtxAC . . . yAG |
| Fungi | 3 | 40-75 (40-500) | GTAnGy . . . CtxAC . . . yAG |
| Yeast | 0.01 | 50-60 (?-?) | GTATGT . . . TACTAAC . . . yAG |

The methods of the invention are thus expected to be useful for expression of DNA libraries derived from both prokaryotic and eukaryotic genomes. Indeed, as described herein, the inventors have demonstrated the use of the antibody to express and screen for human immunoglobulin proteins as well as other proteins such as enzymes. As described above, the methods are capable of expression and discovery of both secreted and intracellular proteins, giving ready access to an extremely large number of genes and proteins.

A further aspect of the invention includes the construction and screening of fungal mutant libraries, and fungal mutant libraries prepared by the methods disclosed herein. The libraries may be obtained by transformation of the fungal hosts according to this invention with any means of integrative or non-integrative transformation, using methods known to those skilled in the art. This library of fungi based on the preferred host strains may be handled and screened for desired properties or activities of exogenous proteins, including any heterologous proteins described herein, in miniaturized and/or high-throughput format screening methods. By property or activity of interest is meant any physical, physicochemical, chemical, biological, or catalytic property, or any improvement, increase, or decrease in such a property, associated with an exogenous protein of a library member. The library may also be screened for metabolites or for a property or activity associated with a metabolite, produced as a result of the presence of exogenous and/or endogenous proteins. The library may also be screened for fungi producing increased or decreased quantities of such protein or metabolites.

In another aspect of this invention, the library of transformed fungi may be screened for the presence of fungal metabolites having desirable properties. Examples of such metabolites include polyketides, alkaloids, and terpenoid natural products. It is anticipated that multiple genes or gene clusters (operons) may be transferred to the host cells of the invention, and that non-protein products generated by the action of the encoded enzymes will then be generated in the host cells. For example, it has been shown that DNA encoding the proteins necessary for production of lovastatin can be transferred to *Aspergillus oryzae* (U.S. Pat. No. 5,362,638; see also U.S. Pat. No. 5,849,541).

In another embodiment of the invention, the library of transformed fungi may be screened for the presence of DNA that hybridizes to a nucleic acid probe of interest. In this embodiment, expression and/or secretion of exogenous proteins is not essential, although it will often still be desirable. Where protein expression is not needed, it will be appreciated that regulatory sequences are not needed in the vector.

In yet another embodiment of the invention, the library of transformed fungi may be screened for some desirable property of the fungi themselves, such as for example tolerance to a physically or chemically extreme environment, or the ability to produce, modify, degrade or metabolize a substance of interest. Such desirable properties may or may not be ascribable to the presence of a single exogenous protein. This embodiment will be of particular utility when employed as part of a process of directed evolution.

The heterologous DNA may be genomic DNA or cDNA, prepared from biological specimens by methods well known in the art. The biological specimen may be an environmental sample (for example, soil, compost, forest litter, seawater, or fresh water), or an extracted, filtered, or centrifuged or otherwise concentrated sample therefrom. Mixed cultures of microorganisms derived from environmental samples may be employed as well. The biological sample may also be derived from any single species of organism, such as a cultured microorganism, or plant, insect, or other animal such as a mammal. In addition, the heterologous DNA may be synthetic or semi-synthetic, for example random DNA sequences or DNA comprising naturally-occurring segments which have been shuffled, mutated, or otherwise altered or engineered. An example of a semi-synthetic nucleic library is found in Wagner et al., WO 00/0632. DNA from environmental samples (or mixed cultures derived therefrom) will be advantageous for the discovery of novel proteins, while the use of DNA from a single species will be advantageous in that (1) an appropriate vector may be more judiciously chosen, and (2) the practitioner will be directed to related or similar species for further screening if a protein of interest is identified. Genetically engineered libraries can include libraries from a variety of sources, and can include combinatorial libraries as described herein.

The heterologous DNA used in the libraries can be further modified to increase the efficiency of expression and screening of the proteins in the fungal system. For example, the DNA libraries can be optimized for the codon usage of the fungal host. In addition, as discussed above, heterologous DNA can be engineered to minimize the presence of processing sites, or when fusion proteins are created that include processing sites, the sites can be engineered to avoid sites that may be similar or duplicated in the heterologous DNA, to avoid inadvertent processing of the heterologous protein. The heterologous DNA can be engineered to reduce glycosylation sites or to result in perfectly glycosylated proteins when produced by the fungal host.

Compared to traditional fungal hosts, transformation, expression and secretion rates are exceedingly high when using a *Chrysosporium* strain exhibiting the compact mycelial morphology of strain UV18-25, and mutants thereof. Thus a recombinant strain according to the invention will preferably exhibit such morphology. The invention however also covers non-recombinant strains or otherwise engineered strains of fungi exhibiting this characteristic.

An attractive embodiment of the invention would employ a recombinant *Chrysosporium* strain exhibiting a viscosity below that of strain NG7C-19, preferably below that of UV18-25 under corresponding or identical culture conditions. We have determined that the viscosity of a culture of UV18-25 is below 10 cP as opposed to that of previously known *Trichoderma reesei* being of the order 200-600 cP, and with that of traditional *Aspergillus niger* being of the order 1500-2000 cP under optimal culture conditions during the middle to late stages of fermentation. Accordingly the invention may employ any engineered or mutant filamentous fungus exhibiting this low-viscosity characteristic, such as the *Chrysosporium* UV18-25 (VKM F-3631D) strain, the *Trichoderma* X 252 strain, or A. sojae pclA (derived from ATCC 11906) or *A. niger* pclA.

The fluidity of filamentous fungal cultures can vary over a wide range, from nearly solid to a free-flowing liquid. Viscosity can readily be quantitated by Brookfield rotational viscometry, use of kinematic viscosity tubes, falling ball viscometer or cup type viscometer. Fermentation broths are non-Newtonian fluids, and the apparent viscosity will be dependent to some extent upon the shear rate (Goudar et al., *Appl. Microbiol. Biotechnol.* 1999 51:310-315). This effect is however much less pronounced for the low-viscosity cultures employed in the present invention.

METHODS OF THE INVENTION

The improved vectors and protease-deficient fungal strains discussed above greatly increase the efficiency of the screening and expression of proteins, particularly proteins expressed by complex DNA libraries. Accordingly, the present invention includes the screening and expression methods described below wherein either an improved vector or a fungus described above (or a combination thereof) is employed to express or screen for a protein or plurality of proteins. The improved vectors and fungal strains described above also allow for the expression and screening of DNA libraries not only to express and screen simple, monomeric proteins, but also to express and screen more complex proteins and/or protein complexes (heterogeneous or heteromultimeric proteins).

The use of such low viscosity cultures in the screening of an expression library according to the method of the invention is highly advantageous. The screening of DNA libraries expressed in filamentous fungi has heretofore been limited to relatively slow and laborious methods. In general, once fungi have been transformed (and the transformants optionally selected for), it has been necessary to prepare spores or conidia, or to mechanically disrupt the mycelia, in order to disperse the library of transformed fungi into individual organisms or reproductive elements. This dispersal is necessary so that the separated organisms can be cultured into clonal colonies or cultures. The spores, conidia, or mycelial fragments are then diluted and "plated out" in standard culture dishes, and the individual colonies are inspected for color, alterations to the substrate, or other detectable indication of the presence of the protein activity or property being sought. In another approach, secreted proteins are blotted from the colonies onto a membrane, and the membrane is probed or examined for an indication of the presence of the protein activity or property of interest. Use of membranes has proved useful where proteolytic degradation of exogenous protein is a problem (Asgeirsdottir et al., *Appl. Environ. Microbiol.* 1999, 65:2250-2252). Such procedures are labor-intensive and have not proven amenable to automation, and as a result high-throughput screening of fungally-expressed proteins has not heretofore been accomplished with conventional filamentous fungi. For purposes of this disclosure, high-throughput screening refers to any partially- or fully-automated screening method or process to search through large or fairly large numbers of substances for desired activity, resulting in less costly and faster processes. In one aspect, high-throughput screening refers to any partially- or fully-automated screening method that is capable of evaluating the proteins expressed by at least about 2, 3, 4, 5, 6, 7, 8, 9 or 10, or more transformants per day, about 100 or more transformants per day, about 250 or more transformants per day, about 500 or more transformants per day, about 750 or more transformants per day, about 1,000 or more transformants per day, and particularly to those methods capable of evaluating 5,000 or more transformants per day, and most particularly to methods capable of evaluating 10,000 or more transformants per day. The invention, however, is not limited to screening large or very large numbers of transformants. For example, the present invention is highly useful for expression and screening of smaller libraries of proteins that have been pre-secreend by another method (e.g., phage display), followed by production of libraries of pre-screened libraries. The present invention enables the identification of the best candidate proteins from a library of any size, including very small to very large.

The automated high-throughput screening of a library of transformed fungi according to the present invention, accordingly, may be carried out in a number of known ways. Methods that are known to be applicable to bacteria or yeast may in general be applied to the low-viscosity fungi of the present invention. This is made possible by the presence of transferable reproductive elements in combination with the low-viscosity phenotype, a consequence of the relatively non-entangled morphology of the hyphae of the mutant fungi employed. In essence, the mutant fungi, and/or their transferable reproductive elements, behave very much like individual bacteria or yeast during the mechanical manipulations involved in automated high-throughput screening. This is in contrast to wild-type fungi, and most industrially-adapted fungi as well, which produce highly entangled mycelia which do not permit the ready separation of the individual organisms from one another.

For example, a dilute suspension of transformed fungi according to the present invention may be aliquotted out through a mechanical micropipette into the wells of a 96-well microplate. It is anticipated that liquid-handling apparatus capable of pipetting into 384- or 1536-well microplates can also be adapted to the task of automated dispersal of the organisms into microplates. The concentration of the suspended organisms can be adjusted as desired to control the average number of organisms (or other transferable reproductive elements) per well. It will be appreciated that where multiple individual organisms are aliquotted into wells, the identification of the desired protein activity or property in that well will be followed by dilution of the contents of the well and culturing the organisms present into individual clonal colonies or cultures. In this manner the throughput of the system may be increased, at the cost of the need for subsequent resolution of the contents of each well that presents a "hit".

In addition, transformed fungi according to the present invention may also be grown and/or screened in larger culture plates, test tubes, shake flasks, small fermentors, etc. to obtain higher protein quantities than from micro titer wells.

In an alternative embodiment, a cell sorter may be interposed in the fluid path, which is capable of directing the flow of the culture to the wells of the microplate upon the detection of an organism or other transferable reproductive element in the detector cell. This embodiment permits the reasonably accurate dispensation of one organism per well. The use of an optically-detectable marker, such as green fluorescent protein, to identify transformants is particularly useful in this embodiment, as it permits the automated selection of transformants by a fluorescence-activated cell sorter.

In yet another embodiment, colonies growing on solid media can be picked by a robotic colony picker, and the organisms transferred by the robot to the wells of a microtiter plate. Well-separated colonies will give rise to single clones in each well.

The dispersed organisms are then permitted to grow into clonal cultures in the microplate wells. Inducers, nutrients, etc. may be added as desired by the automated fluid dispensing system. The system may also be used to add any reagents required to enable the detection of the protein activity or property of interest. For example, chomogenic or fluorogenic substrates can be added so as to permit the spectroscopic or fluorometric detection of an enzyme activity. The low viscosity and submerged growth properties of the cultures in the wells of a microtiter plate permit the rapid diffusion of such reagents into the culture, greatly enhancing the sensitivity and reliability of the assay. Diffusion of oxygen and nutrients is also greatly enhanced, facilitating rapid growth and maximal expression and secretion of exogenous peptides. Certain assays, such as the scintillation proximity assay, rely on the diffusion of soluble components so as to arrive at an equilibrium state; again the low viscosity of the fungal cultures of the present invention makes this high throughput assay possible. Finally, in a highly automated system it will be desirable to automatically pick, aspirate, or pipette clonal cultures of interest from their wells in the microtiter plate, and the low viscosity and submerged growth habit of the cultures will make this possible. All of the above operations would be difficult or impossible given the viscosity of traditional filamentous fungal cultures, especially cultures growing as surface mats in the minimally stirred, shear-free conditions of a microtiter plate well.

In another embodiment, single cells are passed through a microfluidic apparatus, and the property or activity of interest is detected optically (Wada et al., WO 99/67639). Low viscosity is essential to the operation of a microfluidics device, and cultures of the low-viscosity mutant fungi of the present invention are expected to be amenable to microfluidic manipulation. Short et al., in U.S. Pat. No. 6,174,673, have described how fluorogenic substrates may be employed to detect an enzyme activity of interest, and how host cells expressing such an activity may be isolated with a fluorescence-activated cell sorter. The methods of the present invention are compatible with this method of identification of expressed proteins.

In one embodiment, where transformants carry a fluorescent protein as a marker, the fluorescence may be quantitated and employed as a measure of the amount of gene expression and/or expressed protein present in a given culture. In this embodiment, it is possible not only to detect an exogenous protein of interest, but to estimate the specific activity of the protein, as described by Blyna et al. in WO 00/78997. This embodiment will be particularly preferred where the screening method of the invention is employed as part of a process of directed evolution.

In those cases where a greater viscosity is acceptable, a gel-forming matrix may provide certain advantages when culturing fungi, and conducting biochemical assays, in a microplate format, as described by Bochner in U.S. Pat. No. 6,046,021.

Another class of high-thoughput screens is by photometric analysis, by digital imaging spectroscopy, of large numbers of individual colonies growing on a solid substrate. See for example Youvan et al., 1994, *Meth. Enzymol.* 246:732-748. In this method, changes in the overall absorption or emission spectra of specialized reagents are indicative of the presence of a heterologous protein activity or property of interest. The ready dispersal of individual organisms attendant upon the use of low-viscosity mutants also enables the use of filamentous fungi in this method. The tendency for colonies of the mutant fungi of the invention to exhibit less lateral growth, and to produce smooth, compact, and well-defined colonies on solid media, is also advantageous in such a screening system. Furthermore, the superior expression and secretion characteristics of fungi as compared to bacteria provide greater quantities of protein for spectral analysis.

An automated microorganism-handling tool is described in Japanese patent application publication number 11-304666. This device is capable of the transfer of microdroplets containing individual cells, and it is anticipated that the fungal strains of the present invention, by virtue of their morphology, will be amenable to micromanipulation of individual clones with this device.

An automated microbiological high-throughput screening system is described in Beydon et al., *J. Biomol. Screening* 5:13-21 (2000). The robotic system is capable of transferring droplets with a volume of 400 nl to agar plates, and processing 10,000 screening points per hour, and has been used to conduct yeast two-hybrid screens. It is anticipated that the fungal hosts of the present invention will be as amenable as yeast to high-throughput screening with systems of this type.

As an alternative to microtiter plates, transformants can be grown on plates and, in the form of microcolonies, assayed optically as described in WO 00/78997.

In one embodiment, fungal cultures used in the expression and screening methods described herein are conducted under conditions that inhibit proteases. For example, in addition to or as an alternative to using the various fungal strains described herein with low protease activity, culture conditions can include protease inhibition, such as by adding protease inhibitors to culture or screening media and reagents.

Various other techniques can be used in high throughput methods to detect properties of heterologous proteins expressed by the fungal system of the invention, including, but not limited to, Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, or protein microchip, microarray, or any cell-based bioassays.

The development of high throughput screens in general is discussed by Jayawickreme and Kost, *Curr. Opin. Biotechnol.* 8:629-634 (1997). A high throughput screen for rarely transcribed differentially expressed genes is described in von Stein et al., *Nucleic Acids Res.* 35: 2598-2602 (1997).

The low protease *Chrysosporium* strain UV18#100.f and variants of the strain wherein protease genes (e.g., alp1, pep4 and/or alp2) have been disrupted illustrate various aspects of the invention exceedingly well. The invention, however, may employ other mutant or otherwise engineered strains of filamentous fungi that produce transferable reproductive elements in suspension and exhibit low viscosity in culture. For example, various mutants of *Chrysosporium* strain UV18-25 having low protease activity (e.g., UV18#100f $\Delta$alp1, UV18#100f $\Delta$pyr5 $\Delta$alp1, UV18#100.f $\Delta$alp1$\Delta$pep4 $\Delta$alp2, etc.) are described herein. The specific morphology of the fungi may not be critical; the present inventors have observed short, non-entangled mycelia in these two strains but other morphologies, such as close and extensive hyphal branching, may also lead to reduced viscosity. Fungal strains according to the invention are preferred if they exhibit optimal growth conditions at neutral pH and temperatures of 25-43° C. Such screening conditions are advantageous for maintaining the activity of exogenous proteins, in particular those susceptible to degradation or inactivation at acidic pH. Most mammalian proteins, and human proteins in particular, have evolved to function at physiological pH and temperature, and screening for the normal activity of a human enzyme is best carried out under those conditions. Proteins intended for therapeutic use will have to function under such conditions, which also makes these the preferred screening conditions. *Chrysosporium* strains exhibit precisely this characteristic, growing well at neutral pH and 35-40° C., while other commonly employed fungal host species (e.g. *Aspergillus* and *Trichoderma*) grow best at acidic pH, and in some embodiments, at lower temperatures, and may be less suitable for this reason.

Another application of the method of the present invention is in the process of "directed evolution," wherein novel protein-encoding DNA sequences are generated, the encoded proteins are expressed in a host cell, and those sequences encoding proteins exhibiting a desired characteristic are selected, mutated, and expressed again. The process is repeated for a number of cycles until a protein with the desired characteristics is obtained. Gene shuffling, protein engineering, error-prone PCR, site-directed mutagenesis, and combinatorial and random mutagenesis are examples of processes through which novel DNA sequences encoding exogenous proteins can be generated. U.S. Pat. Nos. 5,223,409, 5,780,279 and 5,770,356 provide teaching of directed evolution. See also Kuchner and Arnold, *Trends in Biotechnology*, 15:523-530 (1997); Schmidt-Dannert and Arnold, *Trends in Biotech.*, 17:135-136 (1999); Arnold and Volkov, *Curr. Opin. Chem. Biol.*, 3:54-59 (1999); Zhao et al., *Manual of Industrial*

*Microbiology and Biotechnology*, 2<sup>nd</sup> Ed., (Demain and Davies, eds.) pp. 597-604, ASM Press, Washington D.C., 1999; Arnold and Wintrode, *Encyclopedia of Bioprocess Technology: Fermentation, Biocatalysis, and Bioseparation*, (Flickinger and Drew, eds.) pp. 971-987, John Wiley & Sons, New York, 1999; Minshull and Stemmer, *Curr. Opin. Chem. Biol.* 3:284-290; and Rajpal et al., *PNAS* 2005 102: 8467-8471. Directed evolution is particularly useful for screening combinatorial libraries as described herein. For example, using directed evolution to screen for antibodies is highly desirable, since such methods can mimic the affinity maturation processes through which naturally occurring antibodies progress, and more importantly, can be used to develop and screen for high affinity or high avidity antibodies that bind to particular antigens, including various therapeutic antibodies that are engineered to have desirable characteristics (e.g., neutralizing antibodies, catalytic antibodies, etc.).

An application of combinatorial mutagenesis is disclosed in Hu et al., *Biochemistry.* 1998 37:10006-10015. U.S. Pat. No. 5,763,192 describes a process for obtaining novel protein-encoding DNA sequences by stochastically generating synthetic sequences, introducing them into a host, and selecting host cells with the desired characteristic. Methods for effecting artificial gene recombination (DNA shuffling) include random priming recombination (Z. Shao, et al., *Nucleic Acids Res.*, 26:681-683 (1998)), the staggered extension process (H. Zhao et al., *Nature Biotech.*, 16:258-262 (1998)), and heteroduplex recombination (A. Volkov et al., *Nucleic Acids Res.*, 27:e18 (1999)). Error-prone PCR is yet another approach (Song and Rhee, *Appl. Environ. Microbiol.* 66:890-894 (2000)).

The present invention makes use of any of these and other genetic engineering approaches to modify DNA for directed evolution and screening methods described herein, including, but not limited to, engineering DNA for optimal host expression (e.g., codon optimization); modification of genes to avoid or inhibit protease degradation or protein processing, particularly by the host cells; modification of DNA to provide higher expression levels of proteins, better functionality, and/or improved stability. Genetic engineering methods are well-known in the art and are encompassed by the present invention.

There are two widely-practiced methods of carrying out the selection step in a directed evolution process, although the invention is not limited to these approaches. In one method, the protein activity of interest is somehow made essential to the survival of the host cells. For example, if the activity desired is a cellulase active at pH 8, a cellulase gene could be mutated and introduced into the host cells. The transformants are grown with cellulose as the sole carbon source, and the pH raised gradually until only a few survivors remain. The mutated cellulase gene from the survivors, which presumably encodes a cellulase active at relatively high pH, is subjected to another round of mutation, and the process is repeated until transformants that can grow well on cellulose at pH 8 are obtained. Thermostable variants of enzymes can likewise be evolved, by cycles of gene mutation and high-temperature culturing of host cells (Liao et al., *Proc. Natl. Acad. Sci. USA* 1986 83:576-580; Giver et al., *Proc. Natl. Acad. Sci. USA.* 1998 95:12809-12813). For purposes of this application, mutation of DNA sequences encoding exogenous proteins may be accomplished by any of several methods employed for directed evolution, for example by gene shuffling, in vivo recombination, or cassette mutagenesis.

The chief advantage of this method is the massively parallel nature of the "survival of the fittest" selection step. Millions, or billions, of unsuccessful mutations are simultaneously eliminated from consideration without the need to evaluate them individually. However, it is not always possible to link an enzyme activity of interest to the survival of the host. For example where the desired protein property is selective binding to a target of interest, making the binding property essential to survival is likely to be difficult. Also, survival under forced conditions such as high temperature or extreme pH is likely to be dependent upon multiple factors, and a desirable mutation will not be selected for and will be lost if the host cell is unable to survive for reasons unrelated to the properties of the mutant protein.

An alternative to the massively parallel "survival of the fittest" approach is serial screening. In this approach, individual transformants are screened by traditional methods, such as observation of cleared or colored zones around colonies growing on indicator media, colorimetric or fluorometric enzyme assays, immunoassays, binding assays, etc. See for example Joo et al., *Nature* 399:670-673 (1999), where a cytochrome P450 monooxygenase not requiring NADH as a cofactor was evolved by cycles of mutation and screening; May et al., *Nature Biotech.* 18:317-320 (2000), where a hydantoinase of reversed stereoselectivity was evolved in a similar fashion; and Miyazaki et al., *J. Mol. Biol.* 297:1015-1026 (2000), where a thermostable subtilisin was evolved.

The screening approach has clear advantages over a simple "survival screen," especially if it can be carried out in a high-throughput manner that approaches the throughput of the massively parallel "survival screen" technique. For example, a degree of parallelism has been introduced by employing such measures as digital imaging of the transformed organisms (Joo et al., *Chemistry & Biology,* 6:699-706 (1999)) or digital spectroscopic evaluation of colonies (Youvan et al., 1994, *Meth. Enzymol.* 246:732-748). Serial assays can be automated by the use of cell sorting (Fu et al., *Nature Biotech.*, 17:1109-1111 (1999)). A well-established approach to high-throughput screening involves the automated evaluation of expressed proteins in microtiter plates, using commercially available plate readers, and the method of the present invention is well-suited to the application of this mode of high-throughput screening to directed evolution.

In this embodiment of the invention, a gene encoding a protein of interest is mutated by any known method of generating a plurality of mutants, the mutant protein-encoding DNA is introduced by means of a suitable expression vector into a low-viscosity filamentous fungal host according to the present invention, and the transformants are optionally selected for and cultured. The host cells are then dispersed as described previously into the wells of a microtiter plate, or otherwise spatially separated into resolvable locations, so as to provide individual monoclonal cultures (or polyclonal cultures having fewer than about 100 different clones). The cells are preferably dispersed into the wells of a micro-titer plate. The protein encoded by the mutant DNA is preferably secreted into the medium in the wells of the microtiter plates. Each of the dispersed cultures is screened for the protein activity of interest, and those most strongly exhibiting the desired property are selected. The gene encoding the protein of interest in the selected cultures is mutated again, the mutant DNA is again introduced into the low-viscosity fungal host, and the transformants are re-screened. The mutating and re-screening process is repeated until the value of the property of interest reaches a desired level.

In an alternative embodiment, directed evolution is carried out by mutation and reproduction of the gene of interest in another organism, such as *E. coli*, followed by transfer of the mutant genes to a filamentous fungus according to the present invention for screening. In one embodiment, phage display technology can be combined with screening in a filamentous fungal host. The use of phage display libraries for immunoglobulin screening may be a particularly advantageous combination with the methods of the present invention.

It will be readily appreciated by those skilled in the art that a protein that appears to be of interest based upon the screening assay will not necessarily have all the other properties required for commercial utility. For example, the possession of enzymatic activity, however high the specific activity, will not indicate that the mutant enzyme has the requisite thermal or pH stability, or detergent or protease resistance, or non-immunogenicity, or other property that might be desirable or necessary in a commercially viable product. There is a need for methods of readily determining whether an identified protein has commercially useful properties.

The prior art approaches to screening have not provided a solution to this need, because the host organisms (bacteria and yeast) were not adapted to the production of isolable quantities of protein. It has heretofore been necessary to transfer potentially useful genes from one organism to another, as one proceeded through DNA library preparation, gene expression, screening, expression of research quantities of gene products, and over-expression in industrially suitable production strains. The mutant filamentous fungi of the present invention, on the other hand, are excellent overproducers and secretors of exogenous proteins, especially when employed with the vectors disclosed herein. Sufficient protein may be isolated not only for purposes of characterization, but for evaluation in application trials. Indeed, the strains used in the screening method of the invention are suitable for industrial production as well, since they possess desirable production properties such as low viscosity, high expression rates, and very high protein/biomass ratios.

Accordingly, in a preferred embodiment of the present invention, the method further comprises culturing a clonal colony or culture identified according to the method of the invention, under conditions permitting expression and secretion of the exogenous library protein (or a precursor thereof), and recovering the subsequently produced protein to obtain the protein of interest. As discussed above, expression and secretion of a library protein may be facilitated by creating an in-frame fusion of the cloned gene with the gene for a heterologous protein (or a fragment thereof) with its corresponding signal sequence, or with the signal sequence from a third protein, all operably linked to an expression regulating sequence. By this approach a fusion protein is created that contains heterologous amino acid sequences upstream of the library protein. Subsequently, this fusion precursor protein may be isolated and recovered using purification techniques known in the art. The method may optionally comprise subjecting the secreted fusion protein precursor to a cleavage step to generate the library protein of interest. The cleavage step can be carried out with Kex-2, a Kex-2 like protease, or another selective protease, when the vector is engineered so that a protease cleavage site links a well-secreted protein carrier and the protein of interest.

The ready availability of mutant protein, directly from the screening host organism, has not previously been possible with prior art screening hosts. The present invention thus provides an advantage, in that the mutant proteins deemed of interest based upon the high-throughput screen can be isolated in sufficient quantities (milligrams) for further characterization and even larger quantities (grams to kilograms) for application trials. This particular embodiment of the invention thus permits the practitioner to select mutant proteins for the next round of directed evolution based upon any number of desirable properties, and not merely upon the one property detected in the high-throughput screen. The more stringent selection criteria made possible by the present invention should lead to a more efficient and cost-effective directed evolution process.

The method of production of a recombinant mutant filamentous fungal strain according to the invention comprises introducing a library of DNA sequences comprising nucleic acid sequences encoding heterologous proteins into a low-viscosity mutant filamentous fungus according to the invention, the nucleic acid sequences being operably linked to an expression regulating region. The introduction of the DNA sequences may be carried out in any manner known per se for transforming filamentous fungi. Those skilled in the art will appreciate that there are several well-established methods, such as $CaCl_2$-polyethylene glycol stimulated DNA uptake by fungal protoplasts (Johnstone et al., *EMBO J.*, 1985, 4:1307-1311). A protoplast transformation method is described in U.S. Pat. No. 7,122,330 and the Examples section below. Alternative protoplast or spheroplast transformation methods are known and can be used as have been described in the prior art for other filamentous fungi. Vectors suitable for multicopy integration of heterologous DNA into the fungal genome are well-known; see for example Giuseppin et al., WO 91/00920. The use of autonomously replicating plasmids has long been known as an efficient transformation tool for fungi (Gems et al., *Gene* 1991 98:61-67; Verdoes et al., *Gene* 1994 146:159-165; Aleksenko and Clutterbuck, *Fungal Genetics Biol.* 1997 21:373-387; Aleksenko et al., *Mol. Gen. Genet.* 1996 253:242-246). Details of such methods can be found in many of the cited references, and they are thus incorporated by reference.

GENERAL DEFINITIONS

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000); and Vaccines, S. Plotkin and W. Orenstein, eds., $3^{rd}$ edition (1999).

As used herein, reference to an isolated protein or polypeptide in the present invention, including any of the proteins disclosed herein, such as any of the proteases described above, includes full-length proteins, fusion proteins, or any fragment or homologue of such a protein. More specifically, an isolated protein, such as an enzyme according to the present invention, is a protein (including a polypeptide or peptide) that has been removed from its natural milieu (i.e., that has been subject to human manipulation) and can include purified proteins, partially purified proteins, recombinantly produced proteins, synthetically produced proteins, proteins complexed with lipids, soluble proteins, and isolated proteins associated with other proteins, for example. As such, "isolated" does not reflect the extent to which the protein has been purified. Preferably, an isolated protein of the present invention is produced recombinantly. In addition, and by way of example, a "*C. lucknowens* protein" or "*C. lucknowens* enzyme" refers to a protein (generally including a homologue of a naturally occurring protein) from *Chrysosporium lucknowense* or to a protein that has been otherwise produced from the knowledge of the structure (e.g., sequence) and perhaps the function of a naturally occurring protein from *Chrysosporium lucknowense*. In other words, a *C. lucknowens* protein includes any protein that has substantially similar structure and function of a naturally occurring *C. lucknowens* protein or that is a biologically active (i.e., has biological activity) homologue of a naturally occurring protein from *C. lucknowens* as described in detail herein. As such, a *C. lucknowens* protein can include purified, partially purified, recombinant, mutated/modified and synthetic proteins. According to the present invention, the terms "modification" and "mutation" can be used interchangeably, particularly with regard to the modifications/mutations to the amino acid sequence of a *C. lucknowens* protein (or nucleic acid sequences) described herein. An isolated protein according to the present invention can be isolated from its natural source, produced recombinantly or produced synthetically.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with another compound. Such modifications can be considered to be mutations, for example, if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide), insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in protein homologues, as compared to the wild-type protein, either agonize, antagonize, or do not substantially change, the basic biological activity of the homologue as compared to the naturally occurring protein. Modifications of a protein, such as in a homologue, may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to the present invention, an isolated protein, including a biologically active homologue or fragment thereof, has at least one characteristic of biological activity of a wild-type, or naturally occurring, protein. As discussed above, in general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). The biological activity of a protein of the present invention can include an enzyme activity (catalytic activity and/or substrate binding activity), such as protease activity or any other activity disclosed herein. Methods of detecting and measuring the biological activity of a protein of the invention are known in the art. Such assays include, but are not limited to, measurement of enzyme activity (e.g., catalytic activity), measurement of substrate binding, and the like. It is noted that an isolated protein of the present invention (including homologues) is not required to have a biological activity such as catalytic activity. A protein can be a truncated, mutated or inactive protein, or lack at least one activity of the wild-type enzyme, for example. Inactive proteins may be useful in some screening assays, for example, or for other purposes such as antibody production.

Methods to measure protein expression levels of a protein according to the invention include, but are not limited to: western blotting, immunocytochemistry, flow cytometry or other immunologic-based assays; assays based on a property of the protein including but not limited to, ligand binding or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993);

Schuster et al., Nature 365:343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

Homologues of a protein encompassed by the present invention can comprise, consist essentially of, or consist of, in one embodiment, an amino acid sequence that is at least about 35% identical, and more preferably at least about 40% identical, and more preferably at least about 45% identical, and more preferably at least about 50% identical, and more preferably at least about 55% identical, and more preferably at least about 60% identical, and more preferably at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical, or any percent identity between 35% and 99%, in whole integers (i.e., 36%, 37%, etc.), to an amino acid sequence disclosed herein that represents the amino acid sequence of an enzyme or protein according to the invention (including a biologically active domain of a full-length protein). Preferably, the amino acid sequence of the homologue has a biological activity of the wild-type or reference protein or of a biologically active domain thereof (e.g., a catalytic domain).

In one embodiment, a protein of the present invention comprises, consists essentially of, or consists of an amino acid sequence that is less than 100% identical to an amino acid sequence described herein (e.g., an amino acid sequence selected from: SEQ ID NO:2, SEQ ID NO:5, SEQ ID NO:8) (i.e., a homologue). In another aspect of the invention, a homologue according to the present invention has an amino acid sequence that is less than about 99% identical to any of such amino acid sequences, and in another embodiment, is less than about 98% identical to any of such amino acid sequences, and in another embodiment, is less than about 97% identical to any of such amino acid sequences, and in another embodiment, is less than about 96% identical to any of such amino acid sequences, and in another embodiment, is less than about 95% identical to any of such amino acid sequences, and in another embodiment, is less than about 94% identical to any of such amino acid sequences, and in another embodiment, is less than about 93% identical to any of such amino acid sequences, and in another embodiment, is less than about 92% identical to any of such amino acid sequences, and in another embodiment, is less than about 91% identical to any of such amino acid sequences, and in another embodiment, is less than about 90% identical to any of such amino acid sequences, and so on, in increments of whole integers.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) PSI-BLAST with the standard default parameters (Position-Specific Iterated BLAST; and/or (4) CAZy homology determined using standard default parameters from the Carbohydrate Active EnZymes database (Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12).

It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
 Reward for match=1
 Penalty for mismatch=−2
 Open gap (5) and extension gap (2) penalties
 gap x_dropoff (50) expect (10) word size (11) filter (on)
For blastp, using 0 BLOSUM62 matrix:
 Open gap (11) and extension gap (1) penalties
 gap x_dropoff (50) expect (10) word size (3) filter (on).

A protein of the present invention can also include proteins having an amino acid sequence comprising at least 10 contiguous amino acid residues of any of the sequences described herein (i.e., 10 contiguous amino acid residues having 100% identity with 10 contiguous amino acids of SEQ ID NO:2). In other embodiments, a homologue of a protein amino acid sequence includes amino acid sequences comprising at least 20, or at least 30, or at least 40, or at least 50, or at least 75, or at least 100, or at least 125, or at least 150, or at least 175, or at least 150, or at least 200, or at least 250, or at least 300, or at least 350 contiguous amino acid residues of any of the amino acid sequence represented disclosed herein. Even small fragments of proteins without biological activity are useful in the present invention, for example, in the preparation of antibodies against the full-length protein or in a screening assay (e.g., a binding assay). Fragments can also be used to construct fusion proteins, for example, where the fusion protein comprises functional domains from two or more different proteins (e.g., a domain from one protein linked to a catalytic domain from another protein). In one embodiment, a homologue has a measurable or detectable biological activity associated with the wild-type protein (e.g., enzymatic activity).

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a protein of the present invention, including a homologue, includes a protein having an amino acid sequence that is sufficiently similar to a natural amino acid sequence that a nucleic acid sequence encoding the homologue is capable of hybridizing under moderate, high or very high stringency conditions (described below) to (i.e., with) a nucleic acid molecule encoding the natural protein (i.e., to the complement of the nucleic acid strand encoding the natural amino acid sequence). Preferably, a homologue of a protein of the present invention is encoded by a nucleic acid molecule comprising a nucleic acid sequence that hybridizes under low, moderate, or high stringency conditions to the complement of a nucleic acid sequence that encodes a protein comprising, consisting essentially of, or consisting of, any amino acid sequence described herein, including, but not limited to, an amino acid sequence represented by any of: SEQ ID NO:2, SEQ ID NO:5, SEQ ID NO:8. Such hybridization conditions are described in detail below.

A nucleic acid sequence complement of nucleic acid sequence encoding a protein of the present invention refers to the nucleic acid sequence of the nucleic acid strand that is complementary to the strand that encodes the protein. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence such as SEQ ID NO:2, and/or with the complement of the nucleic acid sequence that encodes an amino acid sequence such as SEQ ID NO:2. Methods to deduce a complementary sequence are known to those skilled in the art. It should be noted that since nucleic acid sequencing technologies are not entirely error-free, the sequences presented herein, at best, represent apparent sequences of the proteins of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

The minimum size of a protein and/or homologue of the present invention is a size sufficient to have biological activity or, when the protein is not required to have such activity, sufficient to be useful for another purpose associated with a protein of the present invention, such as for the production of antibodies that bind to a naturally occurring protein. In one embodiment, the protein of the present invention is at least 20 amino acids in length, or at least about 25 amino acids in length, or at least about 30 amino acids in length, or at least about 40 amino acids in length, or at least about 50 amino acids in length, or at least about 60 amino acids in length, or at least about 70 amino acids in length, or at least about 80 amino acids in length, or at least about 90 amino acids in length, or at least about 100 amino acids in length, or at least about 125 amino acids in length, or at least about 150 amino acids in length, or at least about 175 amino acids in length, or at least about 200 amino acids in length, or at least about 250 amino acids in length, and so on up to a full length of each protein, and including any size in between in increments of one whole integer (one amino acid). There is no limit, other than a practical limit, on the maximum size of such a protein in that the protein can include a portion of a protein or a full-length protein, plus additional sequence (e.g., a fusion protein sequence), if desired.

The present invention also includes a fusion protein that includes a domain of a protein of the present invention (including a homologue) attached to one or more fusion segments, which are typically heterologous in sequence to the protein sequence (i.e., different than protein sequence). Suitable fusion segments for use with the present invention include, but are not limited to, segments that can: enhance a protein's stability; provide other desirable biological activity; and/or assist with the purification of the protein (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the domain of a protein of the present invention and can be susceptible to cleavage in order to enable straight-forward recovery of the protein. Fusion proteins are preferably produced by culturing a recombinant cell transfected with a fusion nucleic acid molecule that encodes a protein including the fusion segment attached to either the carboxyl and/or amino terminal end of a domain of a protein of the present invention. Accordingly, proteins of the present invention also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of a membrane protein, or genes having signal sequences removed which are poorly tolerated in a particular recombinant host).

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived.

In accordance with the present invention, an isolated nucleic acid molecule is a nucleic acid molecule (polynucleotide) that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule, and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. An isolated nucleic acid molecule of the present invention can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a protein of the present invention or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein of the present invention can vary due to degeneracies. It is noted that a nucleic acid molecule of the present invention is not required to encode a protein having protein activity. A nucleic acid molecule can encode a truncated, mutated or inactive protein, for example. In addition, nucleic acid molecules of the invention are useful as probes and primers for the identification, isolation and/or purification of other nucleic acid molecules. If the nucleic acid molecule is an oligonucleotide, such as a probe or primer, the oligonucleotide preferably ranges from about 5 to about 50 or about 500 nucleotides, more preferably from about 10 to about 40 nucleotides, and most preferably from about 15 to about 40 nucleotides in length.

According to the present invention, reference to a gene includes all nucleic acid sequences related to a natural (i.e. wild-type) gene, such as regulatory regions that control production of the protein encoded by that gene (such as, but not limited to, transcription, translation or post-translation control regions) as well as the coding region itself. In another embodiment, a gene can be a naturally occurring allelic variant that includes a similar but not identical sequence to the nucleic acid sequence encoding a given protein. Allelic variants have been previously described above. The phrases "nucleic acid molecule" and "gene" can be used interchangeably when the nucleic acid molecule comprises a gene as described above.

Preferably, an isolated nucleic acid molecule of the present invention is produced using recombinant DNA technology (e.g., polymerase chain reaction (PCR) amplification, cloning, etc.) or chemical synthesis. Isolated nucleic acid molecules include any nucleic acid molecules and homologues thereof that are part of a gene described herein and/or that encode a protein described herein, including, but not limited to, natural allelic variants and modified nucleic acid molecules (homologues) in which nucleotides have been inserted, deleted, substituted, and/or inverted in such a manner that such modifications provide the desired effect on protein biological activity or on the activity of the nucleic acid molecule. Allelic variants and protein homologues (e.g., proteins encoded by nucleic acid homologues) have been discussed in detail above.

A nucleic acid molecule homologue (i.e., encoding a homologue of a protein of the present invention) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a protein is gene shuffling (i.e., molecular breeding) (See, for example, U.S. Pat. No. 5,605,793 to Stemmer; Minshull and Stemmer; 1999, *Curr. Opin. Chem. Biol.* 3:284-290; Stemmer, 1994, *P.N.A.S. USA* 91:10747-10751, all of which are incorporated herein by reference in their entirety). This technique can be used to efficiently introduce multiple simultaneous changes in the protein. Nucleic acid molecule homologues can be selected by hybridization with a gene or polynucleotide, or by screening for the function of a protein encoded by a nucleic acid molecule (i.e., biological activity).

The minimum size of a nucleic acid molecule of the present invention is a size sufficient to encode a protein (including a fragment or homologue of a full-length protein) having biological activity, sufficient to encode a protein comprising at least one epitope which binds to an antibody, or sufficient to form a probe or oligonucleotide primer that is capable of forming a stable hybrid with the complementary sequence of a nucleic acid molecule encoding a natural protein (e.g., under moderate, high, or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein encoding sequence, a nucleic acid sequence encoding a full-length protein (including a gene), including any length fragment between about 20 nucleotides and the number of nucleotides that make up the full length cDNA encoding a protein, in whole integers (e.g., 20, 21, 22, 23, 24, 25 . . . nucleotides), or multiple genes, or portions thereof.

The phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

In one embodiment, the polynucleotide probes or primers of the invention are conjugated to detectable markers. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Preferably, the polynucleotide probes are immobilized on a substrate such as: artificial membranes, organic supports, biopolymer supports and inorganic supports.

According to the present invention, a recombinant nucleic acid molecule typically comprises a recombinant vector and any one or more of the isolated nucleic acid molecules as described herein. According to the present invention, a recombinant vector is an engineered (i.e., artificially produced) nucleic acid molecule that is used as a tool for manipulating a nucleic acid sequence of choice and/or for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is, nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid sequences of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remain separate from the genome for most applications of the invention. The entire vector can remain in place within a host cell, or under certain conditions, the plasmid DNA can be deleted, leaving behind the nucleic acid molecule of the present invention. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest, such as an enzyme of the present invention). In this embodiment, a nucleic acid sequence encoding the product to be produced (e.g., the protein or homologue thereof) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector that enable the transcription and translation of the nucleic acid sequence within the recombinant host cell.

Typically, a recombinant nucleic acid molecule includes at least one nucleic acid molecule of the present invention operatively linked to one or more expression control sequences (e.g., transcription control sequences or translation control sequences). As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence in a manner such that the molecule is able to be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those that are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is generally used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants and describes an inherited change due to the acquisition of exogenous nucleic acids by the microorganism that is essentially synonymous with the term "transfection." Transfection techniques include, but are not limited to, transformation, particle bombardment, electroporation, microinjection, lipofection, adsorption, infection and protoplast fusion.

An encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., filamentous fungi or yeast), plant, insect, or animal cell that can be transfected. Host cells can be either untransfected cells or cells that are already transfected with at least one other recombinant nucleic acid molecule.

Suitable cells (e.g., a host cell or production organism) include any microorganism (e.g., a bacterium, a protist, an alga, a fungus, or other microbe), and is preferably a bacterium, a yeast or a filamentous fungus. Suitable bacterial genera include, but are not limited to, *Escherichia, Bacillus, Lactobacillus, Pseudomonas* and *Streptomyces*. Suitable bacterial species include, but are not limited to, *Escherichia coli, Bacillus subtilis, Bacillus licheniformis, Lactobacillus brevis, Pseudomonas aeruginosa* and *Streptomyces lividans*. Suitable genera of yeast include, but are not limited to, *Saccharomyces, Schizosaccharomyces, Candida, Hansenula, Pichia, Kluyveromyces,* and *Phaffia*. Suitable yeast species include, but are not limited to, *Saccharomyces cerevisiae, Schizosaccharomyces pombe, Candida albicans, Hansenula polymorphs, Pichia pastoris, P. canadensis, Kluyveromyces marxianus* and *Phaffia rhodozyma*.

Suitable fungal genera include, but are not limited to, *Chrysosporium, Thielavia, Neurospora, Aureobasidium, Filibasidium, Piromyces, Corynascus, Cryplococcus, Acremonium, Tolypocladium, Scytalidium, Schizophyllum, Sporotrichum, Penicillium, Gibberella, Myceliophthora, Mucor, Aspergillus, Fusarium, Humicola,* and *Trichoderma*, and anamorphs and teleomorphs thereof. Suitable fungal species include, but are not limited to, *Aspergillus niger, Aspergillus nidulans, Aspergillus japonicus, Absidia coerulea, Rhizopus oryzae, Chrysosporium lucknowense, Neurospora crassa, Neurospora intermedia, Trichoderma reesei, Penicillium canescens, Penicillium solitum, Penicillium funiculosum,* and *Talaromyces flavus*. In one embodiment, the host cell is a fungal cell of the species *Chrysosporium lucknowense*. In one embodiment, the host cell is a fungal cell of Strain C1 (VKM F-3500-D) or a mutant strain derived therefrom (e.g., UV13-6 (Accession No. VKM F-3632 D); NG7C-19 (Accession No. VKM F-3633 D); or UV18-25 (VKM F-3631D)). Host cells can be either untransfected cells or cells that are already transfected with at least one other recombinant nucleic acid molecule. Additional embodiments of the present invention include any of the genetically modified cells described herein.

In one embodiment, one or more protein(s) expressed by an isolated nucleic acid molecule of the present invention are produced by culturing a cell that expresses the protein (i.e., a recombinant cell or recombinant host cell) under conditions effective to produce the protein. In some instances, the protein may be recovered, and in others, the cell may be harvested in whole, either of which can be used in a composition.

Microorganisms used in the present invention (including recombinant host cells or genetically modified microorganisms) are cultured in an appropriate fermentation medium. An appropriate, or effective, fermentation medium refers to any medium in which a cell of the present invention, including a genetically modified microorganism (described below), when cultured, is capable of expressing enzymes useful in the present invention. Such a medium is typically an aqueous medium comprising assimilable carbon, nitrogen and phosphate sources. Such a medium can also include appropriate salts, minerals, metals and other nutrients. Microorganisms and other cells of the present invention can be cultured in conventional fermentation bioreactors. The microorganisms can be cultured by any fermentation process which includes, but is not limited to, batch, fed-batch, cell recycle, and continuous fermentation. The fermentation of microorganisms such as fungi may be carried out in any appropriate reactor, using methods known to those skilled in the art. For example, the fermentation may be carried out for a period of 1 to 14 days, or more preferably between about 3 and 10 days. The temperature of the medium is typically maintained between about 25 and 50° C., and more preferably between 28 and 40° C. The pH of the fermentation medium is regulated to a pH suitable for growth and protein production of the particular organism. The fermentor can be aerated in order to supply the oxygen necessary for fermentation and to avoid the excessive accumulation of carbon dioxide produced by fermentation. In addition, the aeration helps to control the temperature and the moisture of the culture medium. In general the fungal strains are grown in fermentors, optionally centrifuged or filtered to remove biomass, and optionally concentrated, formulated, and dried to produce an enzyme(s) or a multi-enzyme composition that is a crude fermentation product. Particularly suitable conditions for culturing filamentous fungi are described, for example, in U.S. Pat. No. 6,015,707 and U.S. Pat. No. 6,573,086, supra.

Depending on the vector and host system used for production, resultant proteins of the present invention may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced according to the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins of the present invention are preferably retrieved, obtained, and/or used in "substantially pure" form. As used herein, "substantially pure" refers to a purity that allows for the effective use of the protein in any method according to the present invention. For a protein to be useful in any of the methods described herein or in any method utilizing enzymes of the types described herein according to the present invention, it is substantially free of contaminants, other proteins and/or chemicals that might interfere or that would interfere with its use in a method disclosed by the present invention (e.g., that might interfere with enzyme activity), or that at least would be undesirable for inclusion with a protein of the present invention (including homologues) when it is used in a method disclosed by the present invention (described in detail below). Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the protein of interest is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

As used herein, a genetically modified microorganism can include a genetically modified bacterium, yeast, filamentous fungus, or other microbe. Such a genetically modified microorganism has a genome which is modified (i.e., mutated or changed) from its normal (i.e., wild-type or naturally occurring) form such that the desired result is achieved (i.e., increased or modified activity and/or production of a protein or deletion or inactivation of a protein. Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press or *Molecular Cloning: A Laboratory Manual*, third edition (Sambrook and Russel, 2001), (jointly referred to herein as "Sambrook"). The references of Sambrook, ibid., are incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

According to the present invention, the phrase "selectively binds to" refers to the ability of an antibody, antigen binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

Antibodies are characterized in that they comprise immunoglobulin domains and as such, they are members of the immunoglobulin superfamily of proteins. An antibody of the invention includes polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention. Methods for the generation and production of antibodies are well known in the art.

Monoclonal antibodies may be produced according to the methodology of Kohler and Milstein (*Nature* 256:495-497, 1975). Non-antibody polypeptides, sometimes referred to as binding partners, are designed to bind specifically to a protein of the invention. Examples of the design of such polypeptides, which possess a prescribed ligand specificity are given in Beste et al. (*Proc. Natl. Acad. Sci.* 96:1898-1903, 1999), incorporated herein by reference in its entirety. In one embodiment, a binding agent of the invention is immobilized on a substrate such as: artificial membranes, organic supports, biopolymer supports and inorganic supports such as for use in a screening assay.

Each publication or reference cited herein is incorporated herein by reference in its entirety.

The following examples are provided for the purpose of illustration and are not intended to limit the scope of the present invention.

EXAMPLES

Additional examples of fungal strains, library development and expression systems can be found in U.S. Pat. No. 7,122,330, which is incorporated herein by reference in its entirety.

A. Construction of Improved *C. Lucknowense* Host Strains

As described in U.S. Pat. No. 7,122,330, morphological variants of the original *C. lucknowense* strain were isolated during the course of a strain development program for neutral cellulase production. These mutants, of which the prototypical strain is designated UV18-25, are characterized by hypersecretion of protein, low viscosity in fermentation, and hyphal fragmentation. The morphology not only enables the high-level production of proteins, but also the separation of monoclonal elements, called "propagules", from mixed populations. The formation of propagules also results in low viscosity that allows manipulation of cultures using robotic liquid handling systems.

Strain UV18-25, in addition to producing high levels of neutral cellulase, is also characterized by the production of high levels of extracellular proteases. The presence of these proteases often confounds the production of heterologous proteins, presumably by degrading those proteins before they can accumulate to high levels. In order to isolate improved strains for the production of heterologous proteins, low protease variants of UV18-25 were isolated.

The mutants were produced by mutagenesis, followed by selection for low protease producers. Colonies that were characterized by reduced clearing of skim milk in agar plates were isolated and characterized. One such colony, which had ~10% of the protease activity of UV18-25 against casein, was designated UV18#100.f.

The residual extracellular proteases and the conditions under which they were expressed were extensively studied. It was determined that three proteases, whose genes are designated alp1, pep4, and alp2, were responsible for the bulk of the residual activity. Using "reverse genetics" and genomics methods, the corresponding genes were isolated and disrupted with the pyr5 gene, encoding the orotate phosphoribosyl transferase of *C. lucknowense*. The proteases were sequential removed by introducing the disrupted genes into a pyr5 mutant of UV18#100.f requiring uracil and uridine for growth, selecting pyrimidine prototrophs, screening for the lack of the targeted protease, and removing the pyr5 gene from the disruption construct. This ultimately led to pyr5 mutant strains of UV18#100.f containing deletions of one or more of these proteases. The same gene disruption strategy was used to isolate protease deletion variants of other *C. lucknowense* host strains. Strain UV18#100.f Δpyr5 Δalp1 and UV18#100.f Δpyr5 Δalp1Δpep4 Δalp2 were used to test in vitro stability and expression of antibodies in *C. lucknowense*. These strains produced less than 1% of the extracellular protease activity of strain UV18-25.

Host Strains with Reduced Non-Homologous Recombination

For the efficient development of the screening methods described herein, host strains with mutations in one of the genes essential for non-homologous recombination were generated using disruption of the *C. lucknowense* homologue of the human Ku70 gene. This strain showed a highly increased fraction of transformants resulting from homologous recombination. This strain has useful attributes for methods using both the replicative or integrative transformation vectors as described herein. Other strains can be produced using similar methods or by classical mutagenesis and are encompassed by this invention.

The mutated phenotype from this type of host strain may also be beneficial for utilization in classical mutagenesis programs.

B. Production of a Dedicated Vector for Efficient Library Construction and High Throughput Screening in the Hyphal Fungus *Chrysosporium Lucknowense*

Materials and Methods

Transformation

Protoplasts of strains UV18#100.f Δpyr5 and UV18#100.f Δpyr5Δpyr4 were isolated after incubation of mycelium with Caylase C4 (Cayla, Toulouse, France), and. transformants were selected for pyrimidine prototrophy on selective solid or liquid minimal medium. The transformed protoplasts were regenerated in osmotically stabilized (0.67 M sucrose) medium, and after regeneration, were plated on selective solid medium to determine the transformation frequency. The remaining protoplasts were seeded into 100 volumes selective medium and incubated in shake flasks until propagules were formed. The propagules were filtered through Miracloth (Merck Biosciences, Darmstadt, Germany), concentrated by centrifugation, dissolved in physiological salt solution and glycerol was added to a final concentration of 20%. Finally the propagule mix was fractionated and stored at −80° C.

Transformation of *E. coli* was done by electroporation according to standard procedures described by the supplier (Biorad, Veenendaal, The Netherlands).

Medium, Strains and Cultivation Conditions

*C. lucknowense* strains were cultivated on minimal medium (MM). To cultivate the auxotrophic mutants of *C. lucknownse* (Δpyr5 and Δpyr5Δpyr4), uridine and uracil were added to the medium. To stimulate fast propagule formation in microtiter plates, a medium optimized for propagule formation (PFO), in which the glucose concentration was reduced 100-fold, was used. This resulted in a uniform distribution of the number of propagules/ml in deep-well microtiter plates after a short cultivation period even when the initial seeding density was as low as approximately 20 spores/ml. To maintain a constant medium pH during the production of secreted proteins in microtiter plate cultivations, production medium (PM) was used. In PM, the nitrogen source present in MM was replaced by $(NH_4)_2SO4$ and the original $KH_2PO_4$ concentration was increased 5-fold.

Prior to a seeding in microtiter plates, an actual colony count was conducted. The frozen propagule mixture was thawed on ice and a small sample was plated on selective solid medium. Based on these numbers, an appropriate aliquot of the propagule mixture was then added to the propagule formation optimized medium to give a final concentration of approximately five propagules per well when seeded to 96 deep-well microtiter plates. Plates were placed in an incubator shaker (Multitron, Infors, Bottmingen, Switzerland) for 3 days at 35° C. and a rotation speed of 850 rpm. Three µL of the newly formed propagules mixture were transferred to a new plate containing 0.22 mL medium in each well. After 4 days of incubation the mycelium fragments were pelleted by centrifugation and medium samples (10-20 µL) were taken for activity measurements.

Chemicals

Restriction enzymes and T4 DNA ligase were purchased from MBI Fermentas (St. Leon, Germany). SuperTaq polymerase was purchased from SphaeroQ (Leiden, The Netherlands). [α-32P]dCTP was obtained from GE Healthcare (Little Chalfont, UK). All medium chemicals were obtained from Sigma-Aldrich Chemie GmbH (Steinheim, Germany).

DNA Manipulation

For the recovery of the expression cassette and the flanking sequence responsible for plasmid replication and selection in *E. coli* from a fungal transformant the following rescue procedure was set up. One microgram of genomic DNA of the identified transformant was digested to completion with NotI then self-ligated using T4 DNA ligase. The ligated DNA was used for *E. coli* transformation by electroporation using standard conditions and plated to LB-agar plates containing 50 mg/L ampicillin.

For Southern analysis chromosomal DNA was separated on a 0.8% TEA-agarose gel and transferred to a Nylon membrane. The filters were hybridized under stringent conditions with a $^{32}$P-labeled probe using the Rediprime™ II random Prime labelling system from GE Healthcare.

Vector Constructions

The following vectors were constructed to test whether DNA elements like AMA and telomeres could promote autonomous replication in *C. lucknowense* and result in higher transformation frequencies. Heterologous fungal genes that could complement the auxotrophic mutations in the acceptor strains of *C. lucknowense* were used to limit sequence homology between the vectors to be constructed and the genomic DNA of the fungal host strain. The pyrE gene of *A. niger* was cloned as a 5.2 kb SstII fragment in pBluescript (Strategene Europe, Amsterdam, The Netherlands), yielding pBlue-pyrE. The expression cassette conferring kanamycin resistance as present between the two inverted 0.6 kb stretches of the human telomeric repeats[11] was replaced by a synthetic linker containing the recognition site of the meganuclease I-CeuI. The modified cassette was cloned as a 1.2 kb HindIII fragment in pBlue-pyrE yielding pBlue-pyrE tel. The AMA sequence was isolated as a partial HindIII fragment from pHELP[7] and cloned into the corresponding site of pBlue-pyrE, yielding pBlue-pyrE AMA.

The following vectors were constructed to test the characteristics of the developed telomeric vector for robotic high throughput screening in *C. lucknowense*. The vector pPgpdA-TtrpC pyrE tel pyrG (FIG. 2) was constructed using a derivative of pAN52-4[16] called pAN52-NotIΔss (unpublished results). A 3.8 kb NotI-BamHI pyrE fragment derived from pBlue-pyrE was inserted in pAN52-NotIΔss. In this vector, pAN52 pyrE, a blunt ended 1.2 kb telomere fragment was cloned in the StuI site yielding pAN52 pyrE tel. Finally, the pyrG gene from *Aspergillus oryzae*, present on a subcloned 2.8 kb SalI-XhoI fragment, was inserted in the XhoI sites of pAN52 pyrE tel.

The vector pPcbh1-glaA-Tcbh1 pyrE tel pyrG (FIG. 2) contains the full genome sequence of glaA, the glucoamylase (GLA) encoding gene of *A. niger* (accession number #Z32690). The vector pPcbh1-lac1-TtrpC pyrE tel pyrG (FIG. 2) contains a modified laccase encoding cDNA clone from *Pycnoporus* cinnabarinus[16]. This expression cassette was obtained from pLac1-B in which the 21 amino acids of the laccasse signal peptide were replaced by the preprosequence of GLA from *A. niger*[16].

Construction of *C. Lucknowense* Host Strains

As discussed above, the main prerequisites for a successful library construction and screening procedure in fungi are: i) a very high transformation frequency, ii) stable and high level expression of the genes cloned in the expression vector and iii) an efficient procedure to re-isolate the DNA fragment that encodes the (enzymatic) activity screened.

The strain UV18#100.f Δpyr5 was generated by transforming strain UV18#100.f with the pyr5 gene disrupted with the *A. nidulans* amdS gene, selecting for strains able to grow with acetamide as sole nitrogen source, and screening for pyrimidine auxotrophy. Subsequent counterselection for the spontaneous loss of the amdS marker on fluoroacetamide containing medium resulted in the strain UV18#100.fΔpyr5. The uridine requirement could be resolved by the introduction of an integrative vector containing either the pyr5 gene of C1 (pBlue-pyr5) or the *A. nidulans* ortholog pyrE (pBlue-pyrE). The transformation frequency was similar and in both cases transformants have the same phenotype as the parental strain UV18#100.f.

In order to test library construction and screening in *C. lucknowense*, a second specific auxotrophic mutation in the uridine biosynthetic pathway of C1 was introduced by the inactivation of the pyr4 gene. The pyr4 gene encodes the enzyme orotidine-5'-phosphate-decarboxylase. This enzyme converts the reaction product of the pyr5 encoded orotate phosphoribosyltransferase catalyzed reaction into uridine-5-phosphate. By a similar approach as described for UV18#100.f Δpyr5, the strain UV18#100.f Δpyr5Δpyr4 was generated.

Increased Transformation Frequency

To test the ability of either the AMA sequence or the human telomeric sequence to increase the transformation frequency and to facilitate autonomous replication in *C. lucknowense* these genetic elements were introduced in the vector pBlue-pyrE.

The strain UV18#100.f Δpyr5 was transformed with equal amounts of the vectors pBlue-pyrE, pBlue-pyrE AMA1 and pBlue-pyrE tel. A 50 to 100-fold increase in the number of pyr$^+$ transformants was observed for the telomere containing vector. Southern analysis of chromosomal DNA isolated from a set of transformants obtained with the pBlue-pyrE AMA1 vector indicated that the vector did integrate. The morphology of all these transformants was large and smooth.

Figure 3:
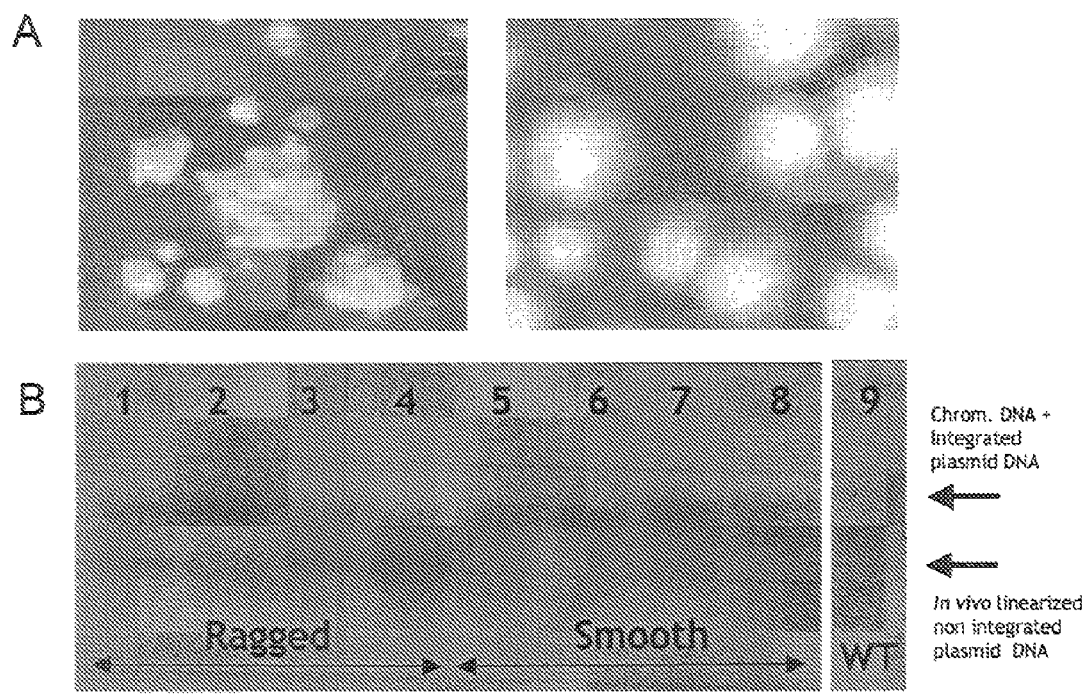
FIGS. 3A and B show the following digital images: (A) Colony morphology of UV18#100.fΔpyr5Δpyr4[pAN52 pyrE tel pyrG] on selective medium of after regeneration (left; ragged) and propagule formation (right, smooth). (B) Southern analysis of genomic DNA isolated from UV18#100.fΔpyr5Δpyr4 (9) and four UV18#100.fΔpyr5Δpyr4[pAN52 pyrE tel pyrG] transformants with a ragged (1-4) and smooth (5-8) phenotype. Genomic DNA was separated on a 0.8% TEA-agarose gel and transferred to a Nylon membrane. The filter was probed with $^{32}$P-labeled vector pAN52 pyrE tel pyrG.

In contrast, more than 90% of the pBlue-pyrE tel transformants displayed a ragged-type colony morphology (FIG. 3A). Southern analysis indicated that the telomeric vector in these *C. lucknowense* transformants was maintained as a non-integrated linear DNA molecule (FIG. 3B). Such ragged-type phenotype was described previously for *A. niger* transformants having an autonomously replicating vector copy of an AMA containing vector[8]. The primary *C. lucknowense* transformants were cultivated in selective liquid medium, the propagules were isolated and plated on selective medium agar-plates (FIG. 3A). A gradual decrease in the number of slow growing, ragged-type colonies indicative for the presence of the linear autonomously replicating vector and the concomitant increase in the number of smooth-type, fast growing colonies indicative for integration, was observed. The suggestion that after prolonged cultivation the linear plasmid finally tends to integrate in the C1 genome was verified by Southern analysis (FIG. 3B). Similar observations were also reported for a telomere vector in *A. nidulans*[11]. The transformation procedure was further optimized by introducing an additional regeneration step in osmotically stabilized medium. Transformation frequencies of up to 13,000 primary transformants per microgram of plasmid DNA were obtained.

Telomeric Vectors for Complex Library Construction in C1

Figure 2:
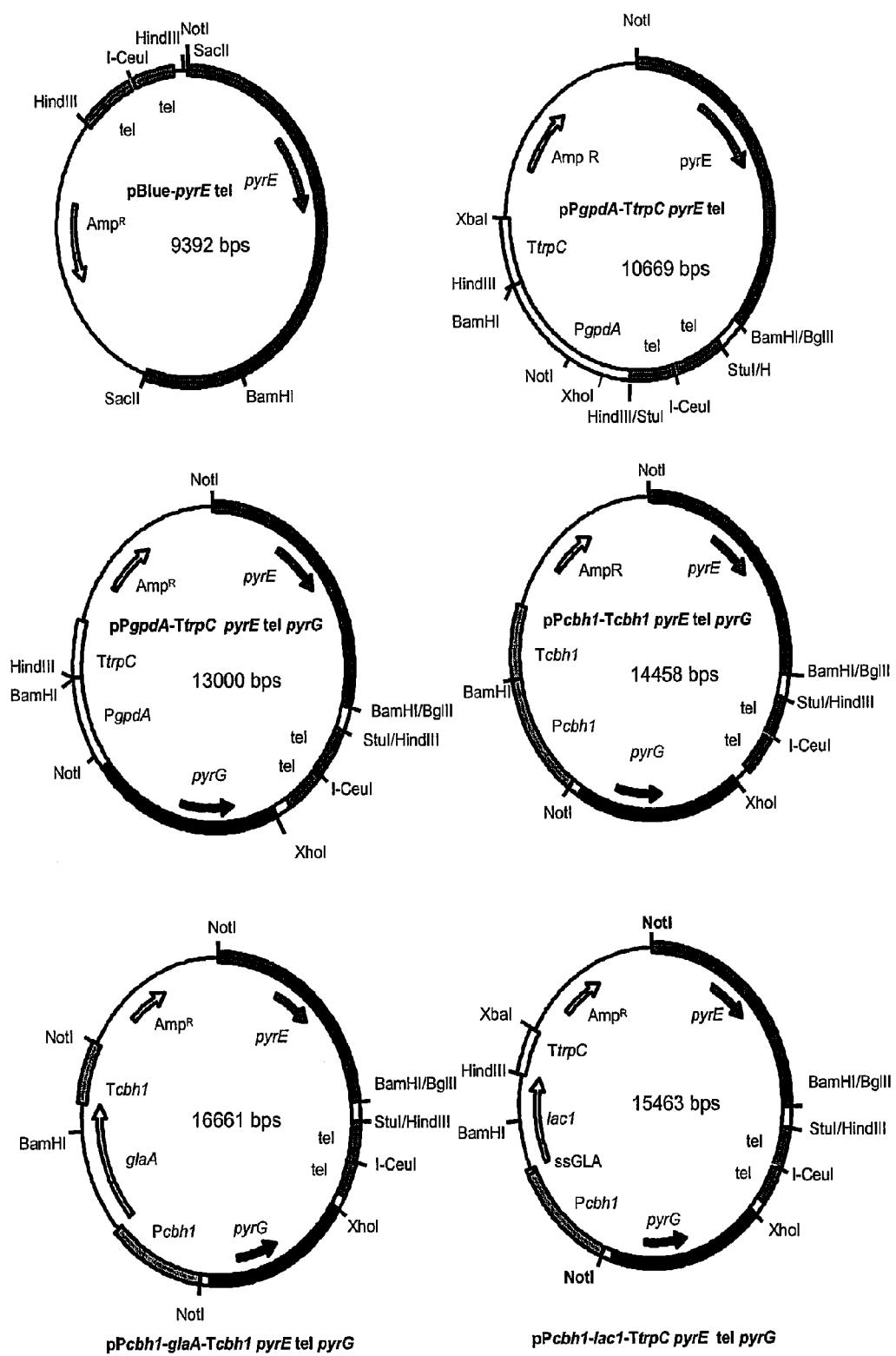
FIG. 2 is a schematic representation of various telomeric vectors described in the Examples (pyrE, orotate phosphoribosyl transferase encoding gene of *Aspergillus niger*; pyrG, orotidine-5'-phosphate-decarboxylase encoding gene of *A. oryzae*; PgpdA, Promoter region of the glyceraldehyde-3-phosphate dehydrogenase gene of *A. nidulans*; TtrpC, trpC terminator of *A. nidulans*; Pcbh1, promoter of the cellobiohydrolase encoding gene of *C. lucknowense*; Tcbh1, terminator of the cellobiohydrolase encoding gene of *C. lucknowense*; glaA, the glucoamylase encoding gene of *A. niger*; lac1, modified laccase encoding cDNA clone from *Pycnoporus cinnabarinus*. Only the restriction sites essential for construction and insert recovery (Bold) are indicated).

AMA containing vectors have been used for gene cloning by complementation in *A. nidulans*[19] and *A. niger*[8]. The disadvantage of this "instant gene bank" approach was the instability of the vector and the uncontrolled recombination between the AMA vector and the complementing DNA fragments. Therefore DNA rescue from AMA derived plasmid molecules via transformation of *E. coli* with total genomic DNA of the *A. niger* transformants was not always possible[8]. The initial high transformation frequency and the controlled stabilization of the telomeric vector after propagule formation as found in *C. lucknowense* fit the demands for the construction of large, complex libraries. The next step was to test the use of the telomeric vector for library construction and screening in *C. lucknowense*. In the first instance the inventors analyzed the complementation of the pyr4 deletion. Chromosomal DNA of C1 was partially digested with Sau3A and fragments from 2-6 kb were isolated and inserted in the unique BamHI site of pPgpdA-TtrpC pyrE tel (FIG. 2). This vector contains in addition to the genetic elements present in pBlue-pyrE tel an expression cassette of the *A. nidulans* glyceraldehyde-3-phosphate dehydrogenase gene (gpdA) promoter and *A. nidulans* trpC terminator. The primary library in *E. coli* DH5α consisted of 190,000 transformants. The transformants were pooled and an aliquot was plated on LB agar plates supplemented with carbenicillin. Cells were harvested after an overnight incubation at 37° C. and plasmid DNA was isolated. Seventy μg of plasmid DNA was used to transform strain UV18#100.f Δpyr5Δpyr4. Simultaneously, the same amount of plasmid DNA was also transformed into strain UV18#100.f Δpyr5 to determine the transformation frequency. About 330,000 Pyr+ transformants were obtained in UV18#100.f Δpyr5 as host and 14 Pyr+ transformants were obtained on selective agar plates using UV18#100.f pyr5Δpyr4 as host. By PCR and sequence analysis we could show that in the latter case all Pyr+ transformants contained an insert with the complete C1 pyr4 gene.

Figure 4:
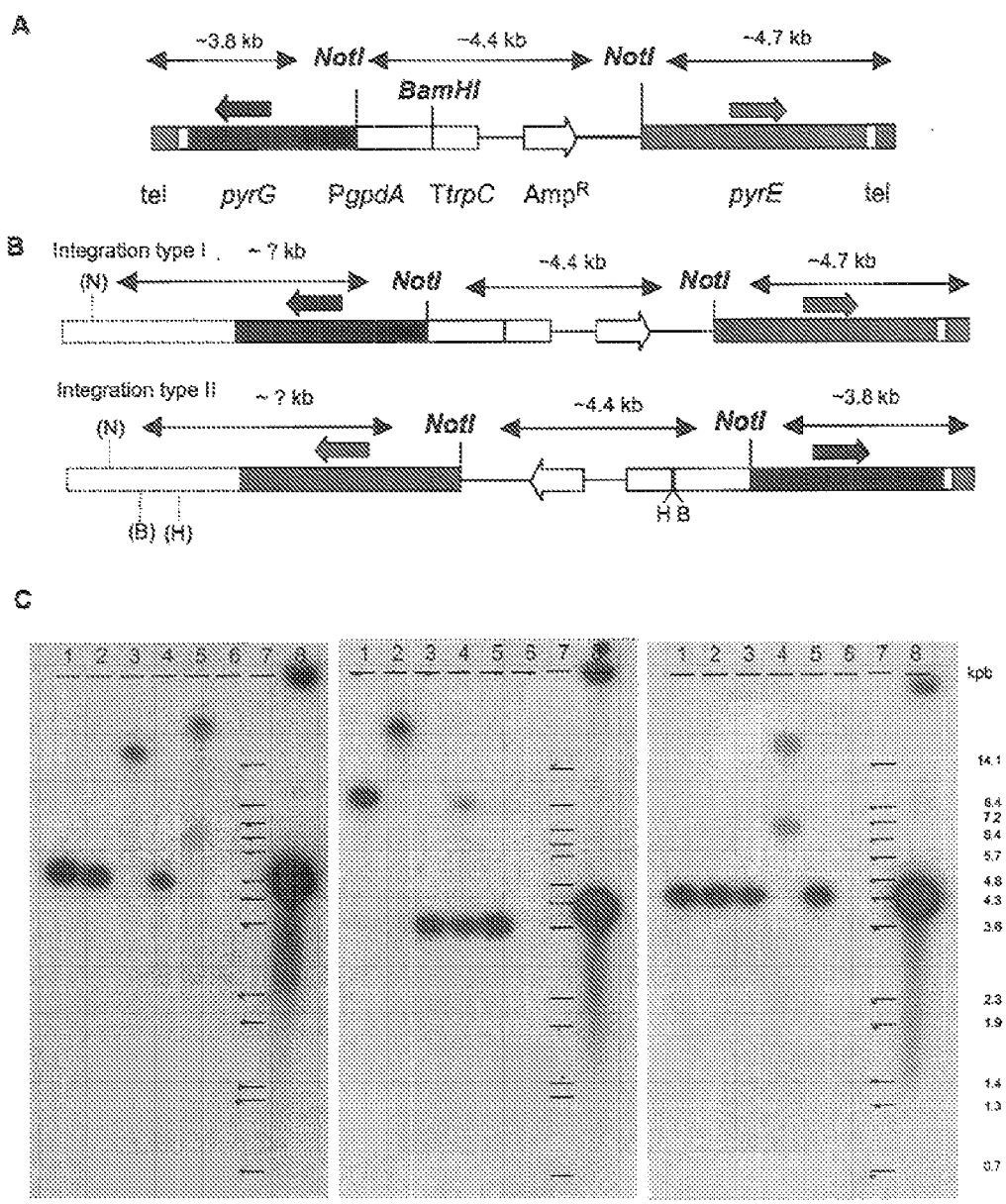
FIGS. 4A-C show the following images: (A) Schematic representation of the in vivo linearized derivative of the telomeric vector pPgpdA-TtrpC pyrE tel pyrG. (B) The schematic representation of situations after stable integration of the telomeric vector within or near the telomeric regions of the *C. lucknowense* chromosomes. (C) A digitized image of a Southern analysis of NotI digested chromosomal DNA of five UV18#100.fΔpyr5Δpyr4[pPgpdA-TtrpC pyrE tel pyrG] transformants probed with specific probes for pyrE (left), pyrG (middle) and PgpdA-TtrpC. The positive control is 10 ng of the vector pPgpdA-TtrpC pyrE tel pyrG digested with I-CeuI and NotI.

Analysis of a set of Pyr+ transformants of UV18#100.f Δpyr5 obtained with the vector pPgpdA-Ttrpc pyrE tel showed that during the integration process part of the linear vector could be lost and that sequences closer to the dominant selection marker (pyrE) were retained more frequently. Based on these observations the vector was redesigned by introducing a second dominant selection marker, the pyrG gene of *A. nidulans*. In this vector, assigned as pPgpdA-TtrpC pyrE tel pyrG (FIG. 2) the promoter and terminator sequences were then flanked by two selection markers. This vector was introduced into strain UV18#100.f Δpyr5Δpyr4. The transformation frequency and ratio of colonies displaying a ragged or smooth colony morphology was comparable to that obtained with the previous telomeric vector pBlue-pyrE tel. Twenty colonies from the pool of propagules of UV18#100.f Δpyr5Δpyr4[pPgpdA-TtrpC pyrE tel pyrG] that grew on selective medium were selected for further analysis. PCR and Southern analysis demonstrated that in all these transformants the expression cassette (PgpdA-TtrpC) was present and intact. Based on the hybridization patterns of chromosomal DNA probed with the fragments for pyrE, pyrG and the expression cassette we could deduce the position of integration (FIG. 4). The vector had integrated into the genome at the end of a chromosome in all transformants. Recombination occurred via one of telomeric regions of pPgpdA-TtrpC pyrE tel pyrG resulting in a situation that either the pyrG (type I) or pyrE (type II) gene was located at the most distal part of a chromosome (FIG. 4B). The difference in size of the restriction fragments of both type I and II transformants shows that integration occurs at different chromosomes. The integrated vectors were genetically stable over several generations even under non-selective cultivation conditions (medium supplied with uridine) in liquid medium. The advantage of this stabilization step during propagule formation in liquid medium is that with our newly designed vector single copy integration occurs within or near the telomeric regions of the C1 chromosomes at a very high frequency. This aspect is important for HTS as it could result in a more uniform expression pattern compared to other integrative vectors.

Validation of Reporter Gene Expression in the Telomeric Vectors

Figure 5:
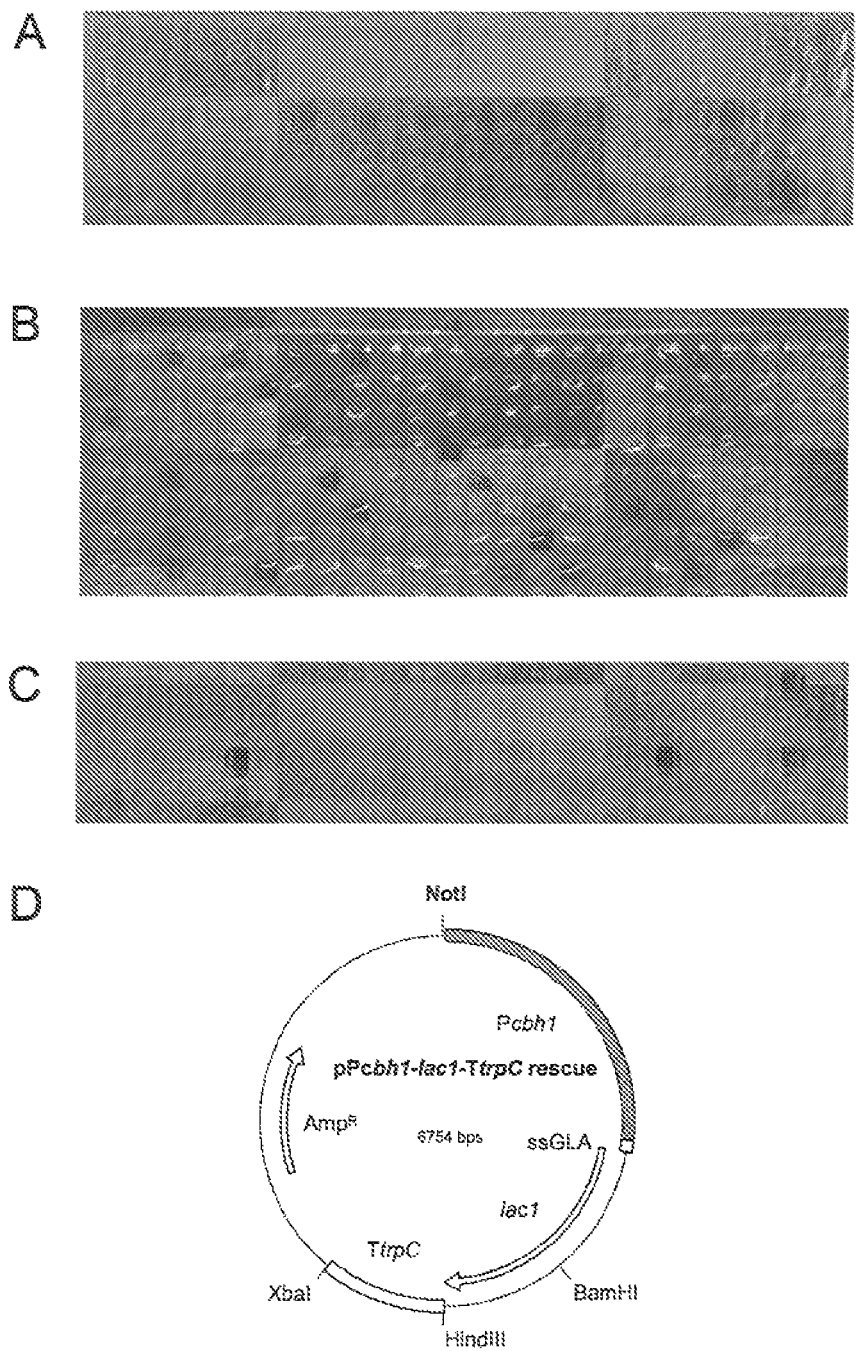
FIGS. 5A-D show ABTS oxidation assay plates of various medium samples. (A) Medium samples of 12 randomly selected UV18#100.fΔpyr5Δpyr4[pPcbh1-Tcbh1 pyrE tel pyrG] (top) and 24 randomly selected UV18#100.fΔpyr5Δpyr4[pPcbh1-lac1-TtrpC pyrE tel pyrG] transformants. (B) Medium samples of a screening plate for laccase activity. Propagules of UV18#100.fΔpyr5Δpyr4 [pAN52 pyrE tel pyrG] and UV18#100.fΔpyr5Δpyr4 [pPcbh1-lac1-TtrpC pyrE tel pyrG] were mixed such that one well in six was expected to have a positive hit. (C) Medium samples of 27 Pyr$^+$ co-transformants of UV18#100.fΔpyr5 [pPcbh1-lac1-TtrpC rescue/pBlue-pyrE].

Two reporter constructs were cloned in the backbone of the pPgpdA-TtrpC pyrE tel pyrG vector (FIG. 2) to evaluate the use of the telomeric vector containing two auxotrophic selection markers for expression and screening. In this procedure the gpdA promoter was replaced with the promoter for the cellobiohydrolase (CBH1) encoding gene cbh1 of *C. lucknowense* to maximize the expression levels for the reporter genes. A high level of expression is essential as the inventors have shown that the integrated telomeric vector is present as a single copy in *C. lucknowense*. The reporter genes used were the glaA gene of *A. niger* and the laccase encoding gene (lac1) of *P. cinnabarinus*. For both enzymatic activities a robot compatible assay was available. The two reporter vectors pPcbh1-lac1-TtrpC pyrE tel pyrG and pPcbh1-glaA-Tcbh1 pyrE tel pyrG and a control vector (pPcbh1-Tcbh1 pyrE tel pyrG) were introduced separately into strain UV18#100.f Δpyr5Δpyr4. The transformation frequencies of the reporter containing vectors were comparable to those obtained with the control vector. Eighteen colonies derived from the propagule pool of UV18#100.f Δpyr5Δpyr4 [pPcbh1-glaA-Tcbh1 pyrE tel pyrG] transformants were randomly selected for further analysis. All contained the Pcbh1-glaA-Tcbh1 expression cassette and produced glucoamylase. In a glucoamylase activity assay based on p-nitrophenyl-β-maltoside 17 transformants had an increased absorbancy value at 405 nm value ($\Sigma_{E405\ nm}$: 1.46±1.10) that was at least 5-fold higher than the value of the control strain UV18#100.f Δpyr5Δpyr4[pPcbh1-Tcbh1 pyrE tel pyrG] (E405 nm: 0.13). Upon introduction of the vector pPcbh1-lac1-TtrpC pyrE tel pyrG into strain UV18#100.f Δpyr5Δpyr4 laccase positive transformants were identified by monitoring the oxidation of ABTS (2,2-azino-bis-[3-ethylthiazoline-6-sulfonat]) (FIG. 5A). Although there is still variation in the production levels both in glucoamylase and laccase case, this variation in expression profile is significantly less than the variation obtained with traditional, ectopic integrative vectors at a single copy level. The variation in reporter gene expression with the telomeric vector might still be the results of the site of integration. This could be a combined effect of the integration at different ends of the chromosomes and the orientation of the expression cassette. In conclusion, using the telomeric vector containing two auxotrophic selection markers more than 95% of the propagules express the reporter genes at clearly detectable level compared to the host strain.

Fungal High Throughput Screening and Insert Recovery

To demonstrate the screening procedure in a fungal high-throughput screening setting using the *C. lucknowense* system and to demonstrate the recovery procedure of the inserts of interest, propagules from a ABTS positive UV18#100.fΔpyr5Δpyr4 [pPcbh1-lac1-TtrpC pyrE tel pyrG] transformant were mixed with propagules from a UV18#1001 Δpyr5Δpyr4[pPcb1-Tcbh1 pyrE tel pyrG] transformant. In the described proof of concept experiment propagules of a laccase transformant (oxidation of ABTS) were mixed with propagules of the control transformant in a ratio of 1:40. An aliquot, containing approximately the number of ABTS positive propagules expected to be present in two 96 wells plates, was plated directly on selective agar plates and 37 ABTS positive colonies were found. The propagule mixture was sampled into the wells of microtiter plates using the Allegro system (Caliper Lifesciences, Hopkinton, USA). When suitable cultivation conditions are applied the propagules will first form mycelium pellets which are then converted in a high density propagules mixture. From this propagule mixtures small aliquots were transferred robotically to a new plate containing production medium. The culture supernatants from the resulting daughter cultures were assayed using a fully automated ABTS oxidation assay in the Staccato robotic system (Caliper Lifesciences, Hopkinton, USA). Thirty-five ABTS positive wells were identified in the two plates seeded with the mixture of propagules (FIG. 5B).

To verify and identify the ABTS positive clone in the propagule mixture a second screening was performed for six positive hits. Firstly, the number of propagules in the well that corresponds to a hit was determined by making serial dilutions and performing colony counting on selective agar plates. The samples were then diluted to an average seeding density of one propagule per well and seeded in the wells of two microtiter plates. The number of pellets formed in each well was scored by visual inspection after two days of cultivation and this number was interpreted as the number of propagules seeded per well. Medium samples were taken after 96 h of cultivation and ABTS oxidation was measured. Using this set up many ABTS positive wells that were seeded with a single propagule were identified (results not shown).

The inventors have tested the recovery of the reporter genes from the positive *C. lucknowense* transformants by PCR using a combination of a specific primer in the promoter and in the terminator region and total genomic DNA as template. However, based on the integration pattern of the vector at the telomeric ends of the C1 chromosomes as described above, the complete expression cassette and the backbone for propagation and selection in *E. coli* should be present on a defined NotI fragment (FIG. 4). Therefore beside the PCR approach, the recovery of the essential parts of the integrated telomere vector should be possible via transformation of *E. coli* with genomic DNA isolated from the positive transformants. The advantages of this approach are that it eliminates the chances of introducing unwanted mutations by PCR and that the recovered vector contains an expression cassette that can be used directly for final hit verification. Several mycelium pellets of ABTS positive wells that were seeded with a single propagule were used to inoculate a shake flask medium culture and from the formed mycelium genomic DNA was isolated. Using a set of Pcbh1 and TtrpC derived primers a specific lac1 containing fragment could be amplified by PCR in all samples. Genomic DNA isolated from a verified positive hit was treated with NotI, self-ligated, and the ligation mixture was introduced into *E. coli*. Plasmid DNA from ampicillin-resistant colonies was analyzed for the presence of the expression cassette. According to PCR and restriction analysis eleven out of 12 colonies tested contained the expected plasmid, pPcbh1-lac1-TtrpC rescue (FIG. 5D).

To verify the advantages of the approach described above, the strain UV18#100.f Δpyr5 was co-transformed with a mixture of the vectors pPcbh1-lac1-TtrpC rescue and pBlue-pyrE. Transformants were selected by growth on minimal agar plates. Individual transformants were tested for their ability to oxidize ABTS. Twenty percent of the Pyr$^+$ transformants were ABTS positive (FIG. 5C). Within this set of transformants the variation in expression level was much more pronounced compared to a set of transformants obtained with the expression cassette present on the telomeric vector (FIG. 20A). As for the production levels obtained in this case in some of the UV18#100.f Δpyr5 [pPlac1T rescue/pBlue-pyrE] transformants a more than 20-fold higher laccase activity was measured. These high levels might be the result of multiple copy integration of the vector, the integration in the genome at a position that facilitates high expression levels or a combination of both. Accordingly, the re-isolated insert DNA encodes the enzymatic activity. In addition, a first generation production strain is produced.

Figure 6:
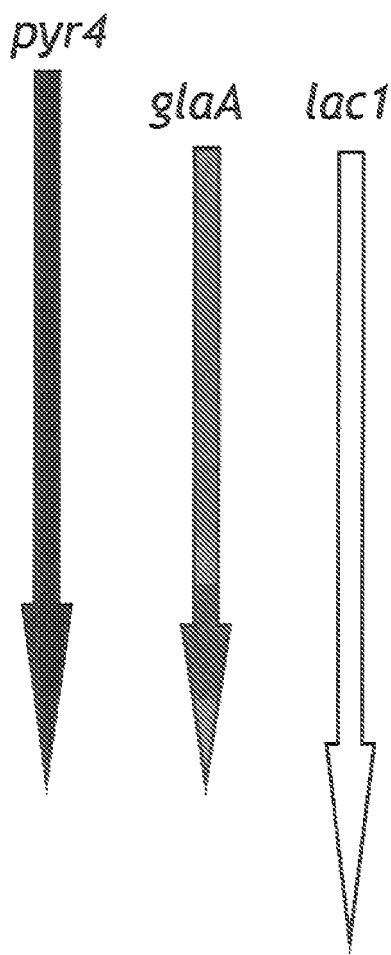
FIG. 6 is a flow chart of the integration of the individual steps for High Throughput Screening in *Chrysosporium lucknowense* C1 using the Allegro™ and Staccato™ robotic liquid handling systems from Caliper Lifesciences (Hopkinton, US UV18#100fΔalp1[88+90 pyrE tel pyrG]#E8, 3—UV18#100fΔalp1[88+90 pyrE tel pyrG]#E2 and 4—negative control strain UV18#100fΔalp1[pyrE tel pyrG]. From left to right in panel C, M—kDa marker, then the first three fractions, respectively, of 1—negative control strain UV18#100fΔalp1[pyrE tel pyrG], 2—transformant UV18#100fΔalp1[88+90 pyrE tel pyrG]#E2, 3—UV18#100fΔalp1[88+90 pyrE tel pyrG]#E2, 4—antibody processing control strain UV18#100fΔalp1[88/90]#58 and 5—two lanes of IgG control protein (14 and 28 ng).
Figure 7:
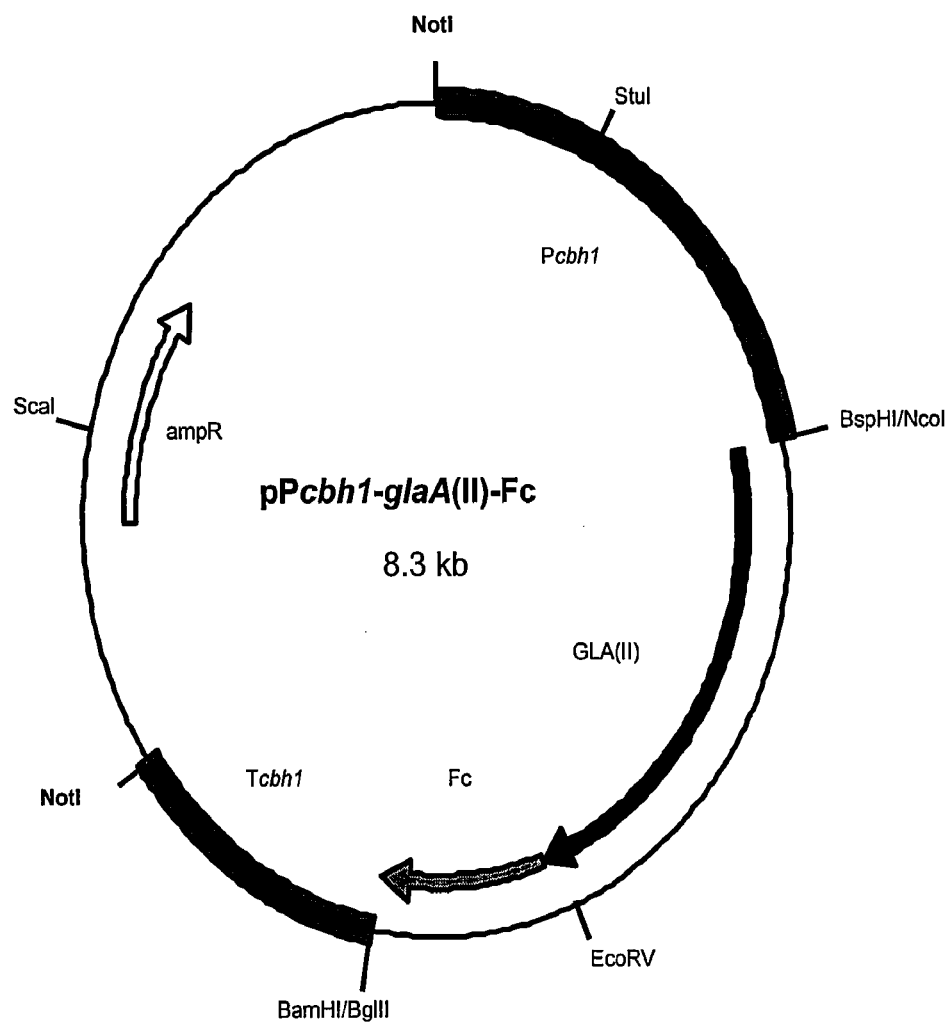
Figure 8:
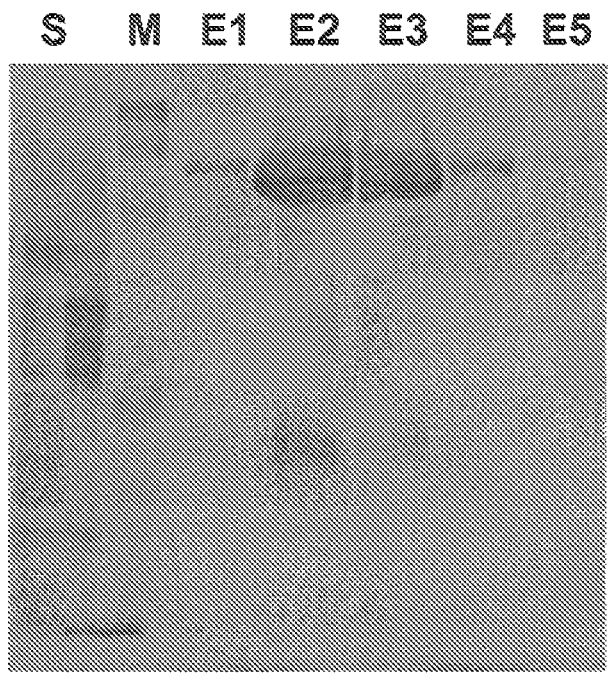
Figure 9:
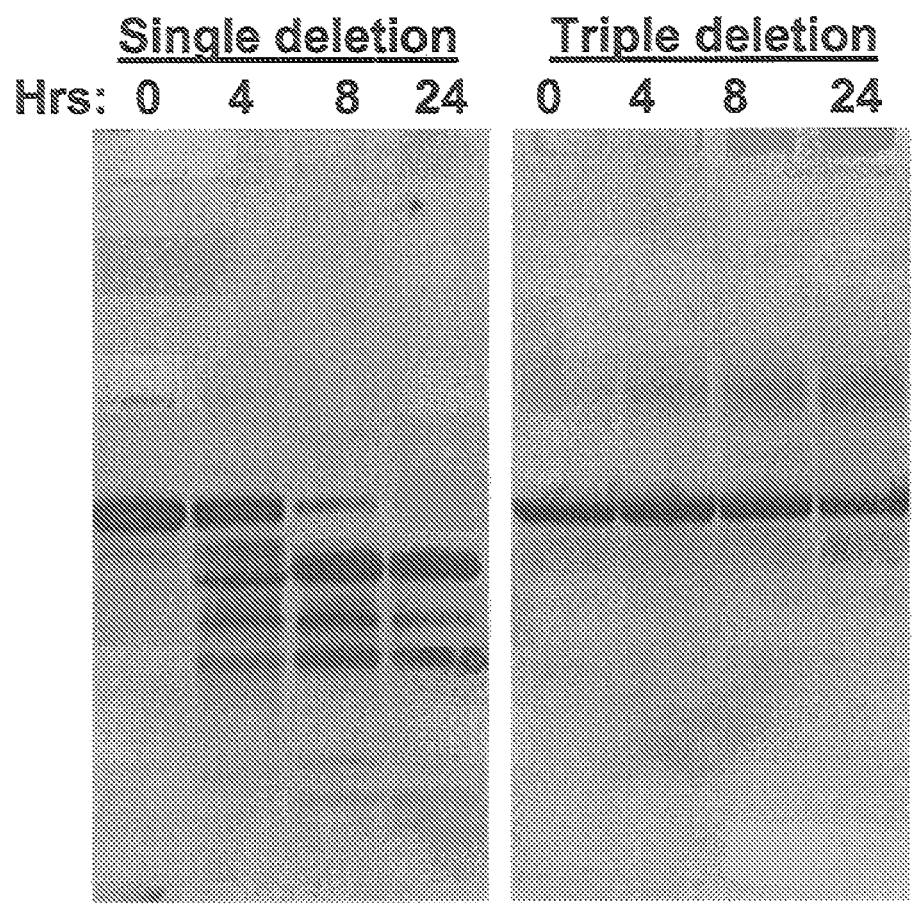
Figure 10:
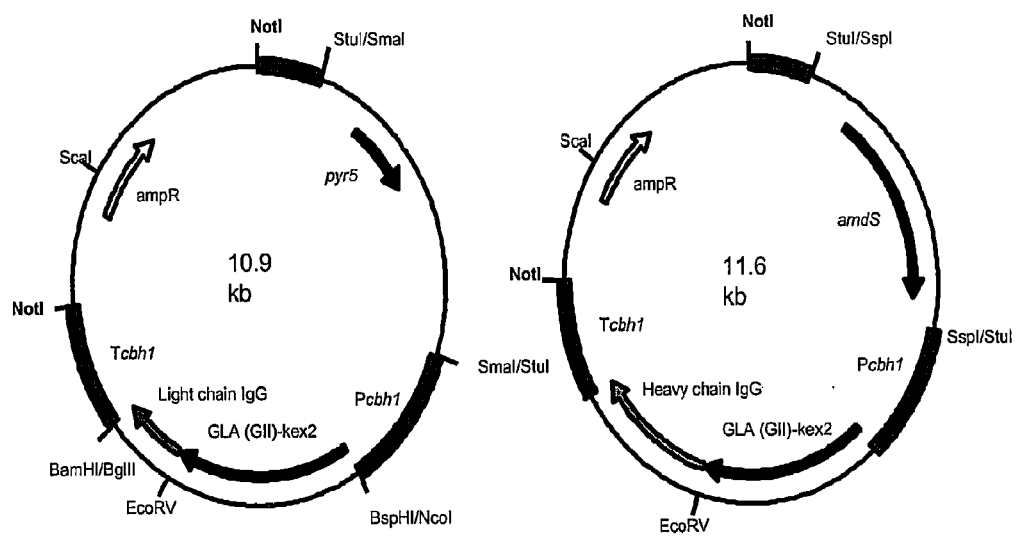
Figure 11:
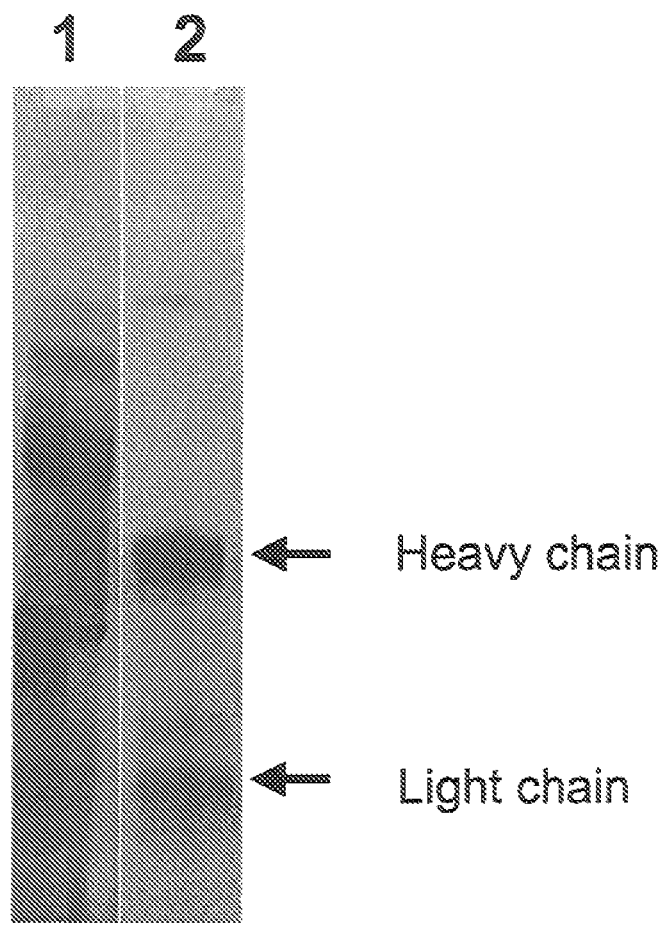

The experiments presented show the successful use of the telomeric vector for library construction and high frequency transformation and the subsequent screening of genomic and of artificial cDNA libraries in a high throughput fashion (FIG. 6). The results support the inventors' concept that this vector, in combination with the screening strategy, will be a powerful tool for the screening of evolved libraries. The need to reduce the variation between individual transformants is provided by the design of the telomeric vector and the DNA stabilization procedure. The actual use of a production strain as host for screening and the use of the rescued plasmid without further modification shortens the time required between screening and product development.

REFERENCES FOR EXAMPLE B

1. Short J M, Keller M. High throughput screening for novel enzymes. U.S. Pat. No. 6,174,673 (2001).
2. Dalboge H, Heldt-Hansen H P. A novel method for efficient expression cloning of fungal enzyme genes. *Mol. Gen. Genet.* 243, 253-260 (1994).
3. Punt P J, van Zeyl C, van den Hondel CAMJJ. High throughput screening of expressed libraries in filamentous fungi. WO 01/79558 (2001).
4. Punt P J, van den Hondel CAMJJ. Transformation of filamentous fungi based on hygromycin B and phleomycin resistance markers. *Methods in Enzymology* 216, 447-457 (1993).
5. Stinchcomb D T, Struhl K, Davies R W. Isolation and characterization of a yeast chromosomal replicator. *Nature* 282, 39-43 (1979).
6. Sohn J H, Choi E S, Kim C H, Agaphonov M O, Ter-Avanesyan M D, Rhee J S and Rhee S K. A novel autonomously replicating sequence (ARS) for multiple integration in the yeast *Hansenula* polymorphs DL-1. *J. Bacteriol.* 178, 4420-4428 (1996).
7. Gems D, Johnstone I L, Clutterbuck A J. An autonomously replicating plasmid transforms *Aspergillus nidulans* at high frequency. *Gene* 98, 61-67 (1991).
8. Verdoes J C, Punt P J, van der Berg P, Debets F, Stouthamer A H, van den Hondel CAMJJ. Characterization of an efficient gene cloning strategy for *Aspergillus niger* based on an autonomously replicating plasmid: cloning of the nicB gene of *A. niger. Gene* 146, 159-165 (1994).

9. Fierro F, Kosalkova K, Gutierrez S, Martin J F. Autonomously replicating plasmids carrying the AMA1 region in *Penicillium chrysogenum*. *Curr. Genet.* 29, 482-489 (1996).

10. Bruckner B, Unkles S E, Weltring K, Kinghorn J R. Transformation of *Gibberella fujikuroi*: effect of the *Aspergillus nidulans* AMA1 sequence on frequency and integration. *Curr. Genet.* 22, 313-316 (1992).

11. Aleksenko A, Ivanova L. In vivo linearization and autonomous replication of plasmids containing human telomeric DNA in *Aspergillus nidulans*. *Mol. Gen. Genet.* 260, 159-164 (1998).

12. Kistler H C, Benny U. Autonomously replicating plasmids and chromosomes rearrangements during transformation of *Nectria haematococca*. *Gene* 117, 81-89 (1992).

13. Javerzat J-P, Bhattacherjee V, Barreau C. Isolation of telomeric DNA from the filamentous fungus *Podospora anserina* and construction of a self replicating linear plasmid showing high transformation frequency. *Nucleic Acids Research* 21, 497-504 (1993).

14. Powell W A, Kistler H C. In vivo rearrangement of foreign DNA by *Fusarium oxysporum* produces linear self-replicating plasmids. *J. Bacteria* 172, 3163-3171 (1990).

15. Bennett J W, Lasure L L. Growth Media. In: More Gene Manipulation in Fungi. Bennett J W, Lasure L L (eds.), pp 444-445. San Diego: Academic Press, Inc. (1991).

16. Record E, Punt P J, Chamkha M, Labat M, van den Hondel CAMJJ, Asther M. Expression of *Pycnoporus cinnabarinus* laccase gene in *Aspergillus niger* and characterization of the recombinant enzyme. *Eur. J. Biochem.* 269, 602-609 (2002).

17. Hynes M J, Corrick C M, King J A. Isolation of genomic clones containing the amdS gene of *Aspergillus nidulans* and their use in the analysis of structural and regulatory mutations. *Mol. Cell. Biol.* 3, 1430-1439 (1983).

18. Hynes M J, Pateman J A. The genetic analysis of regulation of amidase synthesis in *Aspergillus nidulans*. II. Mutants resistant to fluoroacetamide. *Mol. Gen. Genet.* 108, 107-116 (1970).

19. Gems D, Aleksenko A, Beleky 1, Robertson S, Ramsden M, Vinetski Y, Clutterbuck A J. An "instant gene bank" method for the gene cloning by mutant complementation *Mol. Gen. Genet.* 242, 467-471 (1994).

C. Expression of a Glucoamylase-Fc Fusion Protein in *C. Lucknowense*

The plasmid pPcbh1-glaA(II)-Fc was constructed in which the catalytic domain of the glucoamylase gene from *Aspergillus niger* was fused to an Fc gene. Expression of the fusion gene was driven by the cbh1 promoter of *C. lucknowense*. This plasmid is shown in FIG. 7. The large NotI fragment was excised from the plasmid and purified, and this DNA, was cotransformed with another DNA fragment containing the pyr5 gene of *C. lucknowense* into strain UV18#1001 pyr5 Δalp1. Pyrimidine prototrophic strains were selected and screened for the presence of glucoamylase DNA. Among the transformants was a strain that produced about 1 gram per liter of the predicted glucoamylase-Fc fusion protein. The protein was readily purified from culture filtrates of the transformant strain to a purity greater than 90% as shown in FIG. 8. These data indicate that high levels of human Fc can be stably produced as a glucoamylase fusion protein and that the Fc portion of the molecule properly dimerizes and folds as indicated by the binding to protein A.

D. In Vitro Stability of Human IgG1 Against *C. Luckowense Culture Filtrates*

Human IgG1 was incubated with culture filtrate from *C. lucknowense* strains deleted for alp1 (single protease-deleted mutant) or alp1, pep4, and alp2 (triple protease-deleted mutant). Samples were removed after 0, 4, 8, and 24 hours of incubation and subsequently subjected to Western blot analysis using an Fc-specific anti-human IgG1 antibody. The results of this type of analysis are shown in FIG. 9. As seen the antibody is reasonably stable against culture filtrate from the single mutant and more stable against culture filtrate from the triple mutant. In the latter case, no sign of degradation of the heavy chain is seen after 24 hours of incubation. Western analyses against light-chain specific antibodies showed similar results.

E. Expression of Full-Length Antibodies in *C. Lucknowense*

Plasmids expressing the light and heavy chains of a human IgG1 were separately constructed, as shown in FIG. 10. Each plasmid contained genes for the heavy or light chain of the antibody fused to the catalytic subunit of *A. niger* glucoamylase. Between the glucoamylase gene and the antibody gene is a kex2 cleavage site. The presence of this site results in cleavage of the glucoamylase from the antibody chain so that free glucoamylase and antibody are produced. Each glucoamylase-antibody fusion construct was driven by the cbh1 promoter. The light chain-expressing plasmid contained the pyr5 gene as a selection marker. The heavy chain-expressing plasmid contained the *A. nidulans* amdS gene as a selection marker. *C. lucknowense* strains are naturally amdS-negative. The amdS gene encodes an amidase, and introduction of this gene into *C. lucknowense* allows the strain to grow on acetamide as sole nitrogen source. The large NotI fragments were separately isolated and contransformed into UV18#100.f pyr5 Δalp1, selecting for Pyr5-positive AmdS-positive transformants. The transformants were further screened for production of glucoamylase and subsequently for the production of both heavy and light antibody chains.

A number of transformants expressed both the heavy and light chains of the human IgG1. One such transformant was analyzed in detail. Filtrates from fermentation cultures contained approximately 200-400 mg of full-length IgG1 measured by quantitative Western analysis. The antibody was readily purified by chromatography on protein A (FIG. 11), and cell-based bioactivity assays, performed on protein A-purified antibody, indicated that about 200 mg of active IgG was present per liter of culture filtrate. These results indicate that full-length antibodies can be expressed at high titer in a dimerized, properly folded, and active form in *C. lucknowense* strains.

F. Screening for Improved Antibody Affinity Using *C. Lucknowense*

Based on data indicating the antibodies can be stably expressed and proof-of-concept experiments showing that high-throughput screening of expression libraries can be accomplished utilizing *C. lucknowense* host strains, it is possible to produce libraries of libraries containing variants of both heavy and light chains coexpressed in the same host strains. The screening technology will allow arraying of monoclonal cultures, each expressing a distinct antibody into wells of microtiter dishes. Using ELISA or other assays, the antibodies expressed by the separate clones can be assayed for binding and the best binding antibodies screened for. The cultures selected from the screening procedure can be further cultivated for more detailed analysis. DNA from the most promising clones can be retrieved, isolated and sequenced. Using the known sequences, C. lucknowense strains optimized for expression of the antibody can be generated to produce large quantities of those antibodies.

FIG. 12 shows plasmids that can be used for screening of libraries of libraries for antibody binding. Two alternatives are shown. FIG. 12A (left) shows a vector in which libraries of heavy and light chain variable regions ($V_H$ and $V_L$, respectively) are together cloned into a C1-specific replicating vector so that glucoamylase fusions to a single-chain Fv are produced. FIG. 12B (right) shows a vector in which full-length antibody chains are expressed as glucoamylase fusions, each from their own promoter. Numerous possibilities exist for the latter vector. In another aspect, the light and heavy chains could be placed in either order in either orientation. Additionally, although both chains in FIG. 12 are shown utilizing cbh1 promoter and terminator sequences, distinct promoters and terminators could be used to minimize repetitive sequences in the vector. In one aspect, a fusion partner-heavy-light chain fusion protein can be produced in which the three components (fusion partner, heavy and light-chain) are separated by proteolytic processing sites (see FIGS. 13-14). These vectors use human telomeric sequences (hTel) for replication in C. lucknowense and contain two selective markers pyrE and pyrG flanking the expression constructs, and sequences allowing replication in E. coli. Upon introduction into C. lucknowense, the vectors spontaneously linearize between the human telomeric sequences (hTel). The use of doubly marked pyr4-pyr5 mutants of C. lucknowense ensures that integrants contain the entire expression construct. Individual transformants are then separated and screened for binding in a high-throughput fashion. The expression constructs from transformants of interested can be isolated by purifying genomic DNA from those constructs, digesting with NotI, ligating to recircularize, then transforming E. coli and selecting for ampicillin resistance. The resulting E. coli transformants will contain plasmids carrying the antibody expression construct. In the case where full-length antibodies are screened, the expression constructs can be subcloned directly into expression vectors to allow high-level expression of the antibodies as described in Example E. When a single-chain Fv is used in the expression screening, the plasmids can be deconstructed and relevant sequences spliced into full-length heavy and light chains for expression as described in Example E. As an alternative to the replicative vectors, individual vectors carrying the heavy and light chain genes were generated in each using the pyrE or pyrG selection marker.

G. Additional Vectors for Antibody Expression and Screening

One non-limiting example of site-specific recombination technology is Gateway® cloning. "Gateway® cloning" is a cloning method based on the site-specific recombination of lambda bacteriophage. Briefly, the Gateway® technology (Invitrogen, Carlsbad, Calif.), uses a lambda recombinase to catalyze in vitro recombination events between sequences flanked by 25-bp att sites. Often, those sequences are present on two separate plasmids, as when moving an insert from a starting "entry" construct to a "destination" vector. There are also systems for cloning PCR fragments directly into Gateway® plasmids using recombinases. This technology is described, for example, in Mabashi et al., Biosci Biotechnol Biochem. 2006 August; 70(8):1882-9. Various vectors can be produced using any suitable in vitro recombination strategy, of which the Gateway® technology is only one, non-limiting example. The design of vectors that may be produced using in vitro recombination strategies is described herein.

Specifically, the present invention also encompasses the creation of vectors for transformation of fungal host cells as described herein that are designed to allow the efficient transfer of the expression cassette to and/or from a lambda bacteriophage. Exemplary designs for such vectors are illustrated in FIGS. 15-18. While these figures illustrate the use of the vectors to introduce immunoglobulin heavy and light chains, the vectors can similarly be used to express other heterodimeric and heteromultimeric proteins. As discussed above, the technology used to create or implement such vectors can make use of any suitable recombination strategy.

Figure 15:
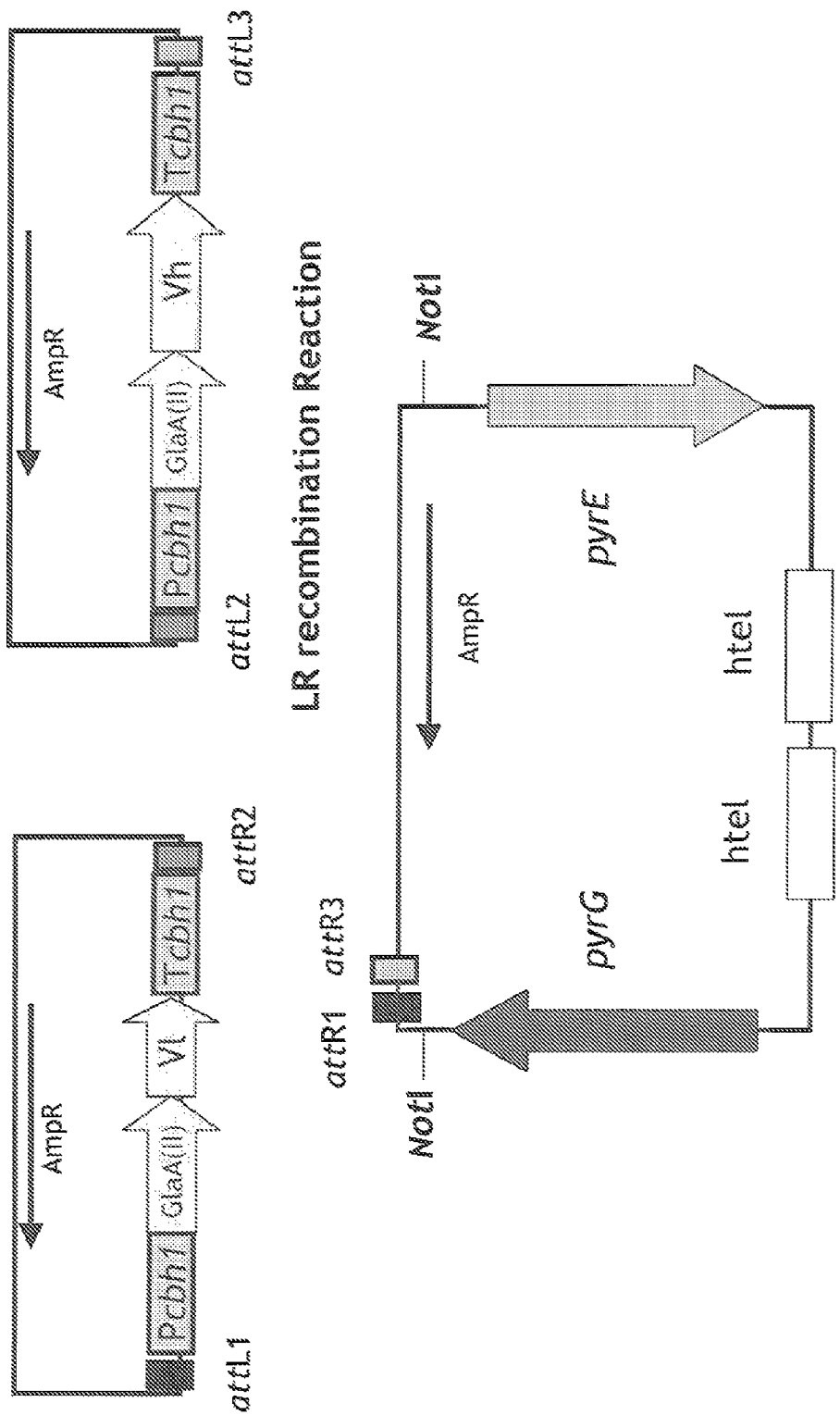
Figure 16:
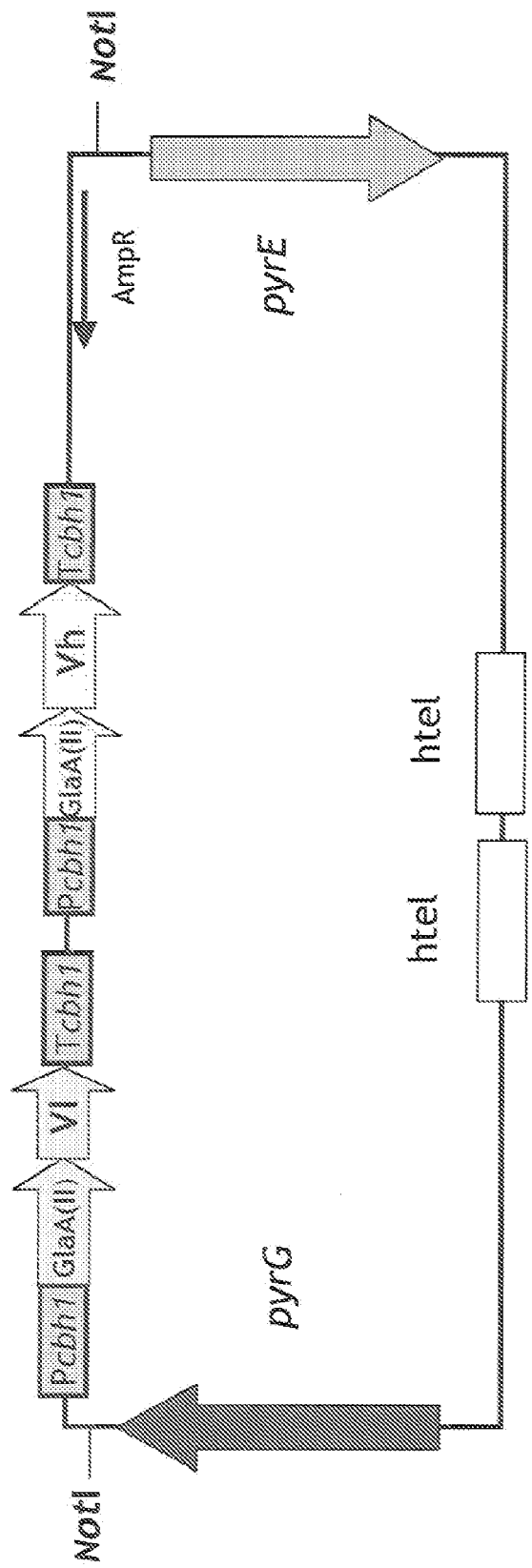

FIGS. 15-16 illustrate a vector of the present invention in which two separate lambda bacteriophage vectors, one comprising an immunoglobulin heavy chain construct and one comprising an immunoglobulin light chain construct, DNA fragments are excised from the lambda bacteriophage vectors and ligated into a fungal expression vector according to the present invention. In this non-limiting example, the 3' end of one construct contains the same att site as the 5' end of the second construct (see attR2 and attL2), such that by a RL (right-left) recombination event, the two constructs are ligated into the fungal vector next to one another, flanked by the remaining att sites from each of the two phage vectors (see attL1 and attR3). The expression cassette can then be excised again for transfer into a phage vector, or excised using distal restriction enzyme sites for, for example, ligation into an E. coli vector. Although both protein chains in this figure are shown utilizing cbh1 promoter and terminator sequences (see FIG. 16), distinct promoters and terminators could be used to minimize repetitive sequences in the vector.

Figure 17:
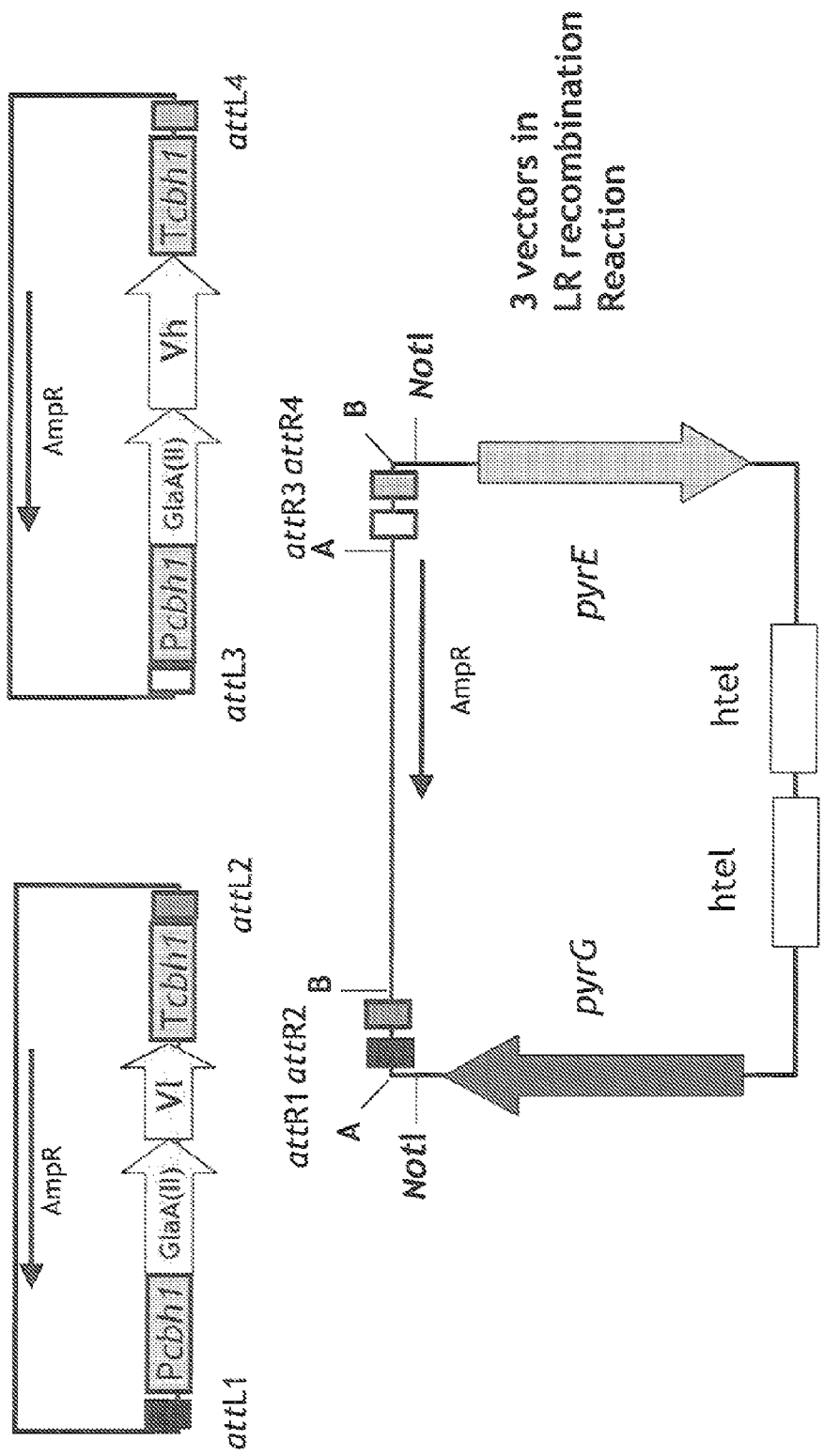
Figure 18:
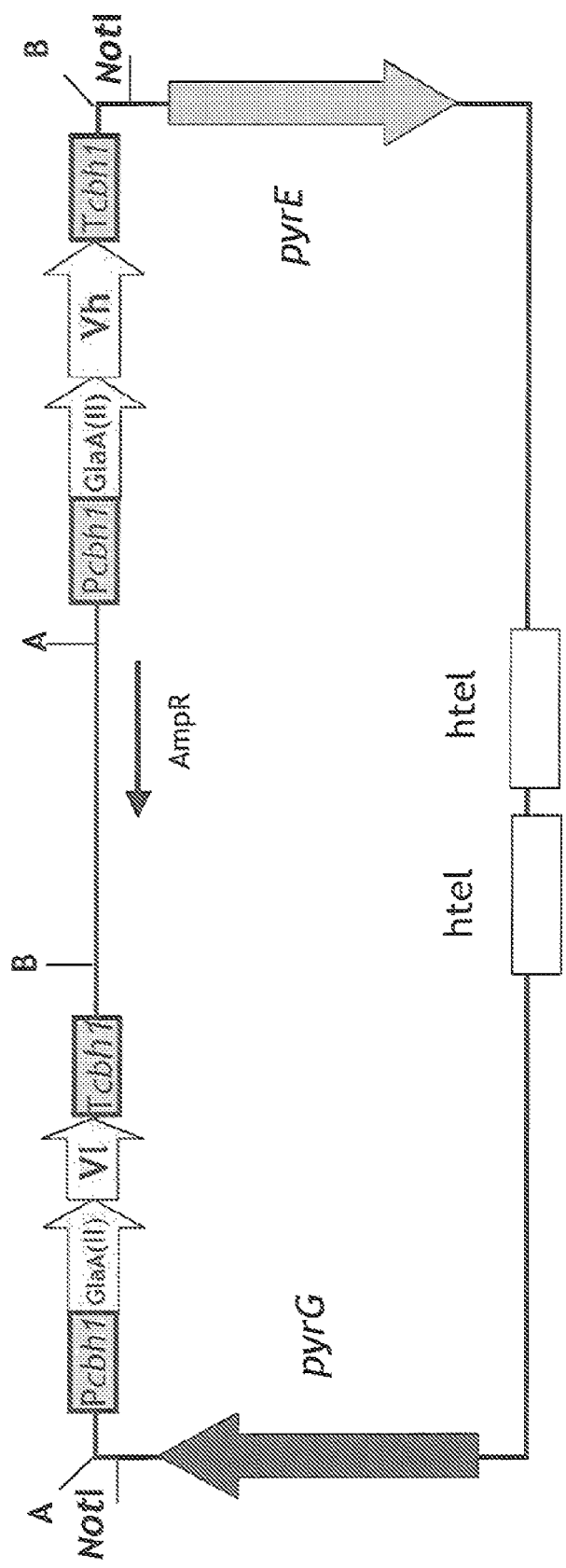

In a second non-limiting example, different right and left att sites are used in each bacteriophage vector, so that the two constructs are excised and then ligated into the fungal vector as separate expression cassettes. This is illustrated in FIGS. 17-18. In this example, each cassette is flanked by different restriction sites (A and B in FIGS. 17 and 18) which will facilitate, if desired, the separate excision of each DNA expression component from the vector. Alternatively, single restriction sites flanking the entire expression cassette are available to facilitate recovery, cloning, and/or transfer of the DNA.

Figure 13:
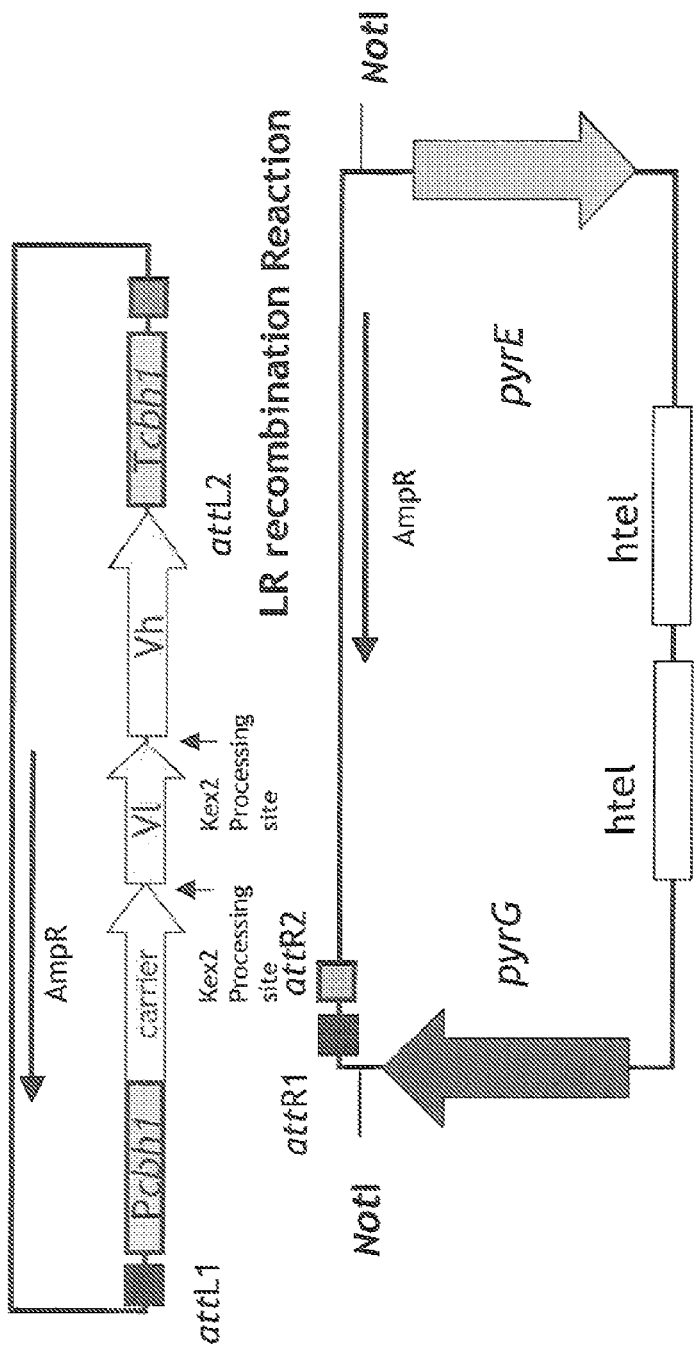
Figure 14:
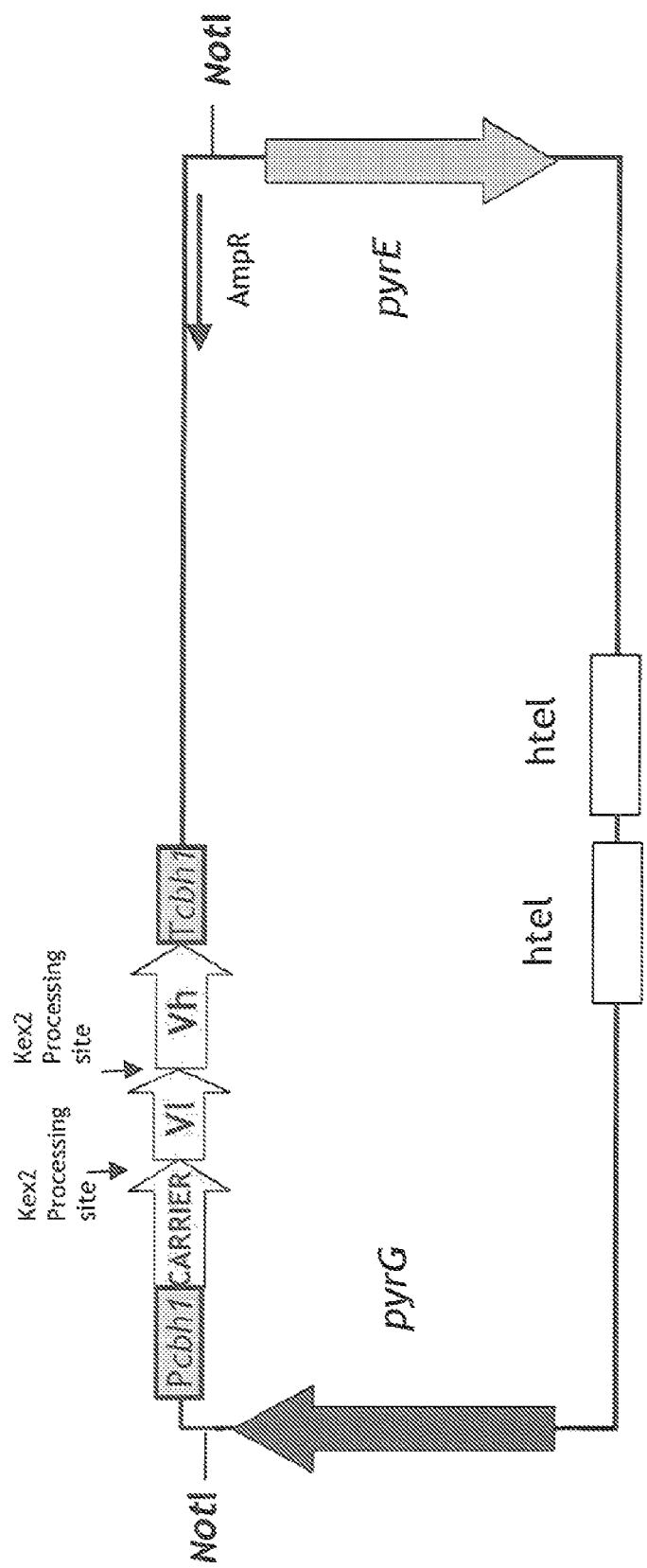

In a third non-limiting example, a strategy similar to that shown in FIGS. 15-16 is used, except that the fusion components (e.g., the fusion partner, heavy chain and light chain) are linked to one another via processing sites. This construct provides additional flexibility in manipulating the components of the vectors as a unit or as individual components and can enhance isolation, cloning, and DNA manipulation strategies. This design is illustrated in FIGS. 13-14.

H. Expression of Full-Length Antibodies in C. Lucknowense

The NotI fragment of the telomere vector flanked with pyrE and pyrG selection markers (example B; FIG. 2) was introduced in the unique NotI site of a vector containing both the expression cassette of the heavy and light chain each fused to the catalytic subunit of A. niger glucoamylase (GLA). Between the GLA encoding gene (glaA) and the antibody genes a kex2 cleavage site is present. The plasmids (FIGS. 20A and B) with the expression cassettes for expressing both the heavy and the light chains of the human IgG1 were used to demonstrate a fungal high throughput robotic screening procedure for improved antibody variants in *C. lucknowense*. The plasmids were introduced into strain UV18#100.fΔpyr5Δpyr4Δalp1.

The primary set of transformants was regenerated at 45 rpm and 33° C. in minimal medium supplemented with 0.67 M sucrose. After 40 hours the mixture was inoculated in shake flasks in minimal medium and incubated at 35° C. for 144 hours. The propagules were harvested by filtration and centrifugation. Diluted aliquots of the resuspended propagule mixtures were plated on selective agar plates. Wells of two microtiter plates containing medium optimized for propagule formation were seeded with small mycelium samples of two times 96 individual colonies. After three days, small aliquots of the formed propagule mixtures were transferred to new plates (daughters) containing production medium. Plates were placed in an incubator shaker (35° C. and a rotation speed of 850 rpm) and after 96 hours culture supernatant was collected. The large majority of transformants produced the dimer of the IgG1 heavy chains as detected by spotblot analysis using an AP-conjugated anti-Fc antibody (FIG. 21A) and by ELISA analysis using a protein A coated plate (FIG. 21B).

Two antibody producing transformants obtained after the introduction of the telomeric vector were analyzed in more detail in fed-batch fermentation simultaneously with a positive-control antibody producing strain and a negative control non-antibody producing strain. Both the heavy and light chains of IgG were detected by Western blot analysis. Filtrates from these controlled fermentation cultures withdrawn after 72 h of glucose feed contained approximately 600 mg of GLA. Antibody was purified from the filtrates using protein A chromatography and the presence of both the light and the heavy chains was verified by Western blot analysis. Protein A column purified antibodies were denatured by heating at 95° C. prior to Western blotting. FIGS. 22A and B shows, from left to right, M—kDa marker, 1—antibody-producing control strain UV18#100fΔalp1[88/90]#58, 2—transformant UV18#100fΔalp1 [88+90 pyrE tel pyrG]#E8, 3—UV18#100fΔalp1[88+90 pyrE tel pyrG]#E2 and 4—negative control strain UV18#100fΔalp1[pyrE tel pyrG]. Western blot detection was performed with antibodies specific for the Ig heavy chain (FIG. 22A) or Ig light chain (FIG. 22B).

Absorption measurements at 280 nm indicated that approximately 150 mg purified antibodies were obtained per liter of fermentation broth. A quantification based on glucoamylase activity indicates that about 200 mg of full-length antibody is produced per liter of fermentation supernatant.

80 ml of each fermentation end sample (96 hours for samples 1-3, 120 hours for sample 4; glucose feed was started after 24 hours of fermentation) was purified on protein A column, this was eluted in eight different fractions of 1 ml each. Glucoamylase activity was detected in two fractions, which were pooled and total protein concentration was determined by absorption at 280 nm. Subsequently, 100 ml portions of the end-of-fermentation (EOF) sample were purified using the same protocol. In four eluted fractions glucoamylase activity was detected, and protein concentration was measured using by absorption at 280 nm. The antibody yields are presented in Table E below. All calculations are based on a 100% recovery from the protein A column.

TABLE E

| | Calculated Ab yield (mg/l) in EOF medium based on 2 ml protein A purified sample | Calculated Ab yield (mg/l) in EOF medium based on 80 ml protein A purified sample | Calculated Ab yield (mg/l) in EOF medium based on 100 ml protein A purified sample |
|---|---|---|---|
| 1: control strain | 0 | 2 | 0.5 |
| 2: ab pyrEtelpyrG E2 | 110 | 55 | 46 |
| 3: ab pyrEtelpyrG E8 | 150 | 38 | 52 |
| 4: ab #58 | 200 | 103 | 330 |

Protein A column purified antibodies from the first three fractions above, along with positive and negative controls, were denatured by heating at 95° C., ran on a gel, then visualized by standard protein staining techniques; FIG. 22C shows, from left to right, M—kDa marker, then the first three fractions, respectively, of 1—negative control strain UV18#100fΔalp1[pyrE tel pyrG], 2—transformant UV18#100fΔalp1[88+90 pyrE tel pyrG]#E2, 3—UV18#100fΔalp1[88+90 pyrE tel pyrG]#E2, 4—antibody processing control strain UV18#100fΔalp1[88/90]#58 and 5—two lanes of IgG control protein (14 and 28 ng).

I. The Effect of C1 Repetitive Sequence (CRS)

The effect of a C1 repetitive sequence (CRS), as present in the terminator region of the cbh1 terminator, was analyzed. DNA fragments containing the eg2 expression cassette (Pcbh1-eg2-Tcbh1) were introduced with and without the CRS in a pyr4 deletion mutant of a Eg3 production strain. Based on the model system the presence of the CRS in Tcbh1 leads to 1) an increase in the average beta-glucanase and CMCase activity in microtiter plate and shake flasks cultures; 2) a set of transformants with the highest enzymatic activities; 3) 15-20% increase in total extracellular protein content under controlled fermentation conditions; and 4) an increase in the number of integrated expression cassettes. In the new Eg3/Eg2 production strains both the beta-glucanase and the CMCase have been increased approximately 2-fold compared to the current Eg3 production strain.

A C1 Repetitive Sequence (CRS) of approximately 340 bp was identified in the terminator region the cbh1 gene (Tcbh1) of *C. lucknowense*. FIG. 23 shows a partial nucleotide sequence of the terminator region of cbh1, with the CRS (SEQ ID NO:12) indicated in gray. In all C1 expression vectors containing the Tcbh1, this CRS was present. Compared to other filamentous fungi like *Aspergillus*, the number of integrated copies of the expression cassette in C1 is rather low. Therefore the effect of the CRS on integration was analyzed using the endoglucanase 2 (Eg2) encoding gene (egg) as model.

Transformation and Selection

From the expression vector pPcbh-eg2-Tcbh (FIG. 24), the expression cassette with the CRS was isolated as 4.4 kb NotI fragment. The expression cassette without a large portion of the CRS was isolated as a 4.1 kb NotI-Bcl1 fragment. The strain UV18[EG3#20]Δpyr4 was selected as the C1 host strain for transformation, although any C1 strain should be adequate for purposes of this example. The expression cassette with and without CRS (10 μg) were each independently introduced by co-transformation with the pyr4 gene (2 μg) as selection marker. Approximately 90 transformants with and without CRS were obtained and purified on selective minimal medium.

Cultivation and Enzyme Activities Microtiter plates containing propagule formation optimized (PFO) medium were inoculated with these transformants and incubated for 72 hours. From these cultures, small propagule samples were transferred to new microplates containing minimal production medium. Supernatant was analyzed after 96 hours of incubation at 35° C. for β-glucanase (Azo-barley) and CMC-ase (AzoCMC) activity.

The results indicated that, compared to the control strains UV18[EG3#20][pyr4], the number of transformants with a more than 2-fold increase in activity was higher in the collection of transformants with the CRS than within the set without the CRS (Table F).

TABLE F

Percentages of Samples with Elevated Activity

|  | Azobarley (>2 x background) | AzoCMC-ase (>2 x background) |
|---|---|---|
| +CRS | 76% | 56%* |
| ΔCRS | 20% | 43% |

*only the samples with >2-fold increase in beta-glucanase activity were tested

Based on these assays, the best producers were selected for further analysis in shake flask cultures. Shake flasks containing 50 ml synthetic minimal medium (NH$_4$, 55 mM PO$_4$, cas, p/s, biotin, 0.5% glucose) were inoculated with 5×10$^7$ spores. After 120 hours, medium samples were analyzed for total extracellular protein content, β-glucanase and CMC-ase activity. Only minor differences in specific β-glucanase activity were detected (results not shown) whereas clear differences in CMC-ase activity levels were found (Table G). In all strains with introduced copies of the eg2 expression cassette, the CMC-ase activity is 2 to 4 fold higher than in the control strains (data are expressed in values relative to the control strains, the averages of which were assigned values of one). Strains co-transformed with the eg2 expression cassette with the CRS (Pcbh eg2 Tcbh/pyr4) displayed a higher activity than strains transformed with the expression cassette without the CRS (Pcbh eg2 TcbhΔCRS/pyr4).

Southern Blot Analysis of eg2 Transformants

Figure 25:
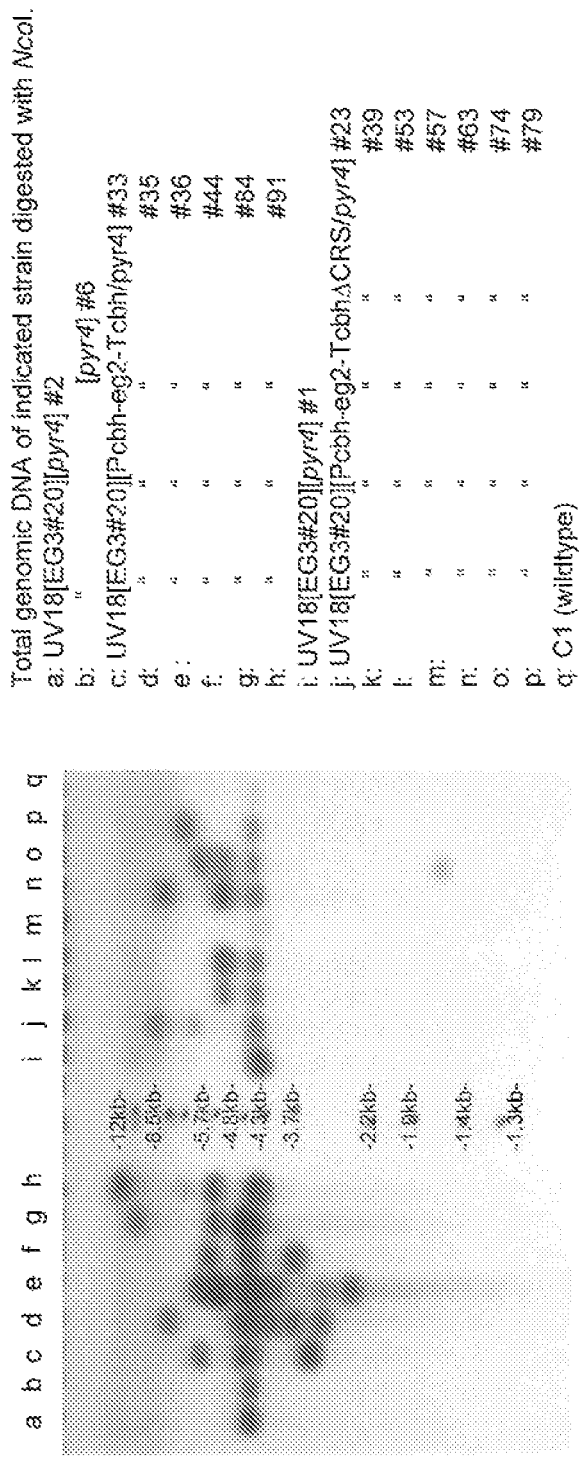
FIG. 25 shows a Southern blot on chromosomal DNA digested with NcoI from UV18[EG3#20[pyr4] and cotransformants with additional copies of an eg2 expression cassette with CRS (left panel) and without CRS in Tcbh1 (right panel) using an internal eg2 (BstEII-EcoRV) fragment as a probe.

Chromosomal DNA was isolated from transformants in order to determine the copy number of the introduced eg2 expression cassette and the integration patterns. Chromosomal DNA was digested with the restriction enzyme NcoI, size fractionated by electrophoresis in an agarose gel, and finally transferred to a nylon membrane. The blot was hybridized with a radioactive labeled internal DNA fragment (BstEII-EcoRV) of the eg2 encoding gene (FIG. 25).

An estimation of the copy number of the eg2 gene was made based on the intensity of the hybridizing fragments (Table G). The copy number is less in the transformants in which the eg2 expression cassette without the CRS was introduced. There is no clear correlation between eg2 copy number and CMCase activity. Most likely, the site of integration plays an important role.

TABLE G

Data overview eg2 multicopy transformants of UV18[Eg3#20]Δpyr4

|  | copy # | Relative CMC-ase 120 hr (u/ml) | Relative Total Protein 120 hr | Relative Specific Activity units/mg |
|---|---|---|---|---|
| C1 (wt) | 1 | — | — |  |
| UV18[EG3#20] |  |  |  |  |
| UV18[pyr4]#2 | 1 | 1 | 1 | 1 |
| UV18[pyr4]#6 | 1 | 1 | 1 | 1 |
| UV18[EG3#20] |  |  |  |  |
| [Pcbh-eg2-Tcbh/pyr4]#33 | 4 | 3.54 | 0.96 | 3.76 |
| [Pcbh-eg2-Tcbh/pyr4]#35 | 6 | 3.38 | 0.86 | 4.00 |
| [Pcbh-eg2-Tcbh/pyr4]#36 | 7 | 4.77 | 1.07 | 4.53 |
| [Pcbh-eg2-Tcbh/pyr4]#44 | 4 | 3.08 | 0.96 | 3.29 |
| [Pcbh-eg2-Tcbh/pyr4]#84 | 4 | 3.38 | 0.98 | 3.53 |
| [Pcbh-eg2-Tcbh/pyr4]#91 | 4 | 2.62 | 0.89 | 3.00 |
| UV18[EG3#20] |  |  |  |  |
| [Pcbh-eg2-TcbhΔCRS/pyr4]#23 | 2 | 4.92* | 1.37 | 3.65 |
| [Pcbh-eg2-TcbhΔCRS/pyr4]#39 | 2 | 4.92* | 1.23 | 4.06 |
| [Pcbh-eg2-TcbhΔCRS/pyr4]#53 | 3 | 3.69 | 1.57 | 2.41 |
| [Pcbh-eg2-TcbhΔCRS/pyr4]#57 | 1 | 2.46 | 1.21 | 2.06 |
| [Pcbh-eg2-TcbhΔCRS/pyr4]#63 | 4 | 2.92 | 1.26 | 2.35 |
| [Pcbh-eg2-TcbhΔCRS/pyr4]#74 | 3 | 3.54 | 1.25 | 2.88 |
| [Pcbh-eg2-TcbhΔCRS/pyr4]#79 | 2 | 2.46 | 1.25 | 2.00 |

*measured in different assay without internal controls

Activity assays and total protein measurements were performed in supernatant from shake flask cultures after 120 hours of incubation.

Controlled Fed Batch Fermentation in Pharma Medium.

Figure 26:
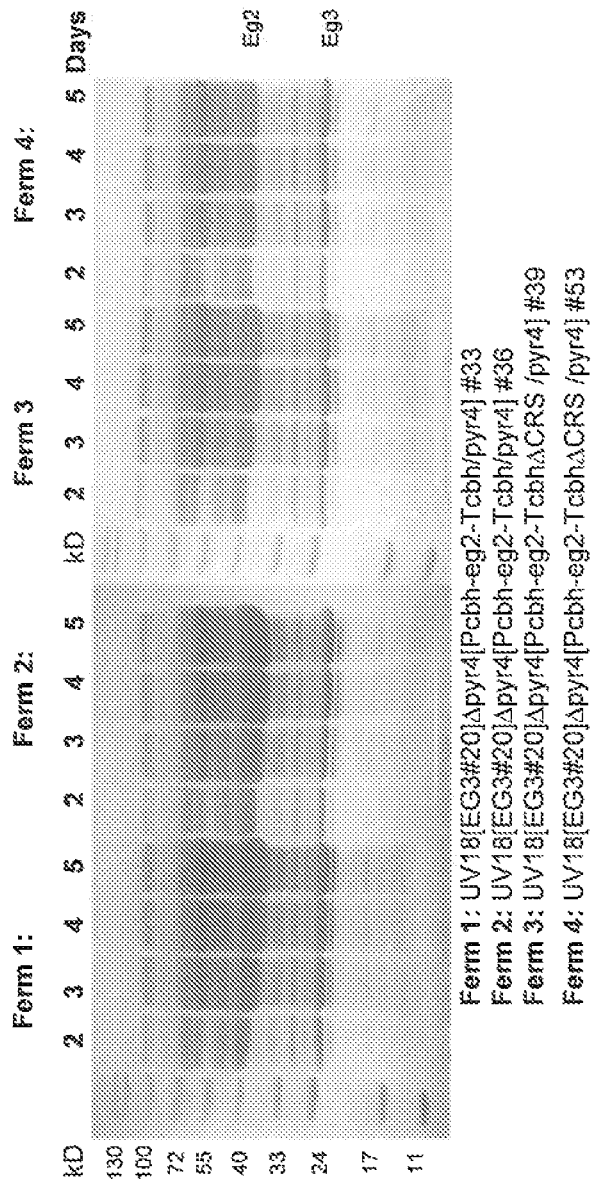
FIG. 26 shows a SDS-page gel on supernatant from fermentations (10 μA loaded on gel from 10× dilution).

Two strains from each set of transformants were selected for additional controlled fermentation runs in production medium. As shown in Table H, a 2-fold increase in specific β-glucanase and CMCase activity was determined in both types of eg2 multicopy strains compared to the pyr4 transformed host strain. However, in fermentor culture supernatant of strains with the CRS, the β-glucanase activity, CMCase activity and total extracellular protein content is 15-20% higher than in the supernatant from strains without the CRS. A PageBlue colored SDS-PAGE gel loaded with end of fermentation (EOF) samples is shown in FIG. 26. In samples of fermentor 1 and 2, an increase in a 40 kDa protein band (Eg2) was observed.

TABLE H

| STRAIN: UV18[EG3#20]Δpyr4 | Relative Beta-glucanase (AzoBarley) U/ml | Relative CMCase activity AzoCMC) U/ml | Relative Total biomass (g) | Relative Extracellular Protein g/L | Relative Beta-glucanase (AzoBarley) u/mg protein | Relative CMCase activity AzoCMC) U/mg protein |
|---|---|---|---|---|---|---|
| [pyr4]#7 | 1 | 1 | 1 | 1 | 1 | 1 |
| [Pcbh-eg2-Tcbh/pyr4]#33 | 1.75 | 1.50 | 1.44 | 0.82 | 2.14 | 1.83 |
| [Pcbh-eg2-Tcbh/pyr4]#36 | 1.92 | 1.51 | 1.66 | 0.77 | 2.49 | 1.96 |
| [Pcbh-eg2-TcbhΔCRS/pyr4]#39 | 1.40 | 1.27 | 1.81 | 0.62 | 2.22 | 2.04 |
| Pcbh-eg2-TcbhΔCRS/pyr4]#53 | 1.52 | 1.06 | 1.74 | 0.59 | 2.57 | 1.79 |

The results indicate that presence of one CRS in the expression cassette has a positive effect on the number of copies of the expression cassette that integrate and thus on the productivity. The effect of multiple copies of CRS on integration, stability and productivity can be tested via a similar approach. New expression cassettes may be constructed with two CRS, the second CRS introduced in the upstream region of the promoter. In addition, multiple expression cassettes in one construct can be flanked by two CRS. The above assays may then be repeated with strains transformed with vectors containing these multiple CRS expression cassettes.

J. Assay for Protease Activity

The following assay may be used to determine the protease activity of enzymes and protease-deficient strains of the present invention.

The protease activity is measured using N,N-dimethylcaseine (Sigma, C 9801) as a substrate. The procedure was fully automated using a Cobas Mira Plus autoanalyser (Roche).

Reagents include N,N-dimethylcaseine (5 g/l in 0.1 M NaAc/Hac (pH=5.5), 5 g/l in 0.1 M $K_2HPO_4$ (pH=7.0), or 5 g/l in 0.1 M $Na_2B_4O_7.10H_2O$ (pH=8.5)); Starter 1 (0.1 M $Na_2B_4O_7.10H_2O$ (pH=9.3)+0.5 g/l $Na_2SO_3$); and Starter 2 (5% TNBS (2,4,6, Trinitrobenzene Sulfonic Acid, Pierce #28997) 2× diluted with water).

2 μl of sample (+13 μl water) is mixed with 75 μl N,N-dimethylcaseine and incubated at 37° C. for 1050 (or 900) seconds. The reaction is stopped by addition of 185 μl starter 1 and 5 μl starter 2. The absorption at 405 nm is measured after 200 seconds. As a standard, a known concentration of glycine is used. Samples are also incubated with water (instead of N,N-dimethylcaseine) to measure the background activity. The sample data are corrected for this background activity. One unit of protease is the amount (in μmol) of peptide bonds cleaved per minute per ml sample at 37° C. at a given pH.

Using the assay above, the protease activity of protease-deficient strains of C. lucknowense was determined, and the results provided in Table I. The results demonstrate the reduced protease activity of strains UV18#100.f, UV18#100.fΔalp1, UV18#100.fΔalp1Δpep4, and UV18#100.fΔalp1Δpep4Δalp2 as compared to the parent strain UV18-25.

TABLE I

Protease Activities

| Strain | Protease Activity | | |
|---|---|---|---|
| | pH5.5 | pH7.0 | pH8.5 |
| UV18-25 | 306 | 415 | 793 |
| UV18#100.f | 104 | 80 | 81 |
| UV18#100.fΔalp1 | 38 | 48 | 18 |
| UV18#100.fΔalp1Δpep4 | 30 | 51 | 21 |
| UV18#100.fΔalp1Δpep4Δalp2 | 8 | 11 | 1 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

We claim:

1. A circular expression vector capable of autonomous replication followed by spontaneous linearization and integration into the genome of a fungal host cell transformed with said vector, comprising in order,
   (a) a first region comprising a telomeric sequence and the selection marker pyrE;
   (b) a second region comprising a promoter operable in a fungal host cell;
   (c) a third region that promotes autonomous replication in a bacterial host cell;
   (d) a fourth region comprising the selection marker pyrG and a telomeric sequence; and
   (e) a fifth intervening region linking the first and fourth regions in the circular form of the expression vector which comprises one or more sites for linearization between the telomeric sequences of said first and fourth regions, but does not comprise a nucleotide sequence encoding a selectable marker operable in a bacterial host cell;
   wherein said telomeric sequences promote autonomous replication and enhance transformation in said fungal host cell;
   wherein said linearization occurs in vivo in the intervening region in the circular form of said expression vector introduced into said fungal host cell;
   wherein said second and third regions may be in any order between said first and fourth regions.

2. The expression vector of claim 1, wherein the telomeric sequences are human telomeric sequences, fungal telomeric sequences, or homologues thereof.

3. The expression vector of claim 1, further comprising a fungal signal sequence.

4. The expression vector of claim 3, wherein the fungal signal sequence is the signal sequence of a fungal gene encoding a protein selected from the group consisting of cellulase, β-galactosidase, xylanase, pectinase, esterase, protease, amylase, chitinase, chitosanase, polygalacturonase and hydrophobin.

5. The expression vector of claim 1, wherein said second region further comprises at least one terminator sequence operably-linked in a 3' direction downstream from at least one of said promoters operable in a fungal host cell.

6. The expression vector of claim 5, wherein the terminator sequence is the trpC terminator of *A. nidulans* (TtrpC) or the terminator of the cellobiohydrolase encoding gene of *C. lucknowense* (Tcbh1).

7. The expression vector of claim 5, wherein the terminator sequence comprises SEQ ID NO:11.

8. The expression vector of claim 1, wherein the vector comprises one or more copies of the C1 Repetitive Sequence (CRS).

9. The expression vector of claim 8, wherein the vector comprises from one to ten copies of the CRS.

10. The expression vector of claim 8, wherein the CRS is located in an upstream region of a promoter within the vector.

11. The expression vector of claim 8, wherein the CRS comprises the nucleic acid sequence of SEQ ID NO:12.

12. The expression vector of claim 1, wherein the promoter sequence is the promoter of the cellobiohydrolase encoding gene of *C. lucknowense* (Pcbh1) or the promoter region of the glyceraldehyde-3-phosphate dehydrogenase gene of *A. nidulans* (PgpdA).

13. The expression vector of claim 5, wherein the vector comprises a nucleic acid sequence encoding a protein between the promoter of the cellobiohydrolase encoding gene of *C. lucknowense* (Pcbh1) and the terminator of the cellobiohydrolase encoding gene of *C. lucknowense* (Tcbh1).

14. The expression vector of claim 13, wherein the protein is a fusion protein.

15. The expression vector of claim 13, wherein the protein is an immunoglobulin light chain or a fragment thereof, or an immunoglobulin heavy chain or a fragment thereof.

16. The expression vector of claim 13, wherein the protein comprises both an immunoglobulin light chain or a fragment thereof, and an immunoglobulin heavy chain or a fragment thereof.

17. The expression vector of claim 1, wherein the vector is pPcbh1 glaA(II) heavy(88) Tcbh1 Pcbh1 glaA(II) light(90) Tcbh1 pyrE tel PyrG.

18. The expression vector of claim 1, wherein the vector comprises the nucleic acid sequence of SEQ ID NO:10.

19. The expression vector of claim 1, wherein said second region comprises one or more nucleic acid sequences encoding a heterogeneous protein or components of a heteromultimeric protein, operably linked to one or more promoters.

20. The expression vector of claim 1, wherein one or more of the promoters operable in a fungal host cell is an inducible promoter.

21. The expression vector of claim 19, wherein each nucleic acid sequence encoding a heterogeneous protein or a component of said heteromultimeric protein is operably linked to a different promoter.

22. The expression vector of claim 19, wherein each nucleic acid sequence encoding a heterogeneous protein or a component of the heteromultimeric protein is operably linked to a different terminator.

23. The expression vector of claim 19, wherein the vector comprises nucleic acid sequences for transfer of the nucleic acid sequences encoding the heterogeneous protein or components of a heteromultimeric protein to or from a non-fungal host cell.

24. The expression vector of claim 19, wherein the vector comprises nucleic acid sequences for transfer of the nucleic acid sequences encoding the heterogeneous proteins or components of a heteromultimeric protein to or from a bacteriophage.

25. The expression vector of claim 19, wherein the vector comprises nucleic acid sequences for transfer of the nucleic acid sequences encoding the components of the heterogeneous or heteromultimeric protein to or from a bacteriophage.

26. The expression vector of claim 23, wherein the nucleic acid sequences for transfer comprise nucleic acid sequences for in vitro homologous recombination.

27. The expression vector of claim 19, wherein the nucleic acid sequences encoding the heterogeneous proteins or components of a heteromultimeric protein are fused to each other and operably-linked to a single promoter.

28. The expression vector of claim 19, wherein the nucleic acid sequences encoding the heterogeneous proteins or components of a heteromultimeric protein are operably-linked to different promoters.

29. The expression vector of claim 19, wherein the vector comprises at least one nucleic acid sequence encoding a fusion partner, wherein the nucleic acid sequence encoding the fusion partner is operably-linked to a nucleic acid sequence encoding a heterogeneous protein or components of a heteromultimeric protein.

30. The expression vector of claim 29, wherein the fusion partner is linked to a component with a protein-processing site.

31. The expression vector of claim 30, wherein the protein-processing site is a kex2 cleavage site.

32. The expression vector of claim 29, wherein each of the heterogeneous proteins or components of a heteromultimeric protein is linked to a different fusion partner.

33. The expression vector of claim 29, wherein each of the heterogeneous proteins or components of a heteromultimeric fusion protein are linked to each other and to a fusion partner.

34. The expression vector of claim 33, wherein the fusion partner and each of the components is linked by a protease processing site.

35. The expression vector of claim 29, wherein the fusion partner enables secretion of the heterogeneous or heteromultimeric protein from the filamentous fungus.

36. The expression vector of claim 19, wherein each of the nucleic acid sequences encoding a component of the multimeric protein is flanked by restriction enzyme sites.

37. The expression vector of claim 19, wherein the nucleic acid sequence comprising all of the nucleic acid sequences encoding the heterogeneous proteins or components of a heteromultimeric protein is flanked by restriction enzyme sites.

38. The expression vector of claim 19, wherein any one or more of the nucleic acid sequences encoding a component of the heterogeneous or heteromultimeric protein is mutated to reduce the presence of protease processing sites recognized by fungal proteases, or wherein any one or more of the nucleic acid sequences encoding the heterogeneous proteins or components of a heteromultimeric protein is selected to have reduced presence of protease processing sites recognized by fungal proteases.

39. The expression vector of claim 19, wherein the nucleic acid sequences encoding the heterogeneous proteins or components of a heteromultimeric protein are optimized to allow efficient transcription, translation, and protein folding in the fungal host.

40. The vector of claim 1, wherein said intervening region comprises a unique target site for linearization in vitro with a restriction endonuclease.

41. The vector of claim 40, wherein said restriction endonuclease is I-Ceul.

42. The vector of claim 1, wherein said intervening region comprises one or more target sites for linearization in vitro with a restriction endonuclease that does not have a target site in other regions of said vector.

43. The vector of claim 40, wherein said restriction endonuclease is EcoRI.

* * * * *